(12) United States Patent
Friedman et al.

(10) Patent No.: US 8,057,804 B2
(45) Date of Patent: *Nov. 15, 2011

(54) HERPES SIMPLEX VIRUS COMBINED SUBUNIT VACCINES AND METHODS OF USE THEREOF

(75) Inventors: Harvey Friedman, Merion, PA (US); Sita Awasthi, Bala Cynwyd, PA (US); John Lubinski, Malvern, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 103 days.

This patent is subject to a terminal disclaimer.

(21) Appl. No.: 12/179,439

(22) Filed: Jul. 24, 2008

(65) Prior Publication Data

US 2009/0148467 A1 Jun. 11, 2009

Related U.S. Application Data

(63) Continuation-in-part of application No. 12/005,407, filed on Dec. 27, 2007.

(60) Provisional application No. 60/877,378, filed on Dec. 28, 2006, provisional application No. 60/929,105, filed on Jun. 13, 2007, provisional application No. 60/996,724, filed on Dec. 3, 2007.

(51) Int. Cl.
*A61K 39/245* (2006.01)

(52) U.S. Cl. .................................... 424/231.1

(58) Field of Classification Search .................... None
See application file for complete search history.

(56) References Cited

U.S. PATENT DOCUMENTS

| | | | |
|---|---|---|---|
| 4,709,011 | A | 11/1987 | Cohen et al. |
| 4,762,708 | A | 8/1988 | Cohen et al. |
| 5,955,088 | A | 9/1999 | Ghiasi et al. |
| 6,193,984 | B1 | 2/2001 | Ghiasi et al. |
| 2003/0129199 | A1 | 7/2003 | Stephenne et al. |

FOREIGN PATENT DOCUMENTS

| | | |
|---|---|---|
| WO | WO 01/08701 A2 | 2/2001 |
| WO | WO01/09361 | 2/2001 |
| WO | WO 02/087614 A2 | 11/2002 |
| WO | WO02/092826 | 11/2002 |

OTHER PUBLICATIONS

Pepose et al (American Journal of Ophthalmology 141:547-557, 2006).*
Stanberry (Herpes 11 Supplement 3: 161A-169A, 2004).*
Bernstein (Expert Review of Vaccines 4:615-627, 2005).*
Jones et al (Expert Review of Vaccines 2:541-549, 2003).*
Stanberry et al (New England Journal of Medicine 347:1652-1661, 2002).*
Judson et al (Journal of Virology 77:12639-12645, 2003).*
Kostavili et al (Journal of Immunology 158:1763-1771, 1997).*
Hook et al (Journal of Virology 80:4038-4046, 2006).*
Ashkenazi et al., 1993, "Immunoadhesins", Int. Rev. Immunol. 10(2-3): 219-27.
Buchwald et al., 1980, "Long-term, continuous intravenous heparin administration by an implantable infusion pump in ambulatory patients with recurrent venous thrombosis", Surgery 88:507.
Caudy AA et al., 2002 "Fragile X-related protein and VIG associate with the RNA interference machinery", Genes & Devel 16:2491-96.
Cheon et al., 1994, "High-affinity binding sites for related fibroblast growth factor ligands reside within different receptor immunoglobulin-like domains", PNAS USA 91(3):989-93.
Dubin G., E. Socolof, I. Frank and H. M. Freidman, 1991, "Herpes simplex virus type 1 Fc receptor protects infected cells from antibody-dependent cellular cytotoxicity", J. Virol 65:7046-50.
Eisenberg RJ et al., 1985, "Localization of epitopes of herpes simplex virus type 1 glycoprotein D", J. Virol 53:634-644.
Evan et al., 1985, "Isolation of Monoclonal Antibodies Specific for Human c-myc Proto-Oncogene Product", Molecular and Cellular Biology 5:3610-3616.
Field et al., 1988, "Purification of a RAS-responsive adenylyl cyclase complex from *Saccharomyces cerevisiae* by use of an epitope addition method", Mol. Cell. Biol. 8:2159-2165.
Friedman H. M., Cohen G. H., Eisenberg R. J., Seidel C. A., and Cines D. B., 1984, "Glycoprotein C of herpes simplex virus 1 acts as a receptor for the C3b complement component on infected cells". Nature 309:633-5.
Friedman et al., 1996, "Immune evasion properties of herpes simplex virus type 1 glycoprotein gC", J. Virol. 70:4253-4260.
Ghiasi et al., "Expression of seven herpes simplex virus type 1 glycoproteins (gB, gC, gD, gE, gG, gH, and gI): Comparative protection against lethal challenge in mice", J, Virol., Apr. 1994, 68(4):2118-26.
Ghiasi et al., "Protection against herpes simplex virus-induced eye disease after vaccination with seven individually expressed herpes simplex virus 1 glycoproteins, Invest. Ophthalmol", Vis. Sci., Jun. 1995, 36(7)1352-1360.
Goldstein and Weller, 1988, "An ICP6::lacZ insertional mutagen is used to demonstrate that the UL52 gene of herpes simplex virus type 1 is required for virus growth and DNA synthesis", J. Virol. 62:2970-2977.
Heidaran et al., 1995, "Beta PDGFR-IgG chimera demonstrates that human beta PDGFR Ig-like domains 1 to 3 are sufficient for high affinity PDGF BB binding", Faseb J. 9(1)140-5.
Hook et al., 2006, "Herpes simplex virus type 1 and 2 glycoprotein C prevents complement-mediated neutralization induced by natural immunoglobulin m antibody", J. Virol. 80:4038-4046.
Hopp et al., 1988, "A Short Polypeptide Marker Sequence Useful for Recombinant Protein Identification and Purification". BioTechnology 6:1204-1210.
International Search Report of Application No. PCT/US07/26352 issued on Mar. 25, 2008.

(Continued)

Primary Examiner — Mary E Mosher
(74) Attorney, Agent, or Firm — Pearl Cohen Zedek Latzer, LLP; Mark S. Cohen

(57) ABSTRACT

This invention provides vaccines comprising two or more recombinant Herpes Simplex Virus (HSV) proteins selected from a gD protein, a gC protein and a gE protein; and methods of impeding immune evasion by HSV thereby vaccinating a subject against HSV and treating, suppressing, inhibiting, and/or reducing an incidence of an HSV infection or a symptom or manifestation thereof, comprising administration of a vaccine of the present invention.

19 Claims, 34 Drawing Sheets

OTHER PUBLICATIONS

Jiang C et al., "Mutations thar decrease DNA binding of the processivity factor of the herpes simplex virus DNA polymerase reduce viral yield, alter the kinetics of viral DNA replication, and decrease the fidelity of DNA replication", J. Virol., Apr. 2007, 81(7):3495-502.

Jones et al., "Vaccination strategies to prevent genital herpes and neonatal herpes simplex virus (HSV) disease", Herpes, Apr. 2004, 11(1):12-17.

Judson KA et al., "Blocking immune evasion as a novel approach for prevention and treatment of herpes simplex virus infection", J. Virol. 77:12639-45, 2003.

Kase at al., 1999, "Human mannan-binding lectin inhibits the infection of influenza A virus without complement", Immunology 97:385-392.

Klepeis et al., 2003, "Integrated computational and experimental approach for lead optimization and design of compstatin variants with improved activity", J. Am. Chem. Soc. 125:8422-8423.

Kostavasili I., Sahu A., Freidman H. M., Eisenberg R. J., Cohen G. H. and Lambris J. D., 1997, "Mechanism of complement inactivation by glycoprotein C of herpes simplex virus", J. Immunol. 158:1763-71.

Labetoulle M et al., "Neuronal propagation of HSV1 from the Oral mucosa to the eye", Invest Ophthalmol Vis Sci. Aug. 2000; 41(9):2600-6.

Lambiase A et al. "Topical treatment with nerve growth factor in an animal model of herpetic keratitis", Grafes Arch Clin. Exp. Ophthalmol., May 4, 2007.

Langur, Supra Sefton, 1987, "Implantable Pumps", CRC Crit. Ref, Biomed. Eng. 14:201.

Larochelle et al., 1995, "Specific receptor detection by a functional keratinocyte growth factor—immunoglobulin chimera", J. Cell Biol. 129(2):357-66.

Lubinski et al., 1998, "Viral interference with antibody and complement", Seminars in Cell & Developmental Biology 9:329-37.

Lubinski et al, 1999, "In vivo role of complement-interacting domains of herpes simplex virus type 1 glycoprotein gC", J. Exper Med 190:1637-46.

Lubinski et al, 2002, "Herpes simplex virus type 1 evades the effects of antibody and complement in vivo", J. Virol 76:9232-41.

Lubinski et al, 1998, "Herpes simplex virus type 1 glycoprotein gC mediates immune evasion in vivo", J. Virol 72:8257-63.

Lutz-Freyermuth et al., 1990, "Quantitative Determination That One of Two Potential RNA-binding Domains of the A Protein Component of the UI Small Nuclear Ribonucleoprotein Complex Binds with High Affinity to Stem-loop II of U1 RNA", Proc. Natl. Acad. Sci. USA, 87:6393-6397.

Majumdar S et al., "Dipeptide monoester ganciclovir prodrugs for treating HSV-1-induced corneal epithelial and stromal keratitis: in vitro and in vivo evaluations", J. Ocul Pharmacol Ther. Dec. 2005; 21(6):463-74.

Martin et al., 1992, "GAP Domains Responsible for Ras p21-Dependent Inhibition of Muscarinic Atrial K+ Channel Currents", Science 255:192-194.

Nagashunmugam et al., "In vivo immune evasion mediated by the herpes simplex virus type 1 immunoglobulin G Fc Receptor", J. Virol. 72:5351-9, 1998.

Nagot et al., "Reduction of HIV-1 RNA levels with therapy to suppress herpes simplex virus", N. Engl. J. Med., Feb. 22, 2007, 356(8):790-9.

Nesburn et al., "Vaccine therapy for ocular herpes simplex virus (HSV) Infection: periocular vaccination reduces spontaneous ocular HSV type 1 shedding in latently infected rabbits", J. Virol., Aug. 1994, 68(8):5084-5092.

Ouedraogo A et al., "Impact of suppressive herpes therapy on genital HIV-1 RNA among women taking antiretroviral therapy: a randomized controlled trial", AIDS, Nov. 28, 2006; 20(18):2305-13.

Paborsky et al., 1990, "Mammalian cell transient expression of tissue factor for the production of antigen", Protein Engineering, 3(6):547-553.

Ramaswamy M et al., "Interactions and management issues in HSV and HIV coinfection", Expert Rev. Anti Infect Ther. Apr. 2007, 5(2):231-43.

Sahu et al., 1996, "Inhibition of human complement by a C3-binding peptide isolated from a phage-displayed random peptide library", J. Immunol. 157:884-891.

Saudek et al., 1989, "A Preliminary Trial of the Programmable Implantable Medication System for Insulin Delivery", N. Engl. J. Med. 321:574.

Skinner et al., 1991, "Use of the Glu-Glu-Phe C-terminal Epitope for Rapid Purification of the Catalytic Domain of Normal and Mutant ras GTPase-activating Proteins", J. Biol. Chem. 266:15163-15166.

Wagner R. W. et al., 1996, "Potent and selective inhibition of gene expression by an antisense heptanucleotide", Nat. Biotechnol. 14:840-844.

Bernstein (2005) "Glycoprotein D adjuvant herpes simplex virus vaccine" Expert Review of Vaccines 4:615-627.

Ghiasi et al. (1996) "Vaccination with a cocktail of seven recombinantly expressed HSV-1 glycoproteins protects against ocular HSV-1 challenge more efficiently than vaccination with any individual glycoprotein" Vaccine 14:107-112.

International Preliminary Report on Patentability (IPRP; Chaper I) for PCT/US07/26352 dated Jul. 9, 2009.

Jones and Cunningham (2003) "Development of prophylactic vaccines for genital and neonatal herpes" Expert Review of Vaccines 2:541-549.

Koelle and Ghiasi (2005) "Prospects for developing an effective vaccine against ocular herpes simplex virus infection" Current Eye Res 30:929-942.

Nass et al. (1998) "Antibody response and protective capacity of plasmid vaccines expressing three different herpes simplex virus glycoproteins." J. Infect. Dis. 178:611-617.

Pepose et al. (2006) "Ocular herpes simplex: changing epidemiology, emerging disease patterns, and the potential of vaccine prevention and therapy" American Journal of Ophthamology 141: 547-557.

Stanberry et al. (2002) "Glycoprotein-D-adjuvant vaccine to prevent genital herpes" New England Journal of Medicine 347:1652-1661.

Chang et al.: "Implications for herpes simplex virus vaccine strategies based on antibodies produced to herpes simplex virus type 1 glycoprotein gC immune evasion domains" Vaccine, Butterworth Scientific. Guildford, GB, vol. 23, No. 38, Sep. 7, 2005, pp. 4658-4665.

Manservigi R et al: "Immunotherapeutic activity of a recombinant combined gB-gD-gE vaccine against recurrent HSV-2 infections in a guinea pig model" Vaccine, Butterworth Scientific, Guildford, GB, vol. 23, No. 7, Jan. 4, 2005, pp. 865-872.

Mukhlis F A et al: "Characterization and immunogenicity of HSV-1 antigens obtained following zwitterionic detergent treatment" Vaccine, Butterworth Scientific. Guildford, GB, vol. 4, No, 3, Sep. 1, 1986, pp. 191-196.

Osorio Yanira et al: "Improved protection from primary ocular HSV-1 infection and establishment of latency using multigenie DNA vaccines." Investigative Ophthalmology & Visual Science Feb. 2004, vol. 45, No. 2, pp. 506-514.

* cited by examiner

A

B

WT VIRUS          gC/gE MUTANT VIRUS gC shields critical domains on gD to protect the virus from antibody neutralization Mutations in gC expose neutralizing epitopes on gD

Figure 47

HERPES SIMPLEX VIRUS COMBINED SUBUNIT VACCINES AND METHODS OF USE THEREOF

CROSS-REFERENCE TO RELATED APPLICATIONS

This application is a continuation-in-part of U.S. application Ser. No. 12/005,407, filed Dec. 27, 2007, which claims the benefit of U.S. Provisional Application Ser. No. 60/877,378, filed Dec. 28, 2006, U.S. Provisional Application Ser. No. 60/929,105, filed Jun. 13, 2007 and U.S. Provisional Application Ser. No. 60/996,724, filed Dec. 3, 2007, which are hereby incorporated by reference in their entirety.

STATEMENT REGARDING FEDERALLY SPONSORED RESEARCH OR DEVELOPMENT

The invention described herein was supported in whole or in part by grants from The National Institutes of Health (Grant No. HL 28220, AI 33063, DE 14152). The government has certain rights in the invention.

FIELD OF INVENTION

This invention provides vaccines comprising two or more recombinant Herpes Simplex Virus (HSV) proteins selected from a gD protein, a gC protein and a gE protein; and methods of impeding immune evasion by HSV thereby vaccinating a subject against HSV and treating, suppressing, inhibiting, and/or reducing an incidence of an HSV infection or a symptom or manifestation thereof, comprising administration of a vaccine of the present invention.

BACKGROUND OF THE INVENTION

Herpes simplex virus type 1 (HSV-1) and Herpes simplex virus type 2 (HSV-2) are common human pathogens and cause a variety of clinical illnesses, including oral-facial infections, genital herpes, ocular infections, herpes encephalitis, and neonatal herpes. HSV-1 is more frequently associated with non-genital infection and is mostly acquired during childhood via nonsexual contact. In the last decade, however, it has become an important cause of genital herpes. HSV-2 is the cause of most cases of genital herpes, and it infects an estimated 500,000 persons annually in the United States. Despite the availability of antiviral agents to treat HSV disease, genital HSV-2 infections have remained a persistent problem with a seroprevalence of approximately 17% among 14-49 year old subjects in the United States, with much greater prevalence rates in parts of South America and Africa.

Methods for preventing primary (first time) infection and preventing recurrences of HSV-1 and HSV-2 are urgently needed in the art.

Herpes simplex virus is also a major risk factor for Human Immunodeficiency Virus (HIV) infection. Individuals who are seropositive for HSV-2 have a 2-fold increased risk of acquiring HIV. Acquisition rates appear greatest following initial HSV-2 infection, when HSV-2 reactivation is most frequent. Treatments and vaccine strategies aimed at reducing HSV infection may prevent HIV transmission, acquisition, and disease progression.

SUMMARY OF THE INVENTION

In one embodiment, the present invention provides a vaccine comprising: (a) a recombinant HSV-2 gD protein or immunogenic fragment thereof; (b) a recombinant HSV-2 gC protein fragment, wherein said fragment comprises a C3b-binding domain thereof, a properdin interfering domain thereof, a C5 interfering domain thereof, or a fragment of said C3b-binding domain, properdin interfering domain, or C5-interfering domain; and (c) an adjuvant.

In another embodiment, the present invention provides a method of inducing an anti-HSV-2 immune response in a subject, the method comprising the step of administering to said subject a vaccine of the present invention.

In another embodiment, the present invention provides a method of treating, suppressing, inhibiting, or reducing an incidence of an HSV-2 infection in a subject, the method comprising the step of administering to said subject a vaccine of the present invention.

In another embodiment, the present invention provides a method of reducing an incidence of a reactivation of a latent HSV-2 infection in a subject, the method comprising the step of administering to said subject the vaccine of the present invention.

In one embodiment, the HSV-2 infection is a primary HSV-2 infection. In one embodiment, the HSV-2 infection is a flare, recurrence, or HSV labialis following a primary HSV-2 infection. In one embodiment, the HSV-2 infection is a genital HSV-2 infection. In one embodiment, the HSV-2 infection is an oral HSV-2 infection. In one embodiment, the HSV-2 infection is HSV encephalitis. In one embodiment, the HSV-2 infection is an HSV neonatal infection. In one embodiment, the subject is HIV-infected. In one embodiment, the vaccine is administered intramuscularly. In another embodiment, the vaccine is administered intravaginally. In one embodiment, the vaccine is administered before exposure to HSV-2. In another embodiment, the vaccine is administered after exposure to HSV-2. In one embodiment, the vaccine is administered multiple times. In one embodiment, the method further comprises administering to said subject a booster vaccination, wherein said booster vaccination (a) comprises said recombinant HSV-2 gD protein or immunogenic fragment thereof; and (b) does not comprise recombinant HSV-2 gC protein or fragment thereof. In another embodiment, the recombinant HSV gD protein or immunogenic fragment thereof is present in the booster vaccination an amount of 2-10 micrograms per dose.

BRIEF DESCRIPTION OF THE FIGURES

FIG. 47: Model of epitope masking. On the left, gC blocks epitopes on gD preventing binding of neutralizing IgG antibodies to WT virus. On the right, gC on the mutant virus fails to block epitopes on gD enabling neutralizing antibodies to bind. Epitope shielding by gE is not shown in the figure; however, our findings support a similar model for gE.

DETAILED DESCRIPTION OF THE INVENTION

Figure 1:
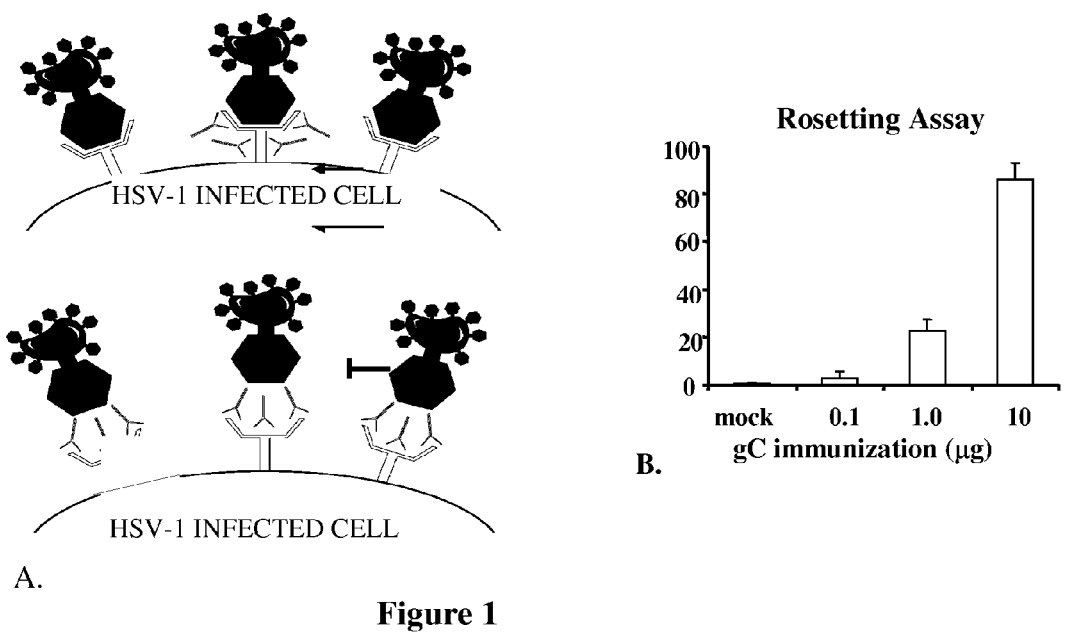
FIG. 1: Rosetting assay to detect antibodies that block C3b binding to gC on HSV-1 infected cells. (A) Top: Symbolic depiction of a resetting assay to measure C3b binding to gC-1. HSV-1 infected Vero cells express gC on the cell surface and bind C3b-coated sheep red blood cells to form rosettes around infected Vero cells. Bottom: Symbolic depiction of antibodies that block resetting. In the presence of anti-gC antibodies, C3b-coated red blood cells fail to bind to gC and no rosettes form. (B) Serum from mock or gC-1 immunized mice was used to block resetting of C3b-coated red blood cells (+/− standard errors).

This invention provides vaccines comprising two or more recombinant Herpes Simplex Virus (HSV) proteins selected from a gD protein, a gC protein and a gE protein; and methods of vaccinating a subject against HSV and treating, impeding, inhibiting, reducing the incidence of, or suppressing an HSV infection or a symptom or manifestation thereof, comprising administration of a vaccine of the present invention. In one embodiment, the vaccine additionally comprises an adjuvant.

In another embodiment, this invention provides vaccines comprising a recombinant Herpes Simplex Virus (HSV) gD protein and a recombinant protein selected from at least one of a HSV gC protein and a HSV gE protein. In one embodiment, the vaccine additionally comprises an adjuvant.

In one embodiment, the present invention provides a vaccine comprising: (a) a recombinant Herpes Simplex Virus-1 (HSV-1) gD protein or fragment thereof; (b) a recombinant HSV-1 gC protein or fragment thereof; and (c) an adjuvant. In another embodiment, administration of the vaccine to a human subject elicits an anti-HSV-1 gC antibody that blocks an immune evasion function of an HSV protein corresponding to the recombinant HSV-1 gC protein. In another embodiment, the gC fragment includes an immune evasion domain thereof. In another embodiment, immunization with gC and gD, or fragments thereof, in combination limits the ability of HSV-1 to evade a host immune response during a subsequent challenge. In another embodiment, immunization with gC or a fragment thereof limits the ability of HSV-1 to evade a host anti-gD immune response during a subsequent challenge. In another embodiment, the host immune response referred to comprises anti-gD antibodies induced by the vaccine.

In another embodiment, "HSV protein" refers to an HSV-1 or HSV-2 protein. In another embodiment, "HSV protein" refers to an HSV-1 protein. In another embodiment, "HSV protein" refers to an HSV-2 protein. In another embodiment, the term refers to an HSV-1 gD protein. In another embodiment, the term refers to a fragment of an HSV-1 gD protein. In another embodiment, the term refers to an HSV-1 gC protein.

In another embodiment, the term refers to a fragment of an HSV-1 gC protein. In another embodiment, the term refers to an HSV-1 gE protein. In another embodiment, the term refers to a fragment of an HSV-1 gE protein. In another embodiment, the term refers to an HSV-2 gD protein. In another embodiment, the term refers to a fragment of an HSV-2 gD protein. In another embodiment, the term refers to an HSV-2 gC protein. In another embodiment, the term refers to a fragment of an HSV-2 gC protein. In another embodiment, the term refers to an HSV-2 gE protein. In another embodiment, the term refers to a fragment of an HSV-2 gE protein. In one embodiment, a fragment referred to herein is an immunogenic fragment. In one embodiment, an "immunogenic fragment" refers to a portion of a oligopeptide, polypeptide or protein that is immunogenic and elicits a protective immune response when administered to a subject.

In one embodiment, "immunogenicity" or "immunogenic" is used herein to refer to the innate ability of a protein, peptide, nucleic acid, antigen or organism to elicit an immune response in an animal when the protein, peptide, nucleic acid, antigen or organism is administered to the animal. Thus, "enhancing the immunogenicity" in one embodiment, refers to increasing the ability of a protein, peptide, nucleic acid, antigen or organism to elicit an immune response in an animal when the protein, peptide, nucleic acid, antigen or organism is administered to an animal. The increased ability of a protein, peptide, nucleic acid, antigen or organism to elicit an immune response can be measured by, in one embodiment, a greater number of antibodies to a protein, peptide, nucleic acid, antigen or organism, a greater diversity of antibodies to an antigen or organism, a greater number of T-cells specific for a protein, peptide, nucleic acid, antigen or organism, a greater cytotoxic or helper T-cell response to a protein, peptide, nucleic acid, antigen or organism, and the like.

In one embodiment, "functional" within the meaning of the invention, is used herein to refer to the innate ability of a protein, peptide, nucleic acid, fragment or a variant thereof to exhibit a biological activity or function. In one embodiment, such a biological function is its binding property to an interaction partner, e.g., a membrane-associated receptor, and in another embodiment, its trimerization property. In the case of functional fragments and the functional variants of the invention, these biological functions may in fact be changed, e.g., with respect to their specificity or selectivity, but with retention of the basic biological function.

Numerous methods for measuring the biological activity of a protein, polypeptide, or molecule are known from the related art, for example, protein assays, which use labeled substrates, substrate analyses by chromatographic methods, such as HPLC or thin-layer chromatography, spectrophotometric methods, etc. (see, e.g., Maniatis et al. (2001) Molecular Cloning: A Laboratory Manual, Cold Spring Harbor Laboratory Press, Cold Spring Harbor, N.Y.).

In one embodiment, the term "fragment" is used herein to refer to a protein or polypeptide that is shorter or comprises fewer amino acids than the full length protein or polypeptide. In another embodiment, fragment refers to a nucleic acid that is shorter or comprises fewer nucleotides than the full length nucleic acid. In another embodiment, the fragment is an N-terminal fragment. In another embodiment, the fragment is a C-terminal fragment. In one embodiment, the fragment is an intrasequential section of the protein, peptide, or nucleic acid. In another embodiment, the fragment is an immunogenic intrasequential section of the protein, peptide or nucleic acid. In another embodiment, the fragment is a functional intrasequential section within the protein, peptide or nucleic acid. In another embodiment, the fragment is an N-terminal immunogenic fragment. In one embodiment, the fragment is a C-terminal immunogenic fragment. In another embodiment, the fragment is an N-terminal functional fragment. In another embodiment, the fragment is a C-terminal functional fragment.

Thus, in one embodiment, an "immunogenic fragment" of a protein as described in the present invention (e.g. gC-1, gC-2, gE-1, gE-2, gD-1, gD-2, etc) refers to a portion of the protein that is immunogenic, in one embodiment and in another embodiment, elicits a protective immune response when administered to a subject.

In one embodiment, any reference to HSV in the composition and methods of the instant invention refers, in one embodiment, to HSV-1, and in another embodiment, to HSV-2, and in another embodiment, to both HSV-1 and HSV-2, and in another embodiment, to HSV-1 or HSV-2.

In another embodiment, the present invention provides a vaccine comprising: (a) a recombinant Herpes Simplex Virus-2 (HSV-2) gD protein or fragment thereof; (b) a recombinant HSV-2 gC protein or fragment thereof; and (c) an adjuvant. In another embodiment, administration of the vaccine to a human subject elicits an anti-HSV-2 gC antibody that blocks an immune evasion function of an HSV protein corresponding to the recombinant HSV-2 gC protein. In another embodiment, the gC fragment includes an immune evasion domain thereof. In another embodiment, immunization with gC and gD, or fragments thereof, in combination limits the ability of HSV-2 to evade a host immune response during a subsequent challenge. In another embodiment, immunization with gC or a fragment thereof, limits the ability of HSV-2 to evade a host anti-gD immune response during a subsequent challenge. In another embodiment, the host immune response referred to comprises anti-gD antibodies induced by the vaccine.

Figure 2:
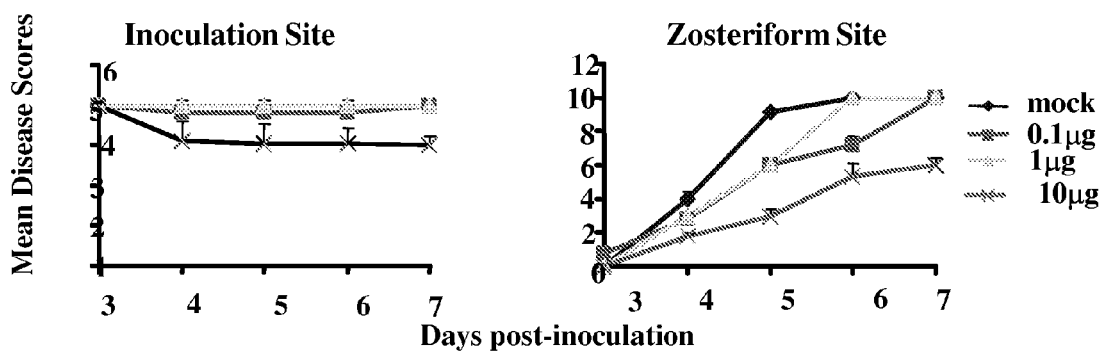
FIG. 2: Disease scores in gC-1 immunized mice challenged by flank infection with a lethal dose of WT virus. Mice were mock immunized or immunized with 0.1, 1 or 10 μg of gC-1. Immunized mice were scored for severity of disease at the inoculation and zosteriform sites from days 3 to 7 post-challenge.
Figure 5:
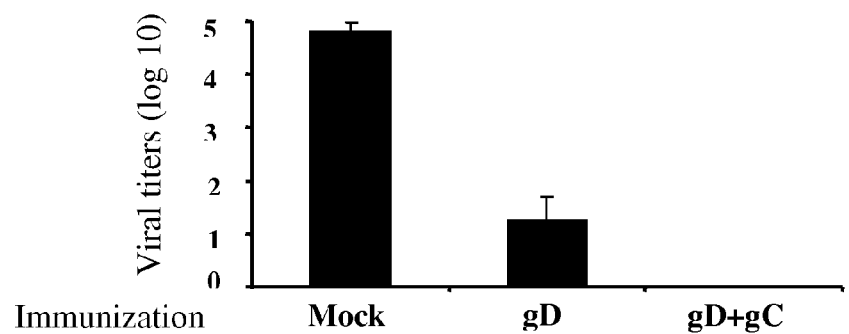
FIG. 5: Recovery of virus from DRG. Mice were either mock immunized, or immunized with gD-1 alone or both gD-1 and gC-1. Each group was then challenged with a lethal dose of HSV-1. Dorsal root ganglia (DRG) were harvested and assayed for infectious virus.

As provided herein, gC-1 subunit vaccines are protective against HSV-1 infection (FIG. 2). Further, in one embodiment, combination gC-1/gD-1 vaccines confer superior protection compared with vaccines containing gD-1 alone (FIG. 3) or gC-1 alone and reduce or prevent infection of dorsal root ganglia (FIG. 5). Further, gC-2 subunit vaccines are protective against HSV-2 infection (FIGS. 20-24), and combination gC-2/gD-2 vaccines confer protection superior to vaccines containing gD-2 alone or gC-2 alone (FIGS. 30-36).

In another embodiment, the present invention provides a vaccine comprising: (a) a recombinant HSV-1 gD protein or fragment thereof; (b) a recombinant HSV-1 gE protein or fragment thereof; and (c) an adjuvant. In another embodiment, administration of the vaccine to a human subject elicits an anti-HSV-1 gE antibody that blocks an immune evasion function of an HSV protein corresponding to the recombinant HSV-1 gE protein. In another embodiment, the gE fragment includes an immune evasion domain thereof. In another embodiment, immunization with gE and gD, or fragments thereof, in combination limits the ability of HSV-1 to evade a host immune response during a subsequent challenge. In another embodiment, immunization with gE or a fragment thereof, limits the ability of HSV-1 to evade a host anti-gD immune response during a subsequent challenge. In another embodiment, the host immune response referred to comprises anti-gD antibodies induced by the vaccine.

In another embodiment, the present invention provides a vaccine comprising: (a) a recombinant HSV-2 gD protein or fragment thereof; (b) a recombinant HSV-2 gE protein or fragment thereof; and (c) an adjuvant. In another embodiment, administration of the vaccine to a human subject elicits an anti-HSV-2 gE antibody that blocks an immune evasion function of an HSV protein corresponding to the recombinant HSV-2 gE protein. In another embodiment, the gE fragment includes an immune evasion domain thereof. In another embodiment, immunization with gE and gD, or fragments thereof, in combination limits the ability of HSV-2 to evade a host immune response during a subsequent challenge. In another embodiment, immunization with gE or a fragment thereof, limits the ability of HSV-2 to evade a host anti-gD immune response during a subsequent challenge. In another embodiment, the host immune response referred to comprises anti-gD antibodies induced by the vaccine.

As provided herein, gE-1 subunit vaccines are protective against HSV-1 infection. Further, combination gE-1/gD-1 vaccines confer superior protection compared with vaccines containing gD-1 alone or gE-1 alone. Further, gE-2 subunit vaccines are protective against HSV-2 infection, and combination gE-2/gD-2 vaccines confer protection superior to vaccines containing gD-2 alone or gE-2 alone.

In another embodiment, the immune-potentiating effect of gC and gE together is greater than the effect of either alone. In another embodiment, the immune-potentiating effects of gC and gE exhibit synergy.

In another embodiment, the present invention provides a vaccine comprising: (a) a recombinant Herpes Simplex Virus-1 (HSV-1) gC protein or fragment thereof; (b) a recombinant HSV-1 gE protein or fragment thereof; and (c) an adjuvant. In another embodiment, administration of the vaccine to a human subject elicits an anti-HSV-1 gC antibody that blocks an immune evasion function of an HSV protein corresponding to the recombinant HSV-1 gC protein. In another embodiment, the gC fragment includes an immune evasion domain thereof. In another embodiment, immunization with gC and gE, or fragments thereof, in combination limits the ability of HSV-1 to evade a host immune response during a subsequent challenge. In another embodiment, immunization with gC, or a fragment thereof, limits the ability of HSV-1 to evade a host anti-gE immune response during a subsequent challenge. In another embodiment, immunization with gE, or a fragment thereof, limits the ability of HSV-1 to evade a host anti-gC immune response during a subsequent challenge. In another embodiment, the host immune response referred to comprises anti-gC antibodies induced by the vaccine. In another embodiment, the host immune response referred to comprises anti-gE antibodies induced by the vaccine.

In another embodiment, the present invention provides a vaccine comprising: (a) a recombinant Herpes Simplex Virus-2 (HSV-2) gC protein or fragment thereof; (b) a recombinant HSV-2 gE protein or fragment thereof; and (c) an adjuvant. In another embodiment, administration of the vaccine to a human subject elicits an anti-HSV-2 gC antibody that blocks an immune evasion function of an HSV protein corresponding to the recombinant HSV-2 gC protein. In another embodiment, the gC fragment includes an immune evasion domain thereof. In another embodiment, immunization with gC and gE, or fragments thereof, in combination limits the ability of HSV-2 to evade a host immune response during a subsequent challenge. In another embodiment, immunization with gC, or a fragment thereof, limits the ability of HSV-2 to evade a host anti-gE immune response during a subsequent challenge. In another embodiment, immunization with gE, or a fragment thereof, limits the ability of HSV-2 to evade a host anti-gC immune response during a subsequent challenge. In another embodiment, the host immune response referred to comprises anti-gC antibodies induced by the vaccine. In another embodiment, the host immune response referred to comprises anti-gE antibodies induced by the vaccine.

In another embodiment, the present invention provides a vaccine comprising: (a) a recombinant HSV-1 gD protein or fragment thereof; (b) a recombinant HSV-1 gC protein or fragment thereof; (c) a recombinant HSV-1 gE protein or fragment thereof; and (d) an adjuvant. In another embodiment, administration of the vaccine to a human subject elicits an anti-HSV-1 gC antibody that blocks an immune evasion function of an HSV protein corresponding to the recombinant HSV-1 gC protein. In another embodiment, administration of the vaccine elicits an anti-HSV-1 gE antibody that blocks an immune evasion function of an HSV protein corresponding to the recombinant HSV-1 gE protein. In another embodiment, the gC fragment includes an immune evasion domain thereof. In another embodiment, the gE fragment includes an immune evasion domain thereof. In another embodiment, immunization with gC, gD, and gE, or fragments thereof, in combination limits the ability of HSV-1 to evade a host immune response during a subsequent challenge. In another embodiment, immunization with gC and gE, or fragments thereof, limits the ability of HSV-1 to evade a host anti-gD immune response during a subsequent challenge. In another embodiment, the host immune response comprises anti-gD antibodies induced by the vaccine. In another embodiment, the immune-potentiating effect of gC and gE, or fragments thereof, together is greater than the effect of either alone. In another embodiment, the immune-potentiating effects of gC and gE exhibit synergy.

In another embodiment, the present invention provides a vaccine comprising: (a) a recombinant HSV-2 gD protein or fragment thereof; (b) a recombinant HSV-2 gC protein or fragment thereof; (c) a recombinant HSV-2 gE protein or fragment thereof; and (d) an adjuvant. In another embodiment, administration of the vaccine to a human subject elicits an anti-HSV-2 gC antibody that blocks an immune evasion function of an HSV protein corresponding to the recombinant HSV-2 gC protein. In another embodiment, administration of the vaccine to a human subject elicits an anti-HSV-2 gE antibody that blocks an immune evasion function of an HSV protein corresponding to the recombinant HSV-2 gE protein. In another embodiment, the gC fragment includes an immune evasion domain thereof. In another embodiment, the gE fragment includes an immune evasion domain thereof. In another embodiment, immunization with gC, gD, and gE, or fragments thereof, in combination limits the ability of HSV-2 to evade a host immune response during a subsequent challenge. In another embodiment, immunization with gC and gE, or fragments thereof, limits the ability of HSV-2 to evade a host anti-gD immune response during a subsequent challenge. In another embodiment, the host immune response comprises anti-gD antibodies induced by the vaccine. In another embodiment, the immune-potentiating effect of gC and gE, or fragments thereof, together is greater than the effect of either alone. In another embodiment, the immune-potentiating effects of gC and gE, or fragments thereof, exhibit synergy.

In another embodiment, the present invention provides a vaccine comprising: (a) a recombinant HSV-1 gD protein or fragment thereof; (b) a recombinant HSV-1 gC protein or fragment thereof; or (c) a recombinant HSV-1 gE protein or fragment thereof. In another embodiment, the present invention provides a vaccine comprising: (a) a recombinant HSV-2 gD protein or fragment thereof; (b) a recombinant HSV-2 gC protein or fragment thereof; or (c) a recombinant HSV-2 gE protein or fragment thereof. In one embodiment, the vaccine further comprises an adjuvant.

In another embodiment, a vaccine of the present invention includes a recombinant HSV-1 gD protein. In another embodiment, the vaccine includes a fragment of an HSV-1 gD protein. In another embodiment, the vaccine includes an HSV-2 gD protein. In another embodiment, the vaccine includes a fragment of an HSV-2 gD protein.

In another embodiment, a gD protein fragment utilized in methods and compositions of the present invention is an immunogenic fragment. In another embodiment, a gD immunoprotective antigen need not be the entire protein. The protective immune response generally involves, in another embodiment, an antibody response. In another embodiment, mutants, sequence conservative variants, and functional conservative variants of gD are useful in methods and compositions of the present invention, provided that all such variants retain the required immuno-protective effect.

In another embodiment, the immunogenic fragment can comprise an immuno-protective gD antigen from any strain of HSV. In another embodiment, the immunogenic fragment can comprise sequence variants of HSV, as found in infected individuals.

In one embodiment, an immunogenic polypeptide is also antigenic. "Antigenic" refers, in another embodiment, to a peptide capable of specifically interacting with an antigen recognition molecule of the immune system, e.g. an immunoglobulin (antibody) or T cell antigen receptor. An antigenic peptide contains, in another embodiment, an epitope of at least about 8 amino acids (AA). In another embodiment, the term refers to a peptide having at least about 9 AA. In another embodiment, the term refers to a peptide having at least about 10 AA. In another embodiment, the term refers to a peptide having at least about 11 AA. In another embodiment, the term refers to a peptide having at least about 12 AA. In another embodiment, the term refers to a peptide having at least about 15 AA. In another embodiment, the term refers to a peptide having at least about 20 AA. In another embodiment, the term refers to a peptide having at least about 25 AA. In another embodiment, the term refers to a peptide having at least about 30 AA. In another embodiment, the term refers to a peptide having at least about 40 AA. In another embodiment, the term refers to a peptide having at least about 50 AA. In another embodiment, the term refers to a peptide having at least about 70 AA. In another embodiment, the term refers to a peptide having at least about 100 AA. In another embodiment, the term refers to a peptide having at least about 150 AA. In another embodiment, the term refers to a peptide having at least about 200 AA. In another embodiment, the term refers to a peptide having at least about 250 AA. In another embodiment, the term refers to a peptide having at least about 300 AA. In certain embodiments, the peptide has an upper limit of 20, 25, 30, 40, 50, 70, 100, 150, 200, 250 or 300 AA. An antigenic portion of a polypeptide, also called herein the epitope in one embodiment, can be that portion that is immunodominant for antibody or T cell receptor recognition, or it can be a portion used to generate an antibody to the molecule by conjugating the antigenic portion to a carrier polypeptide for immunization. A molecule that is antigenic need not be itself immunogenic, i.e., capable of eliciting an immune response without a carrier.

In another embodiment, the gD protein fragment of methods and compositions of the present invention is a gD-1 fragment. In another embodiment, the gD-1 fragment consists of the gD-1 ectodomain. In another embodiment, the gD-1 fragment comprises the gD-1 ectodomain. In another embodiment, the gD-1 fragment consists of a fragment of the gD-1 ectodomain. In another embodiment, the gD-1 fragment comprises a fragment of the gD-1 ectodomain. In another embodiment, the gD-1 fragment is any other gD-1 fragment known in the art.

The gD-1 protein utilized in methods and compositions of the present invention has, in another embodiment, the sequence:

MGGAAARLGAVILFVVIVGLHGVRGKY-ALADASLKLADPNRFRRKDLPVLDQLTDPPGVR RVYHIQAGLPDPFQPPSLPITVYYAV-LERACRSVLLNAPSEAPQIVRGASED-VRKQPYNLTIAWFRM GGNCAIPITVMEYTECSYNK-SLGACPIRTQPRWNYYDSFSAVSEDNLGFLMHAPAFE TAGTYLRLV KINDWTEITQFILEHRAKGSCKYALPL-RIPPSACLSPQAYQQGVTVDSIGML-PRFIPENQRTVAVYSL KIAGWHGPKAPYTSTLLP-PELSETPNATQPELAPEAPEDSALLEDPVGTVAPQIPP NWHIPSIQDAAT PYHPPATPNNMGLIAGAVGGSL-LAALVICGIVYWMRRRTQKAPKRIRL-PHIREDDQPSSHQPLFY (SEQ ID No: 1). In another embodiment, a gD-1 protein utilized in methods and compositions of the present invention is a homologue of SEQ ID No: 1. In another embodiment, the gD-1 protein is an isoform of SEQ ID No: 1. In another embodiment, the gD-1 protein is a variant of SEQ ID No: 1. In another embodiment, the gD-1 protein is a fragment of SEQ ID No: 1. In another embodiment, the gD-1 protein is a fragment of an isoform of SEQ ID No: 1. In another embodiment, the gD-1 protein is a fragment of a variant of SEQ ID No: 1.

In another embodiment, the nucleic acid sequence encoding a gD-1 protein utilized in methods and compositions of the present invention is set forth in a GenBank entry having one of the following Accession Numbers: NC_001806, X14112, E03111, E03023, E02509, E00402, E00401, E00395, AF487902, AF487901, AF293614, L09242, J02217, L09244, L09245, and L09243. In another embodiment, the gD-1 protein is encoded by a nucleotide molecule having a sequence set forth in one of the above GenBank entries. In another embodiment, the gD-1 protein is a homologue of a protein encoded by a sequence set forth in one of the above GenBank entries. In another embodiment, the gD-1 protein is an isoform of a protein encoded by a sequence set forth in one of the above GenBank entries. In another embodiment, the gD-1 protein is a variant of a protein encoded by a sequence set forth in one of the above GenBank entries. In another embodiment, the gD-1 protein is a fragment of a protein encoded by a sequence set forth in one of the above GenBank entries. In another embodiment, the gD-1 protein is a fragment of an isoform of a protein encoded by a sequence set forth in one of the above GenBank entries. In another embodiment, the gD-1 protein is a fragment of a variant of a protein encoded by a sequence set forth in one of the above GenBank entries.

In another embodiment, the gD-1 fragment consists of about amino acids (AA) 26-306. In another embodiment, the gD-1 fragment consists of about AA 36-296. In another embodiment, the fragment consists of about AA 46-286. In another embodiment, the fragment consists of about AA 56-276. In another embodiment, the fragment consists of about AA 66-266. In another embodiment, the fragment consists of about AA 76-256. In another embodiment, the fragment consists of about AA 86-246. In another embodiment, the fragment consists of about AA 96-236. In another embodiment, the fragment consists of about AA 106-226. In another embodiment, the gD-1 fragment consists of about AA 116-216. In another embodiment, the gD-1 fragment consists of about AA 126-206. In another embodiment, the gD-1 fragment consists of about AA 136-196. In another embodiment, the gD-1 fragment consists of about AA 26-286. In another embodiment, the gD-1 fragment consists of about AA 26-266. In another embodiment, the gD-1 fragment consists of about AA 26-246. In another embodiment, the gD-1 fragment consists of about AA 26-206. In another embodiment, the gD-1 fragment consists of about AA 26-166. In another embodiment, the gD-1 fragment consists of about AA 26-126. In another embodiment, the gD-1 fragment consists of about AA 26-106. In another embodiment, the gD-1 fragment consists of about AA 46-306. In another embodiment, the gD-1 fragment consists of about AA 66-306. In another embodiment, the gD-1 fragment consists of about AA 86-306. In another embodiment, the gD-1 fragment consists of about AA 106-306. In another embodiment, the gD-1 fragment consists of about AA 126-306. In another embodiment, the gD-1 fragment consists of about AA 146-306. In another embodiment, the gD-1 fragment consists of about AA 166-306. In another embodiment, the gD-1 fragment consists of about AA 186-306. In another embodiment, the gD-1 fragment consists of about AA 206-306. In alternative embodiments, the gD-1 fragment consists essentially of, or comprises, any of the specified amino acid residues.

In another embodiment, an HSV-1 gD AA sequence is utilized in methods and compositions of the present invention. In another embodiment, an HSV-1 gD protein or peptide is utilized.

In another embodiment, the gD protein fragment of methods and compositions of the present invention is a gD-2 fragment. In another embodiment, the gD-2 fragment consists of the gD-2 ectodomain.

In another embodiment, the gD-2 fragment comprises the gD-2 ectodomain. In another embodiment, the gD-2 fragment consists of a fragment of the gD-2 ectodomain. In another embodiment, the gD-2 fragment comprises a fragment of the gD-2 ectodomain. In another embodiment, the gD-2 fragment is any other gD-2 fragment known in the art.

The gD-2 protein utilized in methods and compositions of the present invention has, in another embodiment, the sequence:

MGRLTSGVGTAALLVVAVGLRVVCAKY-
ALADPSLKMADPNRFRGKNLPVLDQLTDPPGV
KRVYHIQPSLEDPFQPPSIPITVYYAV-
LERACRSVLLHAPSEAPQIVRGASDEAR-
KHTYNLTIAWYR MGDNCAIPITVMEYTECPYNK-
SLGVCPIRTQPRWSYYDSFSAVSEDNLGFLMHAPAFE
TAGTYLRL VKINDWTEITQFILEHRARASCKYALPL-
RIPPAACLTSKAYQQGVTVDSIGML-
PRFIPENQRTVALYS LKIAGWHGPKPPYTSTLLPPELS-
DTTNATQPELVPEDPEDSALLEDPAGTVSSQIPPNWHI
PSIQDVAP HHAPAAPSNPGLIIGALAGSTLAVLVIG-
GIAFWVRRRAQMAPKRLRLPHIRDDDAPPSHQPLFY (SEQ ID No: 2). In another embodiment, a gD-2 protein utilized in methods and compositions of the present invention is a homologue of SEQ ID No: 2. In another embodiment, the protein is an isoform of SEQ ID No: 2. In another embodiment, the protein is a variant of SEQ ID No: 2. In another embodiment, the protein is a fragment of SEQ ID No: 2. In another embodiment, the protein is a fragment of an isoform of SEQ ID No: 2. In another embodiment, the protein is a fragment of a variant of SEQ ID No: 2.

In another embodiment, the nucleic acid sequence encoding a gD-2 protein utilized in methods and compositions of the present invention is set forth in a GenBank entry having one of the following Accession Numbers: NC_001798, E00205, Z86099, AY779754, AY779753, AY779752, AY779751, AY779750, AY517492, AY155225, and K01408. In another embodiment, the gD-2 protein is encoded by a nucleotide molecule having a sequence set forth in one of the above GenBank entries. In another embodiment, the protein is a homologue of a protein encoded by a sequence set forth in one of the above GenBank entries. In another embodiment, the protein is an isoform of a protein encoded by a sequence set forth in one of the above GenBank entries. In another embodiment, the protein is a variant of a protein encoded by a sequence set forth in one of the above GenBank entries. In another embodiment, the protein is a fragment of a protein encoded by a sequence set forth in one of the above GenBank entries. In another embodiment, the protein is a fragment of an isoform of a protein encoded by a sequence set forth in one of the above GenBank entries. In another embodiment, the protein is a fragment of a variant of a protein encoded by a sequence set forth in one of the above GenBank entries.

In another embodiment, the gD-2 fragment consists of about AA 26-306. In another embodiment, the gD-2 fragment consists of about AA 36-296. In another embodiment, the fragment consists of about AA 46-286. In another embodiment, the fragment consists of about AA 56-276. In another embodiment, the fragment consists of about AA 66-266. In another embodiment, the fragment consists of about AA 76-256. In another embodiment, the fragment consists of about AA 86-246. In another embodiment, the fragment consists of about AA 96-236. In another embodiment, the fragment consists of about AA 106-226. In another embodiment, the gD-2 fragment consists of about AA 116-216. In another embodiment, the gD-2 fragment consists of about AA 126-206. In another embodiment, the gD-2 fragment consists of about AA 136-196. In another embodiment, the gD-2 fragment consists of about AA 26-286. In another embodiment, the gD-2 fragment consists of about AA 26-266. In another embodiment, the gD-2 fragment consists of about AA 26-246. In another embodiment, the gD-2 fragment consists of about AA 26-206. In another embodiment, the gD-2 fragment consists of about AA 26-166. In another embodiment, the gD-2 fragment consists of about AA 26-126. In another embodiment, the gD-2 fragment consists of about AA 26-106. In another embodiment, the gD-2 fragment consists of about AA 46-306. In another embodiment, the gD-2 fragment consists of about AA 66-306. In another embodiment, the gD-2 fragment consists of about AA 86-306. In another embodiment, the gD-2 fragment consists of about AA 106-306. In another embodiment, the gD-2 fragment consists of about AA 126-306. In another embodiment, the gD-2 fragment consists of about AA 146-306. In another embodiment, the gD-2 fragment consists of about AA 166-306. In another embodiment, the gD-2 fragment consists of about AA 186-306. In another embodiment, the gD-2 fragment consists of about AA 206-306. In alternative embodiments, the gD-2 fragment consists essentially of, or comprises, any of the specified amino acid residues.

In another embodiment, the recombinant gD protein fragment thereof elicits antibodies that inhibit binding of gD to a cellular receptor. In another embodiment, the receptor is herpesvirus entry mediator A (HveA/HVEM). In another embodiment, the receptor is nectin-1 (HveC). In another embodiment, the receptor is nectin-2 (HveB). In another embodiment, the receptor is a modified form of heparan sulfate. In another embodiment, the receptor is a heparan sulfate proteoglycan. In another embodiment, the receptor is any other gD receptor known in the art.

In another embodiment, the recombinant gD protein or fragment thereof includes AA 26-57. In another embodiment, inclusion of these residues elicits antibodies that inhibit binding to HVEM. In another embodiment, the gD protein or fragment includes Y63. In another embodiment, the gD protein or fragment includes R159. In another embodiment, the gD protein or fragment includes D240. In another embodiment, the gD protein or fragment includes P246. In another embodiment, the recombinant gD protein or fragment includes a residue selected from Y63, R159, D240, and P246. In another embodiment, inclusion of one of these residues elicits antibodies that inhibit binding to nectin-1.

The above nomenclature for gD AA residues includes the residues of the signal sequence. Thus, residue one of the mature protein is referred to as "26."

In another embodiment, an HSV-2 gD AA sequence is utilized in methods and compositions of the present invention. In another embodiment, an HSV-2 gD protein or peptide is utilized.

Each recombinant gD-1 and gD-2 protein or fragment thereof represents a separate embodiment of the present invention.

In another embodiment, a vaccine of the present invention includes a recombinant HSV-1 gC protein. In another embodiment, the vaccine includes a fragment of an HSV-1 gC protein. In another embodiment, the vaccine includes an HSV-2 gD protein. In another embodiment, the vaccine includes a fragment of an HSV-2 gD protein.

The gC-1 protein utilized in methods and compositions of the present invention has, in another embodiment, the sequence:

MAPGRVGLAVVLWGLLWL-GAGVAGGSETASTGPTITAGAVTNASEA-PTSGSPGSAASPEV TPTSTPNPNNVTQNKTTPTE-PASPPTTPKPTSTPKSPPTSTPDPKPKNNTTPAKSGRPT KPPGPVWCD RRDPLARYGSRVQIRCRFRNSTRME-FRLQIWRYSMGPSPPIAPAPDLEEVLT-NITAPPGGLLVYDSAP NLTDPHVLWAEGAGPGADP-PLYSVTGPLPTQRLIIGEVTPATQGMYYLAWGRMDSP HEYGTWVR VRMFR-PPSLTLQPHAVMEGQPFKATCTAAAYYPRNPVEFDWF EDDRQVFNPGQIDTQTHEHPDGF TTVSTVTSEAVG-GQVPPRTFTCQMTWHRDSVTFSRRNAT-GLALVLPRPTITMEFGVRHVVCTAGC VPEGVTFAW-FLGDDPSPAAKSAVTAQESCDHPGLATVRSTLPISYDY SEYICRLTGYPAGIPVLEHH GSHQPPPRDPTER-QVIEAIEWVGIGIGVLAAGVLV-VTAIVYVVRTSQSRQRHRR (SEQ ID No: 3). In another embodiment, a gC-1 protein utilized in methods and compositions of the present invention is a homologue of SEQ ID No: 3. In another embodiment, the protein is an isoform of SEQ ID No: 3. In another embodiment, the protein is a variant of SEQ ID No: 3. In another embodiment, the protein is a fragment of SEQ ID No: 3. In another embodiment, the protein is a fragment of an isoform of SEQ ID No: 3. In another embodiment, the protein is a fragment of a variant of SEQ ID No: 3.

In another embodiment, the nucleic acid sequence encoding a gC-1 protein utilized in methods and compositions of the present invention is set forth in a GenBank entry having one of the following Accession Numbers: NC__001806, X14112, AJ421509, AJ421508, AJ421507, AJ421506, AJ421505, AJ421504, AJ421503, AJ421502, AJ421501, AJ421500, AJ421-499, AJ421-498, AJ421-497, AJ421-496, AJ421-495, AJ421-494, AJ421-493, AJ421-492, AJ421-491, AJ421-490, AJ421-489, AJ421-488, and AJ421-487. In another embodiment, the gC-1 protein is encoded by a nucleotide molecule having a sequence set forth in one of the above GenBank entries. In another embodiment, the protein is a homologue of a protein encoded by a sequence set forth in one of the above GenBank entries. In another embodiment, the protein is an isoform of a protein encoded by a sequence set forth in one of the above GenBank entries. In another embodiment, the protein is a variant of a protein encoded by a sequence set forth in one of the above GenBank entries. In another embodiment, the protein is a fragment of a protein encoded by a sequence set forth in one of the above GenBank entries. In another embodiment, the protein is a fragment of an isoform of a protein encoded by a sequence set forth in one of the above GenBank entries. In another embodiment, the protein is a fragment of a variant of a protein encoded by a sequence set forth in one of the above GenBank entries.

The gC-2 protein utilized in methods and compositions of the present invention has, in another embodiment, the sequence:

MALGRVGLAVGLWGLLWVGVVVVLA-NASPGRTITVGPRGNASNAAPSASPRNASAPRTTP TPPQPRKATKSKASTAKPAPPPKTGPP-KTSSEPVRCNRHDPLARYGSRVQIRCRF-PNSTRTEFRLQIW RYATATDAEIGTAPSLEEVMVN-VSAPPGGQLVYDSAPNRTDPHVIWAEGAGPGASPRLY SVVGPL GRQRLIIEELTLETQGMYYWVWGRTDRP-SAYGTWVRVRVFRPPSLTIHPHAV-LEGQPFKATCTAAT YYPGNRAEFVWFEDGRRVFDPA-QIHTQTQENPDGFSTVSTVTSAAVGGQGPPRTFTCQL TWHRDS VSFSRRNASGTASVLPRPTITMEFT-GDHAVCTAGCVPEGVTFAWFLGDDSS-PAEKVAVASQTSCGR PGTATIRSTLPVSYEQTEYICR-LAGYPDGIPVLEHHGSHQPPPRDPTERQVIRAVEGAG IGVAVLVAV VLAGTAVVYLTHASSVRYRRLR (SEQ ID No: 4). In another embodiment, a gC-2 protein utilized in methods and compositions of the present invention is a homologue of SEQ ID No: 4. In another embodiment, the protein is an isoform of SEQ ID No: 4. In another embodiment, the protein is a variant of SEQ ID No: 4. In another embodiment, the protein is a fragment of SEQ ID No: 4. In another embodiment, the protein is a fragment of an isoform of SEQ ID No: 4. In another embodiment, the protein is a fragment of a variant of SEQ ID No: 4.

In another embodiment, the nucleic acid sequence encoding a gC-2 protein utilized in methods and compositions of the present invention is set forth in a GenBank entry having one of the following Accession Numbers: NC__001798, Z86099, M10053, AJ297389, AF021341, U12179, U12177, U12176, and U12178. In another embodiment, the gC-2 protein is encoded by a nucleotide molecule having a sequence set forth in one of the above GenBank entries. In another embodiment, the protein is a homologue of a protein encoded by a sequence set forth in one of the above GenBank entries. In another embodiment, the protein is an isoform of a protein encoded by a sequence set forth in one of the above GenBank entries. In another embodiment, the protein is a variant of a protein encoded by a sequence set forth in one of the above GenBank entries. In another embodiment, the protein is a fragment of a protein encoded by a sequence set forth in one of the above GenBank entries. In another embodiment, the protein is a fragment of an isoform of a protein encoded by a sequence set forth in one of the above GenBank entries. In another embodiment, the protein is a fragment of a variant of a protein encoded by a sequence set forth in one of the above GenBank entries.

The gC protein fragment utilized in methods and compositions of the present invention is, in another embodiment, an immunogenic fragment. In another embodiment, a gC immunoprotective antigen need not be the entire protein. The protective immune response generally involves, in another embodiment, an antibody response. In another embodiment, mutants, sequence conservative variants, and functional conservative variants of gC are useful in methods and compositions of the present invention, provided that all such variants retain the required immuno-protective effect.

In another embodiment, the immunogenic fragment can comprise an immuno-protective gC antigen from any strain of HSV. In another embodiment, the immunogenic fragment can comprise sequence variants of HSV, as found in infected individuals.

In another embodiment, the gC protein fragment comprises a gC immune evasion domain. In another embodiment, the gC protein fragment comprises a portion of a gC immune evasion domain. In another embodiment, the gC protein fragment is a gC immune evasion domain. In another embodiment, the gC protein fragment is a portion of a gC immune evasion domain. In another embodiment, an HSV-1 gC AA sequence is utilized. In another embodiment, an HSV-1 gC protein or peptide is utilized.

In another embodiment, the gC protein fragment is a C3b-binding domain. In another embodiment, the gC protein fragment is a portion of a C3b-binding domain. "C3b-binding domain" refers, in another embodiment, to a domain that mediates binding of gC with a host C3b molecule. In another embodiment, the term refers to a domain that mediates interaction of gC with a host C3b molecule.

In another embodiment, (e.g. in the case of gC-1), the gC domain consists of approximately AA 26-457. In another embodiment, the domain consists of approximately AA 46-457. In another embodiment, the range is approximately AA 66-457. In another embodiment, the range is approximately AA 86-457. In another embodiment, the range is approximately AA 106-457. In another embodiment, the range is approximately AA 126-457. In another embodiment, the range is approximately AA 146-457. In another embodiment, the range is approximately AA 166-457. In another embodiment, the range is approximately AA 186-457. In another embodiment, the range is approximately AA 206-457. In another embodiment, the domain consists of approximately AA 226-457. In another embodiment, the domain consists of approximately AA 246-457. In another embodiment, the range is approximately AA 26-447. In another embodiment, the range is approximately AA 26-437. In another embodiment, the range is approximately AA 26-427. In another embodiment, the range is approximately AA 26-417. In another embodiment, the range is approximately AA 26-407. In another embodiment, the range is approximately AA 26-387. In another embodiment, the range is approximately AA 26-367. In another embodiment, the range is approximately AA 26-347. In another embodiment, the range is approximately AA 26-327. In another embodiment, the range is approximately AA 26-307. In another embodiment, the range is approximately AA 26-287. In another embodiment, the range is approximately AA 26-267. In another embodiment, the range is approximately AA 26-247. In another embodiment, the range is approximately AA 36-447. In another embodiment, the range is approximately AA 46-437. In another embodiment, the range is approximately AA 56-427. In another embodiment, the range is approximately AA 66-417. In another embodiment, the range is approximately AA 76-407. In another embodiment, the range is approximately AA 86-397. In another embodiment, the range is approximately AA 96-387. In another embodiment, the range is approximately AA 106-377. In another embodiment, the range is approximately AA 116-367. In another embodiment, the range is approximately AA 126-357. In another embodiment, the range is approximately AA 136-347. In another embodiment, the range is approximately AA 147-337. In another embodiment, the domain consists of approximately AA 124-366. In another embodiment, the domain consists of approximately AA 124-137. In another embodiment, the range is approximately AA 223-246. In another embodiment, the range is approximately AA 276-292. In another embodiment, the range is approximately AA 339-366. In alternative embodiments, the gC domain consists essentially of, or comprises, any of the specified amino acid residues.

In another embodiment, the range is approximately AA 124-246. In another embodiment, the range is approximately AA 124-292. In another embodiment, the range is approximately AA 223-292. In another embodiment, the range is approximately AA 223-366. In another embodiment, the gC domain is selected from AA 124-137, 223-246, 276-292, and 339-366. In another embodiment, the domain is selected from AA 124-137 and 223-246. In another embodiment, the domain is selected from AA 124-137 and 276-292. In another embodiment, the domain is selected from AA 124-137 and 339-366. In another embodiment, the domain is selected from AA 223-246 and 276-292. In another embodiment, the domain is selected from AA 223-246 and 339-366. In another embodiment, the domain is selected from AA 276-292 and 339-366. In another embodiment, the domain is selected from AA 124-137, 223-246, and 276-292. In another embodiment, the domain is selected from AA 124-137, 223-246, and 339-366. In another embodiment, the gC domain is selected from AA 124-137, 276-292, and 339-366. In another embodiment, the gC domain is selected from AA 223-246, 276-292, and 339-366. In another embodiment, the range is approximately AA 164-366. In another embodiment, the range is approximately AA 204-366. In another embodiment, the range is approximately AA 244-366. In another embodiment, the range is approximately AA 124-326. In another embodiment, the range is approximately AA 124-286. In another embodiment, the range is approximately AA 124-246. In another embodiment, the range is approximately AA 204-326. In another embodiment, the range is approximately AA 244-326. In another embodiment, the range is approximately AA 204-286. In alternative embodiments, the range consists essentially of, or comprises, any of the specified amino acid residues.

In another embodiment, the gC-1 protein is modified with an antigenic tag. In another embodiment, one of the above gC-1 fragments is modified with an antigenic tag. In another embodiment, the tag is a histidine ("His") tag. In another embodiment, the His tag consists of 5 histidine residues. In another embodiment, the His tag consists of 6 histidine residues. In another embodiment, the His tag consists of another number of histidine residues. In another embodiment, the gC-1 fragment utilized in methods and compositions of the present invention is AA 26-457 modified with a His tag.

In another embodiment, (e.g. in the case of gC-2), the gC domain consists of approximately AA 27-426. In another embodiment, the domain consists of approximately AA 47-426. In another embodiment, the range is approximately AA 67-426. In another embodiment, the range is approximately AA 87-426. In another embodiment, the range is approximately AA 107-426. In another embodiment, the range is approximately AA 127-426. In another embodiment, the range is approximately AA 147-426. In another embodiment, the range is approximately AA 167-426. In another embodiment, the range is approximately AA 187-426. In another embodiment, the range is approximately AA 207-426. In another embodiment, the domain consists of approximately AA 227-426. In another embodiment, the domain consists of approximately AA 247-426. In another embodiment, the range is approximately AA 27-406. In another embodiment, the range is approximately AA 27-386. In another embodiment, the range is approximately AA 27-366. In another embodiment, the range is approximately AA 27-346. In another embodiment, the range is approximately AA 27-326. In another embodiment, the range is approximately AA 27-306. In another embodiment, the range is approximately AA 27-286. In another embodiment, the range is approximately AA 27-266. In another embodiment, the range is approximately AA 27-246. In another embodiment, the range is approximately AA 37-416. In another embodiment, the range is approximately AA 47-406. In another embodiment, the range is approximately AA 57-396. In another embodiment, the range is approximately AA 67-386. In another embodiment, the range is approximately AA 77-376. In another embodiment, the range is approximately AA 87-366. In another embodiment, the range is approximately AA 97-356. In another embodiment, the range is approximately AA 107-346. In another embodiment, the range is approximately AA 117-326. In another embodiment, the range is approximately AA 127-316. In another embodiment, the range is approximately AA 137-306. In another embodiment, the range is approximately AA 147-296. In alternative embodiments, the gC domain consists essentially of, or comprises, any of the specified amino acid residues.

In another embodiment, the domain consists of approximately AA 102-107. In another embodiment, the domain consists of approximately AA 222-279. In another embodiment, the domain consists of approximately AA 307-379. In another embodiment, the range is approximately AA 94-355. In another embodiment, the range is approximately AA 102-279. In another embodiment, the range is approximately AA 102-379. In another embodiment, the range is approximately AA 222-379. In another embodiment, the gC domain is selected from AA 102-107, 222-279, and 307-379. In another embodiment, the domain is selected from AA 102-107 and 222-279. In another embodiment, the domain is selected from AA 102-107 and 307-379. In another embodiment, the domain is selected from AA 222-279 and 307-379. In another embodiment, the range is approximately AA 122-379. In another embodiment, the range is approximately AA 142-379. In another embodiment, the range is approximately AA 162-379. In another embodiment, the range is approximately AA 182-379. In another embodiment, the range is approximately AA 202-379. In another embodiment, the range is approximately AA 222-379. In another embodiment, the range is approximately AA 242-379. In another embodiment, the range is approximately AA 102-359. In another embodiment, the range is approximately AA 102-339. In another embodiment, the range is approximately AA 102-319. In another embodiment, the range is approximately AA 102-299. In another embodiment, the range is approximately AA 102-279. In another embodiment, the range is approximately AA 102-259. In another embodiment, the range is approximately AA 102-239. In another embodiment, the range is approximately AA 112-369. In another embodiment, the range is approximately AA 122-359. In another embodiment, the range is approximately AA 132-349. In another embodiment, the range is approximately AA 142-339. In another embodiment, the range is approximately AA 152-329. In another embodiment, the range is approximately AA 162-319. In another embodiment, the range is approximately AA 172-309. In another embodiment, the range is approximately AA 182-299. In another embodiment, the range is approximately AA 192-289. In another embodiment, the range is approximately AA 202-279. In another embodiment, the range is approximately AA 232-279. In another embodiment, the range is approximately AA 242-279. In another embodiment, the range is approximately AA 252-279. In another embodiment, the range is approximately AA 262-279. In another embodiment, the range is approximately AA 222-269. In another embodiment, the range is approximately AA 222-259. In another embodiment, the range is approximately AA 222-249. In another embodiment, the range is approximately AA 222-239. In another embodiment, the domain consists of approximately AA 227-274. In another embodiment, the domain consists of approximately AA 232-269. In another embodiment, the domain consists of approximately AA 237-264. In another embodiment, the domain consists of approximately AA 242-259. In another embodiment, the domain consists of approximately AA 307-379. In another embodiment, the range is approximately AA 317-379. In another embodiment, the range is approximately AA 327-379. In another embodiment, the range is approximately AA 337-379. In another embodiment, the range is approximately AA 347-379. In another embodiment, the range is approximately AA 357-379. In another embodiment, the range is approximately AA 307-369. In another embodiment, the range is approximately AA 307-359. In another embodiment, the range is approximately AA 307-349. In another embodiment, the range is approximately AA 307-339. In another embodiment, the range is approximately AA 307-329. In another embodiment, the range is approximately AA 312-374. In another embodiment, the range is approximately AA 317-369. In another embodiment, the range is approximately AA 322-364. In another embodiment, the range is approximately AA 327-359. In another embodiment, the range is approximately AA 332-354. In another embodiment, the range is approximately AA 337-349. In alternative embodiments, the gC domain consists essentially of, or comprises, any of the specified amino acid residues.

In another embodiment, the gC-2 protein is modified with an antigenic tag. In another embodiment, one of the above gC-2 fragments is modified with an antigenic tag. In another embodiment, the tag is a histidine ("His") tag. In another embodiment, the His tag consists of 5 histidine residues. In another embodiment, the His tag consists of 6 histidine residues. In another embodiment, the His tag consists of another number of histidine residues. In another embodiment, the gC-2 fragment utilized in methods and compositions of the present invention is AA 27-426 modified with a His tag.

In another embodiment, the gC domain is any other gC domain known in the art to mediate binding or interaction of gC with a host C3b molecule.

In another embodiment, the gC protein fragment is a properdin interfering domain. In another embodiment, the gC protein fragment is a portion of a properdin interfering domain. "Properdin-interfering domain" refers, in another embodiment, to a domain that blocks or inhibits binding of a host C3b molecule with a host properdin molecule. In another embodiment, the term refers to a domain that blocks or inhibits an interaction of a host C3b molecule with a host properdin molecule. In another embodiment, (e.g. in the case of gC-1), the gC domain consists of approximately AA 33-133. In another embodiment, the gC domain consists of approximately AA 33-73. In another embodiment, the gC domain consists of approximately AA 33-83. In another embodiment, the gC domain consists of approximately AA 33-93. In another embodiment, the gC domain consists of approximately AA 33-103. In another embodiment, the gC domain consists of approximately AA 33-113. In another embodiment, the gC domain consists of approximately AA 33-123. In another embodiment, the gC domain consists of approximately AA 43-133. In another embodiment, the gC domain consists of approximately AA 53-133. In another embodiment, the gC domain consists of approximately AA 63-133. In another embodiment, the gC domain consists of approximately AA 73-133. In another embodiment, the gC domain consists of approximately AA 83-133. In another embodiment, the gC domain consists of approximately AA 93-133.

In another embodiment, the gC domain consists of approximately AA 103-133. In another embodiment, the gC domain consists of approximately AA 43-93. In alternative embodiments, the gC domain consists essentially of, or comprises, any of the specified amino acid residues.

In another embodiment, the gC domain is any other gC domain known in the art to interfere with binding of a host C3b molecule with a host properdin molecule.

In another embodiment, the gC protein fragment is a C5 interfering domain. In another embodiment, the gC protein fragment is a portion of a C5 interfering domain. "C5-interfering domain" refers, in another embodiment, to a domain that interferes with binding of a host C3b molecule with a host C5 molecule. In another embodiment, the term refers to a domain that interferes with the interaction of a host C3b molecule with a host C5 molecule. In another embodiment, (e.g. in the case of gC-1), the gC domain consists of approximately AA 33-133. In another embodiment, the gC domain is any other gC domain known in the art to interfere with or inhibit binding or interaction of a host C3b molecule with a host C5 molecule.

Each recombinant gC-1 or gC-2 protein or fragment thereof represents a separate embodiment of the present invention.

In another embodiment, a vaccine of the present invention comprises a recombinant HSV-1 gE protein. In another embodiment, the vaccine comprises a fragment of an HSV-1 gE protein. In another embodiment, the vaccine includes an HSV-2 gE protein. In another embodiment, the vaccine includes a fragment of an HSV-2 gE protein.

The gE-1 protein utilized in methods and compositions of the present invention has, in another embodiment, the sequence:

MDRGAVVGFLLGVCVVSCLAGTPKTSWR-
RVSVGEDVSLLPAPGPTGRGPTQKLLWAVEPL DGCG-
PLHPSWVSLMPPKQVPETVVDAACM-
RAPVPLAMAYAPPAPSATGGLRTDFVWQERAAVVN
RSLVIYGVRETDSGLYTLSVGDIKDPAR-
QVASVVLVVQPAPVPTPPPTPADYDEDD-
NDEGEGEDES LAGTPASGTPRLPPSPAPPRSWPSAPE-
VSHVRGVTVRMETPEAILFSPGEAFSTNVSIHAIAHD
DQTY TMDVVWLRFDVPTSCAEMRIYESCLYH-
PQLPECLSPADAPCAASTWTSRLAVRSY-
AGCSRTNPPPR CSAEAHMEPFPGLAWQAASVNLE-
FRDASPQHSGLYLCVVYVNDHIHAWGHITINTAAQYR
NAVVE QPLPQRGADLAEPTHPHVGAPPHAPPTH-
GALRLGAVMGAALLLSALGLSVWAC-
MTCWRRRAWR AVKSRASGKGPTYIRVADSELYAD-
WSSDSEGERDQVPWLAPPERPDSPSTNGSGFEILSPTA
PSVYP RSDGHQSRRQLTTFGSGRPDRRYSQAS-
DSSVFW (SEQ ID No: 5). In another embodiment, a gE-1 protein utilized in methods and compositions of the present invention is a homologue of SEQ ID No: 5. In another embodiment, the protein is an isoform of SEQ ID No: 5. In another embodiment, the protein is a variant of SEQ ID No: 5. In another embodiment, the protein is a fragment of SEQ ID No: 5. In another embodiment, the protein is a fragment of an isoform of SEQ ID No: 5. In another embodiment, the protein is a fragment of a variant of SEQ ID No: 5.

In another embodiment, the nucleic acid sequence encoding a gE-1 protein utilized in methods and compositions of the present invention is set forth in a GenBank entry having one of the following Accession Numbers: NC_001806, X14112, DQ889502, X02138, and any of AJ626469-AJ626498. In another embodiment, the gE-1 protein is encoded by a nucleotide molecule having a sequence set forth in one of the above GenBank entries. In another embodiment, the protein is a homologue of a protein encoded by a sequence set forth in one of the above GenBank entries. In another embodiment, the protein is an isoform of a protein encoded by a sequence set forth in one of the above GenBank entries. In another embodiment, the protein is a variant of a protein encoded by a sequence set forth in one of the above GenBank entries. In another embodiment, the protein is a fragment of a protein encoded by a sequence set forth in one of the above GenBank entries. In another embodiment, the protein is a fragment of an isoform of a protein encoded by a sequence set forth in one of the above GenBank entries. In another embodiment, the protein is a fragment of a variant of a protein encoded by a sequence set forth in one of the above GenBank entries.

The gE-2 protein utilized in methods and compositions of the present invention has, in another embodiment, the sequence:

MARGAGLVFFVGVWVVSC-
LAAAPRTSWKRVTSGEDVVLLPAPAER-
TRAHKLLWAAEPLD ACGPLRPSWVALWPPRRV-
LETVVDAACMRAPEPLAIAYSPPFPAGDEGLYSELAW
RDRVAVVNES LVIYGALETDSGLYTLSVVGLSDEAR-
QVASVVLVVEPAPVPTPTPDDYDEED-
DAGVTNARRSAFPP QPPPRRPPVAPPTHPRVIPEVSH-
VRGVTVHMETLEAILFAPGETFGTNVSIHAIAHDDGP
YAMDVVW MRFDVPSSCADMRIYEACLYHPQLPE-
CLSPADAPCAVSSWAYRLAVRSYAGCS-
RTTPPPRCFAEAR MEPVPGLAWLASTVN-
LEFQHASPQHAGLYLCVVYVDDHIHAWGHMTISTAA
QYRNAVVEQHLPQ RQPEPVEPTRPHVRAPHPAP-
SARGPLRLGAVLGAALLLAALGLSAWAC-
MTCWRRRSWRAVKSRA SATGPTYIRVADSELYAD-
WSSDSEGERDGSLWQDPPERPDSPSTNGSGFEILSPTA
PSVYPHSEGRKS RRPLTTFGSGSPGRRHSQASYPS-
VLW (SEQ ID No: 6). In another embodiment, a gE-2 protein utilized in methods and compositions of the present invention is a homologue of SEQ ID No: 6. In another embodiment, the protein is an isoform of SEQ ID No: 6. In another embodiment, the protein is a variant of SEQ ID No: 6. In another embodiment, the protein is a fragment of SEQ ID No: 6. In another embodiment, the protein is a fragment of an isoform of SEQ ID No: 6. In another embodiment, the protein is a fragment of a variant of SEQ ID No: 6.

In another embodiment, the nucleic acid sequence encoding a gE-2 protein utilized in methods and compositions of the present invention is set forth in a GenBank entry having one of the following Accession Numbers: NC_001798, Z86099, D00026, X04798, and M14886. In another embodiment, the gE-2 protein is encoded by a nucleotide molecule having a sequence set forth in one of the above GenBank entries. In another embodiment, the protein is a homologue of a protein encoded by a sequence set forth in one of the above GenBank entries. In another embodiment, the protein is an isoform of a protein encoded by a sequence set forth in one of the above GenBank entries. In another embodiment, the protein is a variant of a protein encoded by a sequence set forth in one of the above GenBank entries. In another embodiment, the protein is a fragment of a protein encoded by a sequence set forth in one of the above GenBank entries. In another embodiment, the protein is a fragment of an isoform of a protein encoded by a sequence set forth in one of the above GenBank entries. In another embodiment, the protein is a fragment of a variant of a protein encoded by a sequence set forth in one of the above GenBank entries.

In another embodiment, a gE fragment utilized in methods and compositions of the present invention comprises an IgG Fc-binding domain of the gE protein. In another embodiment, the gE fragment comprises AA 24-224. In another embodiment, the gE fragment comprises a portion of AA 24-224. In another embodiment, the portion is sufficient to elicit antibodies that block immune evasion by the IgG Fc-binding domain of the gE protein.

In another embodiment, the gE fragment comprises a portion of a gE IgG Fc-binding domain. In another embodiment, (e.g. in the case of gE-1) the gE domain consists of about AA 24-409. In another embodiment, the domain consists of about 24-224. In alternative embodiments, the gE domain consists essentially of, or comprises, any of the specified amino acid residue ranges.

In another embodiment, the range is about AA 34-399. In another embodiment, the range is about AA 54-379. In another embodiment, the range is about AA 74-359. In another embodiment, the range is about AA 94-339. In another embodiment, the range is about AA 114-319. In another embodiment, the range is about AA 134-299. In another embodiment, the range is about AA 154-279. In another embodiment, the range is about AA 54-409. In another embodiment, the range is about AA 84-409. In another embodiment, the range is about AA 114-409. In another embodiment, the range is about AA 144-409. In another embodiment, the range is about AA 174-409. In another embodiment, the range is about AA 204-409. In another embodiment, the range is about AA 234-409. In another embodiment, the range is about AA 24-389. In another embodiment, the range is about AA 24-369. In another embodiment, the range is about AA 24-349. In another embodiment, the range is about AA 24-329. In another embodiment, the range is about AA 24-309. In another embodiment, the range is about AA 24-289. In another embodiment, the range is about AA 24-269. In another embodiment, the range is about AA 24-249. In another embodiment, the range is about AA 24-229. In another embodiment, the range is about AA 24-209. In another embodiment, the range is about AA 24-189. In alternative embodiments, the gE domain consists essentially of, or comprises, any of the specified amino acid residue ranges.

In another embodiment, the range is about 223-396. In another embodiment, the range is about AA 230-390. In another embodiment, the range is about AA 235-380. In another embodiment, the range is about AA 245-380. In another embodiment, the range is about AA 255-380. In another embodiment, the range is about AA 265-380. In another embodiment, the range is about AA 275-380. In another embodiment, the range is about AA 285-380. In another embodiment, the range is about AA 295-380. In another embodiment, the range is about AA 305-380. In another embodiment, the range is about AA 235-370. In another embodiment, the range is about AA 235-370. In another embodiment, the range is about AA 235-360. In another embodiment, the range is about AA 235-350. In another embodiment, the range is about AA 235-340. In another embodiment, the range is about AA 235-330. In another embodiment, the range is about AA 235-320. In another embodiment, the range is about AA 235-310. In another embodiment, the range is about AA 235-300. In another embodiment, the range is about AA 322-359. In another embodiment, the range is about AA 327-359. In another embodiment, the range is about AA 332-359. In another embodiment, the range is about AA 337-359. In another embodiment, the range is about AA 322-354. In another embodiment, the range is about AA 322-349. In another embodiment, the range is about AA 322-344. In another embodiment, the range is about AA 327-354. In another embodiment, the range is about AA 332-349. In another embodiment, the gE domain includes AA 380. In alternative embodiments, the gE domain consists essentially of, or comprises, any of the specified amino acid residue ranges.

In another embodiment, the gE protein is modified with an antigenic tag. In another embodiment, one of the above gE fragments is modified with an antigenic tag. In another embodiment, the tag is a histidine ("His") tag. In another embodiment, the His tag consists of 5-6 histidine residues. In another embodiment, the gE fragment utilized in methods and compositions of the present invention is approximately AA 24-409 with a 6 His tag at the C-terminus.

In another embodiment, (e.g. in the case of gE-2) the gE domain consists approximately of AA 218-391. In another embodiment, the range is about AA 223-386. In another embodiment, the range is about AA 228-280. In another embodiment, the range is about AA 230-375. In another embodiment, the range is about AA 228-373. In another embodiment, the range is about AA 238-373. In another embodiment, the range is about AA 248-373. In another embodiment, the range is about AA 258-373. In another embodiment, the range is about AA 268-373. In another embodiment, the range is about AA 278-373. In another embodiment, the range is about AA 288-373. In another embodiment, the range is about AA 298-373. In another embodiment, the range is about AA 308-373. In another embodiment, the range is about AA 228-363. In another embodiment, the range is about AA 228-353. In another embodiment, the range is about AA 228-343. In another embodiment, the range is about AA 228-333. In another embodiment, the range is about AA 228-323. In another embodiment, the range is about AA 228-313. In another embodiment, the range is about AA 228-303. In another embodiment, the range is about AA 238-363. In another embodiment, the range is about AA 248-353. In another embodiment, the range is about AA 258-343. In another embodiment, the gE range is about AA 315-352. In another embodiment, the range is about AA 320-352. In another embodiment, the range is about AA 325-352. In another embodiment, the range is about AA 330-352. In another embodiment, the range is about AA 335-352. In another embodiment, the range is about AA 315-347. In another embodiment, the range is about AA 315-342. In another embodiment, the range is about AA 315-337. In another embodiment, the range is about AA 315-332. In another embodiment, the range is about AA 320-347. In another embodiment, the range is about AA 325-347. In another embodiment, the range is about AA 320-342. In another embodiment, the range is about AA 325-342. In another embodiment, the gE domain includes AA 373. In alternative embodiments, the gE domain consists essentially of, or comprises, any of the specified amino acid residue ranges.

In another embodiment, the gE domain is any other gE domain known in the art to mediate binding to IgG Fc.

In another embodiment, the gE protein comprises a gE domain involved in cell-to-cell spread. In another embodiment, the gE domain consists approximately of AA 256-291. In another embodiment, the gE domain consists approximately of AA 348-380. In another embodiment, the gE domain includes AA 380. In another embodiment, the gE domain is any other gE domain known in the art to be involved in cell-to-cell spread. In another embodiment, the gE domain is known to facilitate cell-to-cell spread. In another embodiment, the gE domain is known to be required for cell-to-cell spread.

In another embodiment, a gE fragment utilized in methods and compositions of the present invention is an immunogenic fragment. "Immunogenic fragment" refers, in another embodiment, to a portion of gE that is immunogenic and elicits a protective immune response when administered to a subject. In another embodiment, a gE immunoprotective antigen need not be the entire protein. The protective immune response generally involves, in another embodiment, an antibody response. In another embodiment, mutants, sequence conservative variants, and functional conservative variants of gE are useful in methods and compositions of the present invention, provided that all such variants retain the required immuno-protective effect.

In another embodiment, the immunogenic fragment can comprise an immuno-protective gE antigen from any strain of HSV. In another embodiment, the immunogenic fragment can comprise sequence variants of HSV, as found in infected individuals.

In another embodiment, the gE fragment comprises an immune evasion domain. In another embodiment, the gE fragment comprises a portion of an immune evasion domain. In another embodiment, the gE fragment is an immune evasion domain. In another embodiment, the gE fragment is a portion of an immune evasion domain. In another embodiment, an HSV-1 gE AA sequence is utilized. In another embodiment, an HSV-1 gE protein or peptide is utilized.

In another embodiment, (e.g. in the case of gE-1) the gE protein fragment consists of about AA 21-419. In another embodiment, the range is about AA 31-419. In another embodiment, the range is about AA 41-419. In another embodiment, the range is about AA 61-419. In another embodiment, the range is about AA 81-419. In another embodiment, the range is about AA 101-419. In another embodiment, the range is about AA 121-419. In another embodiment, the range is about AA 141-419. In another embodiment, the range is about AA 161-419. In another embodiment, the range is about AA 181-419. In another embodiment, the range is about AA 201-419. In another embodiment, the range is about AA 221-419. In another embodiment, the range is about AA 241-419. In another embodiment, the range is about AA 261-419. In another embodiment, the range is about AA 21-399. In another embodiment, the range is about AA 21-379. In another embodiment, the range is about AA 21-359. In another embodiment, the range is about AA 21-339. In another embodiment, the range is about AA 21-319. In another embodiment, the range is about AA 21-299. In another embodiment, the range is about AA 21-279. In another embodiment, the range is about AA 21-259. In another embodiment, the range is about AA 21-239. In another embodiment, the range is about AA 21-219. In another embodiment, the range is about AA 21-199. In another embodiment, the range is about AA 21-179. In another embodiment, the range is about AA 21-159. In another embodiment, the range is about AA 21-139. In another embodiment, the range is about AA 31-409. In another embodiment, the range is about AA 41-399. In another embodiment, the range is about AA 51-389. In another embodiment, the range is about AA 61-379. In another embodiment, the range is about AA 71-369. In another embodiment, the range is about AA 81-359. In another embodiment, the range is about AA 91-349. In another embodiment, the range is about AA 101-339. In another embodiment, the range is about AA 111-329. In another embodiment, the range is about AA 121-319. In another embodiment, the range is about AA 131-309. In another embodiment, the range is about AA 141-299. In another embodiment, the range is about AA 151-279. In another embodiment, the range is about AA 161-269. In another embodiment, the range is about AA 171-259. In another embodiment, the range is about AA 181-249. In another embodiment, the range is about AA 191-239. In alternative embodiments, the gE protein fragment consists essentially of, or comprises, any of the specified amino acid residues.

In another embodiment, (e.g. in the case of gE-2) the gE protein fragment consists of about AA 21-416. In another embodiment, the range is any of the ranges specified in the preceding paragraphs.

Each recombinant gE-1 or gE-2 protein or fragment thereof represents a separate embodiment of the present invention.

"Immune evasion domain" refers, in another embodiment, to a domain that interferes with or reduces in vivo anti-HSV efficacy of anti-HSV antibodies (e.g. anti-gD antibodies). In another embodiment, the domain interferes or reduces in vivo anti-HSV efficacy of an anti-HSV immune response. In another embodiment, the domain reduces the immunogenicity of an HSV protein (e.g. gD) during subsequent infection. In another embodiment, the domain reduces the immunogenicity of an HSV protein during subsequent challenge. In another embodiment, the domain reduces the immunogenicity of HSV during subsequent challenge. In another embodiment, the domain reduces the immunogenicity of an HSV protein in the context of ongoing HSV infection. In another embodiment, the domain reduces the immunogenicity of HSV in the context of ongoing HSV infection.

The present invention also provides for analogs of HSV proteins or polypeptides, or fragments thereof. Analogs may differ from naturally occurring proteins or peptides by conservative amino acid sequence substitutions or by modifications which do not affect sequence, or by both.

For example, conservative amino acid changes may be made, which although they alter the primary sequence of the protein or peptide, do not normally alter its function. Conservative amino acid substitutions typically include substitutions within the following groups: (a) glycine, alanine; (b) valine, isoleucine, leucine; (c) aspartic acid, glutamic acid; (d) asparagine, glutamine; (e) serine, threonine; (f) lysine, arginine; (g) phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also included are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In another embodiment, the present invention provides antibodies to HSV-2, which in one embodiment, are elicited by gC-2 immunization, and in another embodiment, by gC-1 immunization. In another embodiment, the present invention provides a use for such antibodies in treating, inhibiting, or suppressing HSV-2 infection or symptoms thereof, as described herein. In another embodiment, the present invention provides IgG elicited by gC-2 immunization, and in another embodiment, by gC-1. In another embodiment, the present invention provides a use for IgG in treating, inhibiting, or suppressing HSV-2 infection or symptoms thereof, as described herein.

In one embodiment, the vaccines of the present invention comprise an adjuvant, while in another embodiment, the vaccines do not comprise an adjuvant. "Adjuvant" refers, in another embodiment, to compounds that, when administered to an individual or tested in vitro, increase the immune response to an antigen in the individual or test system to which the antigen is administered. In another embodiment, an immune adjuvant enhances an immune response to an antigen that is weakly immunogenic when administered alone, i.e., inducing no or weak antibody titers or cell-mediated immune response. In another embodiment, the adjuvant increases antibody titers to the antigen. In another embodiment, the adjuvant lowers the dose of the antigen effective to achieve an immune response in the individual.

The adjuvant utilized in methods and compositions of the present invention is, in another embodiment, a CpG-containing nucleotide sequence. In another embodiment, the adjuvant is a CpG-containing oligonucleotide. In another embodiment, the adjuvant is a CpG-containing oligodeoxynucleotide (CpG ODN). In another embodiment, the adjuvant is ODN 1826, which in one embodiment, is acquired from Coley Pharmaceutical Group.

"CpG-containing nucleotide," "CpG-containing oligonucleotide," "CpG oligonucleotide," and similar terms refer, in another embodiment, to a nucleotide molecule of 8-50 nucleotides in length that contains an unmethylated CpG moiety. In another embodiment, any other art-accepted definition of the terms is intended.

In another embodiment, a CpG-containing oligonucleotide of methods and compositions of the present invention is a modified oligonucleotide. "Modified oligonucleotide" refers, in another embodiment, to an oligonucleotide in which at least two of its nucleotides are covalently linked via a synthetic internucleoside linkage (i.e., a linkage other than a phosphodiester linkage between the 5' end of one nucleotide and the 3' end of another nucleotide). In another embodiment, a chemical group not normally associated with nucleic acids has been covalently attached to the oligonucleotide. In another embodiment, the synthetic internucleoside linkage is a phosphorothioate linkage. In another embodiment, the synthetic internucleoside linkage is an alkylphosphonate linkage. In another embodiment, the synthetic internucleoside linkage is a phosphorodithioate linkage. In another embodiment, the synthetic internucleoside linkage is a phosphate ester linkage. In another embodiment, the synthetic internucleoside linkage is an alkylphosphonothioate linkage. In another embodiment, the synthetic internucleoside linkage is a phosphoramidate linkage. In another embodiment, the synthetic internucleoside linkage is a carbamate linkage. In another embodiment, the synthetic internucleoside linkage is a carbonate linkage. In another embodiment, the synthetic internucleoside linkage is a phosphate trimester linkage. In another embodiment, the synthetic internucleoside linkage is an acetamidate linkage. In another embodiment, the synthetic internucleoside linkage is a carboxymethyl ester linkage. In another embodiment, the synthetic internucleoside linkage is a peptide linkage.

In another embodiment, the term "modified oligonucleotide" refers to oligonucleotides with a covalently modified base and/or sugar. In another embodiment, modified oligonucleotides include oligonucleotides having backbone sugars covalently attached to low molecular weight organic groups other than a hydroxyl group at the 3' position and other than a phosphate group at the 5' position. In another embodiment, modified oligonucleotides include a 2'-O-alkylated ribose group. In another embodiment, modified oligonucleotides include sugars such as arabinose instead of ribose. In another embodiment, modified oligonucleotides include murine TLR9 polypeptides, together with pharmaceutically acceptable carriers.

In another embodiment, the CpG-containing oligonucleotide is double-stranded. In another embodiment, the CpG-containing oligonucleotide is single-stranded. In another embodiment, "nucleic acid" and "oligonucleotide" refer to multiple nucleotides (i.e., molecules comprising a sugar (e.g. ribose or deoxyribose) linked to a phosphate group and to an exchangeable organic base, which is either a substituted pyrimidine (e.g. cytosine (C), thymine (T) or uracil (U)) or a substituted purine (e.g. adenine (A) or guanine (G)) or a modified base. In another embodiment, the terms refer to oligoribonucleotides as well as oligodeoxyribonucleotides. In another embodiment, the terms include polynucleosides (i.e., a polynucleotide minus the phosphate) and any other organic base-containing polymer. In another embodiment, the terms encompass nucleic acids or oligonucleotides with a covalently modified base and/or sugar, as described herein.

In another embodiment, a CpG-containing oligonucleotide of methods and compositions of the present invention comprises a substituted purine and pyrimidine. In another embodiment, the oligonucleotide comprises standard purines and pyrimidines such as cytosine as well as base analogs such as C-5 propyne-substituted bases. Wagner R W et al., Nat Biotechnol 14:840-844 (1996). In another embodiment, purines and pyrimidines include but are not limited to adenine, cytosine, guanine, thymine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. In another embodiment, CpG-containing oligonucleotide is a linked polymer of bases or nucleotides. In another embodiment, "linked" refers to 2 entities bound to one another by any physicochemical means.

In another embodiment, the CpG nucleotide molecule is 7909, which in one embodiment, is 5' TCGTCGTTTTGTCGTTTTGTCGTT. In another embodiment, the CpG nucleotide molecule is 2216, which in one embodiment, is 5' GGGGGACGATCGTCGGGGGG. In another embodiment, the CpG nucleotide molecule is 8916. In another embodiment, the CpG nucleotide molecule is 1826. In another embodiment, the CpG nucleotide molecule is 2007. In another embodiment, the CpG nucleotide molecule is 10104. In another embodiment, the CpG nucleotide molecule is 2395. In another embodiment, the CpG nucleotide molecule is 2336. In another embodiment, the CpG nucleotide molecule is 2137. In another embodiment, the CpG nucleotide molecule is 2138. In another embodiment, the CpG nucleotide molecule is 2243. In one embodiment, the CpG nucleotide molecule referenced above is acquired from Coley Pharmaceutical Group. In another embodiment, the sequence of the CpG-containing nucleotide molecule is CTAGACGTTAGCGT (SEQ ID No: 7). In another embodiment, the sequence of the CpG-containing nucleotide molecule is TCAACGTT (SEQ ID No: 8). In another embodiment, the sequence TCC ATG ACG TTC CTG ACG TT (SEQ ID No: 9) (fully phosphorothioate backbone). In another embodiment, the sequence is TCG TCG TTT CGT CGT TTT GTC GTT (SEQ ID No: 10) (fully phosphorothioate backbone). In another embodiment, the sequence is TCG TCG TTG TCG TTT TGT CGT T (SEQ ID No: 11) (fully phosphorothioate backbone). In another embodiment, the sequence is TCG TCG TTT TCG GCG CGC GCC G (SEQ ID No: 12) (fully phosphorothioate backbone). In another embodiment, the sequence is TGC TGC TTT TGT GCT TTT GTG CTT (SEQ ID No: 13) (fully phosphorothioate backbone). In another embodiment, the sequence is TCC ATG AGC TTC CTG AGC TT (SEQ ID No: 14) (fully phosphorothioate backbone). In another embodiment, the sequence is G*G*G GAC GAC GTC GTG G*G*G*G*G*G (SEQ ID No: 15) (* denotes phosphorothioate bonds; others are phosphodiester bonds, for this and the next sequence). In another embodiment, the sequence is G*G*G GGA GCA TGC TGG*G*G*G*G*G (SEQ ID No: 16). In another embodiment, the sequence of the CpG-containing nucleotide molecule is any other CpG-containing sequence known in the art. In another embodiment, the CpG nucleotide molecule is any other CpG-containing nucleotide molecule known in the art.

The dose of the CpG oligonucleotide is, in another embodiment, 10 mcg (microgram). In another embodiment, the dose is 15 mcg. In another embodiment, the dose is 20 mcg. In another embodiment, the dose is 30 mcg. In another embodiment, the dose is 50 mcg. In another embodiment, the dose is 70 mcg. In another embodiment, the dose is 100 mcg. In another embodiment, the dose is 150 mcg. In another embodiment, the dose is 200 mcg. In another embodiment, the dose is 300 mcg. In another embodiment, the dose is 500 mcg. In another embodiment, the dose is 700 mcg. In another embodiment, the dose is 1 mg. In another embodiment, the dose is 1.2 mg. In another embodiment, the dose is 1.5 mg. In another embodiment, the dose is 2 mg. In another embodiment, the dose is 3 mg. In another embodiment, the dose is 5 mg. In another embodiment, the dose is more than 5 mg.

In another embodiment, the dose of the CpG oligonucleotide is 10-100 mcg. In another embodiment, the dose is 10-30 mcg. In another embodiment, the dose is 20-100 mcg. In another embodiment, the dose is 30-100 mcg. In another embodiment, the dose is 50-100 mcg. In another embodiment, the dose is 100-200 mcg. In another embodiment, the dose is 100-250 mcg. In another embodiment, the dose is 50-250 mcg. In another embodiment, the dose is 150-300 mcg. In another embodiment, the dose is 200-400 mcg. In another embodiment, the dose is 250-500 mcg. In another embodiment, the dose is 300-600 mcg. In another embodiment, the dose is 500-1000 mcg. In another embodiment, the dose is 700-1500 mcg. In another embodiment, the dose is 0.25-2 mg. In another embodiment, the dose is 0.5-2 mg. In another embodiment, the dose is 1-2 mg. In another embodiment, the dose is 1.5-2 mg. In another embodiment, the dose is 2-3 mg. In another embodiment, the dose is 3-5 mg. In another embodiment, the dose is 5-8 mg.

Methods for use of CpG oligonucleotides are well known in the art and are described, for example, in Sur S et al. (Long term prevention of allergic lung inflammation in a mouse model of asthma by CpG oligodeoxynucleotides. J Immunol. 1999 May 15; 162(10):6284-93); Verthelyi D. (Adjuvant properties of CpG oligonucleotides in primates. Methods Mol Med. 2006; 127:139-58); and Yasuda K et al. (Role of immunostimulatory DNA and TLR9 in gene therapy. Crit Rev Ther Drug Carrier Syst. 2006; 23(2):89-110). Each method represents a separate embodiment of the present invention.

In another embodiment, "nucleic acids" or "nucleotide" refers to a string of at least 2 base-sugar-phosphate combinations. The term includes, in another embodiment, DNA and RNA. "Nucleotides" refers, in one embodiment, to the monomeric units of nucleic acid polymers. RNA is, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al., Genes & Devel 16: 2491-96 and references cited therein). DNA can be, in other embodiments, in form of plasmid DNA, viral DNA, linear DNA, or chromosomal DNA or derivatives of these groups. In addition, these forms of DNA and RNA can be single, double, triple, or quadruple stranded. The term also includes, in another embodiment, artificial nucleic acids that contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothioate nucleic acids and PNA are known to those skilled in the art, and are described in, for example, Neilsen P E, Curr Opin Struct Biol 9:353-57; and Raz N K et al. Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

Each type of modified oligonucleotide represents a separate embodiment of the present invention.

Methods for production of nucleic acids having modified backbones are well known in the art, and are described, for example in U.S. Pat. Nos. 5,723,335 and 5,663,153 issued to Hutcherson et al. and related PCT publication WO95/26204. Each method represents a separate embodiment of the present invention.

In another embodiment, the adjuvant is an aluminum salt adjuvant. In another embodiment, the aluminum salt adjuvant is an alum-precipitated vaccine. In another embodiment, the aluminum salt adjuvant is an alum-adsorbed vaccine. Aluminum-salt adjuvants are well known in the art and are described, for example, in Harlow, E. and D. Lane (1988; Antibodies: A Laboratory Manual Cold Spring Harbor Laboratory) and Nicklas, W. (1992; Aluminum salts. Research in Immunology 143:489-493). In another embodiment, the aluminum salt is hydrated alumina. In another embodiment, the aluminum salt is alumina hydrate. In another embodiment, the aluminum salt is alumina trihydrate (ATH). In another embodiment, the aluminum salt is aluminum hydrate. In another embodiment, the aluminum salt is aluminum trihydrate. In another embodiment, the aluminum salt is alhydrogel. In another embodiment, the aluminum salt is Superfos. In another embodiment, the aluminum salt is Amphogel. In another embodiment, the aluminum salt is aluminum (III) hydroxide. In another embodiment, the aluminum salt is amorphous alumina. In another embodiment, the aluminum salt is trihydrated alumina. In another embodiment, the aluminum salt is trihydroxyaluminum. In another embodiment, the aluminum salt is any other aluminum salt known in the art.

In another embodiment, a commercially available $Al(OH)_3$ (e.g. Alhydrogel or Superfos of Denmark/Accurate Chemical and Scientific Co., Westbury, N.Y.) is used to adsorb proteins in a ratio of 50-200 g protein/mg aluminum hydroxide. Adsorption of protein is dependent, in another embodiment, on the pI (Isoelectric pH) of the protein and the pH of the medium. A protein with a lower pI adsorbs to the positively charged aluminum ion more strongly than a protein with a higher pI. Aluminum salts establishing, in another embodiment, a depot of Ag that is released slowly over a period of 2-3 weeks, nonspecific activation of macrophages and complement activation.

The dose of the alum salt is, in another embodiment, 10 mcg. In another embodiment, the dose is 15 mcg. In another embodiment, the dose is 20 mcg. In another embodiment, the dose is 25 mcg. In another embodiment, the dose is 30 mcg. In another embodiment, the dose is 50 mcg. In another embodiment, the dose is 70 mcg. In another embodiment, the dose is 100 mcg. In another embodiment, the dose is 150 mcg. In another embodiment, the dose is 200 mcg. In another embodiment, the dose is 300 mcg. In another embodiment, the dose is 500 mcg. In another embodiment, the dose is 700 mcg. In another embodiment, the dose is 1 mg. In another embodiment, the dose is 1.2 mg. In another embodiment, the dose is 1.5 mg. In another embodiment, the dose is 2 mg. In another embodiment, the dose is 3 mg. In another embodiment, the dose is 5 mg. In another embodiment, the dose is more than 5 mg. In one embodiment, the dose of alum salt described above is per mcg of recombinant protein.

In another embodiment, the dose of the alum salt is 10-100 mcg. In another embodiment, the dose is 20-100 mcg. In another embodiment, the dose is 30-100 mcg. In another embodiment, the dose is 50-100 mcg. In another embodiment, the dose is 100-200 mcg. In another embodiment, the dose is 150-300 mcg. In another embodiment, the dose is 200-400 mcg. In another embodiment, the dose is 300-600 mcg. In another embodiment, the dose is 500-1000 mcg. In another embodiment, the dose is 700-1500 mcg. In another embodiment, the dose is 1-2 mg. In another embodiment, the dose is 1.5-2 mg. In another embodiment, the dose is 2-3 mg. In another embodiment, the dose is 3-5 mg. In another embodiment, the dose is 5-8 mg. In one embodiment, the dose of alum salt described above is per mcg of recombinant protein.

In another embodiment, the adjuvant is a Montanide ISA adjuvant. In another embodiment, the adjuvant is a trimer of complement component C3d. In another embodiment, the trimer is covalently linked to the protein immunogen. In another embodiment, the adjuvant is MF59. In another embodiment, the adjuvant is a granulocyte/macrophage colony-stimulating factor (GM-CSF) protein. In another embodiment, the adjuvant is a mixture comprising a GM-CSF protein. In another embodiment, the adjuvant is a nucleotide molecule encoding GM-CSF. In another embodiment, the adjuvant is a mixture comprising a nucleotide molecule encoding GM-CSF. In another embodiment, the adjuvant is saponin QS21. In another embodiment, the adjuvant is a mixture comprising saponin QS21. In another embodiment, the adjuvant is monophosphoryl lipid A (MPL). In another embodiment, the adjuvant is a mixture comprising MPL. In another embodiment, the adjuvant is SBAS2. In another embodiment, the adjuvant is a mixture comprising SBAS2. In another embodiment, the adjuvant is an unmethylated CpG-containing oligonucleotide. In another embodiment, the adjuvant is a mixture comprising an unmethylated CpG-containing oligonucleotide. In another embodiment, the adjuvant is an immune-stimulating cytokine. In another embodiment, the adjuvant is a mixture comprising an immune-stimulating cytokine. In another embodiment, the adjuvant is a nucleotide molecule encoding an immune-stimulating cytokine. In another embodiment, the adjuvant is a mixture comprising a nucleotide molecule encoding an immune-stimulating cytokine. In another embodiment, the adjuvant is a mixture comprising a quill glycoside. In another embodiment, the adjuvant is a mixture comprising a bacterial mitogen. In another embodiment, the adjuvant is a mixture comprising a bacterial toxin. In another embodiment, the adjuvant is a mixture comprising any other adjuvant known in the art. In another embodiment, the adjuvant is a mixture of 2 of the above adjuvants. In another embodiment, the adjuvant is a mixture of 3 of the above adjuvants. In another embodiment, the adjuvant is a mixture of more than three of the above adjuvants. In another embodiment, the adjuvant is a mixture of MPL, and 500 μg of alum.

In another embodiment, blocking immune evasion by anti-gC or anti-gE antibodies elicited by a vaccine of the present invention enables a lower dose of adjuvant to be required to elicit an effective anti-gD immune response. In another embodiment, a lower dose of adjuvant is required for a vaccine of the present invention to elicit an effective anti-HSV immune response. In another embodiment, a lower dose of vaccine is required to elicit an effective anti-HSV immune response when an adjuvant is used.

In another embodiment, the adjuvant is a carrier polypeptide. "Carrier polypeptide" refers, in another embodiment, to a protein or immunogenic fragment thereof that can be conjugated or joined with an HSV protein of the present invention to enhance immunogenicity of the polypeptide. Examples of carrier proteins include, but are by no means limited to, keyhole limpet Hemocyanin (KLH), albumin, cholera toxin, heat labile enterotoxin (LT), and the like. In another embodiment, the 2 components are prepared as a chimeric construct for expression as a fusion polypeptide. In another embodiment, chemical cross-linking is used to link an HSV protein with a carrier polypeptide.

In another embodiment, a vaccine of methods and compositions of the present invention comprises recombinant HSV-1 proteins. In another embodiment, the vaccine comprises recombinant HSV-2 proteins. In another embodiment, the vaccine comprises both HSV-1 and HSV-2 proteins.

In another embodiment, a recombinant HSV-1-protein-containing vaccine of methods and compositions of the present invention further comprises a recombinant HSV-2 protein. In another embodiment, the recombinant HSV-2 protein is a gD2 protein or fragment thereof. In another embodiment, the recombinant HSV-2 protein is a gC2 protein or fragment thereof. In another embodiment, the recombinant HSV-2 protein is a gE2 protein or fragment thereof. In another embodiment, the recombinant HSV-1-protein-containing vaccine further comprises a gD2 protein and a gC2 protein or fragments thereof. In another embodiment, the vaccine further comprises a gD2 protein and a gE2 protein or fragments thereof. In another embodiment, the vaccine further comprises a gE2 protein and a gC2 protein or fragments thereof. In another embodiment, the vaccine further comprises a gD2 protein, a gE2 protein, and a gC2 protein or fragments thereof.

In another embodiment, a recombinant HSV-2-protein-containing vaccine of methods and compositions of the present invention further comprises a recombinant HSV-1 protein. In another embodiment, the recombinant HSV-1 protein is a gD1 protein or fragment thereof. In another embodiment, the recombinant HSV-1 protein is a gC1 protein or fragment thereof. In another embodiment, the recombinant HSV-1 protein is a gE1 protein or fragment thereof. In another embodiment, the recombinant HSV-2-protein-containing vaccine further comprises a gD1 protein and a gC1 protein or fragments thereof n. In another embodiment, the vaccine further comprises a gD1 protein and a gE1 protein or fragments thereof. In another embodiment, the vaccine further comprises a gE1 protein and a gC1 protein or fragments thereof. In another embodiment, the vaccine further comprises a gD1 protein, a gE1 protein, and a gC1 protein or fragments thereof.

In another embodiment, a vaccine regimen of the present invention further comprises the step of administering to the subject a booster vaccination, wherein the booster vaccination comprises a recombinant HSV-1 gD protein or immunogenic fragment thereof used in the priming vaccination, but not the other recombinant proteins present in the priming vaccinations. In another embodiment, the booster vaccination contains both and HSV-1 gD protein and an HSV-2 gD protein. In another embodiment, the booster vaccination does not comprise a recombinant HSV-1 gC protein or fragment thereof present in the priming vaccination. In another embodiment, the booster vaccination does not comprise a recombinant HSV-1 gE protein or fragment thereof present in the priming vaccination. In another embodiment, the booster vaccination does not comprise either (a) a recombinant HSV-1 gC protein or fragment thereof or (b) a recombinant HSV-1 gE protein or fragment thereof, both of which are present in the priming vaccination.

In another embodiment, a vaccine regimen of the present invention further comprises the step of administering to the subject a booster vaccination, wherein the booster vaccination comprises a recombinant HSV-1 gE protein or immunogenic fragment thereof used in the priming vaccination, but not the other recombinant proteins contained in the priming vaccinations. In another embodiment, the booster vaccination contains both and HSV-1 gE protein and an HSV-2 gE protein. In another embodiment, the booster vaccination does not comprise a recombinant HSV-1 gC protein or fragment thereof present in the priming vaccination. In another embodiment, the booster vaccination does not comprise a recombinant HSV-1 gD protein or fragment thereof present in the priming vaccination. In another embodiment, the booster vaccination does not comprise either (a) a recombinant HSV-1 gC protein or fragment thereof or (b) a recombinant HSV-1 gD protein or fragment thereof, both of which are present in the priming vaccination.

In another embodiment, a vaccine regimen of the present invention further comprises the step of administering to the subject a booster vaccination, wherein the booster vaccination comprises a recombinant HSV-1 gC protein or immunogenic fragment thereof used in the priming vaccination, but not the other recombinant proteins contained in the priming vaccinations. In another embodiment, the booster vaccination contains both and HSV-1 gC protein and an HSV-2 gC protein. In another embodiment, the booster vaccination does not comprise a recombinant HSV-1 gD protein or fragment thereof present in the priming vaccination. In another embodiment, the booster vaccination does not comprise a recombinant HSV-1 gE protein or fragment thereof present in the priming vaccination. In another embodiment, the booster vaccination does not comprise either (a) a recombinant HSV-1 gD protein or fragment thereof or (b) a recombinant HSV-1 gE protein or fragment thereof, both of which are present in the priming vaccination.

In another embodiment, a vaccine regimen of the present invention further comprises the step of administering to the subject a booster vaccination, wherein the booster vaccination comprises a recombinant HSV-2 gD protein or immunogenic fragment thereof used in the priming vaccination, but not the other recombinant proteins contained in the priming vaccinations. In another embodiment, the booster vaccination contains both and HSV-1 gD protein and an HSV-2 gD protein. In another embodiment, the booster vaccination does not comprise a recombinant HSV-2 gC protein or fragment thereof present in the priming vaccination. In another embodiment, the booster vaccination does not comprise a recombinant HSV-2 gE protein or fragment thereof present in the priming vaccination. In another embodiment, the booster vaccination does not comprise either (a) a recombinant HSV-2 gC protein or fragment thereof or (b) a recombinant HSV-2 gE protein or fragment thereof, both of which are present in the priming vaccination.

In another embodiment, a vaccine regimen of the present invention further comprises the step of administering to the subject a booster vaccination, wherein the booster vaccination comprises a recombinant HSV-2 gE protein or immunogenic fragment thereof used in the priming vaccination, but not the other recombinant proteins contained in the priming vaccinations. In another embodiment, the booster vaccination contains both and HSV-1 gE protein and an HSV-2 gE protein. In another embodiment, the booster vaccination does not comprise a recombinant HSV-2 gC protein or fragment thereof present in the priming vaccination. In another embodiment, the booster vaccination does not comprise a recombinant HSV-2 gD protein or fragment thereof present in the priming vaccination. In another embodiment, the booster vaccination does not comprise either (a) a recombinant HSV-2 gC protein or fragment thereof or (b) a recombinant HSV-2 gD protein or fragment thereof, both of which are present in the priming vaccination.

In another embodiment, a vaccine regimen of the present invention further comprises the step of administering to the subject a booster vaccination, wherein the booster vaccination comprises a recombinant HSV-2 gC protein or immunogenic fragment thereof used in the priming vaccination, but not the other recombinant proteins contained in the priming vaccinations. In another embodiment, the booster vaccination contains both and HSV-1 gC protein and an HSV-2 gC protein. In another embodiment, the booster vaccination does not comprise a recombinant HSV-2 gD protein or fragment thereof present in the priming vaccination. In another embodiment, the booster vaccination does not comprise a recombinant HSV-2 gE protein or fragment thereof present in the priming vaccination. In another embodiment, the booster vaccination does not comprise either (a) a recombinant HSV-2 gD protein or fragment thereof or (b) a recombinant HSV-2 gE protein or fragment thereof, both of which are present in the priming vaccination.

In one embodiment, any of the booster vaccinations described hereinabove is administered following a priming vaccination comprising one or more HSV-1 proteins or immunogenic fragments thereof. In another embodiment, any of the booster vaccinations described hereinabove is administered following a priming vaccination comprising one or more HSV-2 proteins or immunogenic fragments thereof.

In another embodiment, a vaccine regimen of the present invention further comprises the step of administering to the subject a booster vaccination, wherein the booster vaccination consists essentially of a recombinant HSV-1 gD protein or immunogenic fragment thereof. In another embodiment, the booster vaccination consists of a recombinant HSV-1 gD protein or immunogenic fragment thereof and an adjuvant. In one embodiment, the HSV gD protein or immunogenic fragment thereof is an HSV-1 gD protein, while in another embodiment, it's an HSV-2 gD protein, while in another embodiment, it's both an HSV-1 and HSV-2 gD protein. In another embodiment, the booster vaccination consists essentially of a recombinant HSV gE protein or immunogenic fragment thereof. In another embodiment, the booster vaccination consists of a recombinant HSV gE protein or immunogenic fragment thereof and an adjuvant. In one embodiment, the HSV gE protein or immunogenic fragment thereof is an HSV-1 gE protein, while in another embodiment, it's an HSV-2 gE protein, while in another embodiment, it's both an HSV-1 and HSV-2 gE protein. In another embodiment, the booster vaccination consists essentially of a recombinant HSV gC protein or immunogenic fragment thereof. In another embodiment, the booster vaccination consists of a recombinant HSV gC protein or immunogenic fragment thereof and an adjuvant. In one embodiment, the HSV gC protein or immunogenic fragment thereof is an HSV-1 gC protein, while in another embodiment, it's an HSV-2 gC protein, while in another embodiment, it's both an HSV-1 and HSV-2 gC protein.

In another embodiment, the booster vaccination follows a single priming vaccination. "Priming vaccination" refers, in another embodiment, to a vaccination that comprises a mixture of (a) a gD protein and (b) either a gC protein, a gE protein, or a mixture thereof. In another embodiment, a priming vaccination refers to a vaccination that comprises two or more recombinant HSV proteins selected from a gD protein, a gC protein and a gE protein. In another embodiment, the term refers to a vaccine initially administered. In another embodiment, two priming vaccinations are administered before the booster vaccination. In another embodiment, three priming vaccinations are administered before the booster vaccination. In another embodiment, four priming vaccinations are administered before the booster vaccination.

In another embodiment, a single booster vaccination is administered after the priming vaccinations. In another embodiment, two booster vaccinations are administered after the priming vaccinations. In another embodiment, three booster vaccinations are administered after the priming vaccinations.

In one embodiment, gD and gE are administered in a single syringe at the same site, while in another embodiment, gD and gE are administered in separate syringes at separate sites, or in another embodiment, gD and gE are administered simultaneously at a single site and followed by a booster dose of gD without gE.

In one embodiment, gD and gC are administered in a single syringe at the same site, while in another embodiment, gD and gC are administered in separate syringes at separate sites, or in another embodiment, gD and gC are administered simultaneously at a single site and followed by a booster dose of gD without gC.

In one embodiment, gE and gC are administered in a single syringe at the same site, while in another embodiment, gE and gC are administered in separate syringes at separate sites, or in another embodiment, gE and gC are administered simultaneously at a single site and followed by a booster dose of gE without gC or, in another embodiment, followed by a booster dose of gC without gE.

In one embodiment, gD, gC, and gE are administered in a single syringe at the same site, while in another embodiment, gD, gC, and gE are administered in separate syringes at separate sites, or in another embodiment, gD, gC, and gE are administered simultaneously at a single site and followed by a booster dose of gD without gC and gE.

In another embodiment, the dose of recombinant HSV gD-1 utilized in a vaccination or in a booster vaccination is 20 mcg per inoculation, e.g. for a human subject. In another embodiment, the dosage is 10 mcg/inoculation. In another embodiment, the dosage is 30 mcg/inoculation. In another embodiment, the dosage is 25 mcg/inoculation. In another embodiment, the dosage is 22 mcg/inoculation. In another embodiment, the dosage is 18 mcg/inoculation. In another embodiment, the dosage is 16 mcg/inoculation. In another embodiment, the dosage is 15 mcg/inoculation. In another embodiment, the dosage is 14 mcg/inoculation. In another embodiment, the dosage is 13 mcg/inoculation. In another embodiment, the dosage is 12 mcg/inoculation. In another embodiment, the dosage is 11 mcg/inoculation. In another embodiment, the dosage is 10 mcg/inoculation. In another embodiment, the dosage is 9 mcg/inoculation. In another embodiment, the dosage is 8 mcg/inoculation. In another embodiment, the dosage is 7 mcg/inoculation. In another embodiment, the dosage is 6 mcg/inoculation. In another embodiment, the dosage is 5 mcg/inoculation. In another embodiment, the dosage is 4 mcg/inoculation. In another embodiment, the dosage is 3 mcg/inoculation. In another embodiment, the dosage is 2 mcg/inoculation. In another embodiment, the dosage is 1.5 mcg/inoculation. In another embodiment, the dosage is 1 mcg/inoculation. In another embodiment, the dosage is less than 1 mcg/inoculation.

In another embodiment, the dosage is 0.1 mcg/kg body mass (per inoculation). In another embodiment, the dosage is 0.2 mcg/kg. In another embodiment, the dosage is 0.15 mcg/kg. In another embodiment, the dosage is 0.13 mcg/kg. In another embodiment, the dosage is 0.12 mcg/kg. In another embodiment, the dosage is 0.11 mcg/kg. In another embodiment, the dosage is 0.09 mcg/kg. In another embodiment, the dosage is 0.08 mcg/kg. In another embodiment, the dosage is 0.07 mcg/kg. In another embodiment, the dosage is 0.06 mcg/kg. In another embodiment, the dosage is 0.05 mcg/kg. In another embodiment, the dosage is 0.04 mcg/kg. In another embodiment, the dosage is 0.03 mcg/kg. In another embodiment, the dosage is 0.02 mcg/kg. In another embodiment, the dosage is less than 0.02 mcg/kg.

In another embodiment, the dosage is 1-2 mcg/inoculation. In another embodiment, the dosage is 2-3 mcg/inoculation. In another embodiment, the dosage is 2-4 mcg/inoculation. In another embodiment, the dosage is 3-6 mcg/inoculation. In another embodiment, the dosage is 4-8 mcg/inoculation. In another embodiment, the dosage is 5-10 mcg/inoculation. In another embodiment, the dosage is 5-15 mcg/inoculation. In another embodiment, the dosage is 10-20 mcg/inoculation. In another embodiment, the dosage is 20-30 mcg/inoculation. In another embodiment, the dosage is 30-40 mcg/protein/inoculation. In another embodiment, the dosage is 40-60 mcg/inoculation. In another embodiment, the dosage is 2-50 mcg/inoculation. In another embodiment, the dosage is 3-50 mcg/inoculation. In another embodiment, the dosage is 5-50 mcg/inoculation. In another embodiment, the dosage is 8-50 mcg/inoculation. In another embodiment, the dosage is 10-50 mcg/inoculation. In another embodiment, the dosage is 20-50 mcg/inoculation.

Each dose of gD-1 represents a separate embodiment of the present invention.

In another embodiment, the dose of recombinant HSV gD-2 utilized in a vaccination or in a booster vaccination is 10 ng/inoculation, which in one embodiment, is for a human subject. In another embodiment, the dosage is 25 ng/inoculation. In another embodiment, the dosage is 50 ng/inoculation. In another embodiment, the dosage is 100 ng/inoculation. In another embodiment, the dosage is 150 ng/inoculation. In another embodiment, the dosage is 200 ng/inoculation. In another embodiment, the dosage is 250 ng/inoculation. In another embodiment, the dosage is 300 ng/inoculation. In another embodiment, the dosage is 400 ng/inoculation. In another embodiment, the dosage is 500 ng/inoculation. In another embodiment, the dosage is 750 ng/inoculation.

In another embodiment, the dosage is 20 mcg per inoculation. In another embodiment, the dosage is 10 mcg/inoculation. In another embodiment, the dosage is 30 mcg/inoculation. In another embodiment, the dosage is 25 mcg/inoculation. In another embodiment, the dosage is 22 mcg/inoculation. In another embodiment, the dosage is 18 mcg/inoculation. In another embodiment, the dosage is 16 mcg/inoculation. In another embodiment, the dosage is 15 mcg/inoculation. In another embodiment, the dosage is 14 mcg/inoculation. In another embodiment, the dosage is 13 mcg/inoculation. In another embodiment, the dosage is 12 mcg/inoculation. In another embodiment, the dosage is 11 mcg/inoculation. In another embodiment, the dosage is 10 mcg/inoculation. In another embodiment, the dosage is 9 mcg/inoculation. In another embodiment, the dosage is 8 mcg/inoculation. In another embodiment, the dosage is 7 mcg/inoculation. In another embodiment, the dosage is 6 mcg/inoculation. In another embodiment, the dosage is 5 mcg/inoculation. In another embodiment, the dosage is 4 mcg/inoculation. In another embodiment, the dosage is 3 mcg/inoculation. In another embodiment, the dosage is 2 mcg/inoculation. In another embodiment, the dosage is 1.5 mcg/inoculation. In another embodiment, the dosage is 1 mcg/inoculation. In another embodiment, the dosage is less than 1 mcg/inoculation.

In another embodiment, the dosage is 0.1 mcg/kg body mass (per inoculation). In another embodiment, the dosage is 0.2 mcg/kg. In another embodiment, the dosage is 0.15 mcg/kg. In another embodiment, the dosage is 0.13 mcg/kg. In another embodiment, the dosage is 0.12 mcg/kg. In another embodiment, the dosage is 0.11 mcg/kg. In another embodiment, the dosage is 0.09 mcg/kg. In another embodiment, the dosage is 0.08 mcg/kg. In another embodiment, the dosage is 0.07 mcg/kg. In another embodiment, the dosage is 0.06 mcg/kg. In another embodiment, the dosage is 0.05 mcg/kg. In another embodiment, the dosage is 0.04 mcg/kg. In another embodiment, the dosage is 0.03 mcg/kg. In another embodiment, the dosage is 0.02 mcg/kg. In another embodiment, the dosage is less than 0.02 mcg/kg.

In another embodiment, the dosage is 500 ng/kg. In another embodiment, the dosage is 1.25 mcg/kg. In another embodiment, the dosage is 2.5 mcg/kg. In another embodiment, the dosage is 5 mcg/kg. In another embodiment, the dosage is 10 mcg/kg. In another embodiment, the dosage is 12.5 mcg/kg.

In another embodiment, the dosage is 1-2 mcg/inoculation. In another embodiment, the dosage is 2-3 mcg/inoculation. In another embodiment, the dosage is 2-4 mcg/inoculation. In another embodiment, the dosage is 3-6 mcg/inoculation. In another embodiment, the dosage is 4-8 mcg/inoculation. In another embodiment, the dosage is 5-10 mcg/inoculation. In another embodiment, the dosage is 5-15 mcg/inoculation. In another embodiment, the dosage is 10-20 mcg/inoculation. In another embodiment, the dosage is 20-30 mcg/inoculation. In another embodiment, the dosage is 30-40 mcg/protein/inoculation. In another embodiment, the dosage is 40-60 mcg/inoculation. In another embodiment, the dosage is 2-50 mcg/inoculation. In another embodiment, the dosage is 3-50 mcg/inoculation. In another embodiment, the dosage is 5-50 mcg/inoculation. In another embodiment, the dosage is 8-50 mcg/inoculation. In another embodiment, the dosage is 10-50 mcg/inoculation. In another embodiment, the dosage is 20-50 mcg/inoculation.

Each dose of gD-2 represents a separate embodiment of the present invention.

In another embodiment, the dose of recombinant HSV gC-1 utilized in a vaccination or in a booster vaccination is 20 mcg per inoculation, e.g. for a human subject. In another embodiment, the dosage is 10 mcg/inoculation. In another embodiment, the dosage is 30 mcg/inoculation. In another embodiment, the dosage is 25 mcg/inoculation. In another embodiment, the dosage is 22 mcg/inoculation. In another embodiment, the dosage is 18 mcg/inoculation. In another embodiment, the dosage is 16 mcg/inoculation. In another embodiment, the dosage is 15 mcg/inoculation. In another embodiment, the dosage is 14 mcg/inoculation. In another embodiment, the dosage is 13 mcg/inoculation. In another embodiment, the dosage is 12 mcg/inoculation. In another embodiment, the dosage is 11 mcg/inoculation. In another embodiment, the dosage is 10 mcg/inoculation. In another embodiment, the dosage is 9 mcg/inoculation. In another embodiment, the dosage is 8 mcg/inoculation. In another embodiment, the dosage is 7 mcg/inoculation. In another embodiment, the dosage is 6 mcg/inoculation. In another embodiment, the dosage is 5 mcg/inoculation. In another embodiment, the dosage is 4 mcg/inoculation. In another embodiment, the dosage is 3 mcg/inoculation. In another embodiment, the dosage is 2 mcg/inoculation. In another embodiment, the dosage is 1.5 mcg/inoculation. In another embodiment, the dosage is 1 mcg/inoculation. In another embodiment, the dosage is less than 1 mcg/inoculation. In another embodiment, the dosage is 100 mcg/inoculation. In another embodiment, the dosage is 500 mcg/inoculation. In another embodiment, the dosage is 400 mcg/inoculation. In another embodiment, the dosage is 300 mcg/inoculation. In another embodiment, the dosage is 220 mcg/inoculation. In another embodiment, the dosage is 250 mcg/inoculation. In another embodiment, the dosage is 200 mcg/inoculation. In another embodiment, the dosage is 180 mcg/inoculation. In another embodiment, the dosage is 160 mcg/inoculation. In another embodiment, the dosage is 150 mcg/inoculation. In another embodiment, the dosage is 140 mcg/inoculation. In another embodiment, the dosage is 130 mcg/inoculation. In another embodiment, the dosage is 120 mcg/inoculation. In another embodiment, the dosage is 110 mcg/inoculation. In another embodiment, the dosage is 100 mcg/inoculation. In another embodiment, the dosage is 90 mcg/inoculation. In another embodiment, the dosage is 80 mcg/inoculation. In another embodiment, the dosage is 70 mcg/inoculation. In another embodiment, the dosage is 60 mcg/inoculation. In another embodiment, the dosage is 50 mcg/inoculation. In another embodiment, the dosage is 40 mcg/inoculation.

In another embodiment, the dosage is 0.1 mcg/kg body mass (per inoculation). In another embodiment, the dosage is 0.2 mcg/kg. In another embodiment, the dosage is 0.15 mcg/kg. In another embodiment, the dosage is 0.13 mcg/kg. In another embodiment, the dosage is 0.12 mcg/kg. In another embodiment, the dosage is 0.11 mcg/kg. In another embodiment, the dosage is 0.09 mcg/kg. In another embodiment, the dosage is 0.08 mcg/kg. In another embodiment, the dosage is 0.07 mcg/kg. In another embodiment, the dosage is 0.06 mcg/kg. In another embodiment, the dosage is 0.05 mcg/kg. In another embodiment, the dosage is 0.04 mcg/kg. In another embodiment, the dosage is 0.03 mcg/kg. In another embodiment, the dosage is 0.02 mcg/kg. In another embodiment, the dosage is less than 0.02 mcg/kg.

In another embodiment, the dosage is 10-100 ng/inoculation. In another embodiment, the dosage is 50-250 ng/inoculation. In another embodiment, the dosage is 10-250 ng/inoculation. In another embodiment, the dosage is 100-500 ng/inoculation. In another embodiment, the dosage is 200-300 ng/inoculation. In another embodiment, the dosage is 1-2 mcg/inoculation. In another embodiment, the dosage is 2-3 mcg/inoculation. In another embodiment, the dosage is 2-4 mcg/inoculation. In another embodiment, the dosage is 3-6 mcg/inoculation. In another embodiment, the dosage is 4-8 mcg/inoculation. In another embodiment, the dosage is 5-10 mcg/inoculation. In another embodiment, the dosage is 5-15 mcg/inoculation. In another embodiment, the dosage is 10-20 mcg/inoculation. In another embodiment, the dosage is 20-30 mcg/inoculation. In another embodiment, the dosage is 30-40 mcg/protein/inoculation. In another embodiment, the dosage is 40-60 mcg/inoculation. In another embodiment, the dosage is 20-100 mcg/inoculation. In another embodiment, the dosage is 30-100 mcg/inoculation. In another embodiment, the dosage is 50-100 mcg/inoculation. In another embodiment, the dosage is 80-100 mcg/inoculation. In another embodiment, the dosage is 20-200 mcg/inoculation. In another embodiment, the dosage is 30-200 mcg/inoculation. In another embodiment, the dosage is 50-200 mcg/inoculation. In another embodiment, the dosage is 80-200 mcg/inoculation. In another embodiment, the dosage is 100-200 mcg/inoculation. In another embodiment, the dosage is 20-300 mcg/inoculation. In another embodiment, the dosage is 30-300 mcg/inoculation. In another embodiment, the dosage is 50-300 mcg/inoculation. In another embodiment, the dosage is 80-300 mcg/inoculation. In another embodiment, the dosage is 100-300 mcg/inoculation. In another embodiment, the dosage is 200-300 mcg/inoculation. In another embodiment, the dosage is 20-500 mcg/inoculation. In another embodiment, the dosage is 30-500 mcg/inoculation. In another embodiment, the dosage is 50-500 mcg/inoculation. In another embodiment, the dosage is 80-500 mcg/inoculation. In another embodiment, the dosage is 100-500 mcg/inoculation. In another embodiment, the dosage is 200-500 mcg/inoculation. In another embodiment, the dosage is 300-500 mcg/inoculation.

Each dose of gC-1 represents a separate embodiment of the present invention.

In another embodiment, the dose of recombinant HSV gC-2 utilized in a vaccination or in a booster vaccination is 20 mcg per inoculation, e.g. for a human subject. In another embodiment, the dosage is 0.5 mcg/inoculation. In another embodiment, the dosage is 7.5 mcg/inoculation. In another embodiment, the dosage is 10 mcg/inoculation. In another embodiment, the dosage is 30 mcg/inoculation. In another embodiment, the dosage is 25 mcg/inoculation. In another embodiment, the dosage is 22 mcg/inoculation. In another embodiment, the dosage is 18 mcg/inoculation. In another embodiment, the dosage is 16 mcg/inoculation. In another embodiment, the dosage is 15 mcg/inoculation. In another embodiment, the dosage is 14 mcg/inoculation. In another embodiment, the dosage is 13 mcg/inoculation. In another embodiment, the dosage is 12 mcg/inoculation. In another embodiment, the dosage is 11 mcg/inoculation. In another embodiment, the dosage is 10 mcg/inoculation. In another embodiment, the dosage is 9 mcg/inoculation. In another embodiment, the dosage is 8 mcg/inoculation. In another embodiment, the dosage is 7 mcg/inoculation. In another embodiment, the dosage is 6 mcg/inoculation. In another embodiment, the dosage is 5 mcg/inoculation. In another embodiment, the dosage is 4 mcg/inoculation. In another embodiment, the dosage is 3 mcg/inoculation. In another embodiment, the dosage is 2 mcg/inoculation. In another embodiment, the dosage is 1.5 mcg/inoculation. In another embodiment, the dosage is 1 mcg/inoculation. In another embodiment, the dosage is less than 1 mcg/inoculation. In another embodiment, the dosage is 500 mcg/inoculation. In another embodiment, the dosage is 400 mcg/inoculation. In another embodiment, the dosage is 300 mcg/inoculation. In another embodiment, the dosage is 220 mcg/inoculation. In another embodiment, the dosage is 250 mcg/inoculation. In another embodiment, the dosage is 200 mcg/inoculation. In another embodiment, the dosage is 180 mcg/inoculation. In another embodiment, the dosage is 160 mcg/inoculation. In another embodiment, the dosage is 150 mcg/inoculation. In another embodiment, the dosage is 140 mcg/inoculation. In another embodiment, the dosage is 130 mcg/inoculation. In another embodiment, the dosage is 120 mcg/inoculation. In another embodiment, the dosage is 110 mcg/inoculation. In another embodiment, the dosage is 100 mcg/inoculation. In another embodiment, the dosage is 90 mcg/inoculation. In another embodiment, the dosage is 80 mcg/inoculation. In another embodiment, the dosage is 70 mcg/inoculation. In another embodiment, the dosage is 60 mcg/inoculation. In another embodiment, the dosage is 50 mcg/inoculation. In another embodiment, the dosage is 40 mcg/inoculation.

In another embodiment, the dosage is 0.1 mcg/kg body mass (per inoculation). In another embodiment, the dosage is 0.2 mcg/kg. In another embodiment, the dosage is 0.15 mcg/kg. In another embodiment, the dosage is 0.13 mcg/kg. In another embodiment, the dosage is 0.12 mcg/kg. In another embodiment, the dosage is 0.11 mcg/kg. In another embodiment, the dosage is 0.09 mcg/kg. In another embodiment, the dosage is 0.08 mcg/kg. In another embodiment, the dosage is 0.07 mcg/kg. In another embodiment, the dosage is 0.06 mcg/kg. In another embodiment, the dosage is 0.05 mcg/kg. In another embodiment, the dosage is 0.04 mcg/kg. In another embodiment, the dosage is 0.03 mcg/kg. In another embodiment, the dosage is 0.02 mcg/kg. In another embodiment, the dosage is less than 0.02 mcg/kg. In another embodiment, the dosage is 250 mcg/kg. In another embodiment, the dosage is 25 mcg/kg. In another embodiment, the dosage is 50 mcg/kg. In another embodiment, the dosage is 100 mcg/kg. In another embodiment, the dosage is 200 mcg/kg. In another embodiment, the dosage is 300 mcg/kg. In another embodiment, the dosage is 500 mcg/kg.

In another embodiment, the dosage is 1-2 mcg/inoculation. In another embodiment, the dosage is 2-3 mcg/inoculation. In another embodiment, the dosage is 2-4 mcg/inoculation. In another embodiment, the dosage is 3-6 mcg/inoculation. In another embodiment, the dosage is 4-8 mcg/inoculation. In another embodiment, the dosage is 5-10 mcg/inoculation. In another embodiment, the dosage is 5-15 mcg/inoculation. In another embodiment, the dosage is 10-20 mcg/inoculation. In another embodiment, the dosage is 20-30 mcg/inoculation. In another embodiment, the dosage is 30-40 mcg/protein/inoculation. In another embodiment, the dosage is 40-60 mcg/inoculation. In another embodiment, the dosage is 20-100 mcg/inoculation. In another embodiment, the dosage is 30-100 mcg/inoculation. In another embodiment, the dosage is 50-100 mcg/inoculation. In another embodiment, the dosage is 80-100 mcg/inoculation. In another embodiment, the dosage is 20-200 mcg/inoculation. In another embodiment, the dosage is 30-200 mcg/inoculation. In another embodiment, the dosage is 50-200 mcg/inoculation. In another embodiment, the dosage is 80-200 mcg/inoculation. In another embodiment, the dosage is 100-200 mcg/inoculation. In another embodiment, the dosage is 20-300 mcg/inoculation. In another embodiment, the dosage is 30-300 mcg/inoculation. In another embodiment, the dosage is 50-300 mcg/inoculation. In another embodiment, the dosage is 80-300 mcg/inoculation. In another embodiment, the dosage is 100-300 mcg/inoculation. In another embodiment, the dosage is 200-300 mcg/inoculation. In another embodiment, the dosage is 20-500 mcg/inoculation. In another embodiment, the dosage is 30-500 mcg/inoculation. In another embodiment, the dosage is 50-500 mcg/inoculation. In another embodiment, the dosage is 80-500 mcg/inoculation. In another embodiment, the dosage is 100-500 mcg/inoculation. In another embodiment, the dosage is 200-500 mcg/inoculation. In another embodiment, the dosage is 300-500 mcg/inoculation.

Each dose of gC-2 represents a separate embodiment of the present invention.

In another embodiment, the dose of recombinant HSV gE-1 utilized in a vaccination or in a booster vaccination is 20 mcg per inoculation, e.g. for a human subject. In another embodiment, the dosage is 10 mcg/inoculation. In another embodiment, the dosage is 30 mcg/inoculation. In another embodiment, the dosage is 25 mcg/inoculation. In another embodiment, the dosage is 22 mcg/inoculation. In another embodiment, the dosage is 18 mcg/inoculation. In another embodiment, the dosage is 16 mcg/inoculation. In another embodiment, the dosage is 15 mcg/inoculation. In another embodiment, the dosage is 14 mcg/inoculation. In another embodiment, the dosage is 13 mcg/inoculation. In another embodiment, the dosage is 12 mcg/inoculation. In another embodiment, the dosage is 11 mcg/inoculation. In another embodiment, the dosage is 10 mcg/inoculation. In another embodiment, the dosage is 9 mcg/inoculation. In another embodiment, the dosage is 8 mcg/inoculation. In another embodiment, the dosage is 7 mcg/inoculation. In another embodiment, the dosage is 6 mcg/inoculation. In another embodiment, the dosage is 5 mcg/inoculation. In another embodiment, the dosage is 4 mcg/inoculation. In another embodiment, the dosage is 3 mcg/inoculation. In another embodiment, the dosage is 2 mcg/inoculation. In another embodiment, the dosage is 1.5 mcg/inoculation. In another embodiment, the dosage is 1 mcg/inoculation. In another embodiment, the dosage is less than 1 mcg/inoculation. In another embodiment, the dosage is 500 mcg/inoculation. In another embodiment, the dosage is 400 mcg/inoculation. In another embodiment, the dosage is 300 mcg/inoculation. In another embodiment, the dosage is 220 mcg/inoculation. In another embodiment, the dosage is 250 mcg/inoculation. In another embodiment, the dosage is 200 mcg/inoculation. In another embodiment, the dosage is 180 mcg/inoculation. In another embodiment, the dosage is 160 mcg/inoculation. In another embodiment, the dosage is 150 mcg/inoculation. In another embodiment, the dosage is 140 mcg/inoculation. In another embodiment, the dosage is 130 mcg/inoculation. In another embodiment, the dosage is 120 mcg/inoculation. In another embodiment, the dosage is 110 mcg/inoculation. In another embodiment, the dosage is 100 mcg/inoculation. In another embodiment, the dosage is 90 mcg/inoculation. In another embodiment, the dosage is 80 mcg/inoculation. In another embodiment, the dosage is 70 mcg/inoculation. In another embodiment, the dosage is 60 mcg/inoculation. In another embodiment, the dosage is 50 mcg/inoculation. In another embodiment, the dosage is 40 mcg/inoculation.

In another embodiment, the dosage is 0.1 mcg/kg body mass (per inoculation). In another embodiment, the dosage is 0.2 mcg/kg. In another embodiment, the dosage is 0.15 mcg/kg. In another embodiment, the dosage is 0.13 mcg/kg. In another embodiment, the dosage is 0.12 mcg/kg. In another embodiment, the dosage is 0.11 mcg/kg. In another embodiment, the dosage is 0.09 mcg/kg. In another embodiment, the dosage is 0.08 mcg/kg. In another embodiment, the dosage is 0.07 mcg/kg. In another embodiment, the dosage is 0.06 mcg/kg. In another embodiment, the dosage is 0.05 mcg/kg. In another embodiment, the dosage is 0.04 mcg/kg. In another embodiment, the dosage is 0.03 mcg/kg. In another embodiment, the dosage is 0.02 mcg/kg. In another embodiment, the dosage is less than 0.02 mcg/kg.

In another embodiment, the dosage is 0.5-2 mcg/inoculation. In another embodiment, the dosage is 0.5-10 mcg/inoculation. In another embodiment, the dosage is 2.5-7.5 mcg/inoculation. In another embodiment, the dosage is 1-2 mcg/inoculation. In another embodiment, the dosage is 2-3 mcg/inoculation. In another embodiment, the dosage is 2-4 mcg/inoculation. In another embodiment, the dosage is 3-6 mcg/inoculation. In another embodiment, the dosage is 4-8 mcg/inoculation. In another embodiment, the dosage is 5-10 mcg/inoculation. In another embodiment, the dosage is 5-15 mcg/inoculation. In another embodiment, the dosage is 10-20 mcg/inoculation. In another embodiment, the dosage is 20-30 mcg/inoculation. In another embodiment, the dosage is 30-40 mcg/protein/inoculation. In another embodiment, the dosage is 40-60 mcg/inoculation. In another embodiment, the dosage is 20-100 mcg/inoculation. In another embodiment, the dosage is 30-100 mcg/inoculation. In another embodiment, the dosage is 50-100 mcg/inoculation. In another embodiment, the dosage is 80-100 mcg/inoculation. In another embodiment, the dosage is 20-200 mcg/inoculation. In another embodiment, the dosage is 30-200 mcg/inoculation. In another embodiment, the dosage is 50-200 mcg/inoculation. In another embodiment, the dosage is 80-200 mcg/inoculation. In another embodiment, the dosage is 100-200 mcg/inoculation. In another embodiment, the dosage is 20-300 mcg/inoculation. In another embodiment, the dosage is 30-300 mcg/inoculation. In another embodiment, the dosage is 50-300 mcg/inoculation. In another embodiment, the dosage is 80-300 mcg/inoculation. In another embodiment, the dosage is 100-300 mcg/inoculation. In another embodiment, the dosage is 200-300 mcg/inoculation. In another embodiment, the dosage is 20-500 mcg/inoculation. In another embodiment, the dosage is 30-500 mcg/inoculation. In another embodiment, the dosage is 50-500 mcg/inoculation. In another embodiment, the dosage is 80-500 mcg/inoculation. In another embodiment, the dosage is 100-500 mcg/inoculation. In another embodiment, the dosage is 200-500 mcg/inoculation. In another embodiment, the dosage is 300-500 mcg/inoculation.

Each dose of gE-1 represents a separate embodiment of the present invention.

In another embodiment, the dose of recombinant HSV gE-2 utilized in a vaccination or in a booster vaccination is 20 mcg per inoculation, e.g. for a human subject. In another embodiment, the dosage is 10 mcg/inoculation. In another embodiment, the dosage is 30 mcg/inoculation. In another embodiment, the dosage is 25 mcg/inoculation. In another embodiment, the dosage is 22 mcg/inoculation. In another embodiment, the dosage is 18 mcg/inoculation. In another embodiment, the dosage is 16 mcg/inoculation. In another embodiment, the dosage is 15 mcg/inoculation. In another embodiment, the dosage is 14 mcg/inoculation. In another embodiment, the dosage is 13 mcg/inoculation. In another embodiment, the dosage is 12 mcg/inoculation. In another embodiment, the dosage is 11 mcg/inoculation. In another embodiment, the dosage is 10 mcg/inoculation. In another embodiment, the dosage is 9 mcg/inoculation. In another embodiment, the dosage is 8 mcg/inoculation. In another embodiment, the dosage is 7 mcg/inoculation. In another embodiment, the dosage is 6 mcg/inoculation. In another embodiment, the dosage is 5 mcg/inoculation. In another embodiment, the dosage is 4 mcg/inoculation. In another embodiment, the dosage is 3 mcg/inoculation. In another embodiment, the dosage is 2 mcg/inoculation. In another embodiment, the dosage is 1.5 mcg/inoculation. In another embodiment, the dosage is 1 mcg/inoculation. In another embodiment, the dosage is less than 1 mcg/inoculation. In another embodiment, the dosage is 500 mcg/inoculation. In another embodiment, the dosage is 400 mcg/inoculation. In another embodiment, the dosage is 300 mcg/inoculation. In another embodiment, the dosage is 220 mcg/inoculation. In another embodiment, the dosage is 250 mcg/inoculation. In another embodiment, the dosage is 200 mcg/inoculation. In another embodiment, the dosage is 180 mcg/inoculation. In another embodiment, the dosage is 160 mcg/inoculation. In another embodiment, the dosage is 150 mcg/inoculation. In another embodiment, the dosage is 140 mcg/inoculation. In another embodiment, the dosage is 130 mcg/inoculation. In another embodiment, the dosage is 120 mcg/inoculation. In another embodiment, the dosage is 110 mcg/inoculation. In another embodiment, the dosage is 100 mcg/inoculation. In another embodiment, the dosage is 90 mcg/inoculation. In another embodiment, the dosage is 80 mcg/inoculation. In another embodiment, the dosage is 70 mcg/inoculation. In another embodiment, the dosage is 60 mcg/inoculation. In another embodiment, the dosage is 50 mcg/inoculation. In another embodiment, the dosage is 40 mcg/inoculation.

In another embodiment, the dosage is 0.1 mcg/kg body mass (per inoculation). In another embodiment, the dosage is 0.2 mcg/kg. In another embodiment, the dosage is 0.15 mcg/kg. In another embodiment, the dosage is 0.13 mcg/kg. In another embodiment, the dosage is 0.12 mcg/kg. In another embodiment, the dosage is 0.11 mcg/kg. In another embodiment, the dosage is 0.09 mcg/kg. In another embodiment, the dosage is 0.08 mcg/kg. In another embodiment, the dosage is 0.07 mcg/kg. In another embodiment, the dosage is 0.06 mcg/kg. In another embodiment, the dosage is 0.05 mcg/kg. In another embodiment, the dosage is 0.04 mcg/kg. In another embodiment, the dosage is 0.03 mcg/kg. In another embodiment, the dosage is 0.02 mcg/kg. In another embodiment, the dosage is less than 0.02 mcg/kg.

In another embodiment, the dosage is 1-2 mcg/inoculation. In another embodiment, the dosage is 2-3 mcg/inoculation. In another embodiment, the dosage is 2-4 mcg/inoculation. In another embodiment, the dosage is 3-6 mcg/inoculation. In another embodiment, the dosage is 4-8 mcg/inoculation. In another embodiment, the dosage is 5-10 mcg/inoculation. In another embodiment, the dosage is 5-15 mcg/inoculation. In another embodiment, the dosage is 10-20 mcg/inoculation. In another embodiment, the dosage is 20-30 mcg/inoculation. In another embodiment, the dosage is 30-40 mcg/protein/inoculation. In another embodiment, the dosage is 40-60 mcg/inoculation. In another embodiment, the dosage is 20-100 mcg/inoculation. In another embodiment, the dosage is 30-100 mcg/inoculation. In another embodiment, the dosage is 50-100 mcg/inoculation. In another embodiment, the dosage is 80-100 mcg/inoculation. In another embodiment, the dosage is 20-200 mcg/inoculation. In another embodiment, the dosage is 30-200 mcg/inoculation. In another embodiment, the dosage is 50-200 mcg/inoculation. In another embodiment, the dosage is 80-200 mcg/inoculation. In another embodiment, the dosage is 100-200 mcg/inoculation. In another embodiment, the dosage is 20-300 mcg/inoculation. In another embodiment, the dosage is 30-300 mcg/inoculation. In another embodiment, the dosage is 50-300 mcg/inoculation. In another embodiment, the dosage is 80-300 mcg/inoculation. In another embodiment, the dosage is 100-300 mcg/inoculation. In another embodiment, the dosage is 200-300 mcg/inoculation. In another embodiment, the dosage is 20-500 mcg/inoculation. In another embodiment, the dosage is 30-500 mcg/inoculation. In another embodiment, the dosage is 50-500 mcg/inoculation. In another embodiment, the dosage is 80-500 mcg/inoculation. In another embodiment, the dosage is 100-500 mcg/inoculation. In another embodiment, the dosage is 200-500 mcg/inoculation. In another embodiment, the dosage is 300-500 mcg/inoculation.

Each dose of gE-2 represents a separate embodiment of the present invention.

In another embodiment, the booster vaccination comprises an adjuvant. In another embodiment, the adjuvant comprises a CpG oligonucleotide. In another embodiment, the adjuvant comprises an aluminum salt. In another embodiment, the adjuvant comprises both a CpG oligonucleotide and an aluminum salt. In another embodiment, the adjuvant comprises any other adjuvant disclosed hereinabove. In another embodiment, the adjuvant comprises any combination of adjuvants disclosed hereinabove.

The dose of the CpG oligonucleotide in a vaccination or booster vaccination of the present invention is, in another embodiment, 10 mcg (microgram). In another embodiment, the dose is 15 mcg. In another embodiment, the dose is 20 mcg. In another embodiment, the dose is 30 mcg. In another embodiment, the dose is 50 mcg. In another embodiment, the dose is 70 mcg. In another embodiment, the dose is 100 mcg. In another embodiment, the dose is 150 mcg. In another embodiment, the dose is 200 mcg. In another embodiment, the dose is 300 mcg. In another embodiment, the dose is 500 mcg. In another embodiment, the dose is 700 mcg. In another embodiment, the dose is 1 mg. In another embodiment, the dose is 1.2 mg. In another embodiment, the dose is 1.5 mg. In another embodiment, the dose is 2 mg. In another embodiment, the dose is 3 mg. In another embodiment, the dose is 5 mg. In another embodiment, the dose is more than 5 mg.

In another embodiment, the dose of the CpG oligonucleotide is 10-100 mcg. In another embodiment, the dose is 20-100 mcg. In another embodiment, the dose is 30-100 mcg. In another embodiment, the dose is 50-100 mcg. In another embodiment, the dose is 100-200 mcg. In another embodiment, the dose is 150-300 mcg. In another embodiment, the dose is 200-400 mcg. In another embodiment, the dose is 300-600 mcg. In another embodiment, the dose is 500-1000 mcg. In another embodiment, the dose is 700-1500 mcg. In another embodiment, the dose is 1-2 mg. In another embodiment, the dose is 1.5-2 mg. In another embodiment, the dose is 2-3 mg. In another embodiment, the dose is 3-5 mg. In another embodiment, the dose is 5-8 mg.

The dose of the alum salt in the booster vaccination is, in another embodiment, 10 mcg. In another embodiment, the dose is 15 mcg. In another embodiment, the dose is 20 mcg. In another embodiment, the dose is 30 mcg. In another embodiment, the dose is 50 mcg. In another embodiment, the dose is 70 mcg. In another embodiment, the dose is 100 mcg. In another embodiment, the dose is 150 mcg. In another embodiment, the dose is 200 mcg. In another embodiment, the dose is 300 mcg. In another embodiment, the dose is 500 mcg. In another embodiment, the dose is 700 mcg. In another embodiment, the dose is 1 mg. In another embodiment, the dose is 1.2 mg. In another embodiment, the dose is 1.5 mg. In another embodiment, the dose is 2 mg. In another embodiment, the dose is 3 mg. In another embodiment, the dose is 5 mg. In another embodiment, the dose is more than 5 mg.

In another embodiment, the dose of the alum salt is 10-100 mcg. In another embodiment, the dose is 20-100 mcg. In another embodiment, the dose is 30-100 mcg. In another embodiment, the dose is 50-100 mcg. In another embodiment, the dose is 100-200 mcg. In another embodiment, the dose is 150-300 mcg. In another embodiment, the dose is 200-400 mcg. In another embodiment, the dose is 300-600 mcg. In another embodiment, the dose is 500-1000 mcg. In another embodiment, the dose is 700-1500 mcg. In another embodiment, the dose is 1-2 mg. In another embodiment, the dose is 1.5-2 mg. In another embodiment, the dose is 2-3 mg. In another embodiment, the dose is 3-5 mg. In another embodiment, the dose is 5-8 mg.

In another embodiment, the dose of the alum salt is 10 mcg per mcg recombinant protein. In another embodiment, the dose is 15 mcg per mcg recombinant protein. In another embodiment, the dose is 20 mcg per mcg recombinant protein. In another embodiment, the dose is 30 mcg per mcg recombinant protein. In another embodiment, the dose is 50 mcg per mcg recombinant protein. In another embodiment, the dose is 70 mcg per mcg recombinant protein. In another embodiment, the dose is 100 mcg per mcg recombinant protein. In another embodiment, the dose is 150 mcg per mcg recombinant protein. In another embodiment, the dose is 200 mcg per mcg recombinant protein. In another embodiment, the dose is 300 mcg per mcg recombinant protein. In another embodiment, the dose is 500 mcg per mcg recombinant protein. In another embodiment, the dose is 700 mcg per mcg recombinant protein. In another embodiment, the dose is 1 mg. In another embodiment, the dose is 1.2 mg. In another embodiment, the dose is 1.5 mg. In another embodiment, the dose is 2 mg. In another embodiment, the dose is 3 mg. In another embodiment, the dose is 5 mg. In another embodiment, the dose is more than 5 mg.

In another embodiment, the dose of the alum salt is 10-100 mcg per mcg recombinant protein. In another embodiment, the dose is 20-100 mcg per mcg recombinant protein. In another embodiment, the dose is 30-100 mcg per mcg recombinant protein. In another embodiment, the dose is 50-100 mcg per mcg recombinant protein. In another embodiment, the dose is 100-200 mcg per mcg recombinant protein. In another embodiment, the dose is 150-300 mcg per mcg recombinant protein. In another embodiment, the dose is 200-400 mcg per mcg recombinant protein. In another embodiment, the dose is 300-600 mcg per mcg recombinant protein. In another embodiment, the dose is 500-1000 mcg per mcg recombinant protein. In another embodiment, the dose is 700-1500 mcg per mcg recombinant protein. In another embodiment, the dose is 1-2 mg. In another embodiment, the dose is 1.5-2 mg. In another embodiment, the dose is 2-3 mg. In another embodiment, the dose is 3-5 mg. In another embodiment, the dose is 5-8 mg.

In another embodiment, a vaccine of the present invention elicits antibodies that inhibit binding of gD to a cellular receptor. In another embodiment, the receptor is herpesvirus entry mediator A (HveA/HVEM). In another embodiment, the receptor is nectin-1 (HveC). In another embodiment, the receptor is nectin-2 (HveB). In another embodiment, the receptor is a modified form of heparan sulfate. In another embodiment, the receptor is a heparan sulfate proteoglycan. In another embodiment, the receptor is any other gD receptor known in the art.

Figure 17:
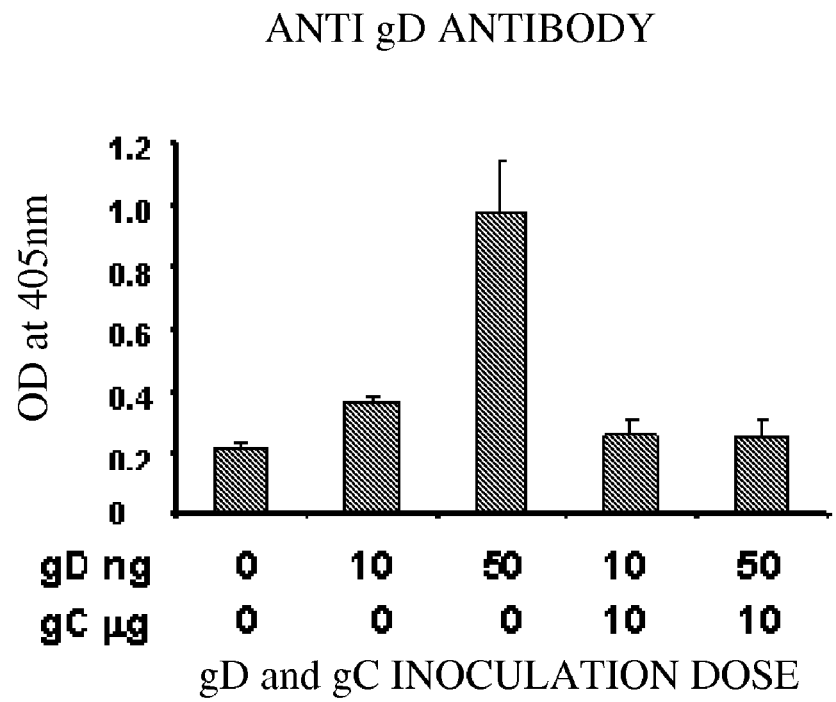
FIG. 17: Anti-gD antibody responses to gD/gC vaccination. Mice were immunized three times with gD alone (first three bars) or gC and gD given together in the same syringe (last 2 bars). Results demonstrate that administering gC and gD simultaneously blunts the antibody response to gD 50 ng.

In another embodiment, inclusion in the vaccine of a gC protein, a gE protein, and/or an adjuvant of the present invention increases the efficaciousness of anti-gD antibodies elicited by the vaccine. In another embodiment, inclusion of a gC protein, a gE protein, and/or an adjuvant of the present invention increases the dose of recombinant gD required to elicit antibodies that inhibit binding of gD to a cellular receptor (FIG. 17). In another embodiment, a gC protein, a gE protein, and/or an adjuvant of the present invention decreases the dose of recombinant gD required to elicit antibodies that inhibit binding of gD to a cellular receptor when a dose of gD is administered separately from the gC protein (FIG. 18A) or gE protein.

In another embodiment, inclusion in the vaccine of a gC protein, a gE protein, and/or an adjuvant of the present invention enhances the effectiveness of an innate immune response. In another embodiment, the innate immune response is an antibody-mediated immune response. In another embodiment, the innate immune response is a non-antibody-mediated immune response. In another embodiment, the innate immune response is an NK (natural killer) cell response. In another embodiment, the innate immune response is any other innate immune response known in the art.

In one embodiment, inclusion in the vaccine of a gC-1 protein, and/or an adjuvant protects from disease and death, while in another embodiment, inclusion in the vaccine of a gC-2 protein, protects from disease and death (for e.g., FIGS. 20-24). In one embodiment, the greatest reduction in inoculation and zosteriform site disease scores reduced is achieved using a dose of 5 mcg. In another embodiment, the reduction in inoculation and zosteriform site disease scores is achieved using a dose of 2 mcg. In one embodiment, the reduction in inoculation and zosteriform site disease scores is achieved using a dose of 1 mcg. In another embodiment, the reduction in inoculation and zosteriform site disease scores is achieved using a dose of 0.5 mcg. In one embodiment, the dose of gC-2 useful in a vaccine for humans is estimated based on mouse experimental data as is known in the art.

In one embodiment, inclusion in the vaccine of a gD-1 protein, and/or an adjuvant protects from disease and death, while in another embodiment, inclusion in the vaccine of a gD-2 protein, protects from disease and death (for e.g., FIGS. 25-29). In one embodiment, the greatest reduction in inoculation and zosteriform site disease scores reduced is achieved using a dose of 250 ng. In one embodiment, the reduction in inoculation and zosteriform site disease scores is achieved using a dose of 100 ng. In another embodiment, the reduction in inoculation and zosteriform site disease scores is achieved using a dose of 50 ng. In another embodiment, the reduction in inoculation and zosteriform site disease scores is achieved using a dose of 25 ng. In another embodiment, the reduction in inoculation and zosteriform site disease scores is achieved using a dose of 10 ng. In one embodiment, the dose of gD-2 useful in a vaccine for humans is estimated based on mouse experimental data as is known in the art.

In another embodiment, a vaccine of the present invention further comprises another HSV glycoprotein involved in cell binding and/or cellular entry. In another embodiment, the glycoprotein is gH. In another embodiment, the glycoprotein is gL. In another embodiment, the glycoprotein is gB.

In another embodiment, a vaccine of the present invention further comprises an additional HSV glycoprotein. In another embodiment, the glycoprotein is gM. In another embodiment, the glycoprotein is gN. In another embodiment, the glycoprotein is gK. In another embodiment, the glycoprotein is gG. In another embodiment, the glycoprotein is gI. In another embodiment, the glycoprotein is gJ.

In one embodiment, vaccines and compositions of the present invention comprise a single recombinant HSV glycoprotein, which in one embodiment is gC, gE, or gD and, optionally, an adjuvant. In one embodiment, the HSV glycoprotein is an HSV-1 glycoprotein, while in another embodiment, the HSV glycoprotein is an HSV-2 glycoprotein. In another embodiment, the present invention provides a recombinant vaccine vector encoding a recombinant HSV glycoprotein.

Figure 18A:
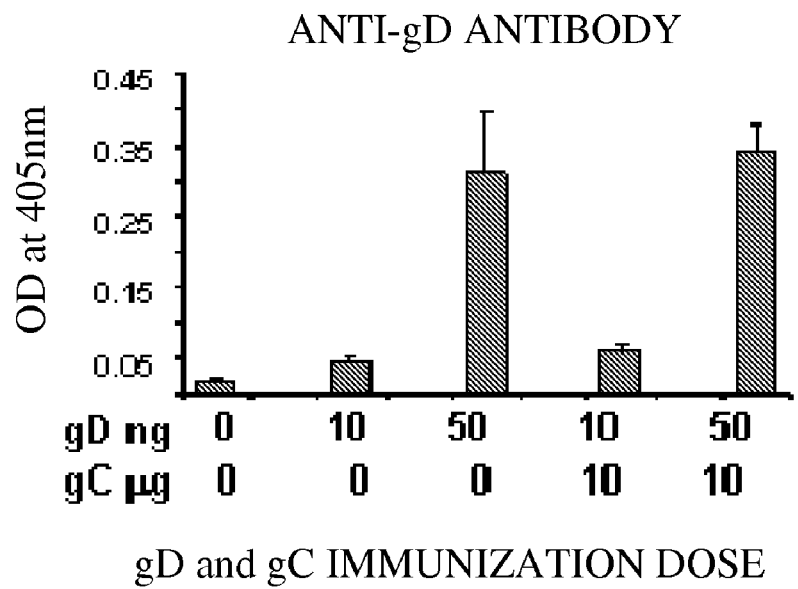
FIG. 18: (A) Mice were immunized as in FIG. 17, and mice that had received 50 ng gD and 10 μg gC were boosted with 50 ng gD. Antibody response to gD improved (last bar). (B) Ability of antisera to inhibit rosette formation by C3b coated erythrocytes.

In another embodiment, inclusion in the vaccine of a gC protein, a gE protein, and/or an adjuvant of the present invention increases the efficaciousness of antibodies elicited by the vaccine against one of the above glycoproteins. In another embodiment, a gC protein, a gE protein, and/or an adjuvant of the present invention decreases the dose of one of the above glycoproteins required to elicit antibodies that inhibit binding of the glycoprotein to a cellular receptor thereof (FIG. 17), when a dose of one of the glycoproteins is administered separately from one of the other glycoproteins (FIG. 18A).

In another embodiment, a vaccine of the present invention is a recombinant nucleotide vaccine. In another embodiment, the vaccine is a recombinant DNA vaccine. In another embodiment, the DNA vaccine encodes an HSV gC protein and an HSV gD protein. In another embodiment, the DNA vaccine encodes an HSV gE protein and an HSV gD protein. In another embodiment, the DNA vaccine encodes an HSV gE protein, an HSV gC protein, and an HSV gD protein. In another embodiment, the recombinant proteins are HSV-2 proteins. In another embodiment, the recombinant proteins are HSV-1 proteins. In another embodiment, the proteins comprise both HSV-1 and HSV-2 proteins.

In another embodiment, a vaccine of the present invention comprises dendritic cells (DCs) loaded with HSV antigens of the present invention. In another embodiment, the DCs have been exposed to HSV antigens of the present invention. In another embodiment, the DCs are loaded with a nucleotide encoding HSV antigens of the present invention. In another embodiment, the DCs have been activated.

In another embodiment, the present invention provides an immunogenic composition comprising a combination of recombinant HSV proteins of the present invention. In another embodiment, the present invention provides an immunogenic composition comprising a nucleotide molecule encoding recombinant HSV proteins of the present invention. In another embodiment, the immunogenic composition further comprises an adjuvant.

In another embodiment, the present invention provides a recombinant vaccine vector encoding recombinant HSV proteins of the present invention. In another embodiment, the present invention provides a recombinant vaccine vector comprising recombinant HSV proteins of the present invention.

In another embodiment, the present invention provides a recombinant vaccine vector comprising a nucleotide molecule of the present invention. In another embodiment, the expression vector is a plasmid. In another embodiment, the present invention provides a method for the introduction of a nucleotide molecule of the present invention into a cell. Methods for constructing and utilizing recombinant vectors are well known in the art and are described, for example, in Sambrook et al. (2001, Molecular Cloning: A Laboratory Manual, Cold Spring Harbor Laboratory, New York), and in Brent et al. (2003, Current Protocols in Molecular Biology, John Wiley & Sons, New York). In another embodiment, the vector is a bacterial vector. In other embodiments, the vector is selected from *Salmonella* sp., *Shigella* sp., BCG, *L. monocytogenes* and *S. gordonii*. In another embodiment, the recombinant HSV proteins are delivered by recombinant bacterial vectors modified to escape phagolysosomal fusion and live in the cytoplasm of the cell. In another embodiment, the vector is a viral vector. In other embodiments, the vector is selected from Vaccinia, Avipox, Adenovirus, AAV, Vaccinia virus NYVAC, Modified vaccinia strain Ankara (MVA), Semliki Forest virus, Venezuelan equine encephalitis virus, herpes viruses, and retroviruses. In another embodiment, the vector is a naked DNA vector. In another embodiment, the vector is any other vector known in the art.

In another embodiment, a nucleotide of the present invention is operably linked to a promoter/regulatory sequence that drive expression of the encoded peptide in cells into which the vector is introduced. Promoter/regulatory sequences useful for driving constitutive expression of a gene are well known in the art and include, but are not limited to, for example, the cytomegalovirus immediate early promoter enhancer sequence, the SV40 early promoter, and the Rous sarcoma virus promoter. In another embodiment, inducible and tissue specific expression of the nucleic acid encoding a peptide of the present invention is accomplished by placing the nucleic acid encoding the peptide under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In another embodiment, a promoter that is induced in response to inducing agents such as metals, glucocorticoids, and the like, is utilized. Thus, it will be appreciated that the invention includes the use of any promoter/regulatory sequence, which is either known or unknown, and which is capable of driving expression of the desired protein operably linked thereto.

In another embodiment, the present invention provides a cell comprising a vector of the present invention. Methods for producing cells comprising vectors and/or exogenous nucleic acids are well-known in the art. See, for example, Sambrook et al. (1989, Molecular Cloning: A Laboratory Manual, Cold Spring Harbor Laboratory, New York), and in Ausubel et al (1997, Current Protocols in Molecular Biology, John Wiley & Sons, New York).

In other embodiments, the vaccines of any of the methods described above have any of the characteristics of a vaccine of compositions of the present invention. Each characteristic represents a separate embodiment of the present invention.

In another embodiment, the present invention provides a method of inhibiting a primary HSV infection in a subject, the method comprising the step of administering to the subject a vaccine of the present invention. In another embodiment, the present invention provides a method of treating an HSV infection in a subject, the method comprising the step of administering to said subject a vaccine of the present invention. In another embodiment, the present invention provides a method of reducing an incidence of an HSV infection in a subject, the method comprising the step of administering to said subject a vaccine of the present invention. In another embodiment, the present invention provides a method of inhibiting a flare following a primary HSV infection in a subject, the method comprising the step of administering to said subject a vaccine of the present invention.

In one embodiment, a "flare" or "recurrence" refers to reinfection of skin tissue following latent neuronal HSV infection. In another embodiment, the terms refer to reactivation of HSV after a latency period. In another embodiment, the terms refer to symptomatic HSV lesions following a non-symptomatic latency period.

In another embodiment, the present invention provides a method of inhibiting spread of HSV. In one embodiment, the spread from DRG to skin is inhibited. In one embodiment, cell-to-cell spread of HSV is inhibited. In one embodiment, anterograde spread is inhibited. In one embodiment, retrograde spread is inhibited. "DRG" refers, in one embodiment, to a neuronal cell body and in another embodiment, contain the neuron cell bodies of nerve fibers. In another embodiment, the term refers to any other definition of "DRG" used in the art. In another embodiment, spread of HSV to neural tissue is inhibited.

In another embodiment, the present invention provides a method of inhibiting a recurrence following a primary HSV infection in a subject, the method comprising the step of administering to said subject a vaccine of the present invention. In another embodiment, the present invention provides a method of preventing a recurrence following a primary HSV infection in a subject, the method comprising the step of administering to said subject a vaccine of the present invention.

In another embodiment, the present invention provides a method of inhibiting an HSV labialis following a primary HSV infection in a subject, the method comprising the step of administering to said subject a vaccine of the present invention.

In another embodiment, the present invention provides a method of preventing a recurrence of an HSV infection, the method comprising the step of administering to said subject a vaccine of the present invention. In another embodiment, the present invention provides a method of diminishing the severity of a recurrence of an HSV infection, the method comprising the step of administering to said subject a vaccine of the present invention. In another embodiment, the present invention provides a method of reducing the frequency of a recurrence of an HSV infection, the method comprising the step of administering to said subject a vaccine of the present invention. In one embodiment, the present invention provides any of the described methods in an HIV-infected subject.

In another embodiment, the present invention provides a method of treating an HSV encephalitis in a subject, the method comprising the step of administering to said subject a vaccine of the present invention. In another embodiment, the present invention provides a method of reducing an incidence of an HSV encephalitis in a subject, the method comprising the step of administering to said subject a vaccine of the present invention. "HSV encephalitis" refers, in one embodiment, to an encephalitis caused by a Herpes Simplex Virus-1 (HSV). In another embodiment, the term refers to an encephalitis associated with HSV. In another embodiment, the term refers to any other type of HSV-mediated encephalitis known in the art.

In another embodiment, the present invention provides a method of treating or reducing an HSV neonatal infection in a subject, the method comprising the step of administering to said subject a vaccine of the present invention.

It is to be understood that reference to HSV herein refers in one embodiment, to HSV-1, while in another embodiment, to HSV-2, while in another embodiment, to HSV-1 and HSV-2.

"HSV-1" refers, in another embodiment, to a Herpes Simplex Virus-1. In another embodiment, the term refers to a KOS strain. In another embodiment, the term refers to an F strain. In another embodiment, the term refers to an NS strain. In another embodiment, the term refers to a CL101 strain. In another embodiment, the term refers to a "17" strain. In another embodiment, the term refers to a "17+syn" strain. In another embodiment, the term refers to a MacIntyre strain. In another embodiment, the term refers to an MP strain. In another embodiment, the term refers to an HF strain. In another embodiment, the term refers to any other HSV-1 strain known in the art.

"HSV-2" refers, in another embodiment, to a Herpes Simplex Virus-2. In another embodiment, the term refers to an HSV-2 333 strain. In another embodiment, the term refers to a 2.12 strain. In another embodiment, the term refers to an HG52 strain. In another embodiment, the term refers to an MS strain. In another embodiment, the term refers to a G strain. In another embodiment, the term refers to an 186 strain. In another embodiment, the term refers to any other HSV-2 strain known in the art.

In another embodiment, the present invention provides a method of vaccinating a subject against an HSV infection, the method comprising the step of administering to said subject a vaccine of the present invention. In another embodiment, the present invention provides a method of suppressing an HSV infection in a subject, the method comprising the step of administering to said subject a vaccine of the present invention. In another embodiment, the present invention provides a method of impeding an HSV infection in a subject, the method comprising the step of administering to said subject a vaccine of the present invention. In another embodiment, the present invention provides a method of impeding a primary HSV infection in a subject, the method comprising the step of administering to said subject a vaccine of the present invention. In another embodiment, the present invention provides a method of impeding neuronal HSV spread in a subject, the method comprising the step of administering to said subject a vaccine of the present invention.

The terms "impeding a HSV infection" and "impeding a primary HSV infection" refer, in another embodiment, to decreasing the titer of infectious virus by 90%. In another embodiment, the titer is decreased by 50%. In another embodiment, the titer is decreased by 55%. In another embodiment, the titer is decreased by 60%. In another embodiment, the titer is decreased by 65%. In another embodiment, the titer is decreased by 70%. In another embodiment, the titer is decreased by 75%. In another embodiment, the titer is decreased by 80%. In another embodiment, the titer is decreased by 85%. In another embodiment, the titer is decreased by 92%. In another embodiment, the titer is decreased by 95%. In another embodiment, the titer is decreased by 96%. In another embodiment, the titer is decreased by 97%. In another embodiment, the titer is decreased by 98%. In another embodiment, the titer is decreased by 99%. In another embodiment, the titer is decreased by over 99%.

In another embodiment, the terms refer to decreasing the extent of viral replication by 90%. In another embodiment, replication is reduced by 50%. In another embodiment, replication is reduced by 55%. In another embodiment, replication is reduced by 60%. In another embodiment, replication is reduced by 65%. In another embodiment, replication is reduced by 70%. In another embodiment, replication is reduced by 75%. In another embodiment, replication is reduced by 80%. In another embodiment, replication is reduced by 85%. In another embodiment, replication is reduced by 92%. In another embodiment, replication is reduced by 95%. In another embodiment, replication is reduced by 96%. In another embodiment, replication is reduced by 97%. In another embodiment, replication is reduced by 98%. In another embodiment, replication is reduced by 99%. In another embodiment, replication is reduced by over 99%.

Methods of determining the extent of HSV replication and HSV infection are well known in the art, and are described, for example, in Lambiase A et al. (Topical treatment with nerve growth factor in an animal model of herpetic keratitis. Graefes Arch Clin Exp Opthalmol. 2007 May 4), Ramaswamy M et al. (Interactions and management issues in HSV and HIV coinfection. Expert Rev Anti Infect Ther. 2007 April; 5(2):231-43), and Jiang C et al. (Mutations that decrease DNA binding of the processivity factor of the herpes simplex virus DNA polymerase reduce viral yield, alter the kinetics of viral DNA replication, and decrease the fidelity of DNA replication. J Virol. 2007 April; 81(7):3495-502). Each method represents a separate embodiment of the present invention.

In another embodiment, the present invention provides a method of reducing an incidence of an HSV-mediated herpetic ocular disease in a subject, the method comprising the step of administering to said subject a vaccine of the present invention. In another embodiment, the present invention provides a method of treating an HSV-1 corneal infection or herpes keratitis in a subject, the method comprising the step of administering to said subject a vaccine of the present invention. In another embodiment, the present invention provides a method of reducing an incidence of an HSV-1 corneal infection or herpes keratitis in a subject, the method comprising the step of administering to said subject a vaccine of the present invention.

Methods for determining the presence and extent of herpetic ocular disease, corneal infection, herpes keratitis are well known in the art, and are described, for example, in Labetoulle M et al. (Neuronal propagation of HSV1 from the oral mucosa to the eye. Invest Opthalmol V is Sci. 2000 August; 41(9):2600-6) and Majumdar S et al. (Dipeptide monoester ganciclovir prodrugs for treating HSV-1-induced corneal epithelial and stromal keratitis: in vitro and in vivo evaluations. J Ocul Pharmacol Ther. 2005 December; 21(6): 463-74). Each method represents a separate embodiment of the present invention.

In another embodiment, the present invention provides a method of treating, suppressing or inhibiting an HSV genital infection, the method comprising the step of administering to said subject a vaccine of the present invention. In another embodiment, the present invention provides a method of treating, suppressing or inhibiting any manifestation of recurrent HSV infection, the method comprising the step of administering to said subject a vaccine of the present invention.

In another embodiment, the present invention provides a method of reducing an incidence of an HSV-mediated genital ulcer disease in a subject, the method comprising the step of administering to said subject a vaccine of the present invention. In another embodiment, the present invention provides a method of impeding an establishment of a latent HSV infection in a subject, the method comprising the step of administering to said subject a vaccine of the present invention.

In one embodiment, the present invention provides a method of treating, suppressing or inhibiting a genital herpes infection in a subject, comprising the step of administering to said subject a vaccine of the present invention. In another embodiment, the present invention provides a method of treating, suppressing or inhibiting an oral herpes infection in a subject, comprising the step of administering to said subject a vaccine of the present invention.

In one embodiment, the present invention provides a method of treating, suppressing or inhibiting an HSV-2 infection in a subject comprising the step of administering to said subject a vaccine of the present invention, which in one embodiment, comprises a gC-1 fragment comprising a C3b binding domain, a properdin interfering domain thereof, a C5 interfering domain thereof, or an antigenic portion of said C3b-binding domain, properdin interfering domain, or C5-interfering domain. In one embodiment, FIG. 31 demonstrates the efficacy of anti-gC-1 antibodies in treating HSV-2 infection.

In another embodiment, the present invention provides a method of treating, suppressing or inhibiting an HSV-2 infection in a subject comprising the step of administering to said subject a vaccine of the present invention, which in one embodiment, comprises a gC-2 fragment comprising a C3b binding domain, a properdin interfering domain thereof, a C5 interfering domain thereof, or an antigenic portion of said C3b-binding domain, properdin interfering domain, or C5-interfering domain. In one embodiment, FIG. 31 demonstrates the efficacy of anti-gC-2 antibodies in treating HSV-2 infection.

In another embodiment, the present invention provides a method of reducing an incidence of an HSV-mediated encephalitis in a subject, the method comprising the step of administering to said subject a vaccine of the present invention.

In another embodiment, the herpes-mediated encephalitis treated or prevented by a method of the present invention is a focal herpes encephalitis. In another embodiment, the herpes-mediated encephalitis is a neonatal herpes encephalitis. In another embodiment, the herpes-mediated encephalitis is any other type of herpes-mediated encephalitis known in the art.

In another embodiment, the present invention provides a method of treating or reducing an incidence of a disease, disorder, or symptom associated with or secondary to a HSV-mediated encephalitis in a subject, the method comprising the step of administering to said subject a vaccine of the present invention.

In another embodiment, the present invention provides a method of treating, reducing the pathogenesis of, ameliorating the symptoms of, ameliorating the secondary symptoms of, reducing the incidence of, prolonging the latency to a relapse of a Herpes Simplex Virus (HSV) infection in a subject, comprising the step of administering to the subject a vaccine of the present invention.

According to any of the methods of the present invention and in one embodiment, the subject is human. In another embodiment, the subject is murine, which in one embodiment, is a mouse, and, in another embodiment, is a rat. In another embodiment, the subject is canine, feline, bovine, ovine, or porcine. In another embodiment, the subject is mammalian. In another embodiment, the subject is any organism susceptible to infection by HSV.

In another embodiment, the present invention provides a method of protecting a subject against formation of a zosteriform lesion or an analogous outbreak in a human subject. In another embodiment, the present invention provides a method of inhibiting the formation of an HSV zosteriform lesion or an analogous outbreak in a human subject.

"Zosteriform" refers, in one embodiment, to skin lesions characteristic of an HSV infection, particularly during reactivation infection, which, in one embodiment, begin as a rash and follow a distribution near dermatomes, commonly occurring in a strip or belt-like pattern. In one embodiment, the rash evolves into vesicles or small blisters filled with serous fluid. In one embodiment, zosteriform lesions form in mice as a result of contact with HSV. In another embodiment, zosteriform lesions form in humans as a result of contact with HSV. "Zosteriform spread" refers, in one embodiment, to an HSV infection that spreads from the ganglia to secondary skin sites within the dermatome. In another embodiment, the term refers to spread within the same dermatome as the initial site of infection. In another embodiment, the term refers to any other definition of "zosteriform spread" known in the art. "Outbreak", in another embodiment, refers to a sudden increase in symptoms of a disease or in the spread or prevalence of a disease, and in one embodiment, refers to a sudden increase in zosteriform lesions, while in another embodiment, "outbreak" refers to a sudden eruption of zosteriform lesions.

In one embodiment, the present invention provides a method of impeding the formation of a dermatome lesion or an analogous condition in a subject. In one embodiment, dermatome lesions form as a result of contact with HSV. In another embodiment, dermatome lesions most often develop when the virus reactivates from latency in the ganglia and in one embodiment, spreads down nerves, in one embodiment, causing a recurrent infection.

It is to be understood that the methods of the present invention may be used to treat, inhibit, suppress, etc an HSV infection or primary or secondary symptoms related to such an infection following exposure of the subject to HSV. In another embodiment, the subject has been infected with HSV before vaccination. In another embodiment, the subject is at risk for HSV infection. In another embodiment, whether or not the subject has been infected with HSV at the time of vaccination, vaccination by a method of the present invention is efficacious in treating, inhibiting, suppressing, etc an HSV infection or primary or secondary symptoms related to such an infection.

In one embodiment, "treating" refers to either therapeutic treatment or prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of the subject viral infection, while in one embodiment, "secondary" refers to a symptom that is derived from or consequent to a primary cause. In one embodiment, the compositions and strains for use in the present invention treat primary or secondary symptoms or secondary complications related to HSV infection.

In another embodiment, "symptoms" may be any manifestation of a HSV infection, comprising blisters, ulcerations, or lesions on the urethra, cervix, upper thigh, and/or anus in women and on the penis, urethra, scrotum, upper thigh, and anus in men, inflammation, swelling, fever, flu-like symptoms, sore mouth, sore throat, pharyngitis, pain, blisters on tongue, mouth or lips, ulcers, cold sores, neck pain, enlarged lymph nodes, reddening, bleeding, itching, dysuria, headache, muscle pain, etc., or a combination thereof.

In another embodiment, the disease, disorder, or symptom is fever. In another embodiment, the disease, disorder, or symptom is headache. In another embodiment, the disease, disorder, or symptom is stiff neck. In another embodiment, the disease, disorder, or symptom is seizures. In another embodiment, the disease, disorder, or symptom is partial paralysis. In another embodiment, the disease, disorder, or symptom is stupor. In another embodiment, the disease, disorder, or symptom is coma. In another embodiment, the disease, disorder, or symptom is any other disease, disorder, or symptom known in the art that is associated with or secondary to a herpes-mediated encephalitis.

Methods of determining the presence and severity of herpes-mediated encephalitis are well known in the art, and are described, for example, in Bonkowsky J L et al. (Herpes simplex virus central nervous system relapse during treatment of infantile spasms with corticotropin. Pediatrics. 2006 May; 117(5):e1045-8) and Khan O A, et al. (Herpes encephalitis presenting as mild aphasia: case report. BMC Fam Pract. 2006 Mar. 24; 7:22). Each method represents a separate embodiment of the present invention.

In another embodiment, the present invention provides a method of treating or reducing an incidence of a disease, disorder, or symptom associated with an HSV infection in a subject, the method comprising the step of administering to said subject a vaccine of the present invention.

In another embodiment, the disease, disorder, or symptom secondary to an HSV infection is oral lesions. In another embodiment, the disease, disorder, or symptom is genital lesions. In another embodiment, the disease, disorder, or symptom is oral ulcers. In another embodiment, the disease, disorder, or symptom is genital ulcers. In another embodiment, the disease, disorder, or symptom is fever. In another embodiment, the disease, disorder, or symptom is headache. In another embodiment, the disease, disorder, or symptom is muscle ache. In another embodiment, the disease, disorder, or symptom is swollen glands in the groin area. In another embodiment, the disease, disorder, or symptom is painful urination. In another embodiment, the disease, disorder, or symptom is vaginal discharge. In another embodiment, the disease, disorder, or symptom is blistering. In another embodiment, the disease, disorder, or symptom is flu-like malaise. In another embodiment, the disease, disorder, or symptom is keratitis. In another embodiment, the disease, disorder, or symptom is herpetic whitlow. In another embodiment, the disease, disorder, or symptom is Bell's palsy. In another embodiment, the disease, disorder, or symptom is herpetic erythema multiforme. In another embodiment, the disease, disorder, or symptom is a lower back symptom (e.g. numbness, tingling of the buttocks or the area around the anus, urinary retention, constipation, and impotence). In another embodiment, the disease, disorder, or symptom is a localized eczema herpeticum. In another embodiment, the disease, disorder, or symptom is a disseminated eczema herpeticum. In another embodiment, the disease, disorder, or symptom is a herpes gladiatorum. In another embodiment, the disease, disorder, or symptom is a herpetic sycosis. In another embodiment, the disease, disorder, or symptom is an esophageal symptom (e.g. difficulty swallowing or burning, squeezing throat pain while swallowing, weight loss, pain in or behind the upper chest while swallowing). In another embodiment, the disease, disorder, or symptom is any other disease, disorder, or symptom that is known in the art. Each disease, disorder, and symptom represents a separate embodiment of the present invention.

Thus, in one embodiment, the compositions and methods of the instant invention treat, suppress, inhibit, or reduce the incidence of the infection itself, while in another embodiment, the compositions and methods of the instant invention treat, suppress, inhibit, or reduce the incidence of primary symptoms of the infection, while in another embodiment, the compositions and methods of the instant invention treat, suppress, inhibit, or reduce the incidence of secondary symptoms of the infection. It is to be understood that the compositions and methods of the instant invention may affect any combination of the infection, the primary symptoms caused by the infection, and secondary symptoms related to the infection.

The HSV infection that is treated or ameliorated by methods and compositions of the present invention is, in another embodiment, a genital HSV infection. In another embodiment, the HSV infection is an oral HSV infection. In another embodiment, the HSV infection is an ocular HSV infection. In another embodiment, the HSV infection is a dermatologic HSV infection.

In another embodiment, the present invention provides a method of reducing an incidence of a disseminated HSV infection in a subject, the method comprising the step of administering to said subject a vaccine of the present invention.

In another embodiment, the present invention provides a method of reducing an incidence of a neonatal HSV infection in an offspring of a subject, the method comprising the step of administering to said subject a vaccine of the present invention.

In another embodiment, the present invention provides a method of reducing a transmission of an HSV infection from a subject to an offspring thereof, the method comprising the step of administering to said subject a vaccine of the present invention.

In another embodiment, the offspring is an infant. In another embodiment, the transmission that is reduced or inhibited is transmission during birth. In another embodiment, transmission during breastfeeding is reduced or inhibited. In another embodiment, the transmission that is reduced or inhibited is any other type of parent-to-offspring transmission known in the art.

In another embodiment, the present invention provides a method of reducing a severity of a neonatal HSV infection in an offspring of a subject, the method comprising the step of administering to said subject a vaccine of the present invention.

In one embodiment, the present invention provides a method of treating, suppressing, inhibiting, or reducing an incidence of an HSV infection in a subject infected with HIV, the method comprising the step of administering to said subject a vaccine comprising: (a) a recombinant HSV gC protein or fragment thereof; (b) a recombinant HSV gE protein or fragment thereof; and (c) an adjuvant. In another embodiment, the present invention provides a method of treating, suppressing, inhibiting, or reducing an incidence of an HSV infection in a subject infected with HIV, the method comprising the step of administering to said subject a vaccine comprising: (a) a recombinant HSV gC protein or fragment thereof, wherein said fragment comprises either a C3b-binding domain thereof, a properdin interfering domain thereof, a C5 interfering domain thereof, or a fragment of said C3b-binding domain, properdin interfering domain, or C5-interfering domain; (b) a recombinant HSV gE protein or fragment thereof, wherein said fragment comprises AA 24-409 or a fragment thereof; and (c) an adjuvant.

In another embodiment, the present invention provides a method of treating an HSV infection in a subject infected with HIV, the method comprising the step of administering to said subject a vaccine of the present invention. In another embodiment, the present invention provides a method of suppressing an HSV infection in a subject infected with HIV, the method comprising the step of administering to said subject a vaccine of the present invention. In another embodiment, the present invention provides a method of inhibiting an HSV infection in a subject infected with HIV, the method comprising the step of administering to said subject a vaccine of the present invention. In another embodiment, the present invention provides a method of reducing an incidence of an HSV infection in a subject infected with HIV, the method comprising the step of administering to said subject a vaccine of the present invention. In another embodiment, the present invention provides a method of preventing an HIV infection, the method comprising the step of administering to said subject an HSV vaccine of the present invention. In one embodiment, HSV infection increases the risk of HIV infection, and protection against HSV infection decreases the risk of HIV infection. Thus, in one embodiment, present invention provides a method of decreasing the risk of an HIV infection, the method comprising the step of administering to said subject a vaccine of the present invention.

In one embodiment, the vaccine for use in the methods of the present invention elicits an immune response against HSV. In another embodiment, the vaccine for use in the methods of the present invention elicits an immune response against HSV-1. In another embodiment, the vaccine for use in the methods of the present invention elicits an immune response against HSV-2. In another embodiment, the vaccine comprises recombinant gD and gC proteins. In another embodiment, the vaccine comprises recombinant gE and gD proteins. In another embodiment, the vaccine comprises recombinant gC and gE proteins. In another embodiment, the vaccine comprises recombinant gE, gD, and gC proteins. In another embodiment, the vaccine comprises recombinant gE, gD, or gC protein. In another embodiment, the recombinant proteins are HSV-1 proteins. In another embodiment, the recombinant proteins are HSV-2 proteins. In another embodiment, the proteins comprise both HSV-1 and HSV-2 proteins.

It is to be understood that, in one embodiment, a subject according to any of the embodiments described herein may be a subject infected with, or in another embodiment, susceptible to infection with HSV. In one embodiment, a subject may be infected with, or in another embodiment, susceptible to infection with at least one other pathogen. In one embodiment, a subject may be immunocompromised. In one embodiment, the subject is infected by HSV, while in another embodiment, the subject is at risk for infection by HSV, which in one embodiment, is a subject who is a neonate, in another embodiment, immunocompromised, in another embodiment, elderly, and in another embodiment, an immunocompromised neonate or an immunocompromised elderly subject.

In another embodiment, the compositions or vaccines of the present invention and their related uses may suppress, inhibit, prevent or treat an HIV infection in a subject. In one embodiment, the compositions or vaccines of the present invention and their related uses may treat secondary complications of HIV infection, which in one embodiment, are opportunistic infections, neoplasms, neurologic abnormalities, or progressive immunologic deterioration. In another embodiment, the methods comprise treating acquired immunodeficiency syndrome (AIDS). In another embodiment, the methods comprise treating a decline in the number of $CD4^+$ T lymphocytes.

In another embodiment, the present invention provides a method of reducing HIV-1 transmission to an offspring, the method comprising the step of administering to a subject a vaccine of the present invention. As is known in the art, HSV-2 infection increases HIV-1 viral shedding in genital secretions (Nagot N et al., Reduction of HIV-1 RNA levels with therapy to suppress herpes simplex virus. N Engl J Med. 2007 Feb. 22; 356(8):790-9). Thus, methods of the present invention of inhibiting HSV-2 infection are also efficacious for reducing HIV-1 transmission to an offspring. In another embodiment, the mutant HSV strain is an HSV-1 strain. In another embodiment, the mutant HSV strain is an HSV-2 strain.

In another embodiment, the present invention provides a method of reducing HIV-1 transmission to a sexual partner, the method comprising the step of administering to a subject a vaccine of the present invention. As function of gE. In another embodiment, a further enhanced anti-HSV immune response is enabled by combination of gD with both an adjuvant of the present invention and a gE immunogen that induces antibodies that block an immune evasion function of gE.

In another embodiment, a further enhanced anti-gD immune response is enabled by combination of gD with both a gE immunogen that induces antibodies that block an immune evasion function of gE and a gC immunogen that induces antibodies that block an immune evasion function of gC. In another embodiment, a further enhanced anti-gD immune response is enabled by combination of gD with: (a) an adjuvant of the present invention, (b) a gE immunogen that induces antibodies that block an immune evasion function of gE, and (c) a gC immunogen that induces antibodies that block an immune evasion function of gC.

In another embodiment, a further enhanced anti-HSV immune response is enabled by combination of gD with both a gE immunogen that induces antibodies that block an immune evasion function of gE and a gC immunogen that induces antibodies that block an immune evasion function of gC. In another embodiment, a further enhanced anti-HSV immune response is enabled by combination of gD with: (a) an adjuvant of the present invention, (b) a gE immunogen that induces antibodies that block an immune evasion function of gE, and (c) a gC immunogen that induces antibodies that block an immune evasion function of gC.

The dose of recombinant HSV gD protein utilized in methods and compositions of the present invention is, in another embodiment, 20 mcg per inoculation. In one embodiment, "protein" refers to a recombinant HSV glycoprotein or, in another embodiment, to a fragment thereof. In another embodiment, the dosage is 10 mcg/inoculation. In another embodiment, the dosage is 30 mcg/inoculation. In another embodiment, the dosage is 25 mcg/inoculation. In another embodiment, the dosage is 22 mcg/inoculation. In another embodiment, the dosage is 18 mcg/inoculation. In another embodiment, the dosage is 16 mcg/inoculation. In another embodiment, the dosage is 15 mcg/inoculation. In another embodiment, the dosage is 14 mcg/inoculation. In another embodiment, the dosage is 13 mcg/inoculation. In another embodiment, the dosage is 12 mcg/inoculation. In another embodiment, the dosage is 11 mcg/inoculation. In another embodiment, the dosage is 10 mcg/inoculation. In another embodiment, the dosage is 9 mcg/inoculation. In another embodiment, the dosage is 8 mcg/inoculation. In another embodiment, the dosage is 7 mcg/inoculation. In another embodiment, the dosage is 6 mcg/inoculation. In another embodiment, the dosage is 5 mcg/inoculation. In another embodiment, the dosage is 4 mcg/inoculation. In another embodiment, the dosage is 3 mcg/inoculation. In another embodiment, the dosage is 2 mcg/inoculation. In another embodiment, the dosage is 1.5 mcg/inoculation. In another embodiment, the dosage is 1 mcg/inoculation. In another embodiment, the dosage is less than 1 mcg/inoculation. In another embodiment, the dosage is 10 ng/inoculation. In another embodiment, the dosage is 25 ng/inoculation. In another embodiment, the dosage is 50 ng/inoculation. In another embodiment, the dosage is 100 ng/inoculation. In another embodiment, the dosage is 150 ng/inoculation. In another embodiment, the dosage is 200 ng/inoculation. In another embodiment, the dosage is 250 ng/inoculation. In another embodiment, the dosage is 300 ng/inoculation. In another embodiment, the dosage is 400 ng/inoculation. In another embodiment, the dosage is 500 ng/inoculation. In another embodiment, the dosage is 750 ng/inoculation.

In another embodiment, the dosage is 0.1 mcg/kg body mass (per inoculation). In another embodiment, the dosage is 0.2 mcg/kg. In another embodiment, the dosage is 0.15 mcg/kg. In another embodiment, the dosage is 0.13 mcg/kg. In another embodiment, the dosage is 0.12 mcg/kg. In another embodiment, the dosage is 0.11 mcg/kg. In another embodiment, the dosage is 0.09 mcg/kg. In another embodiment, the dosage is 0.08 mcg/kg. In another embodiment, the dosage is 0.07 mcg/kg. In another embodiment, the dosage is 0.06 mcg/kg. In another embodiment, the dosage is 0.05 mcg/kg. In another embodiment, the dosage is 0.04 mcg/kg. In another embodiment, the dosage is 0.03 mcg/kg. In another embodiment, the dosage is 0.02 mcg/kg. In another embodiment, the dosage is less than 0.02 mcg/kg. In another embodiment, the dosage is 500 ng/kg. In another embodiment, the dosage is 1.25 mcg/kg. In another embodiment, the dosage is 2.5 mcg/kg. In another embodiment, the dosage is 5 mcg/kg. In another embodiment, the dosage is 10 mcg/kg. In another embodiment, the dosage is 12.5 mcg/kg.

In another embodiment, the dosage is 1-2 mcg/inoculation. In another embodiment, the dosage is 2-3 mcg/inoculation. In another embodiment, the dosage is 2-4 mcg/inoculation. In another embodiment, the dosage is 3-6 mcg/inoculation. In another embodiment, the dosage is 4-8 mcg/inoculation. In another embodiment, the dosage is 5-10 mcg/inoculation. In another embodiment, the dosage is 5-15 mcg/inoculation. In another embodiment, the dosage is 10-20 mcg/inoculation. In another embodiment, the dosage is 20-30 mcg/inoculation. In another embodiment, the dosage is 30-40 mcg/protein/inoculation. In another embodiment, the dosage is 40-60 mcg/inoculation. In another embodiment, the dosage is 2-50 mcg/inoculation. In another embodiment, the dosage is 3-50 mcg/inoculation. In another embodiment, the dosage is 5-50 mcg/inoculation. In another embodiment, the dosage is 8-50 mcg/inoculation. In another embodiment, the dosage is 10-50 mcg/inoculation. In another embodiment, the dosage is 20-50 mcg/inoculation.

In another embodiment, the dosage is 0.01-0.02 mcg/kg body mass (per injection). In another embodiment, the dosage is 0.02-0.03 mcg/kg. In another embodiment, the dosage is 0.02-0.04 mcg/kg. In another embodiment, the dosage is 0.03-0.06 mcg/kg. In another embodiment, the dosage is 0.04-0.08 mcg/kg. In another embodiment, the dosage is 0.05-0.1 mcg/kg. In another embodiment, the dosage is 0.05-0.15 mcg/kg. In another embodiment, the dosage is 0.1-0.2 mcg/kg. In another embodiment, the dosage is 0.2-0.3 mcg/kg. In another embodiment, the dosage is 0.3-0.4 mcg/kg. In another embodiment, the dosage is 0.4-0.6 mcg/kg. In another embodiment, the dosage is 0.5-0.8 mcg/kg. In another embodiment, the dosage is 0.8-1 mcg/kg.

In another embodiment, the dosage of gD protein for human vaccination is determined by extrapolation from animal studies to human data. In another embodiment, the dosage of gD protein is determined by using a ratio of protein efficacious in human vs. mouse studies. In another embodiment, the ratio is 1:400 (ratio of gD-1 protein used in the present Examples to gD-2 used in human vaccination). In another embodiment, the ratio is 1:100. In another embodiment, the ratio is 1:150. In another embodiment, the ratio is 1:300. In another embodiment, the ratio is 1:500. In another embodiment, the ratio is 1:600. In another embodiment, the ratio is 1:700. In another embodiment, the ratio is 1:800. In another embodiment, the ratio is 1:900. In another embodiment, the ratio is 1:1000. In another embodiment, the ratio is 1:1200. In another embodiment, the ratio is 1:1500. In another embodiment, the ratio is 1:2000. In another embodiment, the ratio is 1:3000. In another embodiment, the ratio is 1:4000. In another embodiment, the dosage of gD protein for human vaccination is determined empirically. In another embodiment, the ratio is 1:5000.

In another embodiment, the dosage of total recombinant gD protein (gD-1 protein and gD-2 protein) is one of the above amounts. In another embodiment, utilization of an adjuvant of the present invention enables a lower effective dosage of gD. In another embodiment, a lower effective dosage of gD is enabled by combination of gD with a gC immunogen that induces antibodies that block an immune evasion function of gC. In another embodiment, a still lower effective dosage of gD is enabled by combination of gD with both an adjuvant of the present invention and a gC immunogen that induces antibodies that block an immune evasion function of gC.

In another embodiment, a lower effective dosage of gD is enabled by combination of gD with a gE immunogen that induces antibodies that block an immune evasion function of gE (e.g. 10 mcg instead of 20 mcg per dose is required in humans). In another embodiment, 15 mcg instead of 20 mcg is required. In another embodiment, 12 mcg instead of 20 mcg is required. In another embodiment, 8 mcg instead of 20 mcg is required. In another embodiment, 7 mcg instead of 6 mcg is required. In another embodiment, 5 mcg instead of 20 mcg is required. In another embodiment, 3 mcg instead of 20 mcg is required. In another embodiment, the reduction in amount required is any amount mentioned herein.

In another embodiment, a lower effective dosage of gD is enabled by combination of gD with both an adjuvant of the present invention and a gE immunogen that induces antibodies that block an immune evasion function of gE.

In another embodiment, a lower effective dosage of gD is enabled by combination of gD with both a gE immunogen that induces antibodies that block an immune evasion function of gE and a gC immunogen that induces antibodies that block an immune evasion function of gC. In another embodiment, a still lower effective dosage of gD is enabled by combination of gD with: (a) an adjuvant of the present invention, (b) a gE immunogen that induces antibodies that block an immune evasion function of gE, and (c) a gC immunogen that induces antibodies that block an immune evasion function of gC.

In another embodiment, one of the above gD doses is utilized in a priming vaccination of the present invention. In another embodiment, the gD doses hereinabove may refer to doses of gD-1, gD-2, or a combination thereof. Each possibility and each dosage of gD represents a separate embodiment of the present invention.

The dose of recombinant HSV gC protein utilized in methods and compositions of the present invention is, in another embodiment, 20 mcg per inoculation. In one embodiment, "protein" refers to a recombinant HSV glycoprotein or, in another embodiment, to a fragment thereof. In another embodiment, the dosage is 25 mcg/inoculation. In another embodiment, the dosage is 30 mcg/inoculation. In another embodiment, the dosage is 40 mcg/inoculation. In another embodiment, the dosage is 50 mcg/inoculation. In another embodiment, the dosage is 60 mcg/inoculation. In another embodiment, the dosage is 70 mcg/inoculation. In another embodiment, the dosage is 80 mcg/inoculation. In another embodiment, the dosage is 90 mcg/inoculation. In another embodiment, the dosage is 100 mcg/inoculation. In another embodiment, the dosage is 110 mcg/inoculation. In another embodiment, the dosage is 100 mcg/inoculation. In another embodiment, the dosage is 120 mcg/inoculation. In another embodiment, the dosage is 130 mcg/inoculation. In another embodiment, the dosage is 140 mcg/inoculation. In another embodiment, the dosage is 150 mcg/inoculation. In another embodiment, the dosage is 160 mcg/inoculation. In another embodiment, the dosage is 170 mcg/inoculation. In another embodiment, the dosage is 180 mcg/inoculation. In another embodiment, the dosage is 200 mcg/inoculation. In another embodiment, the dosage is 220 mcg/inoculation. In another embodiment, the dosage is 250 mcg/inoculation. In another embodiment, the dosage is 270 mcg/inoculation. In another embodiment, the dosage is 300 mcg/inoculation. In another embodiment, the dosage is 350 mcg/inoculation. In another embodiment, the dosage is 400 mcg/inoculation. In another embodiment, the dosage is 450 mcg/inoculation. In another embodiment, the dosage is 500 mcg/inoculation. In another embodiment, the dosage is 10 mcg/inoculation. In another embodiment, the dosage is 30 mcg/inoculation. In another embodiment, the dosage is 25 mcg/inoculation. In another embodiment, the dosage is 22 mcg/inoculation. In another embodiment, the dosage is 18 mcg/inoculation. In another embodiment, the dosage is 16 mcg/inoculation. In another embodiment, the dosage is 15 mcg/inoculation. In another embodiment, the dosage is 14 mcg/inoculation. In another embodiment, the dosage is 13 mcg/inoculation. In another embodiment, the dosage is 12 mcg/inoculation. In another embodiment, the dosage is 11 mcg/inoculation. In another embodiment, the dosage is 10 mcg/inoculation. In another embodiment, the dosage is 9 mcg/inoculation. In another embodiment, the dosage is 8 mcg/inoculation. In another embodiment, the dosage is 7 mcg/inoculation. In another embodiment, the dosage is 6 mcg/inoculation. In another embodiment, the dosage is 5 mcg/inoculation. In another embodiment, the dosage is 4 mcg/inoculation. In another embodiment, the dosage is 3 mcg/inoculation. In another embodiment, the dosage is 2 mcg/inoculation. In another embodiment, the dosage is 1.5 mcg/inoculation. In another embodiment, the dosage is 1 mcg/inoculation. In another embodiment, the dosage is 0.5 mcg/inoculation. In another embodiment, the dosage is less than 1 mcg/inoculation.

In another embodiment, the dosage is 0.1 mcg/kg body mass (per inoculation). In another embodiment, the dosage is 0.2 mcg/kg. In another embodiment, the dosage is 0.15 mcg/kg. In another embodiment, the dosage is 0.13 mcg/kg. In another embodiment, the dosage is 0.12 mcg/kg. In another embodiment, the dosage is 0.11 mcg/kg. In another embodiment, the dosage is 0.09 mcg/kg. In another embodiment, the dosage is 0.08 mcg/kg. In another embodiment, the dosage is 0.07 mcg/kg. In another embodiment, the dosage is 0.06 mcg/kg. In another embodiment, the dosage is 0.05 mcg/kg. In another embodiment, the dosage is 0.04 mcg/kg. In another embodiment, the dosage is 0.03 mcg/kg. In another embodiment, the dosage is 0.02 mcg/kg. In another embodiment, the dosage is less than 0.02 mcg/kg.

In another embodiment, the dosage is 30-60 mcg/inoculation. In another embodiment, the dosage is 40-80 mcg/inoculation. In another embodiment, the dosage is 50-100 mcg/inoculation. In another embodiment, the dosage is 50-150 mcg/inoculation. In another embodiment, the dosage is 100-200 mcg/inoculation. In another embodiment, the dosage is 200-300 mcg/inoculation. In another embodiment, the dosage is 300-400 mcg/protein/inoculation. In another embodiment, the dosage is 1-2 mcg/inoculation. In another embodiment, the dosage is 2-3 mcg/inoculation. In another embodiment, the dosage is 2-4 mcg/inoculation. In another embodiment, the dosage is 3-6 mcg/inoculation. In another embodiment, the dosage is 4-8 mcg/inoculation. In another embodiment, the dosage is 5-10 mcg/inoculation. In another embodiment, the dosage is 5-15 mcg/inoculation. In another embodiment, the dosage is 10-20 mcg/inoculation. In another embodiment, the dosage is 20-30 mcg/inoculation. In another embodiment, the dosage is 30-40 mcg/protein/inoculation. In another embodiment, the dosage is 40-60 mcg/inoculation.

In another embodiment, the dosage is 0.01-0.02 mcg/kg body mass (per injection). In another embodiment, the dosage is 0.02-0.03 mcg/kg. In another embodiment, the dosage is 0.02-0.04 mcg/kg. In another embodiment, the dosage is 0.03-0.06 mcg/kg. In another embodiment, the dosage is 0.04-0.08 mcg/kg. In another embodiment, the dosage is 0.05-0.1 mcg/kg. In another embodiment, the dosage is 0.05-0.15 mcg/kg. In another embodiment, the dosage is 0.1-0.2 mcg/kg. In another embodiment, the dosage is 0.2-0.3 mcg/kg. In another embodiment, the dosage is 0.3-0.4 mcg/kg. In another embodiment, the dosage is 0.4-0.6 mcg/kg. In another embodiment, the dosage is 0.5-0.8 mcg/kg. In another embodiment, the dosage is 0.8-1 mcg/kg.

In another embodiment, the dosage of gC protein for human vaccination is determined by extrapolation from animal studies to human data. In another embodiment, the dosage for humans is determined by using a ratio of protein efficacious in human vs. mouse studies. In another embodiment, the ratio is 1:400. In another embodiment, the ratio is 1:100. In another embodiment, the ratio is 1:150. In another embodiment, the ratio is 1:300. In another embodiment, the ratio is 1:500. In another embodiment, the ratio is 1:600. In another embodiment, the ratio is 1:700. In another embodiment, the ratio is 1:800. In another embodiment, the ratio is 1:900. In another embodiment, the ratio is 1:1000. In another embodiment, the ratio is 1:1200. In another embodiment, the ratio is 1:1500. In another embodiment, the ratio is 1:2000. In another embodiment, the ratio is 1:3000. In another embodiment, the ratio is 1:4000. In another embodiment, the dosage of gC protein for human vaccination is determined empirically. In another embodiment, the ratio is 1:5000.

In another embodiment, the dosage of total recombinant gC protein (gC-1 protein and gC-2 protein) is one of the above amounts. In another embodiment, utilization of an adjuvant of the present invention enables a lower effective dosage of total recombinant gC protein.

In another embodiment, utilization of an adjuvant of the present invention enables a lower effective dosage of gC. In another embodiment, a lower effective dosage of gC is enabled by combination of gC with a gE immunogen that induces antibodies that block an immune evasion function of gE. In another embodiment, a still lower effective dosage of gC is enabled by combination of gC with both an adjuvant of the present invention and a gE immunogen that induces antibodies that block an immune evasion function of gE.

In another embodiment, one of the above gC doses is utilized in a priming vaccination of the present invention. In another embodiment, the gC doses hereinabove may refer to doses of gC-1, gC-2, or a combination thereof. Each possibility and each dosage of gC represents a separate embodiment of the present invention.

The dose of recombinant HSV gE protein utilized in methods and compositions of the present invention is, in another embodiment, 20 mcg per inoculation. In one embodiment, "protein" refers to a recombinant HSV glycoprotein or, in another embodiment, to a fragment thereof. In another embodiment, the dosage is 25 mcg/inoculation. In another embodiment, the dosage is 30 mcg/inoculation. In another embodiment, the dosage is 40 mcg/inoculation. In another embodiment, the dosage is 50 mcg/inoculation. In another embodiment, the dosage is 60 mcg/inoculation. In another embodiment, the dosage is 70 mcg/inoculation. In another embodiment, the dosage is 80 mcg/inoculation. In another embodiment, the dosage is 90 mcg/inoculation. In another embodiment, the dosage is 100 mcg/inoculation. In another embodiment, the dosage is 110 mcg/inoculation. In another embodiment, the dosage is 100 mcg/inoculation. In another embodiment, the dosage is 120 mcg/inoculation. In another embodiment, the dosage is 130 mcg/inoculation. In another embodiment, the dosage is 140 mcg/inoculation. In another embodiment, the dosage is 150 mcg/inoculation. In another embodiment, the dosage is 160 mcg/inoculation. In another embodiment, the dosage is 170 mcg/inoculation. In another embodiment, the dosage is 180 mcg/inoculation. In another embodiment, the dosage is 200 mcg/inoculation. In another embodiment, the dosage is 220 mcg/inoculation. In another embodiment, the dosage is 250 mcg/inoculation. In another embodiment, the dosage is 270 mcg/inoculation. In another embodiment, the dosage is 300 mcg/inoculation. In another embodiment, the dosage is 350 mcg/inoculation. In another embodiment, the dosage is 400 mcg/inoculation. In another embodiment, the dosage is 450 mcg/inoculation. In another embodiment, the dosage is 500 mcg/inoculation. In another embodiment, the dosage is 10 mcg/inoculation. In another embodiment, the dosage is 30 mcg/inoculation. In another embodiment, the dosage is 25 mcg/inoculation. In another embodiment, the dosage is 22 mcg/inoculation. In another embodiment, the dosage is 18 mcg/inoculation. In another embodiment, the dosage is 16 mcg/inoculation. In another embodiment, the dosage is 15 mcg/inoculation. In another embodiment, the dosage is 14 mcg/inoculation. In another embodiment, the dosage is 13 mcg/inoculation. In another embodiment, the dosage is 12 mcg/inoculation. In another embodiment, the dosage is 11 mcg/inoculation. In another embodiment, the dosage is 10 mcg/inoculation. In another embodiment, the dosage is 9 mcg/inoculation. In another embodiment, the dosage is 8 mcg/inoculation. In another embodiment, the dosage is 7 mcg/inoculation. In another embodiment, the dosage is 6 mcg/inoculation. In another embodiment, the dosage is 5 mcg/inoculation. In another embodiment, the dosage is 4 mcg/inoculation. In another embodiment, the dosage is 3 mcg/inoculation. In another embodiment, the dosage is 2 mcg/inoculation. In another embodiment, the dosage is 1.5 mcg/inoculation. In another embodiment, the dosage is 1 mcg/inoculation. In another embodiment, the dosage is less than 1 mcg/inoculation.

In another embodiment, the dosage is 0.1 mcg/kg body mass (per inoculation). In another embodiment, the dosage is 0.2 mcg/kg. In another embodiment, the dosage is 0.15 mcg/kg. In another embodiment, the dosage is 0.13 mcg/kg. In another embodiment, the dosage is 0.12 mcg/kg. In another embodiment, the dosage is 0.11 mcg/kg. In another embodiment, the dosage is 0.09 mcg/kg. In another embodiment, the dosage is 0.08 mcg/kg. In another embodiment, the dosage is 0.07 mcg/kg. In another embodiment, the dosage is 0.06 mcg/kg. In another embodiment, the dosage is 0.05 mcg/kg. In another embodiment, the dosage is 0.04 mcg/kg. In another embodiment, the dosage is 0.03 mcg/kg. In another embodiment, the dosage is 0.02 mcg/kg. In another embodiment, the dosage is less than 0.02 mcg/kg.

In another embodiment, the dosage is 30-60 mcg/inoculation. In another embodiment, the dosage is 40-80 mcg/inoculation. In another embodiment, the dosage is 50-100 mcg/inoculation. In another embodiment, the dosage is 50-150 mcg/inoculation. In another embodiment, the dosage is 100-200 mcg/inoculation. In another embodiment, the dosage is 200-300 mcg/inoculation. In another embodiment, the dosage is 300-400 mcg/protein/inoculation. In another embodiment, the dosage is 1-2 mcg/inoculation. In another embodiment, the dosage is 2-3 mcg/inoculation. In another embodiment, the dosage is 2-4 mcg/inoculation. In another embodiment, the dosage is 3-6 mcg/inoculation. In another embodiment, the dosage is 4-8 mcg/inoculation. In another embodiment, the dosage is 5-10 mcg/inoculation. In another embodiment, the dosage is 5-15 mcg/inoculation. In another embodiment, the dosage is 10-20 mcg/inoculation. In another embodiment, the dosage is 20-30 mcg/inoculation. In another embodiment, the dosage is 30-40 mcg/protein/inoculation. In another embodiment, the dosage is 40-60 mcg/inoculation.

In another embodiment, the dosage is 0.01-0.02 mcg/kg body mass (per injection). In another embodiment, the dosage is 0.02-0.03 mcg/kg. In another embodiment, the dosage is 0.02-0.04 mcg/kg. In another embodiment, the dosage is 0.03-0.06 mcg/kg. In another embodiment, the dosage is 0.04-0.08 mcg/kg. In another embodiment, the dosage is 0.05-0.1 mcg/kg. In another embodiment, the dosage is 0.05-0.15 mcg/kg. In another embodiment, the dosage is 0.1-0.2 mcg/kg. In another embodiment, the dosage is 0.2-0.3 mcg/kg. In another embodiment, the dosage is 0.3-0.4 mcg/kg. In another embodiment, the dosage is 0.4-0.6 mcg/kg. In another embodiment, the dosage is 0.5-0.8 mcg/kg. In another embodiment, the dosage is 0.8-1 mcg/kg.

In another embodiment, the dosage of gE protein for human vaccination is determined by extrapolation from animal studies to human data. In another embodiment, the dosage for humans is determined by using a ratio of protein efficacious in human vs. mouse studies. In another embodiment, the ratio is 1:400. In another embodiment, the ratio is 1:100. In another embodiment, the ratio is 1:150. In another embodiment, the ratio is 1:300. In another embodiment, the ratio is 1:500. In another embodiment, the ratio is 1:600. In another embodiment, the ratio is 1:700. In another embodiment, the ratio is 1:800. In another embodiment, the ratio is 1:900. In another embodiment, the ratio is 1:1000. In another embodiment, the ratio is 1:1200. In another embodiment, the ratio is 1:1500. In another embodiment, the ratio is 1:2000. In another embodiment, the ratio is 1:3000. In another embodiment, the ratio is 1:4000. In another embodiment, the dosage of gE protein for human vaccination is determined empirically. In another embodiment, the ratio is 1:5000.

In another embodiment, the dosage of total recombinant gE protein (gE-1 protein and gE-2 protein) is one of the above amounts. In another embodiment, utilization of an adjuvant of the present invention enables a lower effective dosage of total recombinant gE protein.

In another embodiment, utilization of an adjuvant of the present invention enables a lower effective dosage of gE. In another embodiment, a lower effective dosage of gE is enabled by combination of gE with a gC immunogen that induces antibodies that block an immune evasion function of gC. In another embodiment, a still lower effective dosage of gE is enabled by combination of gE with both an adjuvant of the present invention and a gC immunogen that induces antibodies that block an immune evasion function of gC.

In another embodiment, one of the above gE doses is utilized in a priming vaccination of the present invention. In another embodiment, the gE doses hereinabove may refer to doses of gE-1, gE-2, or a combination thereof. Each possibility and each dosage of gE represents a separate embodiment of the present invention.

In another embodiment, the dosage of recombinant gE protein is one of the above amounts. In another embodiment, utilization of an adjuvant of the present invention enables a lower effective dosage of gE. In another embodiment, a lower effective dosage of gE is enabled by combination of gE with a gC immunogen that induces antibodies that block an immune evasion function of gC. In another embodiment, a still lower effective dosage of gE is enabled by combination of gE with both an adjuvant of the present invention and a gC immunogen that induces antibodies that block an immune evasion function of gC. Each possibility and each dosage of gE represents a separate embodiment of the present invention.

"Effective dose" of a glycoprotein refers, in another embodiment, the dose required to elicit antibodies that significantly block an immune evasion function of an HSV virus during a subsequent challenge. In another embodiment, the term refers to the dose required to elicit antibodies that effectively block an immune evasion function of an HSV virus during a subsequent challenge. In another embodiment, the term refers to the dose required to elicit antibodies that significantly reduce infectivity of an HSV virus during a subsequent challenge.

Each dosage of each recombinant glycoprotein, and each combination thereof, represents a separate embodiment of the present invention.

Methods for measuring the dose of an immunogen (e.g. in human subjects) are well known in the art, and include, for example, dose-escalating trials. Each method represents a separate embodiment of the present invention.

In another embodiment, the strategy demonstrated herein is utilized for another virus and/or another pathogen. In another embodiment, a combined subunit vaccine is utilized, containing both a first protein that plays a role in infection and a (or more than one) second protein with an immune evasion function, whereby antibodies elicited against the second protein by the vaccine block the immune evasion function.

In another embodiment, the present invention provides a method for improvement of an existing HSV-1 vaccine, the method comprising the steps of (1) screening a combination of recombinant gC-1 proteins and adjuvants for ability to block an immune evasion property of gC-1; and (2) adding recombinant gD protein, and comparing the resulting vaccine to a vaccine containing adjuvant and gD protein alone.

In another embodiment, the present invention provides a method for improvement of an existing HSV-1 vaccine, the method comprising the steps of (1) screening a combination of recombinant gE-1 proteins and adjuvants for ability to block immune evasion property of gE-1; and (2) adding recombinant gD protein, and comparing the resulting vaccine to a vaccine containing adjuvant and gD protein alone.

In another embodiment, the present invention provides a method for improvement of an existing HSV-1 vaccine, the method comprising the steps of (1) screening a combination of recombinant gC-1 proteins, recombinant gE-1 proteins, and adjuvants for ability to block immune evasion property of gC-1 and gE-1; and (2) adding recombinant gD protein, and comparing the resulting vaccine to a vaccine containing adjuvant and gD protein alone.

In another embodiment, the present invention provides a method for improvement of an existing HSV-2 vaccine, the method comprising the steps of (1) screening a combination of recombinant gC-2 proteins and adjuvants for ability to block immune evasion property of gC-2; and (2) adding recombinant gD protein, and comparing the resulting vaccine to a vaccine containing adjuvant and gD protein alone.

In another embodiment, the present invention provides a method for improvement of an existing HSV-2 vaccine, the method comprising the steps of (1) screening a combination of recombinant gE-2 proteins and adjuvants for ability to block immune evasion property of gE-2; and (2) adding recombinant gD protein, and comparing the resulting vaccine to a vaccine containing adjuvant and gD protein alone.

In another embodiment, the present invention provides a method for improvement of an existing HSV-2 vaccine, the method comprising the steps of (1) screening a combination of recombinant gC-2 proteins, recombinant gE-2 proteins, and adjuvants for ability to block immune evasion property of gC-2 and gE-2; and (2) adding recombinant gD protein, and comparing the resulting vaccine to a vaccine containing adjuvant and gD protein alone.

In some embodiments, any of the HSV vaccines of and for use in the methods of this invention will comprise an HSV protein or combination of HSV proteins of the present invention, in any form or embodiment as described herein. In some embodiments, any of the HSV vaccines of and for use in the methods will consist of an HSV protein or combination of HSV proteins of the present invention, in any form or embodiment as described herein. In some embodiments, the HSV vaccines of this invention will consist essentially of a an HSV protein or combination of HSV proteins of the present invention, in any form or embodiment as described herein. In some embodiments, the term "comprise" refers to the inclusion of other recombinant HSV proteins, as well as inclusion of other proteins that may be known in the art. In some embodiments, the term "consisting essentially of" refers to a vaccine, which has the specific HSV protein or fragment thereof. However, other peptides may be included that are not involved directly in the utility of the HSV protein(s). In some embodiments, the term "consisting" refers to a vaccine having a particular HSV protein or fragment or combination of HSV proteins or fragments of the present invention, in any form or embodiment as described herein.

In another embodiment, the present invention provides a composition for treating HSV-1 or a symptom or manifestation thereof, the composition comprising a vaccine of the present invention.

In another embodiment, the present invention provides a composition for treating HSV-2 or a symptom or manifestation thereof, the composition comprising a vaccine of the present invention.

In another embodiment, of methods of the present invention, a vaccine of the present invention is administered as a single inoculation. In another embodiment, the vaccine is administered twice. In another embodiment, the vaccine is administered three times. In another embodiment, the vaccine is administered four times. In another embodiment, the vaccine is administered at least four times. In another embodiment, the vaccine is administered more than four times. In another embodiment, the vaccine is administered at separate sites with gD separate from gC or gE. In another embodiment, the vaccine is administered at 1 week intervals. In another embodiment, the vaccine is administered at 2 week intervals. In another embodiment, the vaccine is administered at 3 week intervals. In another embodiment, the vaccine is administered at 4 week intervals. In another embodiment, the vaccine is administered at 1 month intervals.

It is to be understood that the compositions/vaccines, and methods of the present invention may be used in non-HSV herpesvirus as well, which in one embodiment, comprise gD, gE, or gC proteins that are, in one embodiment, 70% homologous, in another embodiment, 80% homologous, in another embodiment, 85% homologous, in another embodiment, 90% homologous, in another embodiment, 95% homologous, in another embodiment, 98% homologous, and in another embodiment, 100% homologous to the gD, gE, or gC proteins of HSV-1, or in another embodiment, of HSV-2. In one embodiment, such vaccines may be useful in suppressing, inhibiting, preventing, or treating, cancers, or in another embodiment, tumors. In one embodiment, non-HSV herpesvirus comprise Varicella Zoster Virus (VZV), Epstein-Barr virus (EBV), EBNA, cytomegalovirus (CMV), and human herpesvirus-6 (HHV-6).

In another embodiment, a recombinant protein of the present invention is homologous to a sequence set forth hereinabove, either expressly or by reference to a GenBank entry. The terms "homology," "homologous," etc, when in reference to any protein or peptide, refer, in one embodiment, to a percentage of AA residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

Homology is, in another embodiment, determined by computer algorithm for sequence alignment, by methods well described in the art. For example, computer algorithm analysis of nucleic acid sequence homology can include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID No: 1-6 of greater than 70%. In another embodiment, "homology" refers to identity to a sequence selected from SEQ ID No: 1-6 of greater than 72%. In another embodiment, "homology" refers to identity to one of SEQ ID No: 1-6 of greater than 75%. In another embodiment, "homology" refers to identity to a sequence selected from SEQ ID No: 1-6 of greater than 78%. In another embodiment, "homology" refers to identity to one of SEQ ID No: 1-6 of greater than 80%. In another embodiment, "homology" refers to identity to one of SEQ ID No: 1-6 of greater than 82%. In another embodiment, "homology" refers to identity to a sequence selected from SEQ ID No: 1-6 of greater than 83%. In another embodiment, "homology" refers to identity to one of SEQ ID No: 1-6 of greater than 85%. In another embodiment, "homology" refers to identity to one of SEQ ID No: 1-6 of greater than 87%. In another embodiment, "homology" refers to identity to a sequence selected from SEQ ID No: 1-6 of greater than 88%. In another embodiment, "homology" refers to identity to one of SEQ ID No: 1-6 of greater than 90%. In another embodiment, "homology" refers to identity to one of SEQ ID No: 1-6 of greater than 92%. In another embodiment, "homology" refers to identity to a sequence selected from SEQ ID No: 1-6 of greater than 93%. In another embodiment, "homology" refers to identity to one of SEQ ID No: 1-6 of greater than 95%. In another embodiment, "homology" refers to identity to a sequence selected from SEQ ID No: 1-6 of greater than 96%. In another embodiment, "homology" refers to identity to one of SEQ ID No: 1-6 of greater than 97%. In another embodiment, "homology" refers to identity to one of SEQ ID No: 1-6 of greater than 98%. In another embodiment, "homology" refers to identity to one of SEQ ID No: 1-6 of greater than 99%. In another embodiment, "homology" refers to identity to one of SEQ ID No: 1-6 of 100%.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y.). In other embodiments, methods of hybridization are carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA.

Protein and/or peptide homology for any AA sequence listed herein is determined, in another embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and, in another embodiment, employ the use of the Smith and Waterman algorithms, and/or global/local or BLOCKS alignments for analysis, for example. Each method of determining homology represents a separate embodiment of the present invention.

In one embodiment, "variant" refers to an amino acid or nucleic acid sequence (or in other embodiments, an organism or tissue) that is different from the majority of the population but is still sufficiently similar to the common mode to be considered to be one of them, for example splice variants. In one embodiment, the variant may a sequence conservative variant, while in another embodiment, the variant may be a functional conservative variant. In one embodiment, a variant may comprise an addition, deletion or substitution of 1 amino acid. In one embodiment, a variant may comprise an addition, deletion, substitution, or combination thereof of 2 amino acids. In one embodiment, a variant may comprise an addition, deletion or substitution, or combination thereof of 3 amino acids. In one embodiment, a variant may comprise an addition, deletion or substitution, or combination thereof of 4 amino acids. In one embodiment, a variant may comprise an addition, deletion or substitution, or combination thereof of 5 amino acids. In one embodiment, a variant may comprise an addition, deletion or substitution, or combination thereof of 7 amino acids. In one embodiment, a variant may comprise an addition, deletion or substitution, or combination thereof of 10 amino acids. In one embodiment, a variant may comprise an addition, deletion or substitution, or combination thereof of 2-15 amino acids. In one embodiment, a variant may comprise an addition, deletion or substitution, or combination thereof of 3-20 amino acids. In one embodiment, a variant may comprise an addition, deletion or substitution, or combination thereof of 4-25 amino acids.

In one embodiment, "isoform" refers to a version of a molecule, for example, a protein, with only slight differences to another isoform of the same protein. In one embodiment, isoforms may be produced from different but related genes, or in another embodiment, may arise from the same gene by alternative splicing. In another embodiment, isoforms are caused by single nucleotide polymorphisms.

In another embodiment, methods and compositions of the present invention utilize a chimeric molecule, comprising a fusion of a recombinant HSV protein with a tag polypeptide that provides an epitope to which an anti-tag antibody can selectively bind. The epitope tag is placed, in other embodiments, at the amino- or carboxyl-terminus of the protein or in an internal location therein. The presence of such epitope-tagged forms of the recombinant HSV protein is detected, in another embodiment, using an antibody against the tag polypeptide. In another embodiment, inclusion of the epitope tag enables the recombinant HSV protein to be readily purified by affinity purification using an anti-tag antibody or another type of affinity matrix that binds to the epitope tag. Various tag polypeptides and their respective antibodies are known in the art. Examples include poly-histidine (poly-his) or poly-histidine-glycine (poly-his-gly) tags; the flu HA tag polypeptide and its antibody 12CA5 (Field et al., Mol. Cell. Biol., 8: 2159-2165 (1988)); the c-myc tag and the 8F9, 3C7, 6E10, G4, B7 and 9E10 antibodies thereto (Evan et al., Molecular and Cellular Biology, 5: 3610-3616 (1985)); and the Herpes Simplex virus glycoprotein D (gD) tag and its antibody (Paborsky et al., Protein Engineering, 3(6): 547-553 (1990)). Other tag polypeptides include the Flag-peptide (Hopp et al., BioTechnology, 6: 1204-1210 (1988)); the KT3 epitope peptide (Martin et al., Science, 255: 192-194 (1992)); a tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87: 6393-6397 (1990)). In another embodiment, the chimeric molecule comprises a fusion of the recombinant HSV protein with an immunoglobulin or a particular region of an immunoglobulin. Methods for constructing fusion proteins are well known in the art, and are described, for example, in LaRochelle et al., J. Cell Biol., 139(2): 357-66 (1995); Heidaran et al., FASEB J., 9(1): 140-5 (1995); Ashkenazi et al., Int. Rev. Immunol., 10(2-3): 219-27 (1993) and Cheon et al., PNAS USA, 91(3): 989-93 (1994).

In another embodiment, the present invention provides a kit comprising a vaccine utilized in performing a method of the present invention. In another embodiment, the present invention provides a kit comprising a vaccine of the present invention.

"Administering," in another embodiment, refers to directly introducing into a subject by injection or other means a composition of the present invention. In another embodiment, "administering" refers to contacting a cell of the subject's immune system with a vaccine or recombinant HSV protein or mixture thereof.

Pharmaceutical Compositions and Methods of Administration

In another embodiment, methods of the present invention comprise administering a recombinant HSV protein and a pharmaceutically acceptable carrier. The pharmaceutical compositions containing the vaccine can be, in another embodiment, administered to a subject by any method known to a person skilled in the art, such as parenterally, transmucosally, transdermally, intramuscularly, intravenously, intradermally, intra-nasally, subcutaneously, intra-peritonealy, intra-ventricularly, intra-cranially, or intra-vaginally. In another embodiment, vaccines of the instant invention are administered via epidermal injection, in another embodiment, intramuscular injection, in another embodiment, subcutaneous injection, and in another embodiment, intra-respiratory mucosal injection.

In another embodiment, of methods and compositions of the present invention, the pharmaceutical compositions are administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment, of the present invention, the vaccine is formulated in a capsule. In another embodiment, compositions of the present invention comprise a hard gelating capsule.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intramuscularly and are thus formulated in a form suitable for intra-muscular administration.

In another embodiment, the pharmaceutical compositions are administered topically to body surfaces and are thus formulated in a form suitable for topical administration. Suitable topical formulations include gels, ointments, creams, lotions, drops and the like.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of antigen agent over a period of time.

In another embodiment, the vaccine is delivered in a vesicle, e.g. a liposome.

In other embodiments, carriers or diluents used in methods of the present invention include, but are not limited to, a gum, a starch (e.g. corn starch, pregeletanized starch), a sugar (e.g. lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g. Tris-HCL, acetate, phosphate) of various pH and ionic strength, additives such as albumin or gelatin to prevent absorption to surfaces, detergents (e.g. Tween 20, Tween 80, Pluronic F68, bile acid salts), protease inhibitors, surfactants (e.g. sodium lauryl sulfate), permeation enhancers, solubilizing agents (e.g. glycerol, polyethylene glycerol), anti-oxidants (e.g. ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g. Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g. poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e., compositions in which the antigen is released over a period of time after administration. Controlled- or sustained-release compositions include formulation in lipophilic depots (e.g. fatty acids, waxes, oils). In another embodiment, the composition is an immediate-release composition, i.e., a composition in which all the antigen is released immediately after administration.

In another embodiment, the pharmaceutical composition is delivered in a controlled release system. In another embodiment, the agent is administered using intravenous infusion, an implantable osmotic pump, a transdermal patch, liposomes, or other modes of administration. In another embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant.

The compositions also include, in another embodiment, incorporation of the active material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications also increase, in another embodiment, the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

The preparation of pharmaceutical compositions that contain an active component, for example by mixing, granulating, or tablet-forming processes, is well understood in the art. An active component is, in another embodiment, formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Each of the above additives, excipients, formulations and methods of administration represents a separate embodiment of the present invention.

It is to be understood that the present invention also encompasses compositions comprising one or more recombinant Herpes Simplex Virus (HSV) proteins selected from a gD protein, a gC protein and a gE protein, as described for vaccines herein.

EXPERIMENTAL DETAILS SECTION

Example 1

HSV-1 gC-1 Subunit Vaccines are Protective Against HSV-1 Infection

Materials and Experimental Methods (Examples 1-2)

Rosette Inhibition Assays

Vero cells were infected with WT HSV-1 at a multiplicity of infection (MOI) of 2 for 20 h. IgG was added to the infected cells for 1 h at room temperature. C3b-coated sheep erythrocytes were added for 1 h at 37° C. and viewed by light microscopy for rosettes. The percentage of cells that form rosettes of C3b-coated erythrocytes is calculated as (number of cells that have four or more erythrocytes bound divided by total number of cells counted times 100%). Inhibition of C3b-coated rosettes indicates that antibodies are present that block C3b binding to gC-1.

Murine Flank Model

BALB/c or C57Bl/6 female mice (Charles River, Wilmington, Mass.) or C3 knockout mice 5-7 weeks old were anesthetized, and flanks of the mice were shaved and chemically denuded. 16-20 h later, mice were infected with purified HSV-1 WT virus by adding 10 μl containing $5 \times 10^4$ or $5 \times 10^5$ PFU and scratching the skin with the bevel of a 30-gauge needle. Disease at the inoculation site was scored as follows. Erythema or swelling with no vesicles was assigned 0.5 points, and individual vesicles were scored as 1 point each, with a total maximum daily score of 5. If lesions coalesced, up to 5 points were assigned based on the size of the lesions. Zosteriform disease was scored similarly, except that the maximum daily score was 10, because more lesions could be counted over the larger skin area involved. For some experiments with HSV-2 (FIGS. 16A and 16B) the scoring system was modified to distinguish among animals at the severe end of the disease spectrum, since HSV-2 causes more severe flank disease than HSV-1. At the inoculation site, scores range from 0-3, with 0 representing no disease, 1 for redness or isolated lesions, 2 for ulcers, and 3 for areas with tissue necrosis. At the zosteriform site, scores range from 0-4, with 0 for no disease, 1 for isolated lesions, 2 for confluent lesions, 3 for ulcers, and 4 for areas with tissue necrosis.

Vaccines

Vaccines contained recombinant HSV-1 bac-gD-1(306t) (AA 26-306 with a C-terminal 6 His tag) and an HSV-1 bac-gC-1 fragment (AA 26-457 modified with a 5 His tag).

Results

Optimum dose of gC-1 subunit vaccine: This experiment defined the dose of gC-1 immunization that generates anti-gC antibodies capable of blocking immune evasion, measured by inhibiting C3b binding to gC-1. Mice were mock-immunized or immunized with 0.1, 1, or 10 μg of gC-1, and resulting sera was tested for ability to block C3b binding, using a resetting assay (FIG. 1, left panel). Mice immunized with 10 μg of gC-1 produced anti-gC antibodies that blocked resetting by 85% (FIG. 1, right panel). Mice were then challenged with a lethal dose of HSV-1 and scored for disease at the inoculation and zosteriform sites from days 3 to 7 post-challenge (FIGS. 2A and B). Inoculation site disease was not altered significantly by gC-1 immunization, but zosteriform disease was reduced (P<0.001) compared with mock-immunized mice.

Mock and gC-1 immunized mice were scored for survival for 14 days post-challenge. At 10 μg gC-1, 40% survived, compared with none at the lower doses. Therefore, immunization with 10 μg gC-1 generates antibodies that protect mice from zosteriform disease and death.

Example 2

Figure 3:
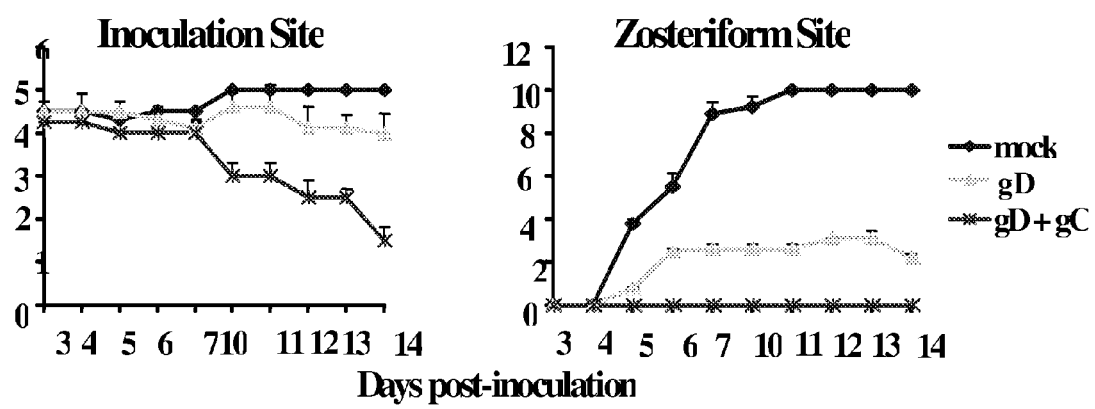
FIG. 3: Disease scores in mice immunized and then challenged by flank infection with a lethal dose of WT virus. Mice were either mock immunized or immunized with gD-1 alone, or both gD-1 and gC-1. Mice were scored for disease severity at the inoculation and zosteriform sites from 3 to 14 days post-challenge.
Figure 4:
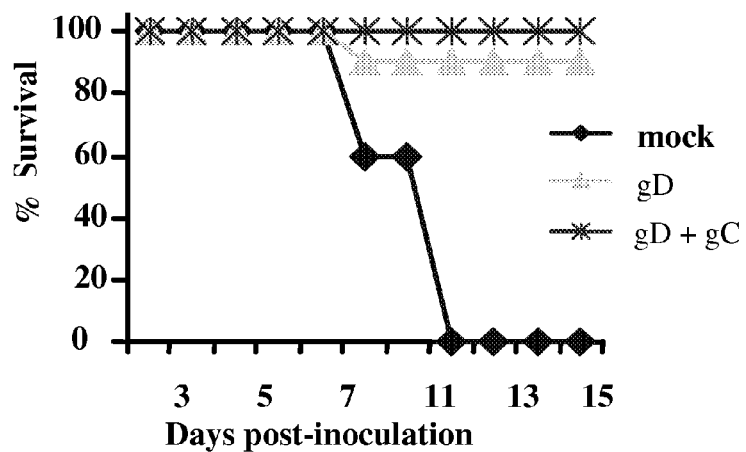
FIG. 4: Survival in mice immunized and then challenged with a lethal dose of WT virus. Mice were either mock immunized, or immunized with gD-1 alone, or both gD-1 and gC-1. Survival was monitored from 3-15 days post-challenge.

Combination gC-1/gD-1 Vaccines Confer Protection Superior to Vaccines Containing gD-1 or gC-1 Alone Optimum dose of gD-1 subunit vaccine: The mouse flank model was used to define a gD-1 dose that partially protects mice from disease, to simulate a partially protective gD-1 subunit vaccine. Based on these studies, a gD-1 dose of 50 ng was chosen; which provided minimal protection at the inoculation site and moderate protection against zosteriform disease (results included in FIG. 3).

gD-1 and gC-1 combined subunit vaccine: Mice were either mock-immunized or immunized with gD-1 alone (50 ng), or with both gD-1 (50 ng) and gC-1 (10 μg) and challenged with a lethal dose of HSV-1 (FIG. 3). Disease severity was significantly reduced at the inoculation site (P<0.02), and zosteriform site disease was completely prevented in mice administered the gD-1/gC-1 combination vaccine, a significant result (P<0.001) compared with gD-1 alone or gC-1 alone (FIGS. 2A and 2B). Further, the combination vaccine conferred survival upon 100% of the mice (FIG. 4).

Thus, combination gC-1/gD-1 vaccines confer superior protection, compared with vaccines containing gD-1 alone or gC-1 alone.

Example 3

Combination gC-1/gD-1 Vaccines Prevent Infection of Dorsal Root Ganglia

Materials and Experimental Methods

Harvesting of DRG was performed at 5 days post-infection. The mice were euthanized, and the ganglia that innervate the inoculated skin were identified under a magnifying dissecting microscope. The ganglia were removed and homogenized in DMEM, and virus in the ganglia was titrated by plaque assay.

Results

HSV-1 develops latency in the neuronal cell bodies within dorsal root ganglia (DRG). To test whether immunization with gD-1 and gC-1 prevents infection of DRG, DRG were harvested at 5 days post-challenge (the time of peak titers) with a lethal dose of HSV-1. No infectious virus was found in mice immunized with gD-1 and gC-1, while virus was recovered from mock or gD-1 immunized mice (FIG. 5).

Thus, combination gC-1/gD-1 vaccines better protect mice from disease, death and DRG infection than immunization with gD-1 or gC-1 alone.

Example 4

Combination gC-1/gD-1 Vaccines Prevent Recurrent Infection in HSV-1 Infected Subjects Combination gC-1/gD-1 vaccines (e.g. those described in Examples 2-3) are assessed for their ability to prevent recurrent HSV-1 infection (e.g. as assessed by occurrence of flares) in the mouse flank model. Following infection, mice are immunized up to 5 times with gC-1/gD-1 vaccines, vaccines containing gC-1 or gD-1 alone, or are mock-immunized, then monitored for recurrent infection. The combination gC-1/gD-1 vaccines are believed to confer protection that compares favorably with gC-1 or gD-1 vaccines.

Example 5

Protection Mediated by Anti-gC-1 IgG in Mice Immunized with gD-1 & gC-1 is Dependent on C3b Materials and Experimental Methods Flank Model Experiments were performed to demonstrate that anti-gC-1 IgG protection of mice occurs by blocking the interaction between gC-1 and C3b. Mice were immunized three times IM with 5 µg of gC-1 mixed with CpG (#1826, Coley Pharmaceuticals Group) (50 µg/mice) and alum (25 µg/µg protein) (Accurate Chemicals and Scientific Corp). Serum was obtained 2 weeks after the third immunization and shown to interact with gC-1 protein by Western blot (result not shown) and to block C3b rosetting on HSV-1 infected cells (as described in FIG. 1). IgG was purified from the mouse serum on a protein G column (Hi-Trap™, Amersham Biosciences, Uppsala, Sweden) and tested for neutralizing antibody activity. An anti-gD1 monoclonal antibody DL11 (Eisenberg, R J et al. J. Virol 53: 634-644, 1985), anti-gC-1 monoclonal antibody 1C8 that binds to the domain on gC-1 that interacts with C3b and blocks C3b rosetting to HSV-1 infected cells (Judson K A et al. J Virol 77:12639-45, 2003), and non-immune murine IgG were included as controls. Approximately 80 PFU of HSV-1, strain NS was incubated with anti-gC-1 IgG obtained from immunized mice, or with DL11, 1C8 or non-immune murine IgG for 1 hour at 37° C. Virus titers were then determined by plaque assay on Vero cells.

To test the ability of the anti-gC-1 IgG to protect mice, complement-intact mice (C57B1/6) or C3 knockout mice (C3KO) were passively immunized with 200 µg/mouse of anti-gC-1 IgG 24 hours before flank infection with $5 \times 10^5$ HSV-1. Mice were evaluated for inoculation and zosteriform site disease for 11 days. Controls included passive transfer of (200 µg/mice) 1C8 or non-immune murine IgG (200 µg/mice). The scoring system for disease at the inoculation site was 0 for no disease and a score of 1-5 depending on the size of the lesion(s) at the inoculation site. The scoring system for disease at the zosteriform site was 0 for no disease and score of 1 for each lesion up to a maximum score of 10. Animals that died before the end of the experiment were assigned the score at the last evaluation for the duration of the study period.

Results

Figure 6:
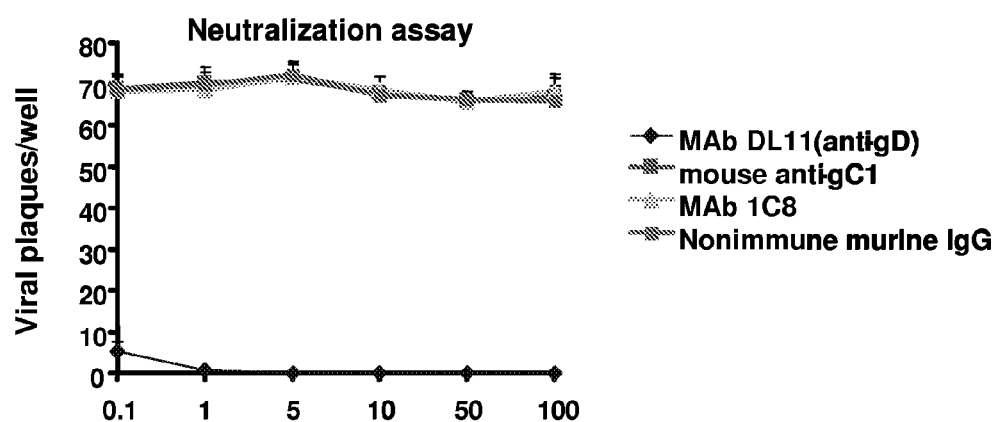
FIG. 6: Anti-gC-1 IgG does not neutralize HSV-1. Mice were immunized three times intramuscularly (IM) with 5 µg of gC-1 mixed with CpG (50 µg/mice) and alum (25 µg/µg protein). Serum was obtained 2 weeks after the third immunization, IgG was purified from the mouse serum on a protein G column and tested for neutralizing antibody activity. As controls, neutralization was performed using anti-gD1 monoclonal antibody DL11, anti-gC-1 monoclonal antibody 1C8 that binds to the domain on gC-1 that interacts with C3b and blocks C3b resetting to HSV-1 infected cells, and non-immune murine IgG. Approximately 80 PFU of HSV-1, strain NS was incubated with anti-gC-1 IgG obtained from immunized mice or with DL11, 1C8 or non-immune murine IgG for 1 hour at 37° C. Virus titers were then determined by plaque assay on Vero cells.

DL11 was highly effective at neutralizing HSV-1, even at 0.1 µg/ml, while anti-gC-1 IgG failed to neutralize HSV-1 when used at 100 µg/ml, which is 3 $\log_{10}$ higher concentrations (FIG. 6). Anti-gC-1 monoclonal antibody 1C8 and non-immune murine IgG also failed to neutralize HSV-1. Mouse anti-gC-1 IgG failed to neutralize HSV-1, indicating that protection offered by this antibody cannot be attributed to its neutralizing activity.

Figure 7:
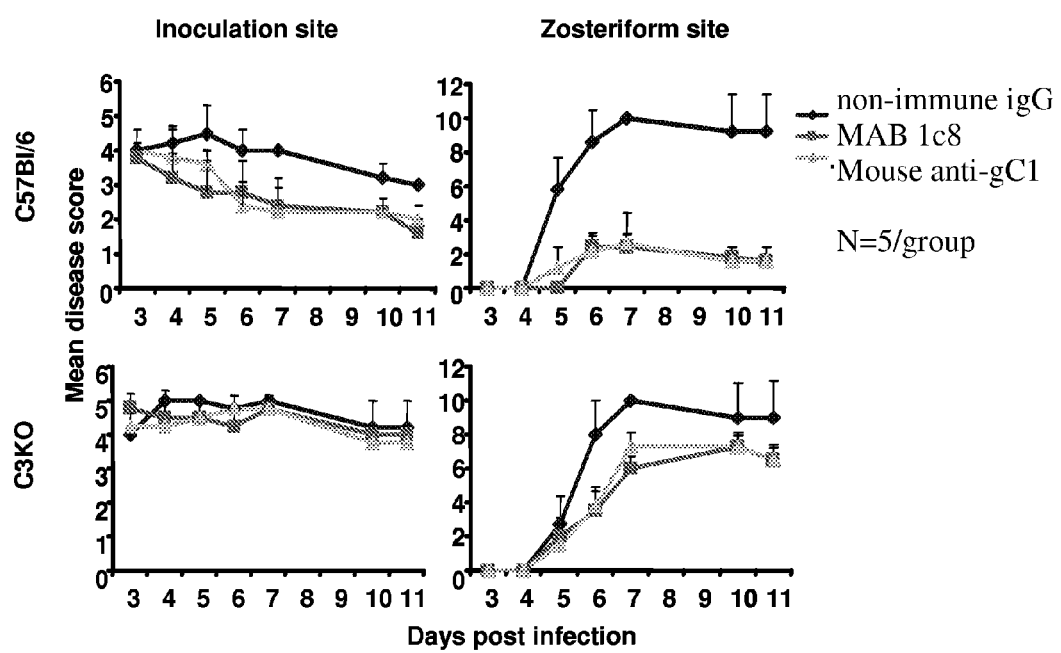
FIG. 7: Complement-intact mice (C57B1/6) or C3knockout mice (C3KO) were passively immunized with 200 µg/mice of anti-gC-1 IgG, 1C8 (200 µg/mice), or non-immune murine IgG (200 µg/mice) 24 hours before flank infection with $5 \times 10^5$ HSV-1. Mice were evaluated for inoculation and zosteriform site disease for 11 days.

FIG. 7 shows protection by passive immunization with anti-gC1 IgG or monoclonal anti-gC-1 1C8 in complement intact C57B1/6 mice or C3 knockout (C3KO) mice. Passive immunization with anti-gC1 IgG or monoclonal anti-gC-1 1C8 had little effect on inoculation site disease (not statistically different from non-immune IgG); however, anti-gC1 IgG or monoclonal anti-gC-1 1C8 greatly reduced zosteriform site disease in C57B1/6 mice (P<0.001 for anti-gC-1 or 1C8 compared with non-immune IgG). In contrast, anti-gC-1 IgG or 1C8 had little effect in C3KO mice (no statistical differences comparing anti-gC-1 or 1C8 with non-immune IgG at the inoculation or zosteriform sites).

We conclude from these experiments that anti-gC-1 IgG does not neutralize HSV-1 and that the protective effect detected in complement intact mice is dependent on complement. These results support our findings presented in FIGS. 1-5 that addition of gC-1 to gD-1 immunization improves vaccine efficacy by preventing gC-mediated immune evasion.

Example 6 gC2 from Multiple Strains Protects HSV-2 from Complement-Mediated Neutralization by Normal Human Serum Materials and Experimental Methods (Examples 6-12)

Cells and Viruses

African green monkey kidney cells (Vero) were grown in Dulbecco's modified Eagle's medium supplemented with 10% heat-inactivated fetal bovine serum, 10 mM HEPES (pH 7.3), 2 mM L-glutamine, 20 µg/ml gentamicin, and 1 µg/ml Fungizone (Life Technologies, Rockville, Md.). Purified virus pools were prepared by infecting Vero cells at a multiplicity of infection of 0.005. Supernatant fluids at 48 h postinfection were harvested for cell-free virus and centrifuged onto a 5% to 70% sucrose gradient.

The HSV-1 gC deletion mutant NS-gCnull was derived from strain NS and is referred to as NS-gC1null. The gC1 protein-coding region is replaced with a β-galactosidase expression cassette under the control of the HSV-1 infected-cell protein 6 (ICP6) early promoter (Friedman et al., 1996. J. Virol. 70:4253-4260; Goldstein and Weller, 1988. J. Virol. 62:2970-2977). Wild-type HSV-2 strains include HSV-2(G), HSV-2(333), and HSV-2.12, a low-passage HSV-2 isolate obtained from a genital lesion of an 18-year-old female. The HSV-2 gC deletion mutants were derived from HSV-2 strain G and strain 333 and are referred to as G-gC2null and 333-gC2Δ, respectively. The G-gC2null virus contains the β-galactosidase gene in place of gC2, while the 333-gC2Δ virus contains a 130-base-pair deletion in gC2, corresponding to 0.613 to 0.626 map units, that results in no gC2 protein expression. A gC2-null strain was constructed from HSV-2.12 by cotransfecting Vero cells with HSV-2.12 DNA and a flanking sequence vector expressing an ICP6::lacZ expression cassette flanked by 848 bp on the 5' end and 738 bp on the 3' end of gC2 sequence that replaced most of the gC2 protein-coding region starting −1 bp prior to the start site and extending to 16 bp prior to the stop site. Recombinant viruses were generated and 2.12-gC2null was isolated by selection of blue plaques and triple plaque-purified prior to use.

Complement Reagents

The source of complement was HSV-1- and HSV-2-non-immune human serum (referred to as normal human serum [NHS]) obtained from four healthy adult volunteers. Blood was clotted at room temperature for 20 min and overnight at 4° C., and serum was then separated, aliquoted, and frozen at −80° C. The absence of HSV-1- and HSV-2-specific IgG antibodies was verified by HSV enzyme-linked immunosorbent assay (ELISA) performed by the Clinical Virology Laboratory at the Children's Hospital of Philadelphia, and by virus neutralization assays as described below. Serum from each donor had normal concentrations of immunoglobulins, as measured by the Clinical Immunology Laboratory at the Hospital of the University of Pennsylvania. For donor 1, IgA was 131 mg/dl (normal, 50 to 500 mg/dl); IgG was 984 mg/dl (normal, 650 to 2,000 mg/dl); and IgM was 55 mg/dl (normal, 40 to 270 mg/dl). For donor 2, IgA was 147 mg/dl; IgG was 1023 mg/dl; and IgM was 205 mg/dl. For donor 3, IgA was 170 mg/dl; IgG was 905 mg/dl; and IgM 237 mg/dl. For donor 4, IgA was 253 mg/dl; IgG was 1,140 mg/dl; and IgM was 155 mg/dl.

When indicated, NHS was heated to 56° C. for 30 min to inactivate complement. To identify the complement pathways responsible for virus neutralization, NHS was treated with 10 mM EDTA to inactivate the classical, mannan-binding lectin, and alternative pathways; 8 mM EGTA and 2 mM $Mg^{2+}$ to inactivate the classical and mannan-binding lectin pathways; and 100 mM D-mannose to interfere with activation of the mannan-binding lectin pathway. To interfere with C3 activation, NHS was treated with the small synthetic peptide compstatin (4W9A; Hook, et al. 2006. J. Virol. 80:4038-4046; Sahu, et al. 1996, J. Immunol. 157:884-891; Kase, et al. 1999, Immunology 97:385-392; Klepeis, et al. 2003, J. Am. Chem. Soc. 125:8422-8423) at a concentration of 40 µM, while 40 µM linear compstatin was used as an inactive control.

Depletion of IgM and Complement Components from NHS

NHS was IgM depleted by adding 30 mM EDTA and passing the serum over an anti-human IgM column (Sigma, St. Louis, Mo.). The IgM purification was repeated twice to remove 90 to 95% of IgM. Serum was then dialyzed against phosphate-buffered saline (PBS) containing 1 mM EDTA to reduce the EDTA concentrations and supplemented with 1 mM $Mg^{2+}$ and 2 mM $Ca^{2+}$ prior to use in neutralization experiments.

To deplete NHS of complement components C1q, C5, and C6, immunoadsorbant columns were prepared by coupling IgG fractions of sheep or goat antiserum prepared against C1q, C5, or C6 to cyanogen bromide-Sepharose (Amersham Pharmacia Biotech, Piscataway, N.J.) at a final concentration of 10 mg/ml IgG. Isolated protein fractions were concentrated and dialyzed against PBS containing 0.1 mM EDTA to reduce EDTA concentrations and to remove sodium azide. The original volume of serum was restored with dialysis buffer and supplemented with 1 mM $Mg^{2+}$ and 2 mM $Ca^{2+}$ prior to use. Complement-depleted NHS was reconstituted with 550 µg/ml IgM, 100 µg/ml C1q, 75 µg/ml C5, or 60 µg/ml C6 (Sigma, St. Louis, Mo.) to restore physiologic concentrations.

Purified IgM

IgM was purified from NHS using an anti-IgM column (Sigma, St. Louis, Mo.). Protein-containing fractions were pooled, dialyzed against PBS at 4° C., concentrated by ultracentrifugation using membranes with a 50-kDa cutoff, and stored in aliquots at −80° C.

Neutralization Assay

Purified virus was incubated with the NHS or with heat- or EDTA-inactivated serum or PBS as controls for 1 h at 37° C. Viral titers were determined by plaque assay on Vero cells.

Assay for Classical Complement Pathway Hemolytic Activity

The total hemolytic complement activity ($CH_{50}$) of NHS or complement component-depleted serum was determined by incubating serial twofold dilutions of serum with antibody-sensitized sheep erythrocytes (EA) (Sigma, St. Louis, Mo.) for 45 min at 37° C. in 96-well microtiter plates. Intact EA were removed by centrifugation for 3 min at 120×g, the supernatant fluids were transferred to a new 96-well plate, and the percentage of EA lysed was determined by spectrophotometry at 405 nm.

ELISA to Measure IgM Binding to G-gC2Null Virus

Sucrose gradient-purified G-gC2null virus was added to 96-well High Binding Costar microtiter plates (Corning Incorporated, Corning, N.Y.) at $2×10^6$ PFU/well in Dulbecco's PBS (pH 7.1), incubated for 2 h at room temperature, and blocked overnight at 4° C. with 5% (wt/vol) nonfat milk. Serial twofold dilutions of heat-inactivated NHS diluted in PBS/0.05% Tween 20 were added for 1 h at 37° C. to virus-coated wells or to control wells coated with nonfat milk in PBS-Tween. Bound IgM was detected at an optical density of 405 nm using horseradish peroxidase-conjugated goat F(ab')$_2$ IgG anti-human IgM µ-chain (Sigma, St. Louis, Mo.). The endpoint titer was the serum dilution resulting in an optical density greater than 0.1 and at least twice the optical density of control wells.

Western Blot Analysis

Infected-cell extracts were run on 4 to 15% sodium dodecyl sulfate (SDS)-polyacrylamide gel electrophoresis (PAGE), transferred to Immobilon-P transfer membranes (Millipore Corp., Bedford, Mass.), and reacted with rabbit anti-gC2 antibody R81 and rabbit anti-VP5 antibody.

Statistical Analysis

The area under the curve (AUC) was used to compare percent virus neutralization. Student's t test (Microsoft Excel software) was used to determine P values. Results were considered significant at a probability (P) of <0.05.

Results

Figure 8:
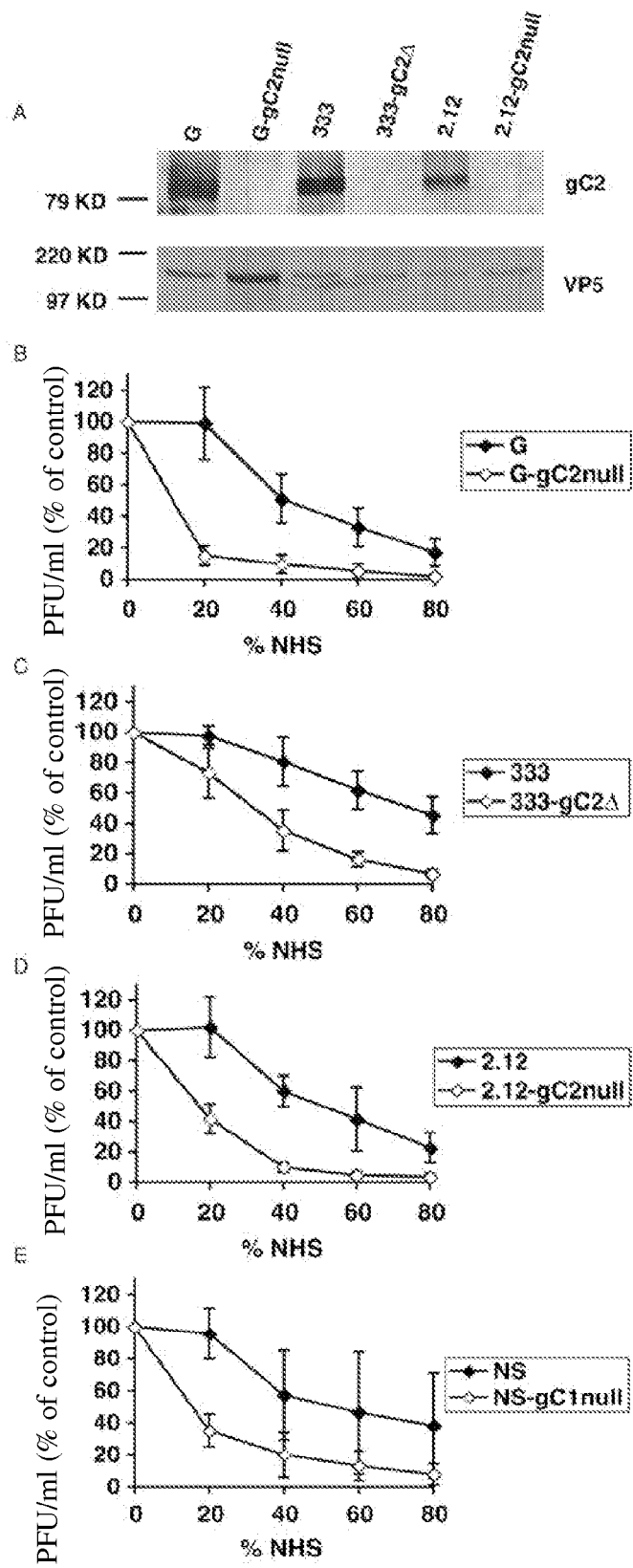
FIG. 8: (A) Western blot analysis of gC2 expression in HSV-2 wild-type- and gC2-null-infected cell extracts. The blot was probed with rabbit anti-gC2 antibody R81 or rabbit anti-VP5 as a loading control. (B to E) Neutralization of HSV-1 (NS) and HSV-2 (G, 333, and 2.12) wild-type and gC-null strains by normal human serum (NHS). Viruses were incubated with PBS (control) or NHS as the source of complement at the concentrations indicated for 1 h at 37° C. Results are expressed as PFU/ml (% of control) and were calculated as follows: (PFU with NHS/PFU with PBS)×100. Results represent the mean titers±standard deviations of 4 separate experiments for strain G and of three experiments for strains 333, 2.12, and NS. Area under the curve (AUC) comparing wild-type and gC-null viruses: P<0.0001 for strain G, P<0.002 for strain 333, P<0.001 for strain 2.12, and P<0.05 for strain NS.

The protective effects conferred by gC2 in multiple HSV-2 strains, including strains G, 333, and 2.12, were examined. Western blots confirmed expression of gC2 in wild-type—but not in gC2-null-infected cells (FIG. 8A). Neutralization assays were performed by incubating each virus with increasing concentrations of NHS as the source of complement for 1 h at 37° C. Virus incubated with PBS served as the control. All three wild-type HSV-2 viruses were more resistant to complement-mediated neutralization than the gC2-null viruses (FIG. 8B to D). Similar results were obtained with HSV-1 wild-type and gC1-null viruses (FIG. 8E). Although little or no neutralization of HSV-2 wild-type viruses occurred at a concentration of 20% NHS, the titers of 333-gCΔ, 2.12-gC2null, and G-gC2null were reduced approximately 25%, 75%, and 85%, respectively (FIG. 8B to D). The increased susceptibility to complement neutralization of gC2-null viruses persisted over the range of complement concentrations evaluated. Generally, fourfold or greater concentrations of NHS were required to achieve similar levels of neutralization of wild-type virus compared with gC2-null virus. The results indicate that gC2 protects the virus from complement-mediated neutralization.

Example 7

Neutralization of gC-Null Viruses Involves C1q

Figure 9:
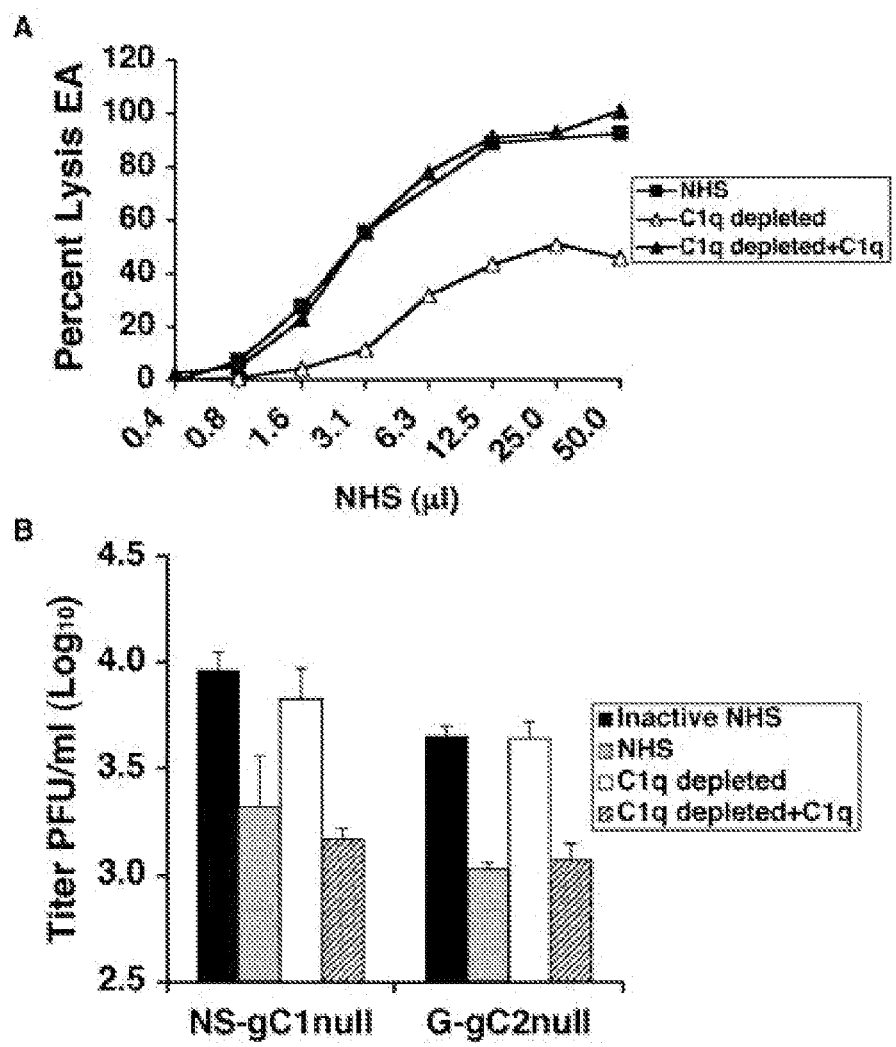
FIG. 9: (A) Total hemolytic complement activity of NHS, NHS depleted of C1q (C1q depleted), and C1q-depleted serum reconstituted with C1q (C1q depleted+C1q). EA (Sheep erythrocyte coated with IgM) were incubated with serum and the percentage of EA lysed was determined. (B) gC1-null and gC2-null viruses are neutralized by the classical complement pathway. Neutralization experiments were performed with 20% NHS that was C1q depleted or reconstituted. Results depicted represent mean titers±standard deviations of three independent experiments. P<0.02, comparing heat-inactivated NHS and either NHS or C1q-restored serum for NS-gC1null and G-gC2null. In contrast, values are not significant, P<0.23 and 0.86, comparing heat-inactivated NHS with C1q-depleted serum for NS-gC1null and G-gC2null, respectively.

To determine whether C1q, the first component of the classical complement pathway, is required to neutralize HSV-1 or HSV-2 gC-null virus, C1q was depleted from NHS, which resulted in a reduction of total hemolytic complement activity that was restored upon reconstitution with C1q (FIG. 9A). C1q-depleted serum showed residual activity despite being depleted by greater than 95%, indicating that relatively small C1q concentrations are sufficient to initiate the classical complement cascade and lyse antibody-coated erythrocytes. Neutralization experiments were performed to compare 20% NHS, C1q-depleted NHS, and C1q-depleted NHS reconstituted with C1q. As a control, virus was incubated with 20% NHS that had been heat inactivated. C1q-depleted serum did not neutralize NS-gC1null or G-gC2null, while serum reconstituted with C1q restored neutralization (FIG. 9B). Thus, neutralization of the gC-null viruses involves C1q and occurs through activation of the classical complement pathway.

Example 8

NHS from Multiple Donors Neutralizes gC-Null Viruses

Figure 10:
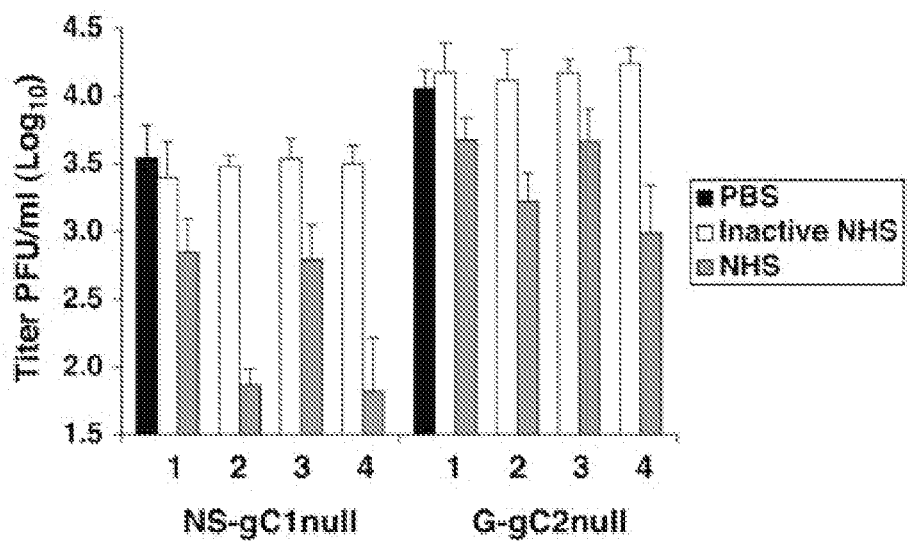
FIG. 10: Neutralization of HSV-1 and HSV-2 gC-null viruses by NHS from 4 donors occurs in the absence of specific antibodies against HSV. Neutralization experiments were performed on virus incubated with PBS, heat-inactivated NHS (inactive NHS), or 20% NHS. The four serum samples are labeled 1 to 4. Results shown represent the mean titers±standard deviations of three separate experiments. P was <0.001 for all four sera, comparing PBS with NHS for NS-gC1null, and P ranged from 0.006 to <0.001 for G-gC2null viruses. In contrast, values were not significant for PBS versus heat-inactivated NHS.

Complement neutralization of NS-gC1null and G-gC2null was measured using four HSV-1 and HSV-2 seronegative human donors, to determine whether NHS neutralization varies among subjects. All samples neutralized the gC-null viruses at 20% NHS, while heat-inactivated NHS failed to neutralize; thus, all samples exhibited complement-mediated neutralization of the gC-null viruses (FIG. 10).

Example 9

Neutralization of gC-Null Viruses Involves Activation of C3

Figure 11:
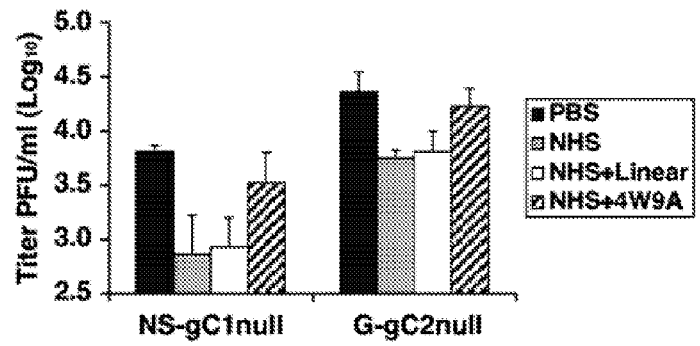
FIG. 11: Neutralization of HSV-1 and HSV-2 gC-null viruses is dependent upon C3 activation. Neutralization experiments were performed on virus treated with PBS, 20% NHS, or NHS treated with either inactive compstatin (NHS+Linear) or active compstatin (NHS+4W9A). Results represent mean titers±standard deviations of three independent experiments for NS-gC1null and three independent experiments for G-gC2null. For both viruses, differences were significant between PBS and NHS (P<0.01) and PBS and NHS treated with inactive compstatin (P<0.05). However, no significant differences were detected between PBS and NHS treated with active compstatin.

C3 is a component of all three complement pathways. High concentrations of C3 present in NHS make it difficult to deplete; therefore, compstatin was used to inhibit C3 activation and determine whether C3 is necessary to neutralize gC-null viruses. Compstatin (4W9A) is a small synthetic peptide that interferes with complement at low concentrations by binding C3, preventing its activation. Experiments were performed to examine neutralization following treatment with 20% NHS or 20% NHS treated with either active (4W9A) or inactive (linear) compstatin. As a control, virus was left untreated. NS-gC1null and G-gC2null viruses were neutralized following treatment with NHS or NHS treated with inactive compstatin (FIG. 11). NHS treated with active compstatin did not reduce viral titers, indicating that neutralization of the gC-null viruses involves C3 activation.

Example 10

Neutralization of G-gC2Null Virus Involves C5

Figure 12:
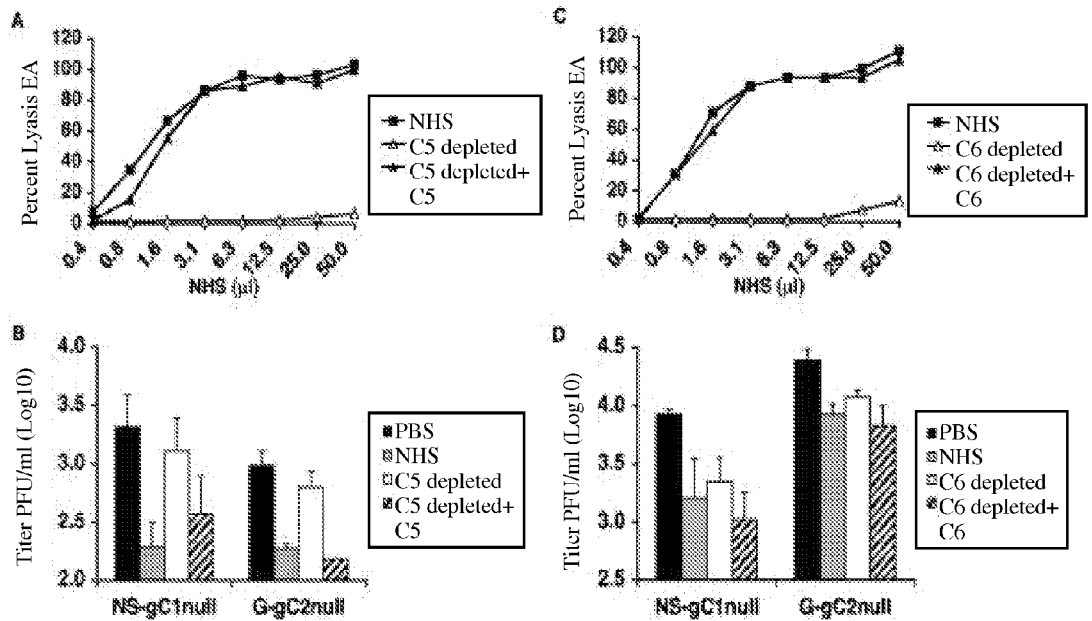
FIG. 12: (A) Total hemolytic complement activity of NHS, NHS depleted of C5 (C5 depleted), and C5-restored serum (C5 depleted+C5). (B) Neutralization of gC1-null and gC2-null viruses requires the presence of C5. Virus was incubated with PBS, 20% NHS, 20% NHS depleted of C5 (C5 depleted), or C5-restored serum (C5 depleted+C5). Results are expressed as the mean titers±standard deviations of 4 independent experiments for NS-gC1null and 2 for G-gC2null. P<0.005 for both viruses, comparing NHS and C5-restored NHS with PBS. No significant differences were detected between PBS and C5-depleted NHS. (C) Total hemolytic complement activity of NHS, NHS depleted of C6 (C6 depleted), and C6-restored serum (C6 depleted+C6). (D) Neutralization of gC1-null or gC2-null virus is not dependent on the presence of C6. Neutralization assays were performed on virus treated with PBS, 20% NHS, C6-depleted NHS (C6 depleted), and C6-restored serum (C6 depleted+C6). The results represent the mean titers±standard deviations of three independent experiments for NS-gC1null and seven experiments for G-gC2null. P<0.01 for both viruses, comparing PBS with NHS, C6-depleted, and C6-reconstituted serum.

It was next determined whether G-gC2null neutralized involves C5-dependent antibody-independent complement neutralization. Depletion of C5 from NHS reduced the total hemolytic activity, which was restored when C5 was reconstituted (FIG. 12A). NS-gC1null and G-gC2null were incubated with 20% NHS, serum depleted of C5, and C5-reconstituted serum. C5-depleted serum did not neutralize the viruses, while NHS and reconstituted serum did (FIG. 12B). Thus, G-gC2null neutralization involves C5.

Additional studies showed that neutralization of G-gC1null and G-gC2null viruses did not require activation of the alternative complement pathway, activation of the mannan-binding lectin complement pathway, or C6 (C6 result shown in FIGS. 12C and 12D).

Example 11

Natural IgM Antibody is Involved in Neutralizing gC-Null Viruses

Figure 13:
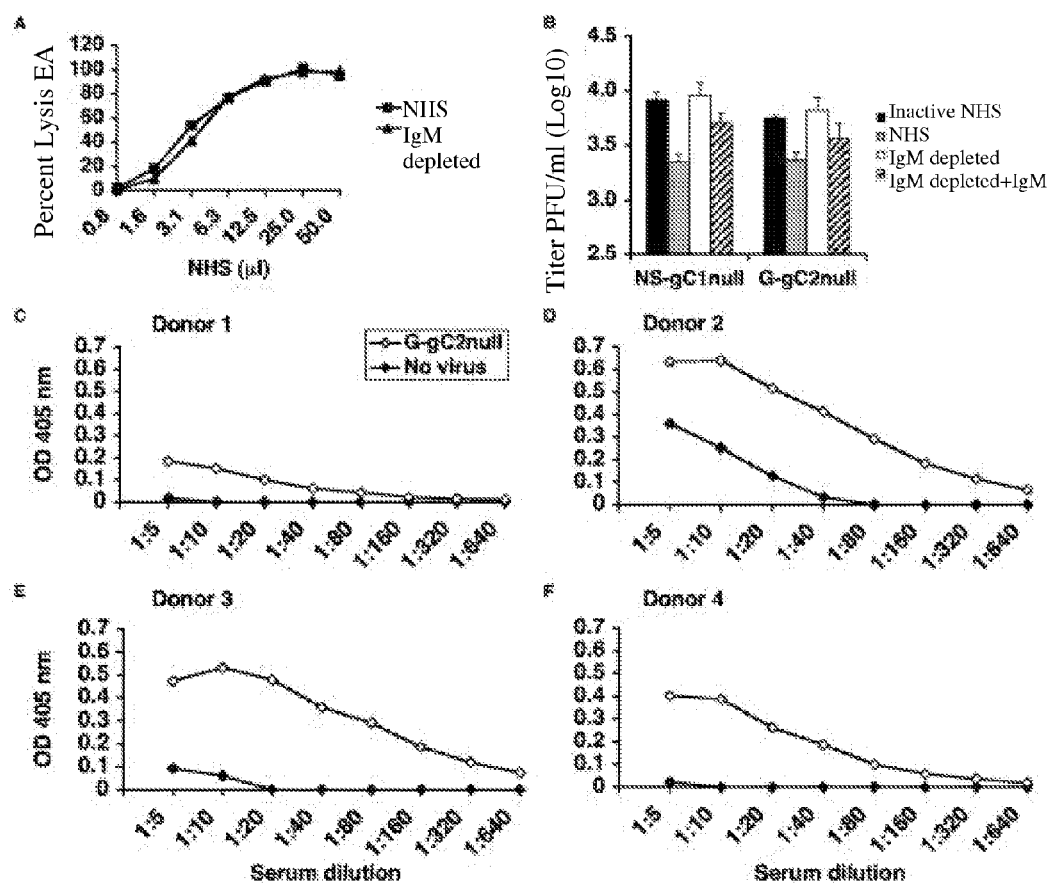
FIG. 13: (A) Total hemolytic complement activity using NHS and NHS depleted of IgM (IgM depleted). Hemolytic assays were performed using antibody-coated sheep erythrocytes to demonstrate an intact classical complement pathway in IgM-depleted serum. (B) Natural IgM antibody is required for neutralization of HSV-1 and HSV-2 gC-null viruses. The gC-null viruses were incubated with 20% NHS, heat-inactivated NHS (inactive NHS), 20% NHS depleted of IgM (IgM depleted), and IgM-restored serum (IgM depleted+IgM). The results shown represent the mean titers±standard deviations of 4 independent experiments. P<0.05, comparing IgM-depleted with reconstituted sera for NS-gC1null and G-gC2null. In contrast, values were not significant when comparing PBS with IgM-depleted serum for NS-gC1null and G-gC2null, P 0.83 and 0.31, respectively. (C to F) ELISA detects natural IgM antibody binding to gC2-null virus. Heat-inactivated 20% NHS from 4 donors was serially diluted and added to microtiter wells coated with G-gC2null or control wells. The experiment was performed twice with similar results. Results of 1 experiment are depicted.

Activation of the classical complement pathway occurs when C1q binds to IgM or two IgG molecules on the virion surface. Activation can also occur when C1q binds directly to viral membrane proteins, as reported for human cytomegalovirus and human T-cell lymphotropic virus. The role of natural IgM antibody in mediating complement neutralization was evaluated. NHS was depleted of IgM, which resulted in no loss of total hemolytic complement activity, indicating that classical complement pathway components were not depleted along with the IgM (FIG. 13A). Experiments were performed comparing neutralization after treatment with 20% NHS, 20% NHS depleted of IgM, and IgM-restored NHS. IgM-depleted serum did not neutralize NS-gC1null or G-gC2null, while NHS or IgM-reconstituted NHS neutralized these viruses (FIG. 13B). Therefore, both IgM and complement participate in neutralization of gC-null viruses.

Example 12

IgM Antibody Binds to G-gC2Null Virus

ELISA was utilized to measure binding of IgM in heat-inactivated NHS to G-gC2null. Serial twofold dilutions of serum, starting with 20% NHS, were incubated with G-gC2null or control wells. IgM in NHS from each of four donors was detected bound to G-gC2null (FIG. 13C-F). End-point titers varied among the 4 donors (donor 1, 1:20; donors 2 and 3, 1:320; and donor 4, 1:80), which correlated with the IgM concentrations in the sera (donor 1, 55 mg/dl; donor 2, 205 mg/dl; donor 3, 237 mg/dl; and donor 4, 155 mg/dl). Thus, IgM binds to G-gC2null virus.

Example 13

Identification of gE Domains Involved in Fc Receptor Activity

FcγR (IgG Fc receptor) activity and virus spread are 2 functions of gE that are carried out by overlapping but distinct domains. HSV-1 gE mediates virus spread from one epithelial cell to another, and transport within neurons. To delineate contributions of the HSV FcγR to recurrent infections, a mutant virus defective in FcγR activity but intact for spread functions was utilized; namely, an HSV-1 gE mutant virus with 4 AA (ALEG) inserted after gE amino acid 264 (NS-gE264).

NS-gE264 mutant in the murine flank model: The murine flank model measures virus spread without consideration of FcγR function, since murine IgG Fc does not bind to the HSV-1 FcγR. Therefore the HSV-1 FcγR phenotype has no impact on virulence in mice. The murine flank model was modified to assess FcγR function by passively immunizing mice with IgG from humans or rabbits, since the Fc domain of human and rabbit IgG binds to the HSV-1 FcγR. In the absence of passive immunization, zosteriform disease can be used as an indicator of the virus spread phenotype. Therefore, if NS-gE264 causes zosteriform disease similar to WT virus, spread phenotype is intact. NS-gE264 is FcγR negative, as evidenced by lack of rosettes formation by IgG-coated erythrocytes around NS-gE264-infected cells. The spread phenotype of NS-gE264 was evaluated in the mouse flank model.

Figure 14:
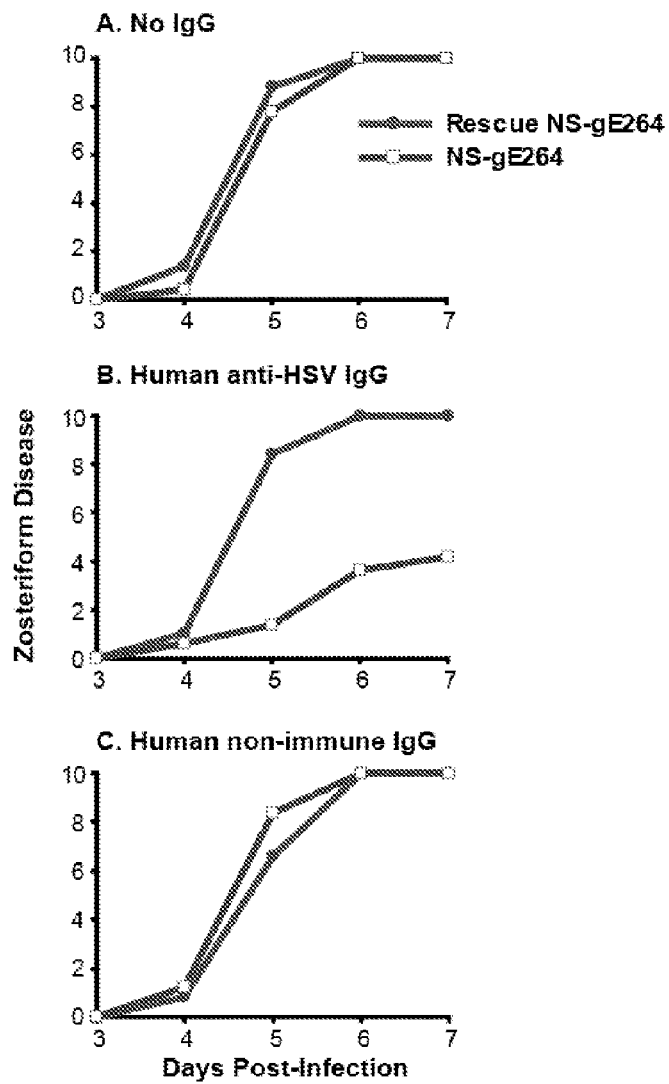
FIG. 14: NS-gE264 disease in the murine flank model. Mice were infected at $5 \times 10^5$ PFU with NS-gE264 or rescue NS-gE264 and scored for zosteriform disease days 3-7 post-infection. (A) No passive transfer of IgG: NS-gE264 causes comparable disease as the rescue virus. (B) Passive transfer of human anti-HSV IgG: NS-gE264 disease scores were significantly lower than the rescue strain (P<0.001). (C) Passive transfer of human non-immune IgG: No significant differences were present between NS-gE264 and the rescue strain. N=5 mice per group, except N=10 for the NS-gE264 with no IgG.

Mice were inoculated on the flank with $5 \times 10^5$ PFU of NS-gE264 or rescue NS-gE264, which restores the WT gE gene. Animals were scored for zosteriform disease on days 3-7 post infection (pi) by assigning 1 point for each lesion up to a maximum of 10 per day. NS-gE264 exhibited an intact spread phenotype, since zosteriform disease scores were similar in the mutant and rescue strains (FIG. 14A). To evaluate FcγR activity, mice were passively immunized with human immune (anti-HSV) IgG (capable of binding to HSV antigens by the $F(ab')_2$ domain and to the HSV-1 FcγR by the Fc domain, which blocks IgG Fc activities) or with nonimmune human IgG as a control (capable of binding only by the Fc domain to the FcγR). 16 hours later, mice were infected and evaluated for zosteriform disease on days 3-7 post-infection. Less disease was present in NS-gE264 than rescue NS-gE264 infected mice passively immunized with human anti-HSV IgG (FIG. 14B). Therefore, HSV antibody is more effective against the FcγR mutant than the rescue strain. Non-immune human IgG had no effect against either virus (FIG. 14C).

Thus, NS-gE264 has an intact spread but impaired FcγR phenotype, and the lack of an FcγR renders the virus susceptible to clearance by HSV antibodies.

Example 14 gC-1 Contributes to Virulence In Vivo

In the murine flank model, virus spreads from the inoculation site to neurons within DRG, replicates and spreads to adjacent neurons, and then returns to the skin to produce lesions in a band-like (zosteriform) distribution. In complement intact mice, an HSV-1 mutant strain defective in C3b binding (NS-gCΔC3; Δ275-367) caused less disease than WT virus at the flank inoculation and zosteriform sites, while in C3KO mice the disease was comparable to WT virus at both the inoculation and zosteriform sites.

Figure 15:
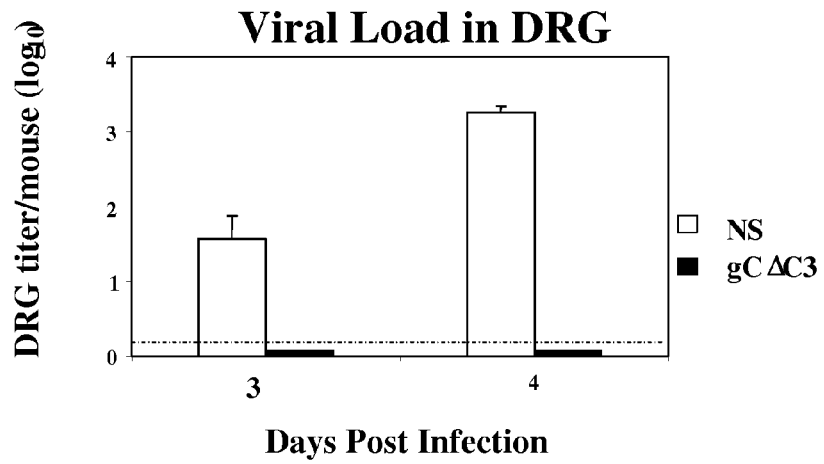
FIG. 15: Virus titers in DRG 3 and 4 dpi. Balb/C mice were inoculated in the flank with $10^5$ PFU NS (WT) or $5 \times 10^5$ PFU NS-gCΔC3. DRG from each mouse was titered separately. Results represent the average±SE of three mice per group. Line reflects the lower limit of detection (2 PFU).

To determine the contribution of gC to viral infection of DRG during primary (acute) infection, BALB/c mice were infected by scratch inoculation of the flank with $5 \times 10^5$ PFU of WT virus (NS) or NS-gCΔC3, an HSV-1 mutant virus that lacks gC-1 (AA 275-367) and does not bind C3b. At 3 and 4 days post-infection, mice were euthanized, DRG harvested and tissues titered for infectious virus (FIG. 15). By day 4, 3 $\log_{10}$ of WT virus were recovered from DRG, while no gC mutant virus was detected. The inoculation titer of NS-gCΔC3 was increased to $3 \times 10^6$ PFU and compared with NS at $5 \times 10^5$ PFU at day 5. At the higher inoculum, NS-gCΔC3 was detected in the DRG; however, titers were still 1000-fold lower than NS, indicating that gC provides at least 3 orders of magnitude protection in enabling virus to infect DRG.

Thus, under the conditions utilized, complement accounts for the decrease in DRG infection and gC-mediated immune evasion accounts for the contribution of gC-1 to virulence.

Example 15 gC-2 Contributes to HSV-2 Virulence In Vivo

Figure 16:
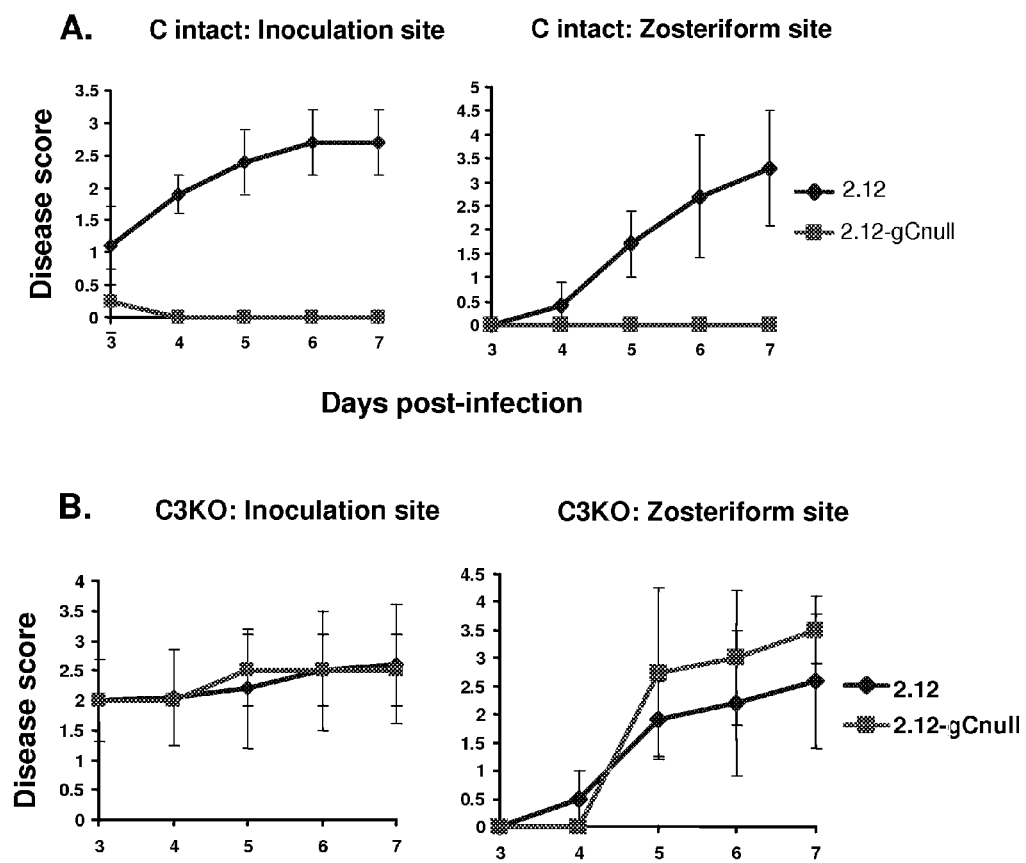
FIG. 16 (A) 2.12-gC null is less virulent than 2.12 in complement-intact mice. HSV-2 strain 2.12 and 2.12-gCnull were scratch-inoculated at $5 \times 10^5$ PFU onto the flanks of complement intact C57B1/6 mice (n=10), and disease was scored from days 3-7 pi. 2.12-gCnull caused significantly less disease at the inoculation (left panel) and zosteriform (right panel) sites (P<0.001). (B) 2.12-gCnull is as virulent as 2.12 in C3KO mice. The same experiment was performed in C3KO mice (n=4). No differences were detected between 2.12-gCnull and 2.12. Error bars represent SD.

To determine the role of HSV-2 gC in protecting the virus against complement attack in vivo, complement-intact C57B1/6 or C3KO mice were scratch-inoculated on the flank with $5 \times 10^5$ PFU WT HSV-2 strain 2.12 or a gC-2 null mutant, 2.12-gCnull, then scored for inoculation and zosteriform site disease from days 3-7 post-infection. The scoring system was modified to distinguish among animals at the severe end of the disease spectrum, since HSV-2 causes more severe flank disease than HSV-1. At the inoculation site, scores range from 0-3, with 0 representing no disease, 1 for redness or isolated lesions, 2 for ulcers, and 3 for areas with tissue necrosis. At the zosteriform site, scores range from 0-4, with 0 for no disease, 1 for isolated lesions, 2 for confluent lesions, 3 for ulcers, and 4 for areas with tissue necrosis. Disease scores of 2.12-gCnull compared with 2.12 were markedly reduced in complement intact mice (FIG. 16A), but were comparable to WT virus in C3KO mice (FIG. 16B).

Thus, HSV-2 gC mediates immune evasion, including evasion of complement, in vivo.

Example 16

Defining an Effective Immunization Dose and Schedule of HSV-1 gD and gC

Materials and Experimental Methods

Balb/C mice were inoculated intraperitoneally with three doses of gD at 10 ng/dose with or without gC at 10 microgram (μg)/dose or gD at 50 ng/dose, with or without gC at 10 μg/dose. Injections were given at 14-day intervals. The first inoculation was with Freund's complete adjuvant and the two subsequent inoculations were with Freund's incomplete adjuvant. The mock-vaccinated mice (0 gD or 0 gC) received adjuvant alone. After three inoculations serum was obtained, and analyzed for anti-gD and anti-gC antibody responses by ELISA. Rosette inhibition assays were performed as described for Example 1.

Results

Figure 18B:
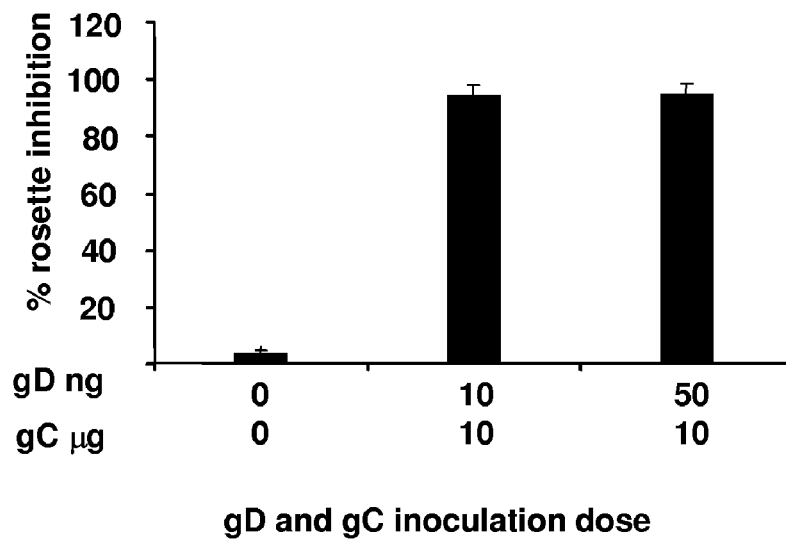

Three inoculations with 50 ng of gD in the absence of gC generated a robust anti-gD antibody response, which was reduced when 10 μg of gC was administered with the gD (FIG. 17). To improve the anti-gD response, mice were inoculated with a fourth dose of 50 ng gD in the absence of gC. Two weeks later, sera were collected, and the antibody response to gD and gC was analyzed. The fourth dose of gD significantly increased the anti-gD antibody response (FIG. 18A, bar furthest to right). In addition, the gC antibody induced following the fourth dose was able to block C3b binding, as evidenced by 85-90% inhibition of rosette formation relative to the mock group (FIG. 18B), further confirming the efficacy of this vaccine regimen.

Thus, inoculation with recombinant gC+a second HSV antigen, followed by inoculation with the second antigen alone, is an effective method for induction of anti-HSV antibody responses. Alternatively, the gC protein and the second antigen can be administered at separate sites or at separate times.

Example 17

Use of CpG+Alum as an Adjuvant for gD and gC

Materials and Experimental Methods

Mice were inoculated three times at 14-day intervals with 2 µg of gC per inoculation (a five-fold lower concentration than used with Freund's adjuvant above), 50 µg of CpG (ODN no. 1826) per inoculation and 25 µg of alum (Alhydragel® (Aluminum Hydroxide gel-Adjuvant, Accurate Chemical and Scientific Corp., Westbury N.Y., 11590) per µg of protein inoculated (final amount 50 µg alum). Serum was collected after the 2nd and 3rd inoculations.

Results

Figure 19A:
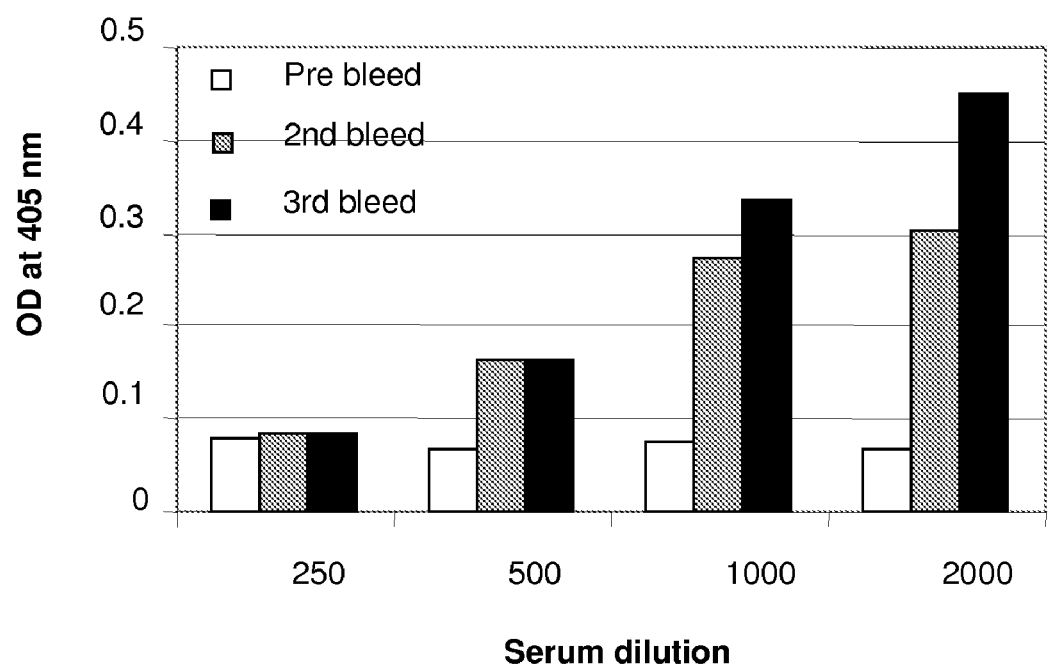
FIG. 19: (A) ELISA antibody responses to immunization with gC mixed with CpG and alum as adjuvants. (B) Ability of antisera to inhibit rosette formation of C3b-coated erythrocytes.
Figure 19B:
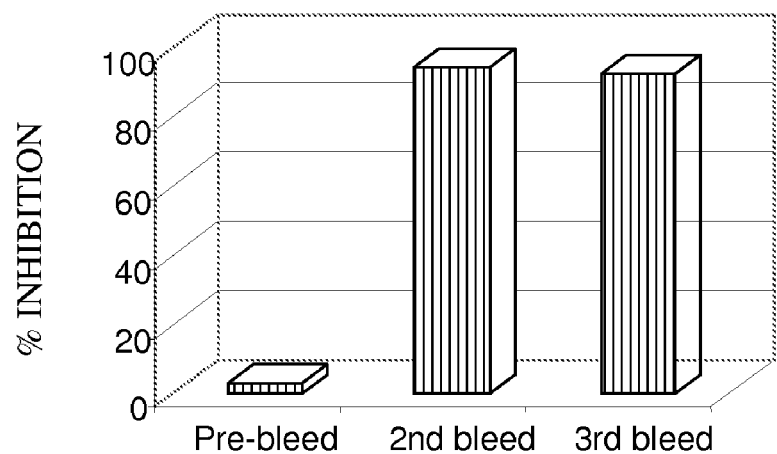

The ability of gC+alum+CpG oligonucleotide vaccines to elicit anti-gC antibodies was tested. The vaccines elicited robust antibody responses, as measured after both the $2^{nd}$ and $3^{rd}$ inoculations (FIG. 19A). Moreover, the antisera exhibited ability to potently block C3b binding site resetting (FIG. 19B).

Thus, vaccination with recombinant HSV proteins in combination with alum+CpG oligonucleotide vaccines is an effective means of eliciting anti-gC antibodies. Further, combining recombinant HSV proteins with alum+CpG oligonucleotides enables effective vaccination at a lower antigen dose than used with other adjuvants.

Example 18

HSV-2 gC-2 Subunit Vaccines are Protective Against HSV-2 Infection in Murine Flank and Vaginal HSV-2 Models Flank Model Balb/C mice were immunized intramuscularly (IM) in the gastrocnemius muscle three times at two-week intervals with 0.5, 1, 2, or 5 µg of gC-2 using CpG (50 µg/mice) mixed with alum (25 µg/µg protein), or mock-immunized with CpG (50 µg/mice) and alum (25 µg/µg) but without gC-2. Fourteen days after the third immunization, mice were challenged on the shaved and chemically denuded flank by scratch inoculation with $4 \times 10^5$ PFU of HSV-2 strain 2.12. Survival was recorded from days 0-14 and animals were scored for disease severity at the inoculation and zosteriform sites from days 3-14 (N=5 mice per group). The scoring system for disease at the inoculation and zosteriform sites was as described in the anti-gC-1 passive transfer experiments.

Vaginal Model

Balb/C mice were mock-immunized IM in the gastrocnemius muscle with CpG (#1826, Coley Pharmaceuticals Group) (50 µg/mice) and alum (25 µg/µg protein) (Accurate Chemicals) or immunized with 1, 2, or 5 µg of gC-2 with CpG and alum at two-week intervals. Five animals in each group were immunized three times, except one group was immunized with the 5 µg dose twice [labeled as 5 µg (2×) in contrast to the group labeled 5 µg (3×)]. Nine days after the third immunization or 23 days after the 5 µg (2×) immunization, mice were injected IP with Depo Provera® (a 150 mg aqueous suspension of medroxyprogesterone acetate for depot injection by Pfizer; 2 mg/mouse) to synchronize the estrus cycle. Five days later, mice were challenged intra-vaginally with $2 \times 10^5$ PFU of HSV-2 strains 2.12.

Animals were observed for mortality from days 0-14 and for disease scores from days 3-14 post-challenge. The scoring system for vaginal disease assigned one point for each of the following: redness or swelling, exudate, loss of hair around the vaginal and anal areas, and necrosis. The maximum score per day was four points. Animals that died before the end of the experiment were assigned the score at the last evaluation for the duration of the study period. Vaginal swabs were performed daily from days 1-11. The swabs were placed in one ml DMEM and viral titers were performed by plaque assay on Vero cells.

Results

Figure 20:
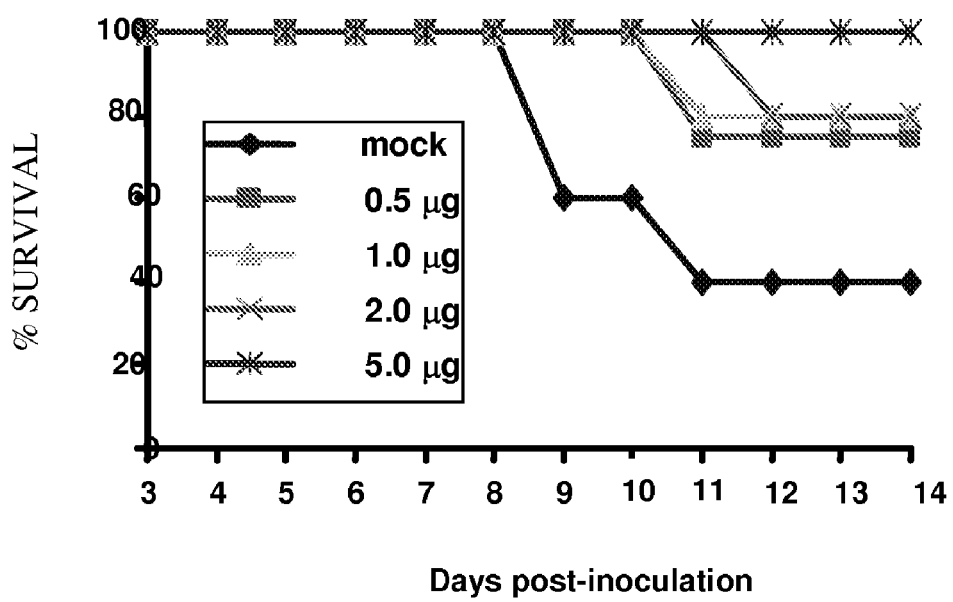
FIG. 20: Survival in gC-2-immunized mice after flank exposure to HSV-2. Balb/C mice were immunized IM in the gastrocnemius muscle three times at two-week intervals with 0.5, 1, 2, or 5 μg of gC-2 using CpG (50 μg/mice) mixed with alum (25 μg/μg protein), or mock-immunized with CpG and alum but without gC-2. Fourteen days after the third immunization, mice were challenged on the shaved and chemically denuded flank by scratch inoculation with $4 \times 10$ PFU of HSV-2 strain 2.12. Survival was recorded from days 0-14.

For flank inoculation, mice were protected against death at each gC-2 immunization dose compared with mock-immunized mice. However, 100% survival was only observed at the 5 µg dose, which was the highest dose tested (FIG. 20).

Figure 21:
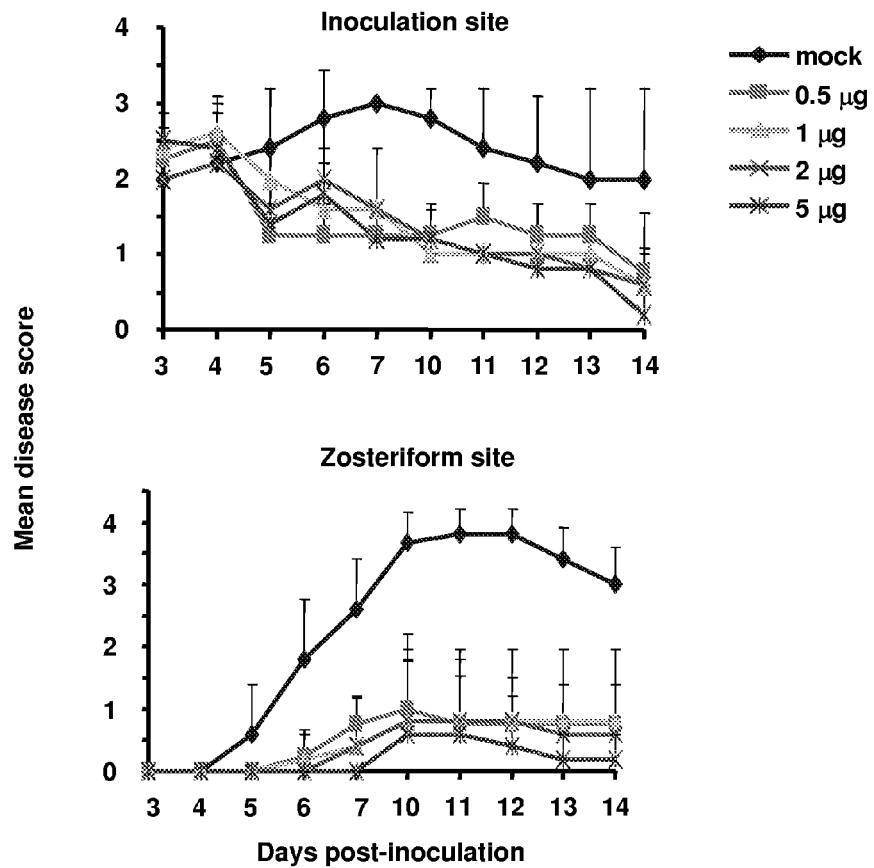
FIG. 21: Disease severity at the inoculation and zosteriform sites in gC-2-immunized mice after flank exposure to HSV-2. Experiments were performed as in FIG. 20. After scratch inoculation challenge with $4 \times 10^5$ PFU of HSV-2 strain 2.12, animals were scored for disease severity at the inoculation and zosteriform sites from days 3-14 (N=5 mice per group).

FIG. 21 demonstrates that inoculation and zosteriform site disease scores were reduced in mice immunized with 0.5 µg, 1 µg, 2 µg, and 5 µg of gC-2 compared with mock-immunized mice from days 3-14 post-challenge with the greatest reduction at the zosteriform site noted with the 5 µg dose (comparing Area Under the Curve for the 5 µg dose with mock-immunized mice at the inoculation and zosteriform sites, P<0.01).

Figure 22:
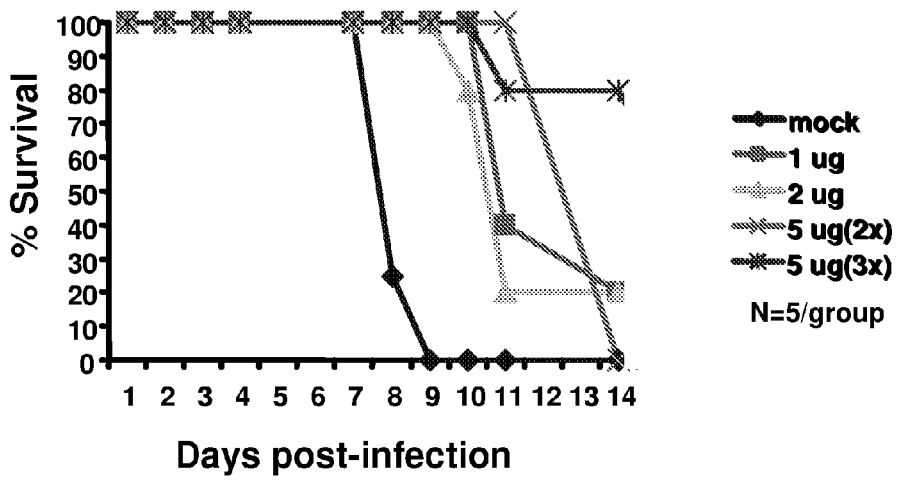
FIG. 22. Survival in gC-2-immunized mice after vaginal exposure to HSV-2. Balb/C mice were mock-immunized IM in the gastrocnemius muscle with CpG (50 μg/mice) and alum (25 μg/μg protein) or immunized with 1, 2, or 5 μg of gC-2 with CpG and alum at two-week intervals. Five animals in each group were immunized three times, except one group was immunized with the 5 μg dose twice [labeled as 5 μg (2×)], while another group of five mice was immunized three times [labeled as 5 μg (3×)]. Nine days after the third immunization or 23 days after the 5 μg (2×) immunization, mice were injected intraperitoneally (IP) with Depo Provera® (2 mg/mouse) to synchronize the estrus cycle. Five days later, mice were challenged intra-vaginally with $2 \times 10^5$ PFU of HSV-2 strain 2.12. Animals were observed for mortality from days 0-14.

For intra-vaginal inoculation, all mock-immunized mice died, while immunization with gC-2 5 µg (3×) offered the best protection against death. All mice immunized with gC-2 5 µg (2×) died, although time to death was delayed compared with mock-immunized mice. Mice immunized three times with 1 or 2 µg survived slightly longer and fewer died compared to mock-immunized mice, but protection was not as good as with gC-2 5 µg (3×) (FIG. 22).

Figure 23:
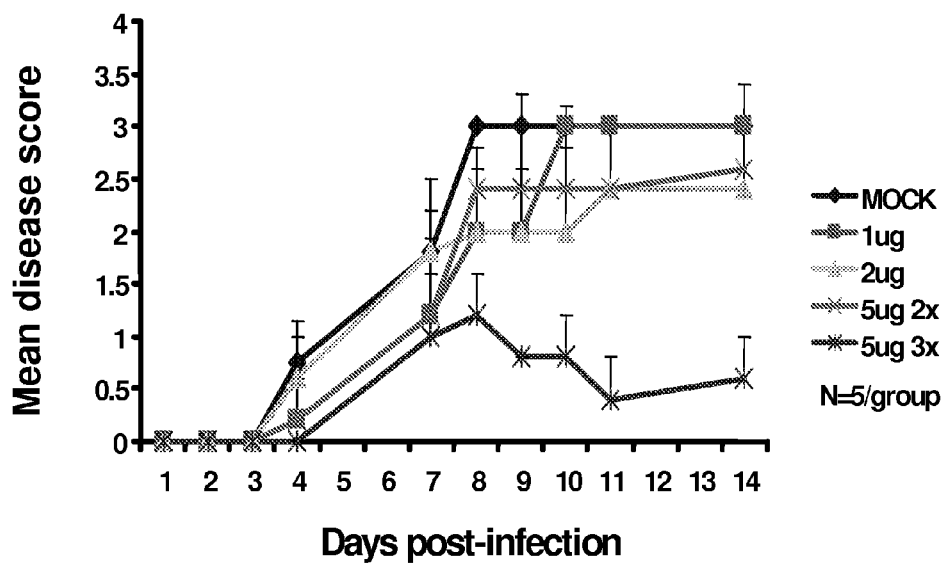
FIG. 23: Mean disease score in gC-2-immunized mice after vaginal exposure to HSV-2. Experiments were performed as in FIG. 22. After intra-vaginal challenge with $2 \times 10^5$ PFU of HSV-2 strain 2.12, animals were scored for disease severity from days 3-14.

Disease scores of mock-immunized or gC-2-immunized mice challenged intravaginally with $2 \times 10^5$ PFU of HSV-2 strains 2.12 are shown in FIG. 23. All mice died in the mock-immunized group by day 8; therefore, the score at the last evaluation was assigned from days 9-14. Immunization with 1 or 2 µg of gC-2 provided little protection from vaginal disease, while immunization with gC-2 at 5 µg (3×) provided significant protection, P<0.01.

Figure 24:
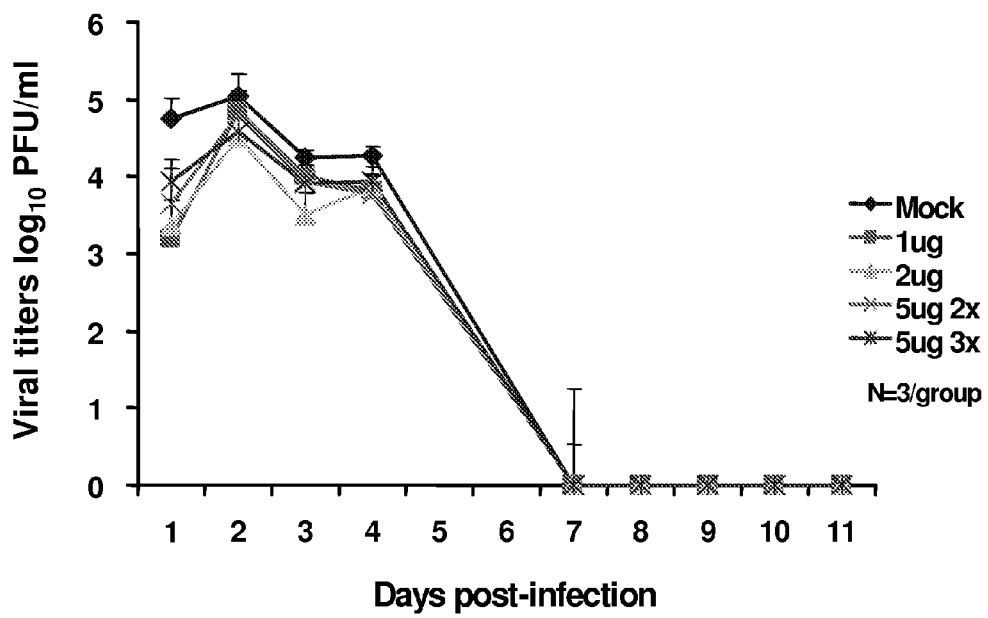
FIG. 24: Vaginal HSV-2 viral titers in gC-2-immunized mice after vaginal exposure to HSV-2. Experiments were performed as in FIG. 22. Vaginal swabs were obtained daily from days 1-11 post-challenge, and viral titers were determined.

Vaginal swabs were obtained daily from days 1-11 post-challenge (FIG. 24). Results shown are the average titers of three mice per group. Immunizations with gC-2 reduced vaginal titers by 1-2 $\log_{10}$ on day 1 post-challenge, but had little effect on subsequent days.

Example 19

HSV-2 gD-2 Subunit Vaccines are Protective Against HSV-2 Infection in Murine Flank and Vaginal HSV-2 Models Materials and Experimental Methods Flank Model Balb/C mice were mock immunized or immunized IM in gastrocnemius muscle three times as described above for gC-2 except that the gD-2 doses were 10, 25, 50, or 100 ng combined with CpG (50 µg/mice) and alum (25 µg/µg protein). Mice were challenged with $4 \times 10^5$ PFU/10 ml of HSV-2 strain 2.12. Five mice per group were inoculated.

Vaginal Model

Balb/C mice were immunized IM three times (3×) with 50, 100, or 250 ng of gD-2 or twice (2×) with 250 ng of gD-2. The gD-2 was combined with CpG (50 µg/mice) and alum (25 µg/µg protein) prior to inoculation with $2 \times 10^5$ PFU of HSV-2 strain 2.12. Mice were treated with Depo Provera® and challenged as described above for gC-2 immunization and evaluated for survival and disease severity. Each group comprised five animals. Vaginal swabs were obtained daily from days 1-11 post-challenge, with three mice in each group.

Results

Figure 25:
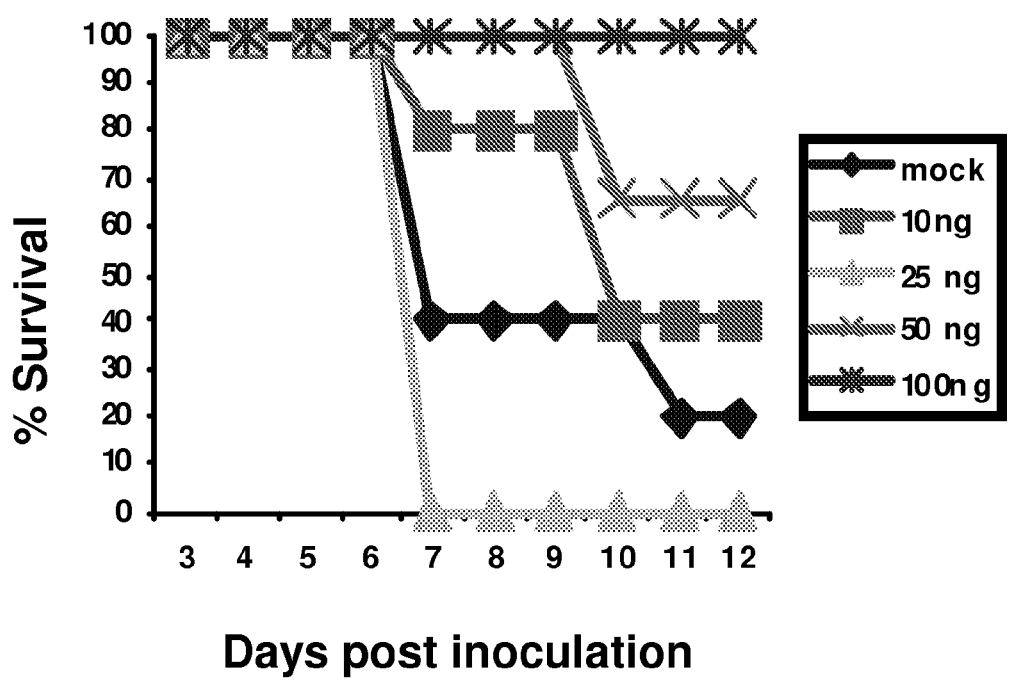
FIG. 25: Survival in gD-2-immunized mice after flank exposure to HSV-2. Balb/C mice were mock immunized or immunized IM in gastrocnemius muscle three times with 10, 25, 50, or 100 ng of gD-2 with CpG (50 μg/mice) and alum (25 μg/μg protein). Mice were challenged by flank inoculation with $4 \times 10^5$ PFU/10 ml of HSV-2 strain 2.12.

For flank inoculation, the highest rate of survival was observed in mice immunized with 100 ng gD-2 and then in mice immunized with 50 ng (FIG. 25).

Figure 26:
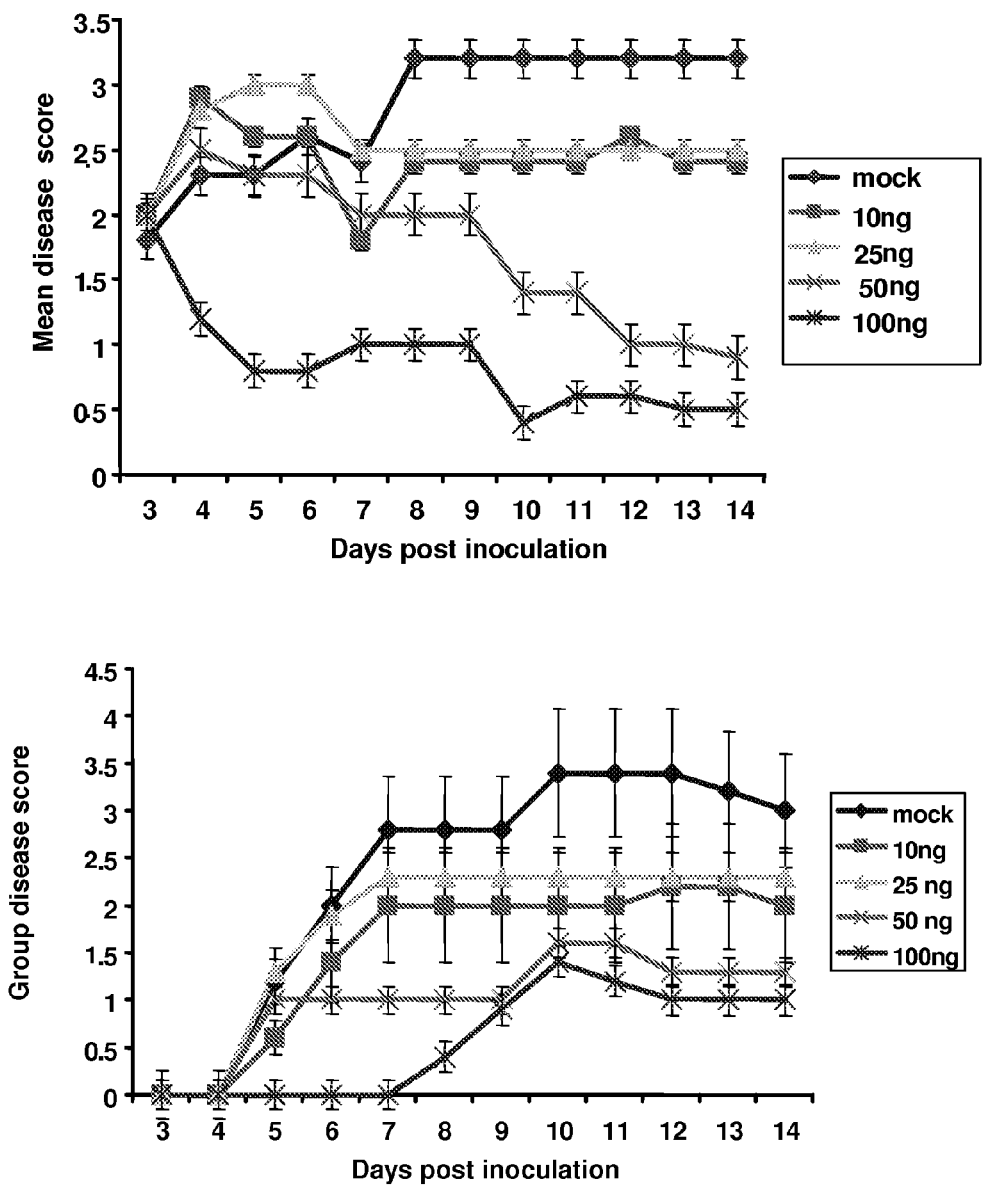
FIG. 26: Mean disease score in gD-2-immunized mice after flank exposure to HSV-2. Experiments were conducted as described in FIG. 25. After flank inoculation with $4 \times 10^5$ PFU/10 ml of HSV-2 strain 2.12, animals were scored for disease severity at the inoculation and zosteriform sites from days 3-14.

Immunizations with gD-2 at 10 ng and 25 ng doses provided minimal protection against inoculation or zosteriform site disease; however, at 50 ng and 100 ng doses disease scores were significantly reduced ($P<0.01$ comparing mock and the 50 ng dose at the inoculation and zosteriform sites, $P<0.001$ comparing mock and the 100 ng dose at the inoculation and zosteriform sites) (FIG. 26).

Figure 27:
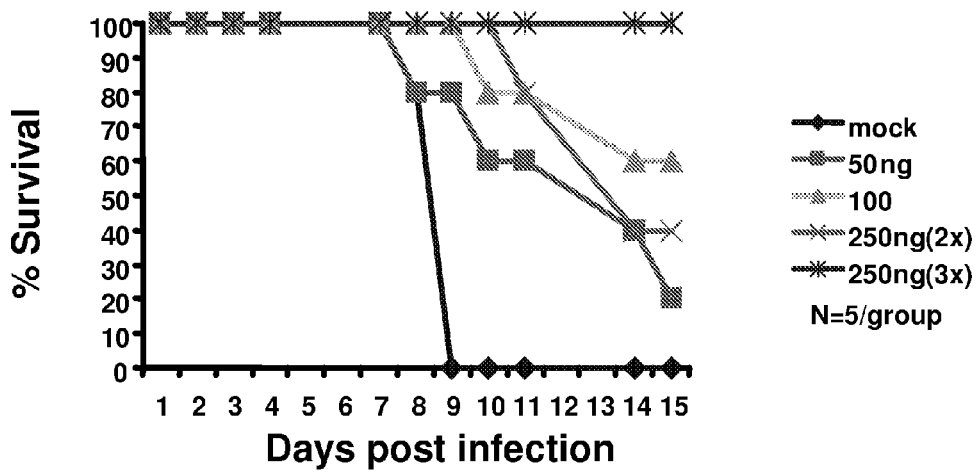
FIG. 27: Survival in gD-2-immunized mice after vaginal exposure to HSV-2. Balb/C mice were immunized IM three times (3×) with 50, 100, or 250 ng (3×) of gD-2 or twice (2×) with 250 ng of gD-2. The gD-2 was combined with CpG (50 μg/mice) and alum (25 μg/μg protein) prior to inoculation as described in FIG. 22 for gC-2. Mice were treated with Depo Provera® and challenged with $2 \times 10^5$ PFU of HSV-2 strain 2.12 as described in FIG. 22 for gC-2 immunization and evaluated for survival and disease severity.

For intravaginal inoculation, none of the mice survived in the mock-immunized group beyond day 9 (FIG. 27). Immunization with 50 ng, 100 ng and 250 ng 2× of gD-2 provided some protection; however, 250 ng 3× provided complete protection against death.

Figure 28:
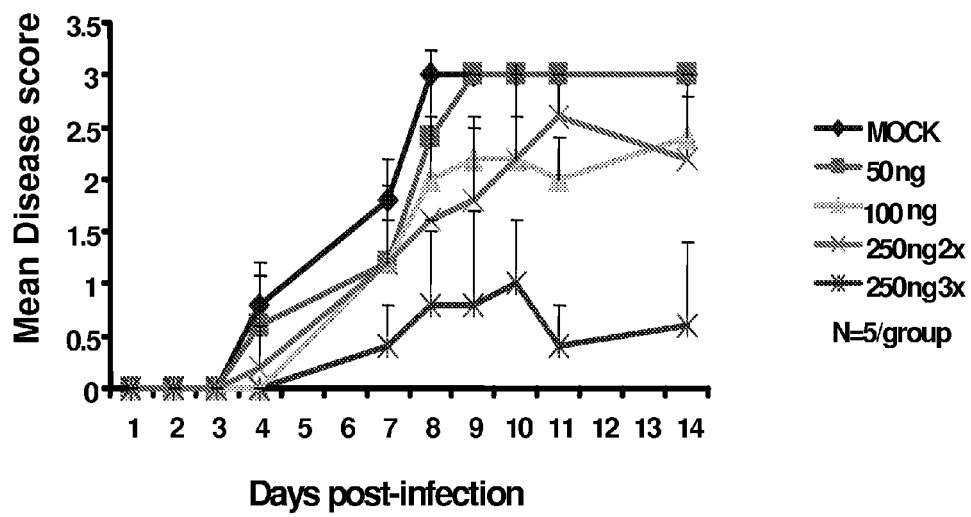
FIG. 28: Mean disease score in gD-2-immunized mice after vaginal exposure to HSV-2. Experiments were conducted as described in FIG. 27. After intra-vaginal challenge with $2 \times 10^5$ PFU of HSV-2 strain 2.12, animals were scored for disease severity from days 3-14.

Only mice immunized with gD-2 at 250 ng 3× were significantly protected from vaginal disease (comparing Area Under the Curve of mock and gD-2 250 ng 3×, $P<0.001$) (FIG. 28).

Figure 29:
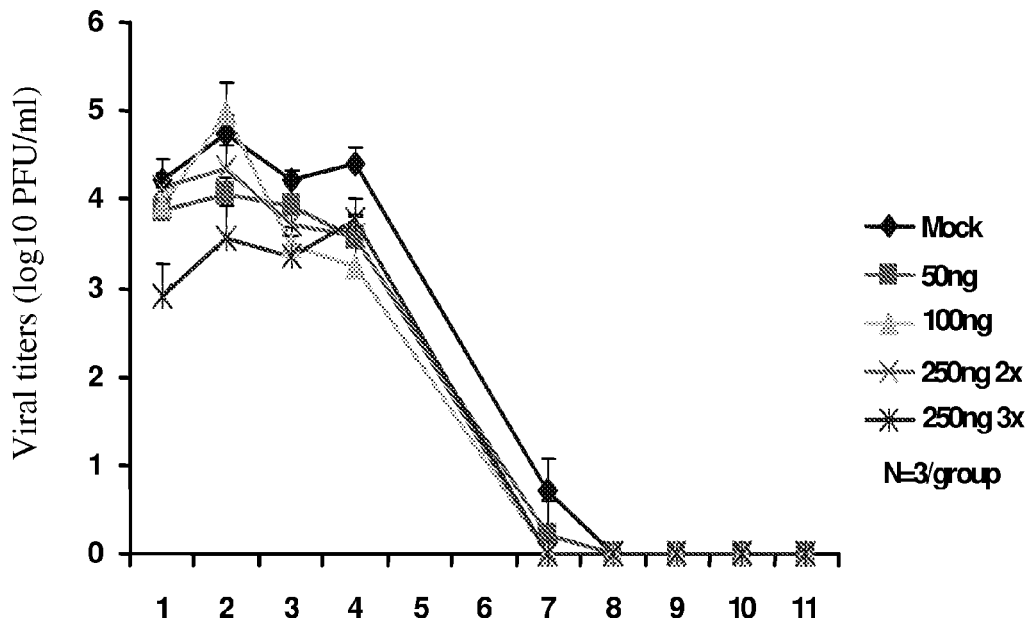
FIG. 29: Vaginal HSV-2 viral titers in gD-2-immunized mice after vaginal exposure to HSV-2. Experiments were performed as in FIG. 27. Vaginal swabs were obtained daily from days 1-11 post-challenge, with three mice in each group.

Immunizations with gD-2 250 ng 3× reduced vaginal titers by ~1 $\log_{10}$ on days 1-7 post-challenge ($P<0.001$ compared with mock-immunized mice), while the other doses had a smaller effect compared with mock-immunized mice (p values not significantly different) (FIG. 29).

The experiments in Examples 18 and 19 described a dose of gC-2 (5 µg) and gD-2 (250 ng) for immunization capable of protecting mice against HSV-2-mediated death, and inoculation and zosteriform site disease in both flank and vaginal models of HSV-2.

Example 20

Combination gC-2/gD-2 Vaccines Confer Protection Superior to Vaccines Containing gD-2 Alone Materials and Experimental Methods Vaginal Model: Balb/C mice were mock immunized or immunized with 5 µg gC-2 alone, 250 ng gD-2 alone, or combined 5 µg gC-2 & 250 ng of gD-2 three times at two week intervals. The antigens were mixed with CpG and Alum as adjuvants as described earlier. Each glycoprotein was incubated in a separate tube with CpG and Alum, and for the combined gC-2 and gD-2 immunization, the materials were mixed together just prior to the time of intramuscular (IM) inoculation. Serum was taken two weeks after the third immunization and tested for antibody to gC-2 and gD-2. Mice were treated with Depo Provera® (2 mg/mouse) 5 days before intravaginal challenge with HSV-2 strain 2.12 ($10^5$ PFU in 5 µl inoculation volume). Mice were observed daily for 14 days for survival. Mice were scored and swabbed daily for vaginal disease and vaginal titers for 11 days. In a parallel but identical set of experiments, sacral ganglia were isolated on day 4 post infection and titered on Vero cells.

Flank Model: Balb/C mice were mock immunized or immunized with 5 µg gC-2 alone, 250 ng gD-2 alone, or combined 5 µg gC-2 & 250 ng gD-2 three times at two week intervals. The antigens were mixed with CpG and Alum adjuvants as described above for the vaginal infection model. Fourteen days after the third IM immunization, mice were challenged on the shaved and chemically denuded flank by scratch inoculation with $2 \times 10^5$ PFU of HSV-2 strain 2.12. Survival was recorded from days 0-14 and animals were scored for disease severity at the inoculation and zosteriform sites from days 3-14 (N=5 mice per group). The scoring system for disease at the inoculation and zosteriform sites was as described for HSV-1 studies.

Results

Vaginal Model

Figure 30:
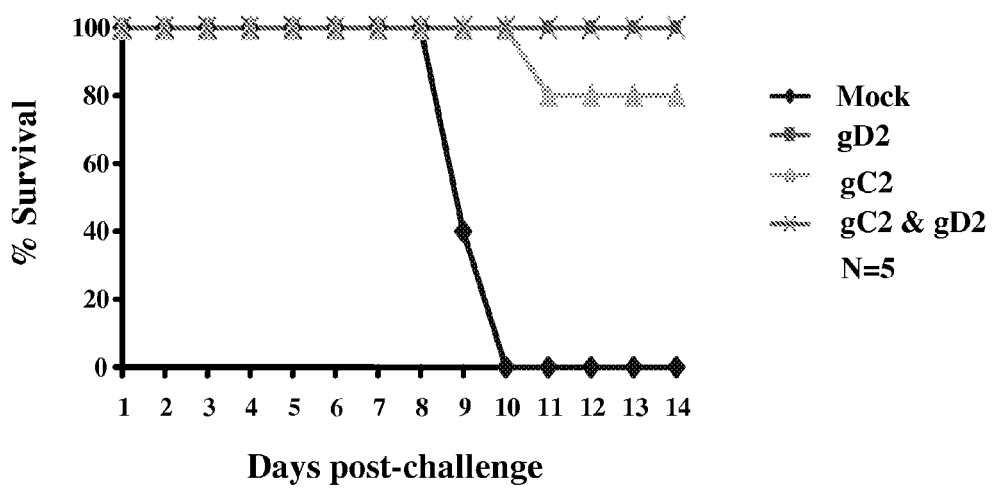
FIG. 30: Survival of mice immunized with gC-2, gD-2 or gC-2 & gD-2 and challenged with $10^5$ PFU of HSV-2 (strain 2.12) by vaginal inoculation (N=5 per group).
Figure 31:
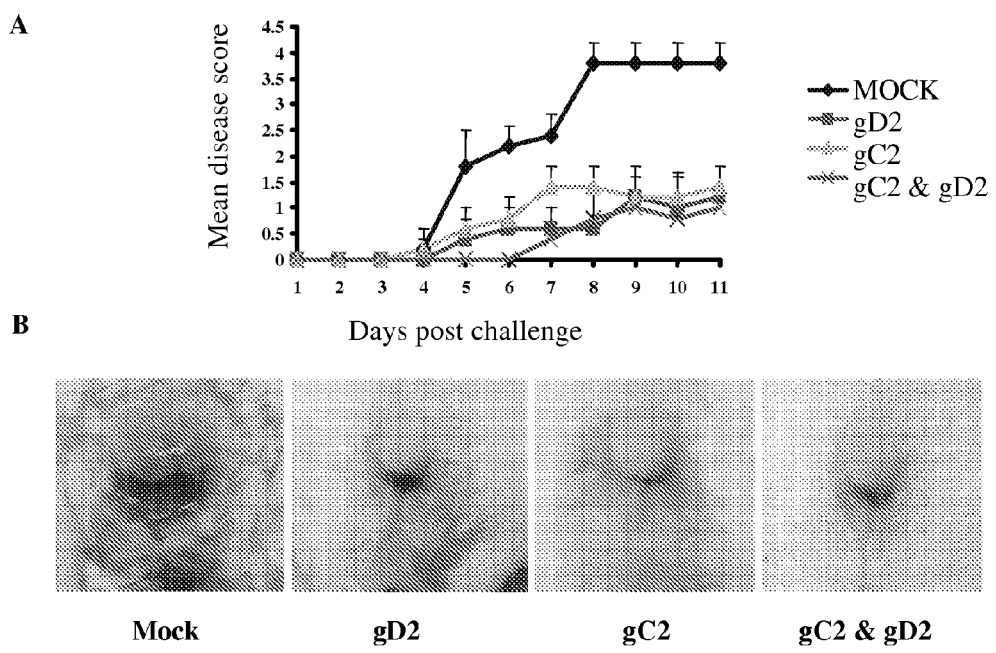
FIG. 31: Vaginal disease scores. A. Mice were immunized with gC-2, gD-2 or gC-2 & gD-2 and challenged with 10 PFU of HSV-2 (strain 2.12) by vaginal inoculation. B. Images of vaginal disease of one mouse in each group taken 7 days post challenge. The results represent the mean±SEM of 5 mice in each group.

All mock-immunized mice died, while survival in the gC-2 alone group was 80%, and in the gD-2 alone or combined gC-2 & gD-2 group survival was 100% (FIG. 30).

Vaginal disease scores are shown in FIG. 31A. Mock-immunized mice showed extensive vaginal disease, while the gC-2 alone, gD-2 alone and combined gC-2 & gD-2 groups were significantly protected from the vaginal disease ($P<0.001$ comparing mock to each treatment group; gC-2 or gD-2 are not significantly different from the gC-2 & gD-2 combined group, $P>0.05$). The combined group showed delayed onset of disease that first appeared on day 7 as hair loss around the base of the tail. Images of vaginal disease are shown on day 7 post-infection (FIG. 31B). One representative animal from each group is shown. The mock group developed severe disease, while gC-2 or gD-2 immunized mice had very mild disease, and the combined immunization group had the least disease.

Figure 32:
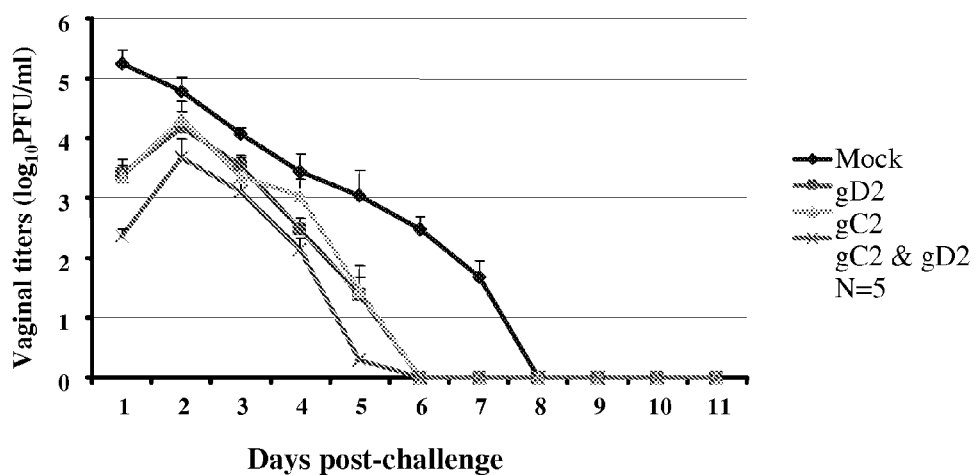
FIG. 32: The vaginal viral titers from mock-immunized and each immunization group after vaginal challenge with HSV-2 ($10^5$ PFU). The results represent the mean±SEM of 5 mice in each group.

The vaginal viral titers are shown in FIG. 32. The mock-immunized mice had ~5-6 $\log_{10}$ titers on day one which gradually declined over 8 days. Immunization with gC-2 or gD-2 reduced viral titers by ~2 $\log_{10}$ on day one, which became undetectable by day 6. The combined gC-2 & gD-2 group had reduced viral titers by ~3 $\log_{10}$ on day one ($P<0.001$ comparing the combined group to mock, gD-2 or gC-2 alone group) and cleared virus more rapidly ($P<0.001$ comparing day 5 viral titers from the combined group to mock, gD-2, or gC-2 alone group).

Figure 33:
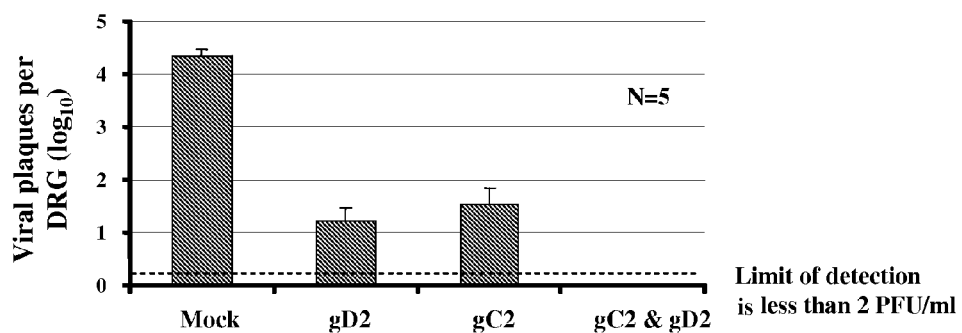
FIG. 33: Protection of sacral DRG by gC-2 & gD-2 immunization. Results represent the mean±SEM of 5 mice in each group.

To examine whether the combined gC-2 and gD-2 immunization protected DRG from infection, we performed viral plaque assays on homogenized sacral DRG as described in Example 3. Approximately 4 $\log_{10}$ PFU were detected in the mock-immunized mice (FIG. 33). Immunization with gD-2 or gC-2 alone reduced the viral titers in DRG 2-3 $\log_{10}$; however, no infectious viral titer was detected in mice immunized with the combined gC-2 & gD-2 ($P<0.001$ comparing the combined group to mock, gD-2, or gC-2 mice).

Flank Model

Figure 34:
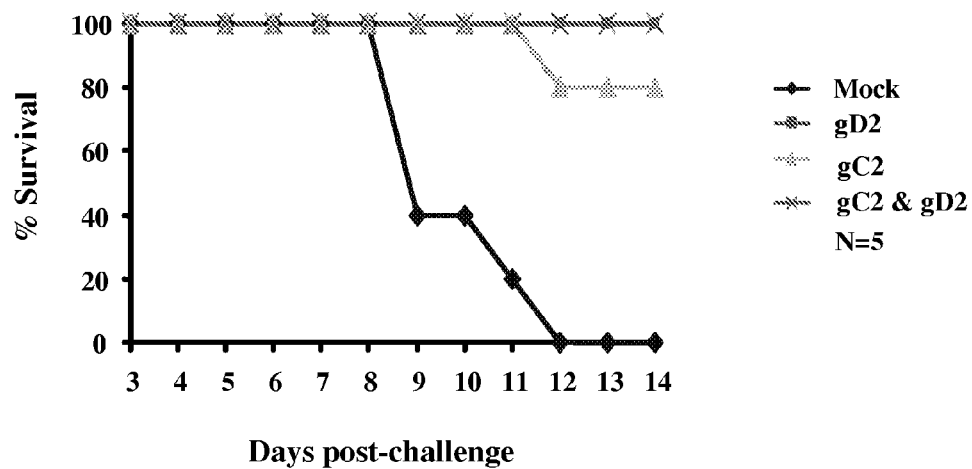
FIG. 34: Survival of mice immunized with gC-2, gD-2 or gC-2 & gD-2 and challenged with $2 \times 10^5$ PFU of HSV-2 (strain 2.12) by epidermal scratch inoculation (N=5 per group).

All mock-immunized mice died, while 80% survived when immunized with gC-2 alone, and 100% survived when gD-2 alone or the combined gC-2 & gD-2 immunizations were administered (FIG. 34).

Figure 35:
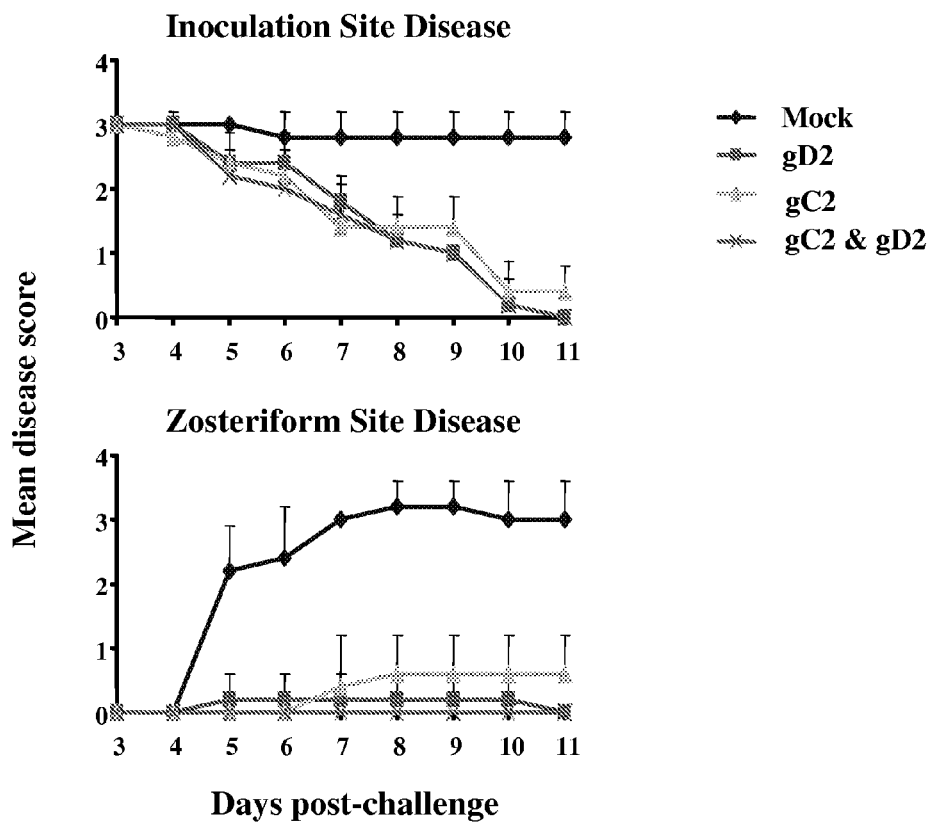
FIG. 35: Inoculation and zosteriform site disease scores of mice immunized with gD-2, gC-2, or gC-2 & gD-2 and challenged with $2 \times 10^5$ PFU of HSV-2 (strain 2.12). The results represent the mean±standard error of 5 mice in each group.

Inoculation site disease scores were reduced in mice immunized with gC-2, gD-2 or the combined gC-2 & gD-2 compared with mock-immunized mice (FIG. 35, $P<0.001$). There were no significant differences among the three immunization groups. Zosteriform site disease was significantly reduced in gC-2 or gD-2 alone groups ($P<0.001$ compared with mock). No zosteriform disease was observed in the combined gC-2 & gD-2 immunization group.

Figure 36:
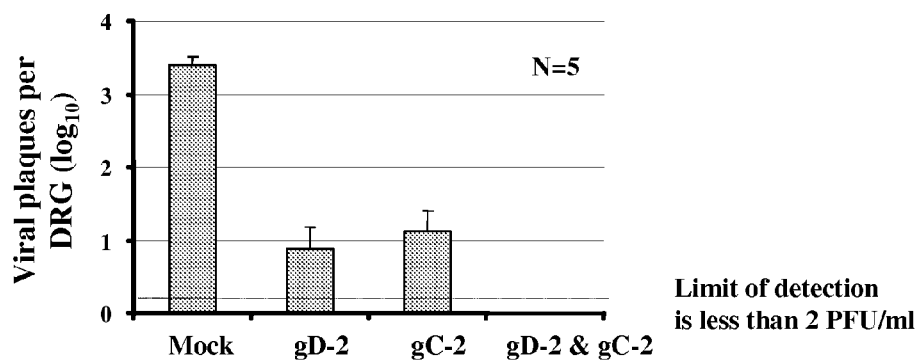
FIG. 36: Protection of DRG by gC-2 & gD-2 immunization. Results represent the mean±SEM of 5 mice in each group.

To examine whether the combined gC-2 & gD-2 immunization protected DRG from infection, we performed viral plaque assays on homogenized DRG (FIG. 36). Approximately 3.5 $\log_{10}$ PFU were detected in the mock-immunized mice. Immunization with gD-2 or gC-2 alone reduced the viral titers in DRG by about 2 $\log_{10}$; however, no infectious virus was detected in mice immunized with the combined gC-2 & gD-2 (P<0.001 comparing the combined group to mock, gD-2, or gC-2 mice).

Example 21

Immunization with gC-2 Induces HSV-2 Neutralizing Antibody

To obtain anti gC-2 IgG, mice were immunized three times IM with 5 µg of gC-2 mixed with CpG and alum, as described above. Serum was obtained two weeks after the third immunization and shown to interact with gC-2 protein by Western blot and ELISA (results not shown). IgG was purified from the mouse serum on a protein G column (Hi-Trap™, Amersham Biosciences, Uppsala, Sweden) and tested for neutralizing antibody activity. As controls, gD-2 antibody was evaluated for neutralizing activity as was non-immune murine IgG. Approximately 250 PFU of HSV-2, strain 2.12 was incubated with anti-gC-2 IgG obtained from immunized mice, or with anti-gD-2, non-immune murine IgG or anti-gD-1 MAb DL11, an antibody that shows potent neutralizing activity against HSV-1 (described hereinabove). Viruses were incubated with antibody for 1 hour at 37° C.; then virus titers were then determined by plaque assay on Vero cells.

Results

Figure 37:
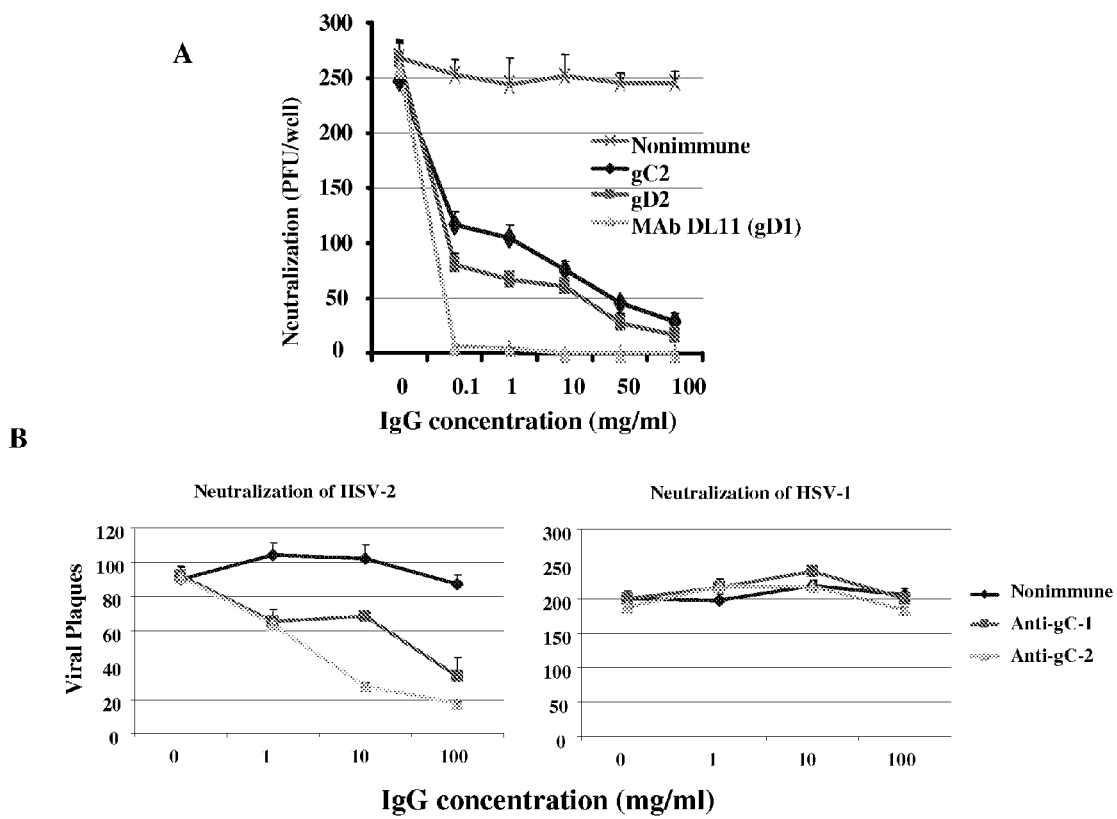
FIG. 37: A. Anti-gC-2 IgG neutralizes HSV-2. Virus was incubated with murine anti-gC-2 or anti-gD-2 IgG or murine nonimmune IgG, and titers determined by plaque assay on Vero cells. B. Anti-gC-2 or anti-gC-1 IgG neutralize HSV-2 (left panel) but not HSV-1 (right panel). Each data point represents mean±SEM of two separate assays each performed in triplicate.

Anti-gC-2 IgG neutralized HSV-2 virus at comparable IgG concentrations as anti-gD-2 IgG (although 20-fold higher concentrations of gC-2 than gD-2 was used for immunization) (FIG. 37A). As expected, DL11 demonstrated potent neutralizing activity and murine non-immune IgG failed to neutralize HSV-2.

Additional experiments were performed using IgG purified from mice immunized with gC-1, gC-2 or murine non-immune IgG. Antibodies to gC-1 neutralized HSV-2, although not as effectively as antibodies to gC-2 (FIG. 37B, left panel). Anti-gC-1 IgG or anti-gC-2 IgG failed to neutralize HSV-1 (FIG. 37B, right panel). Therefore, neutralizing antibodies are produced to HSV-2 after gC-1 or gC-2 immunization, but not to HSV-1 after gC-1 or gC-2 immunization.

Example 22

Anti-gC-2 IgG Blocks C3B Binding to GC-2

Figure 38A:
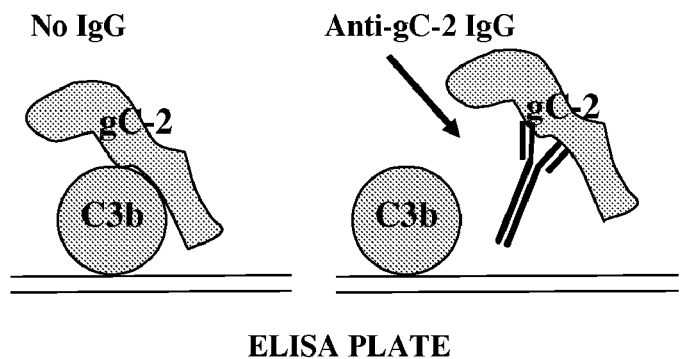
FIG. 38: A. Schematic showing gC-2 binding to C3b (left side) and anti-gC-2 IgG blocking gC-2 binding to C3b (right side). B. Anti-gC-2 IgG blocks C3b binding to gC-2. ELISA was performed to demonstrate that anti-gC-2 IgG blocks gC-2 binding to C3b (left panel), while anti-gD-2 IgG fails to block gC-2 binding to C3b (right panel). C. Anti-gC-2 and anti-gD-2 IgG neutralization of HSV-2 WT and HSV-2 gCnull in the presence of absence of 2.5% human serum as the source of complement. D. Anti-gC-1 and anti-gD-1 neutralization of HSV-1 WT and HSV-1 gCnull in presence or absence of 2.5% human serum. Each experiment in B-D was performed once.
Figure 38B:
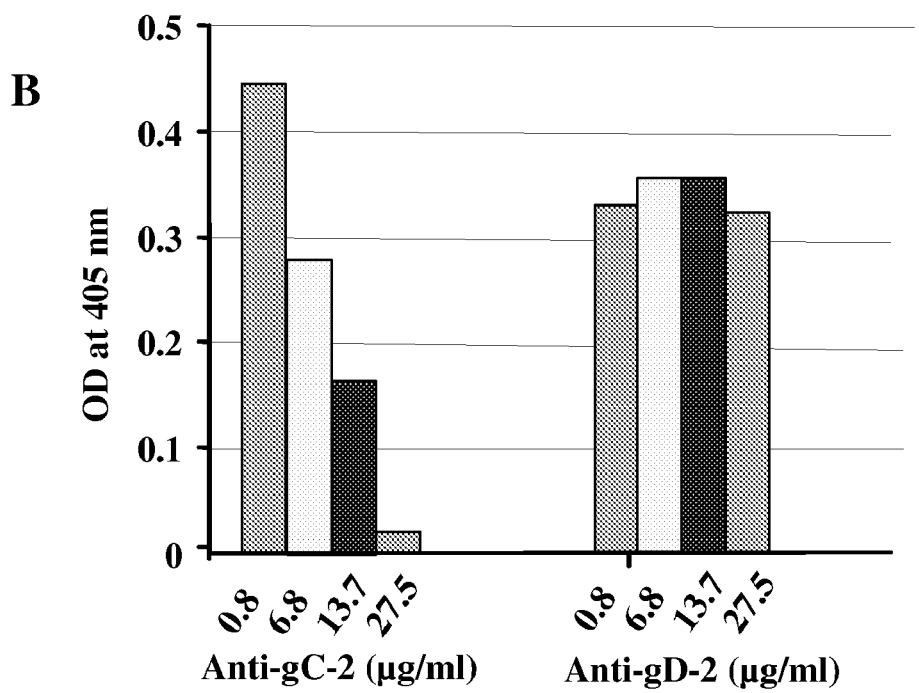

We previously demonstrated that anti-gC-1 IgG blocks the binding of gC-1 to C3b (Example 5). We examined whether anti-gC-2 IgG also blocks the binding of gC-2 to C3b. Wells of an ELISA plate were coated with 200 ng C3b. gC-2 at 50 ng/ml was incubated with serial two-fold dilutions of anti-gC-2 IgG, or anti-gD-2 IgG as a control, for 60 min at 37° C.; then the antibody-gC-2 mix was added to the C3b coated wells. gC-2 that bound to C3b was detected using rabbit anti-gC-2 IgG and HRP-conjugated anti-rabbit IgG. FIG. 38A is a cartoon of the assay demonstrating anti-gC-2 IgG blocking gC-2 binding to C3b. FIG. 38B demonstrates that increasing concentrations of anti-gC-2 IgG resulted in decreased binding of gC-2 to C3b, while anti-gD-2 IgG had no effect on gC-2 binding.

Figure 38C:
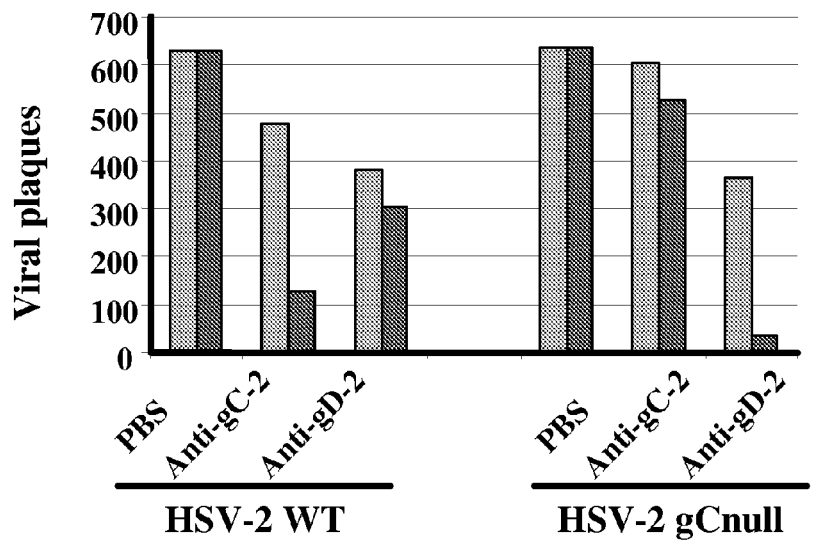

We next evaluated whether complement enhances anti-gC-2 or anti-gD-2 neutralization of HSV-2 WT or HSV-2 gCnull. Each virus was incubated with 10 µg anti-gC-2 or anti-gD-2 IgG in the presence of absence of 2.5% human serum (obtained from an HSV-1 and HSV-2 seronegative individual) as the source of complement. At 2.5% concentration, complement alone had no neutralizing activity against HSV-2 WT virus or HSV-2 gCnull virus (FIG. 38C, left bars). In contrast, complement greatly enhanced the neutralizing activity of anti-gC-2 IgG against HSV-2 WT virus, while having no effect against HSV-2 gCnull virus (FIG. 38C, middle bars). Complement had very little effect on neutralization by anti-gD-2 IgG against HSV-2 WT virus, but a considerable effect against HSV-2 gCnull virus (FIG. 38C, right bars).

Interpretation of results: We previously demonstrated that complement neutralizes HSV-2 gCnull more actively than HSV-2 WT, but neutralization is minimal at serum concentrations <20% (Hook L M et al, J Virol 80:4038-46, 2006). Therefore, it was not unexpected that complement alone at 2.5% had little effect against either virus. Anti-gC-2 IgG binds to gC-2 and blocks complement C3b binding to gC-2; therefore, anti-gC-2 IgG prevents HSV-2 evasion from complement attack. Anti-gC-2 IgG binds to HSV-2 WT gC-2, activates complement, which results in enhanced neutralization of the WT virus (FIG. 37C, middle bars of HSV-2 WT). In contrast, anti-gC-2 IgG cannot bind to HSV-2 gCnull; therefore, complement is not activated and we detect no enhanced neutralization of HSV-2 gCnull (FIG. 38C, middle bars of HSV-2 gCnull). Anti-gD-2 IgG neutralizes HSV-2, but complement adds little because gC-2 binds complement C3b and inhibits complement activation (FIG. 38C, right bars of HSV-2 WT). In contrast, complement greatly enhances the neutralizing activity of anti-gD-2 IgG against HSV-2 gCnull virus because gC-2 is not present to inhibit complement activation (FIG. 38C, right bars of HSV-2 gCnull).

Figure 38D:
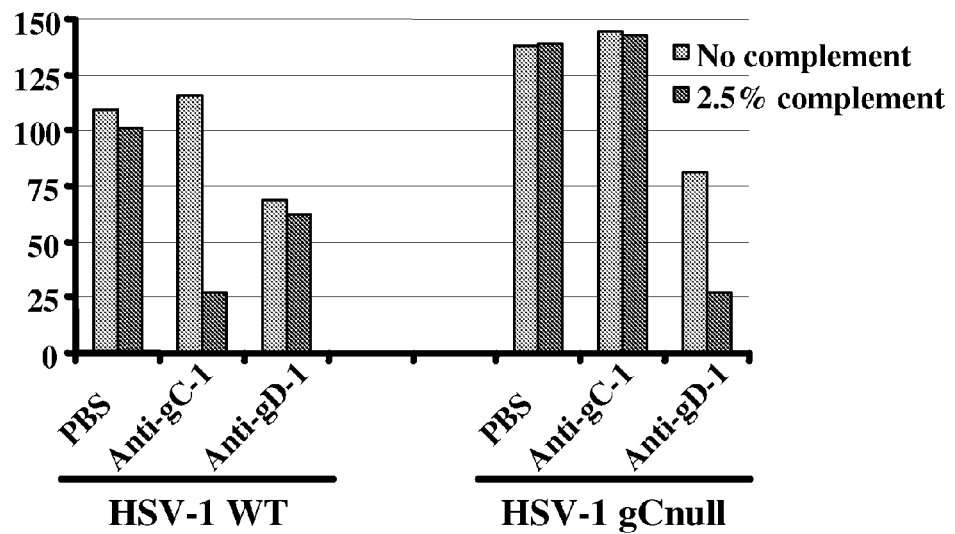

We performed a similar experiment with HSV-1 WT or HSV-1gCnull virus using anti-gC-1 or anti-gD-1 IgG. Results shown in FIG. 38D are comparable to those shown in 38C and indicate that anti-gC-1 IgG blocks immune evasion from complement mediated by gC-1, and that gC-1 on WT virus inhibits complement-enhanced neutralization.

Example 23

Anti-gC-2 IgG Protection in Mice is Mediated by Antibody Blocking Immune Evasion from Complement C57B1/6 or C3 knockout mice (C3KO) were passively immunized by intraperitoneal injection with anti-gC-2 IgG, or nonimmune IgG (200 µg/mice), which were administered 24 hours before flank scratch inoculation with $2 \times 10^5$ PFU of HSV-2 strain 2.12. Mice were evaluated for inoculation and zosteriform site disease on day 3-11 post-infection. The scoring system for disease is as described above.

Results

Figure 39:
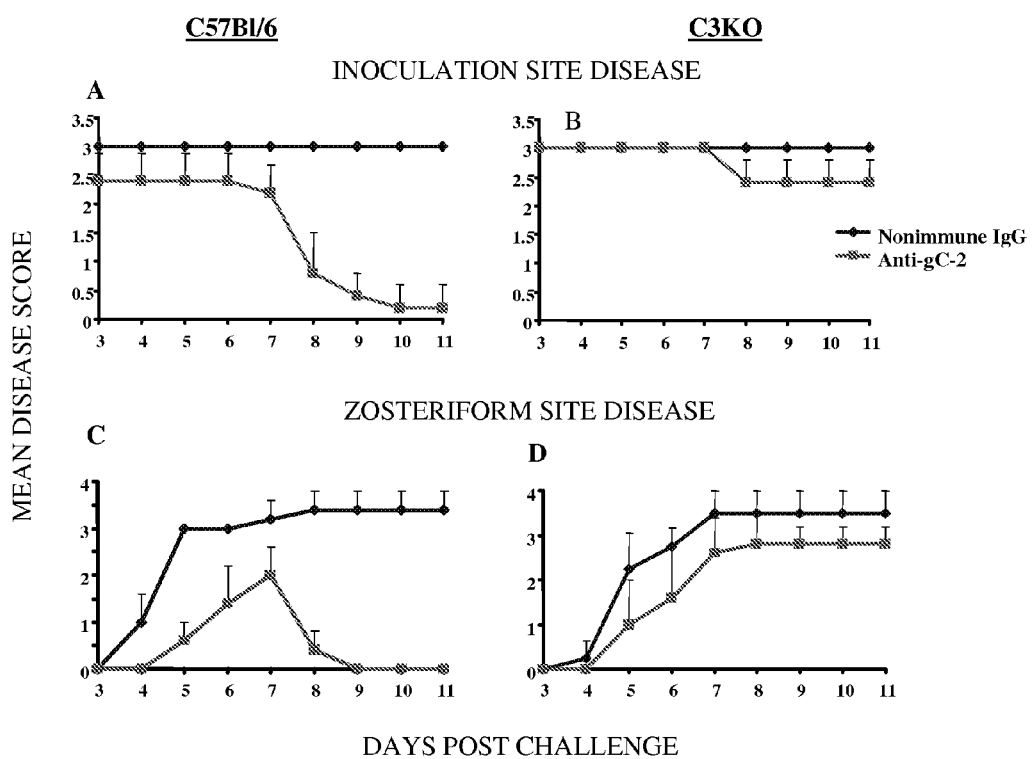
FIG. 39: Inoculation site (A-B) and zosteriform site (C-D) disease scores in C57B1/6 and C3 knockout (C3KO) mice passively immunized with murine anti-gC-2 IgG or murine nonimmune IgG followed by HSV-2 epidermal challenge. The results represent the mean±SEM of 5 mice in each group.

Anti-gC-2 IgG protected complement intact C57B1/6 mice from inoculation site disease (P<0.01) (FIG. 39A) but failed to protect C3KO mice (P>0.05) (FIG. 39B). Anti-gC-2 IgG reduced zosteriform site disease in C57B1/6 mice (P<0.001) (FIG. 39C). In contrast, anti-gC-2 IgG had little effect in C3KO mice (P>0.05) (FIG. 39D). Therefore, the protective effect of anti-gC-2 IgG is detected in complement intact but not in C3KO mice. We detected a slight reduction in zosteriform site disease in passively immunized C3KO mice, which may be attributable to the neutralizing activity of anti-gC-2 IgG. The results support our hypothesis that gC-2 immunization improves the effectiveness of a gD-2 vaccine by preventing gC-2 mediated immune evasion of complement.

Example 24

Combination gC-2/gD-2 Vaccines Prevent Recurrent Infection in HSV-2 Infected Subjects Combination gC-2/gD-2 vaccines (e.g. those described in Examples 2-3) are assessed for ability to prevent recurrent HSV-2 infection (e.g. as assessed by occurrence of flares). Following infection, mice are immunized up to 5 times with gC-2/gD-2 vaccines, vaccines containing gC-2 or gD-2 alone, or are mock-immunized, then monitored for recurrent infection. The combination gC-2/gD-2 vaccines are believed to confer protection that compares favorably with gC-2 or gD-2 vaccines.

Example 25

Immunization with gE-1 Induces Antibodies that Bind gE and Block gE Immune Evasion Domains Materials and Experimental Methods Cell Cultures and Virus Strains COS-1 cells were grown at 37° C. in 5% $CO_2$ in an humidified incubator in Dulbecco's modified Eagle's medium (DMEM) supplemented with 10% heat-inactivated fetal bovine serum, 20 µg of gentamicin per ml and 20 mM HEPES (pH 7.3). Cells were infected with HSV-1 wild-type strain, NS. Virus pools were prepared using African green monkey kidney (Vero) cells.

Construction of bac-gE24-224, bac-gE225-398 and bac-gE24-409 Viruses

Baculoviruses bac-gE24-224, bac-gE225-398 and bac-gE24-409 were constructed using ThermalAce DNA polymerase (Invitrogen Corp., Carlsbad, Calif.) PCR to amplify gE AA 24-224, 225-398 and 24-409 from pCMV3-gE. A six histidine-tag was incorporated into the 3' primer in front of a stop codon. BamH1 and Pst1 sequences were included on the 5' and 3' primers, respectively, and the BamH1-Pst1 fragment was cloned into pVT-Bac using a rapid DNA ligation kit (Roche Diagnostics, Indianapolis, Ind.). This subcloning strategy placed gE24-224, gE225-398 and gE24-409 sequences immediately 3' of the honeybee mellitin signal sequence and under the control of the baculopolyhedrin promoter. Sf9 insect cells (Gibco BRL, Grand Island, N.Y.) were co-transfected with pVT-Bac constructs and Baculogold® DNA (PharMingen, San Diego, Calif.) to produce bac-gE24-224, bac-gE225-398 and bac-gE24-409 viruses.

Purification and Identification of gE24-224, gE225-398 and gE24-409

Baculoviruses were grown in Sf9 insect cells for the first three passages, and in H5 insect cells (Gibco BRL) to obtain higher yields of protein expression at passage 4. The supernatants from 150 ml of infected H5 cells were tested for protein expression by Western Blot, and used for protein purification. The supernatant fluids were passed through a nickel column (QIAGEN Inc., Valencia, Calif.), and eluted with 50-250 mM imidazole. Eluted fragments were concentrated with an Ultrafree-15® centrifugal filter device (Millipore Corp., Bedford, Mass.), and identified on a 4-15% SDS-PAGE using GelCode® Blue Stain Reagent (Pierce). Samples of the purified proteins were electrophoresed on a 4-15% SDS-PAGE, transferred to a nitrocellulose membrane, and probed with a mouse anti-His tag monoclonal antibody (MAb), 1BA10, that recognizes gE sequences between AA 103-120 or rabbit polyclonal antibody R575 against gE AA 1-409.

Immunizations with gE Fragments

Five 8-9-week-old female BALB/c mice (Charles River Laboratories, Wilmington, Mass.) were immunized intraperitoneally with 10 µg of purified gE24-224, gE225-398 or gE24-409, and three mice were injected with PBS as controls. Complete Freund's adjuvant was used for primary immunizations and incomplete Freund's adjuvant for booster injections at intervals of 10 to 14 days. Serum was collected two weeks after the third to fifth immunization. Two rabbits each were immunized with purified gE24-224, gE225-398 or gE24-409 (COCALICO Biologicals, Inc., Reamstown, Pa.), and serum was collected after the fourth to sixth immunization.

Antibody Detection by ELISA

Purified gE24-224, gE225-398 and gE24-409 fragments were diluted to 2 µg/ml in Dulbecco's phosphate buffered saline (DuPBS), pH 7.1, and 200 ng was used to coat Covalink® NH 96 well-microtiter plates (Nalge Nunc International, Naperville, Ill.). Coated plates were incubated overnight at 4° C. and blocked for 2 h at 37° C. with 5% (w/v) nonfat milk in DuPBS. IgG samples were diluted to 2 µg/100 µl in DuPBS and 0.1% BSA. A 1:1000 dilution of horseradish peroxidase (HRPO)-conjugated, affinity-purified donkey anti-rabbit IgG (H+L) or sheep anti-mouse IgG (H+L) (Amersham Life Science, Piscataway, N.J.) was prepared in DuPBS and 0.01% BSA. The reaction was developed by adding 1 mg/ml ABTS in buffer solution (Roche, Mannheim, Germany) for 10 min at room temperature, and the optical density (OD) was measured at 405 nm using an ELISA plate reader (Dynatech, Chantilly, Va.).

Flow Cytometry Assays

The assay to determine whether antibodies block IgG Fc binding to HSV-1 infected cells included two components; first measuring whether antibodies bind to HSV-1 infected cells, then determining if the bound antibodies block biotin-labeled non-immune human IgG binding to the HSV-1 FcγR. For antibody binding, COS-1 cells were infected with wild-type virus at an M.O.I. of 2 for 16 h, dispersed with cell dissociation buffer (Life Technologies Inc., Rockville, Md.), and treated with 0.05 U neuraminidase (Sigma Chemical Co., St. Louis, Mo.), which enhances IgG Fc binding. Binding of IgG antibodies to HSV-1 infected cells surface was measured using fluorescein isothiocyanate (FITC)-conjugated $F(ab')_2$ fragments against mouse or rabbit IgG or against rabbit IgG $F(ab')_2$ fragments. Cells were fixed with 1% paraformaldehyde and analyzed by FACScan flow cytometry (Becton-Dickinson, San Jose, Calif.). Antibody binding was reported as mean fluorescence intensity (MFI). For assays to measure blocking of IgG binding, neuraminidase-treated HSV-1 infected cells were incubated with IgG or $F(ab')_2$ fragments and then 10 µg of biotin-labeled nonimmune human IgG was added, which was detected using streptavidin-R-phycoerythrin (PE) (Sigma). Percent blocking was calculated as: ((MFI without blocking antibody−MFI with blocking antibody)/MFI without blocking antibody)×100.

Results

Production of gE fragments in baculovirus. To determine whether gE immunization can induce antibodies that bind to gE by the F(ab')₂ domains, three gE fragments were prepared that span almost the entire gE ectodomain, gE24-224, gE225-398, and gE24-409. The gE225-398 fragment spans much, or perhaps all, of the IgG Fc domain. gE24-409 contains sequences included in each of the smaller fragments.

Supernatant fluids of baculovirus infected cells yielded 6-8 mg/L of fragments gE24-224, gE225-398 and gE24-409, which were purified on a nickel column and concentrated to 1 mg/ml. Purity was ≧95%, as shown by GelCode Blue® staining on SDS-PAGE. The gE24-224 and gE24-409 fragments reacted with anti-His MAb, anti-gE MAb 1BA10, and rabbit polyclonal antibody R575. Fragment gE225-398 reacted with anti-His MAb, rabbit polyclonal antibody R575, and as expected, not with MAb 1BA10, which recognizes AA sequences between 103 and 120.

Figure 40:
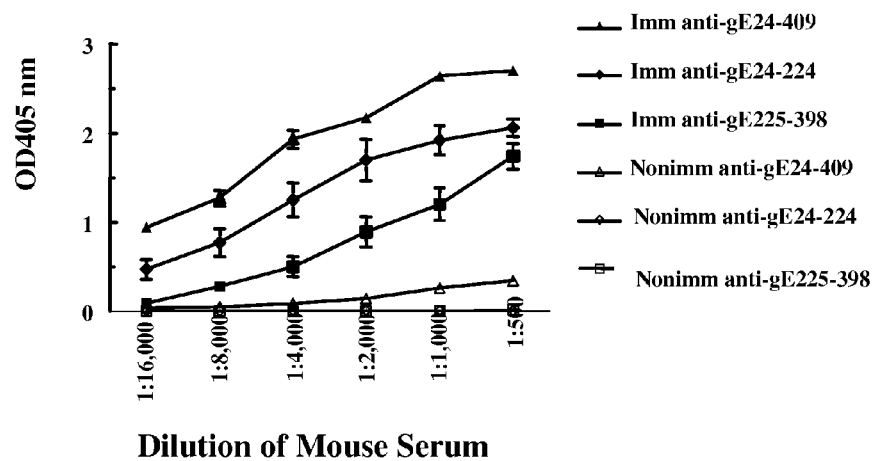
FIG. 40: Antibodies in mouse serum measured against the inducing immunogen. Data are plotted as mean±standard error of the mean of 5 mice immunized with bac-gE fragments or three mock-immunized mice.

Baculovirus gE immunization of mice. To determine whether the elicited antibodies block IgG Fc binding to the HSV-1 FcγR, mice were immunized with gE24-224, gE225-398, gE24-409 or mock-immunized as controls. Mouse serum was collected after the fifth immunizations with gE24-224 and gE225-398 or third immunizations with gE24-409, and tested for antibody titers by ELISA against the corresponding immunogens. Immunized, but not mock-immunized, mice produced antibodies that reacted with the immunizing antigen. Antibody levels were highest against the gE24-409 fragment (FIG. 40).

Blocking the HSV-1 FcγR using mouse antibodies. Flow cytometry assays were performed 16 h post-infection to evaluate whether antibodies bind to gE expressed on HSV-1 infected cells. Antibodies from gE24-224 and gE24-409 immunized mice bound to gE (FIG. 41A), while antibodies from gE225-398 immunized mice exhibited lower levels of binding. Unlike human or rabbit IgG, murine IgG Fc does not bind to the HSV-1 FcγR; therefore, binding by mouse antibodies can only be mediated by the IgG F(ab')₂ domain. Thus, gE expressed on infected cells binds to F(ab')₂ domains of antibodies elicited by gE24-224 and gE24-409, and to a lesser extent gE225-398. Under the conditions utilized, the conformation of gE225-398 epitope expressed on the infected cell either differs from the gE conformation in the baculovirus fragment, or this epitope is hidden on infected cells.

Figure 41:
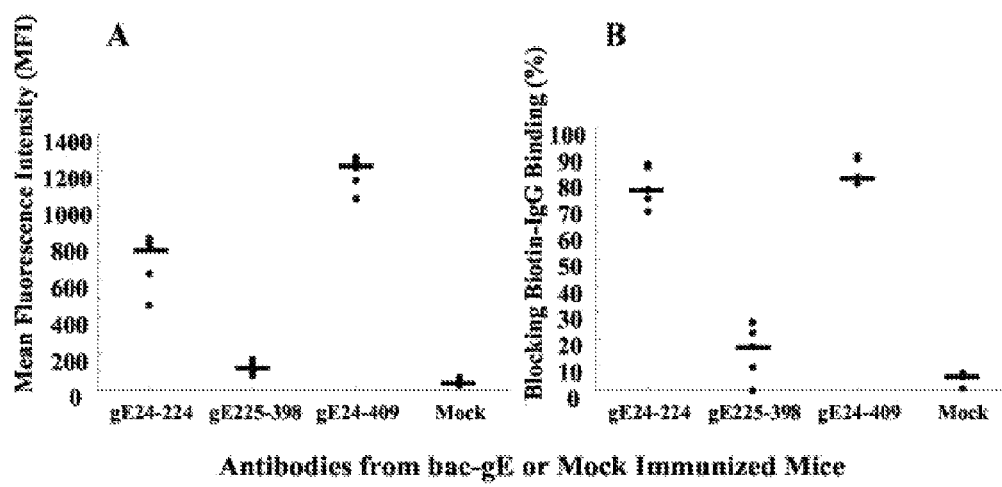
FIG. 41: Murine and rabbit antibody binding to gE and blocking biotin-labeled nonimmune human IgG binding to the FcγR. (A) Infected cells were incubated with serum from immunized mice (n=5 per group) or mock-immunized controls (n=3). Serum (1:10 dilution) was evaluated for binding to gE on infected cells by flow cytometry. (B) Serum (undiluted) was added to infected cells to block binding of 10 μg of biotin-labeled nonimmune human IgG. Bars indicate median values for each group.

Undiluted serum from the immunized mice was tested for ability to block binding of biotin-labeled nonimmune human IgG to the HSV-1 FcγR. Antibodies elicited by gE24-224 and gE24-409 blocked the HSV-1 FcγR (median blocking 76% and 80%, respectively), while antibodies to gE225-398 exhibited little blocking (median blocking 17%) (FIG. 41B). Therefore, antibodies to gE24-224 and gE24-409 bind to gE by their F(ab')₂ domains and block IgG Fc binding to the HSV-1 FcγR.

Example 26 gE-1/gD-1 Vaccines are Immunogenic and Protective Against HSV-1 Infection

Materials and Experimental Methods

Combination gE-1/gD-1 vaccines (e.g. AA 24-409 of gE-1 with a C-terminal 6 His tag and AA 26-306 of gD-1 with a C-terminal 6 His tag) are administered to mice and immunogenicity is assessed as described for gC-1/gD-1 vaccines in Examples 2-3 and 14.

Results

Combination gE-1/gD-1 vaccines are compared to vaccines containing gE-1 alone or gD-1 alone for immunogenicity. The immunogenicity of the combination vaccines is believed to compare favorably with gE-1 or gD-1 vaccines. Next, the vaccines are compared for their ability to confer protection against HSV-1. The protection conferred by the combination vaccines is believed to compare favorably with gE-1 or gD-1 vaccines.

Next, combination gE-1/gD-1/gC-1 vaccines are compared to gE-1/gD-1 and gD-1/gC-1 vaccines for immunogenicity. The immunogenicity of the gE-1/gD-1/gC-1 combination vaccines is believed to compare favorably with gE-1/gD-1 and gD-1/gC-1 vaccines. Next, the vaccines are compared for their ability to confer protection against HSV-1. The protection conferred by the gE-1/gD-1/gC-1 combination vaccines is believed to compare favorably with gE-1/gD-1 and gD-1/gC-1 vaccines.

Example 27 gE-2/gD-2 Subunit Vaccines are Protective Against HSV-2 Infection

Combination gE-2/gD-2 vaccines (e.g. AA 24-409 of gE-2 with a C-terminal 6 His tag and AA 26-306 of gD-2 with a C-terminal 6 His tag) are compared to vaccines containing gE-2 alone or gD-2 alone for immunogenicity. The immunogenicity of the combination vaccines is believed to compare favorably with gE-2 or gD-2 vaccines. Next, the vaccines are compared for their ability to confer protection against HSV-2. The protection conferred by the combination vaccines is believed to compare favorably with gE-2 or gD-2 vaccines.

Next, combination gE-2/gD-2/gC-2 vaccines are compared to gE-2/gD-2 and gD-2/gC-2 vaccines for immunogenicity. The immunogenicity of the gE-2/gD-2/gC-2 combination vaccines is believed to compare favorably with gE-2/gD-2 and gD-2/gC-2 vaccines. Next, the vaccines are compared for their ability to confer protection against HSV-2. The protection conferred by the gE-2/gD-2/gC-2 combination vaccines is believed to compare favorably with gE-2/gD-2 and gD-2/gC-2 vaccines.

Example 28

HSV Glycoproteins gC- and gE-Mediated Immune Evasion in HIV-Infected Subjects

Materials and Experimental Methods

Sera Isolation

Sera from HIV subjects at various stages of HIV disease (CD4 count <200/µl, 200-500/µl, >500/µl) were obtained from the Clinical Core Laboratory of the University of Pennsylvania Center for AIDS Research. Sera were tested for antibodies to HSV-1 and HSV-2 by HerpeSelect™ 1 and 2 ELISA IgG (Focus Technologies, Cypress, Calif.), which is a gG-based assay that can detect type-specific IgG antibodies. Subjects were 75% male: 56% African-American, 35% Caucasian, 7% Hispanic, and 2% Other; with an average age of 41 years. Subject risks for HIV infection included 51% men who have sex with men, 5% intravenous drug users, 41% heterosexual, and 3% unknown. HIV seronegative sera were obtained from healthy volunteers who participated in the GlaxoSmithKline HSV-2 gD2 vaccine trial. Enrolled subjects were seronegative to HIV, HSV-1 and HSV-2 prior to receiving either the gD2 vaccine or adjuvant alone (placebo group).

IgG Purification

Patient IgG was purified from sera using the HiTrap™ protein G column according to the manufacturer's instructions (Amersham Biosciences, Uppsala, Sweden). Fractions containing protein were pooled, dialyzed against PBS at 4° C., concentrated, and stored in aliquots at −20° C. Rabbit IgG was purified from pre-immune rabbit serum or from rabbits inoculated with purified baculovirus proteins gB, gD, or gH/gL.

Assay for Classical Complement Pathway Hemolytic Activity ($CH_{50}$)

Serum total hemolytic complement activity ($CH_{50}$) was measured in HIV subjects with CD4 T-cell counts <200/μl, 200-500 μl, and >500/μl and from HIV uninfected controls. Serial dilutions of serum were incubated with antibody sensitized sheep erythrocytes for 1 h at 37° C. in 96-well microtiter plates. Plates were centrifuged for 3 min at 120×g, the supernatants transferred to fresh plates, and the extent of hemolysis was measured by spectrophotometry at 405 nm.

Antibody and Complement Neutralization Assays

Approximately $10^5$ plaque-forming units (PFU) of purified virus were incubated with IgG, HSV 1+/2− serum, HSV 1+/2− serum treated with EDTA to inactivate complement, or PBS for 1 h at 37° C. Viral titers remaining were determined by plaque assay on Vero cells. Neutralization mediated by antibody alone or antibody and complement was calculated as the difference in titer when virus was incubated with PBS and EDTA-treated serum (antibody alone), or PBS and serum without EDTA (antibody and complement).

Results

Serum was tested for antibodies to HSV-1 and HSV-2 from the first 133 subjects enrolled in the Center for AIDS Research Clinical Core database from whom both serum and CD4 T-cell counts were available to identify HIV subjects co-infected with HSV-1 (HSV 1+/2−). Overall, 39% had CD4 T-cell counts >500 μl, 28% 200-500 μl, and 33%<200/μl. Sixty-nine percent were HSV-1 seropositive (41% HSV 1+/2+ and 28% HSV 1+/2−), and 64% were HSV-2 seropositive (41% HSV 1+/2+ and 23% HSV 1−/2+). Eight percent of subjects were seronegative to both HSV-1 and HSV-2. Sera from HSV 1+/2− subjects were selected for further studies.

Figure 42A:
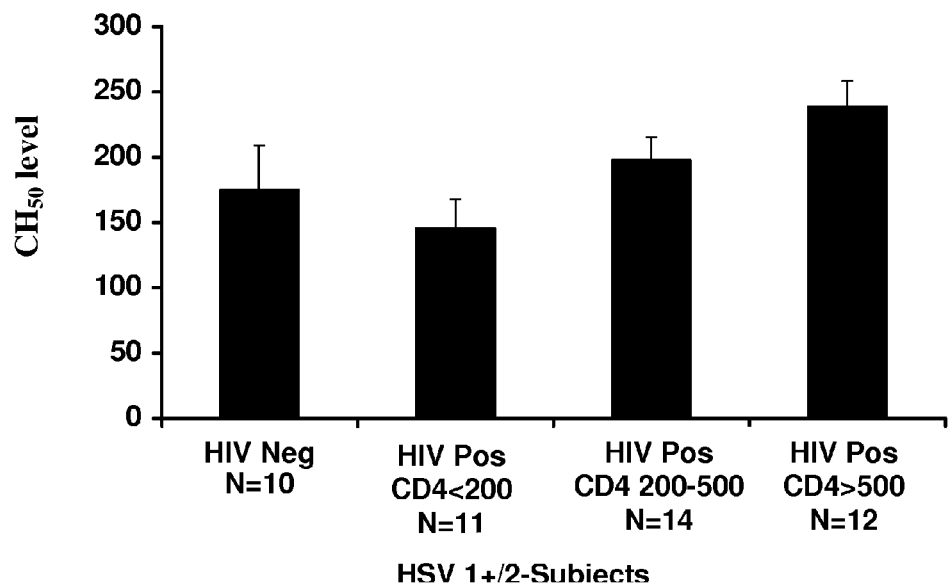
FIG. 42: (A) Complement levels are maintained in HIV/HSV-1+/2-co-infected subjects. Serum total hemolytic complement activity ($CH_{50}$) was measured in HIV-positive subjects with CD4 T-cell counts <200/μl, 200-500/μl, and >500/μl and from HIV uninfected controls. Results shown represent mean+/−standard error (SE). (B) Neutralization of HSV-1 WT and gC/gE mutant viruses by antibody alone or antibody and complement. WT or gC/gE mutant virus was incubated for 1 h at 37° C. with PBS, 1% serum treated with EDTA to inactivate complement (labeled as Ab), or 1% serum containing active complement (labeled as Ab&C).

Total hemolytic serum complement ($CH_{50}$) levels in HSV 1+/2− subjects who were not infected with HIV or in HIV/HSV-1 co-infected subjects at various stages of HIV disease were measured (FIG. 42A). Serum total hemolytic complement levels were maintained, even in HIV/HSV-1 co-infected subjects with advanced disease.

Figure 42B:
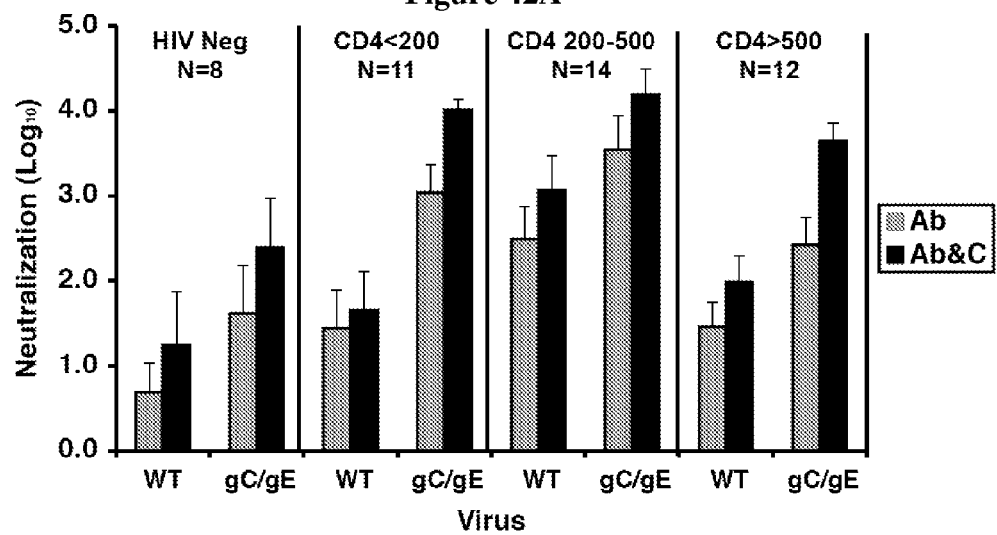

Next, antibody-mediated neutralization was measured using 1% serum treated with EDTA to inactivate complement. Antibody neutralized both WT and gC/gE mutant viruses at all stages of HIV disease, including in subjects with CD4 T-cells <200/μl (FIG. 42B gray bars).

The effects of antibody and complement on neutralizing WT and gC/gE mutant viruses using 1% serum and active complement (without EDTA treatment) were compared. Neutralization of the gC/gE mutant virus was greater than WT virus in the HIV negative controls and the HIV infected subjects all levels of CD4 T-cell counts (FIG. 42B, black bars). These results were surprising, because earlier studies reported that gC and gE inhibit virus neutralization via inhibition of complement activation (Lubinski et al., Seminars in Cell & Developmental Biology 9:329-37; Nagashunmugam et al., J Virol 72:5351-9). Therefore, further experiments were performed to evaluate additional mechanisms by which gC and gE mediate immune evasion.

Example 29

HSV gC and gE Epitopes on Viral Glycoproteins Increases Efficacy of Immune Evasion by Blocking Antibody Access to Glycoproteins Involved in Virus Entry Materials and Experimental Methods Cells and Viruses African green monkey kidney cells (Vero) were grown in Dulbecco's modified Eagle's medium supplemented with 10% heat-inactivated fetal bovine serum, 2 mM L-glutamine, 10 mM HEPES (pH 7.3), 20 μg/ml gentamicin, and 1 μg/ml Fungizone (Life Technologies, Rockville, Md.). Pools of purified virus were prepared by infecting Vero cells at a multiplicity of infection of 2-5. Supernatant fluids 24 h post-infection were harvested for cell free virus and centrifuged onto a 5% to 70% sucrose gradient. Virus-containing fractions were isolated and dialyzed against Dulbecco's phosphate buffered saline with Ca2+ and Mg2+ (PBS), aliquoted, and stored at −70° C.

The WT strain, HSV-1 NS, is a low passage clinical isolate obtained from an infected child. Mutant viruses derived from the NS strain, NS-gCΔC3, NS-gE339, and the double mutant, NS-gCΔC3, gE339, have been described previously. The gC mutant virus, NS-gCΔC3, has a deletion from amino acid 275 to 367, resulting in a loss of C3b binding. The gE mutant virus, NS-gE339, has a 4 amino acid insert at gE amino acid 339, resulting in loss of IgG Fc binding. The gC/gE double mutant virus, NS-gCΔC3, gE339, contains both the gC and gE mutations in a single virus.

Antibody and Complement Neutralization Assays

Approximately $10^5$ plaque-forming units (PFU) of purified virus were incubated with pooled human IgG (Michigan State Health Laboratories) or rabbit antibodies to purified baculovirus proteins gB, gC, gD, gH/gL, or gI were used. The antibody to gI was produced in rabbits using as antigen baculovirus-expressed gI amino acids 24-264 (HMF, unpublished).

Western Blot and Densitometry Analyses

Approximately $2 \times 10^6$ PFU of purified virus was run on a 4-15% SDS-PAGE, transferred to Immobilon-P Transfer Membranes (Millipore Corp., Bedford, Mass.), and detected using polyclonal rabbit antibodies to gB, gC, gD, gE, gH/gL, gI, and VP5. Horseradish peroxidase-conjugated goat anti-rabbit IgG and enhanced chemiluminescence (Amersham Pharmacia, Piscataway, N.J.) were used to visualize the primary antibodies. Densitometry analyses were performed using ScanMaker i900 (Microtek Lab Inc., Carson, Calif.) to compare protein levels.

Viral ELISA

Approximately $10^6$ PFU of purified WT or NS-gCΔC3, gE339 virus was diluted in 50 μl PBS, added to Costar® high-binding 96-well plates and incubated at 4° C. overnight. As controls, some wells were incubated with 50 μl PBS without virus. Wells were blocked at room temperature for 2 h with 5% milk and 0.05% Tween20 in PBS. Serial dilutions of purified rabbit IgG against gB, gD, gH/gL, or pre-immune rabbit IgG were prepared in blocking buffer and added at decreasing concentrations ranging from 2 ug to 0.015 ug in 50 μl of blocking buffer. Antibody was incubated at room temperature for 1 h, washed three times with 0.05% Tween20 in PBS and incubated with horseradish peroxidase conjugated donkey anti-rabbit IgG (Amersham Bioscience) at a 1:1,000 dilution in blocking buffer for 30 min. Plates were washed twice with 0.05% Tween20 in PBS and once with PBS alone, then ABTS substrate (Roche) was added and after 25 min read at 405 nm. For some experiments, anti-gD serum from chickens was used in the viral ELISA. Chickens were immunized and boosted four times with a baculovirus-gD construct and serum obtained as a source of IgY antibodies. The serum had high antibody titers to gD as measured by ELISA on a gD-coated plate.

Results

Figure 43:
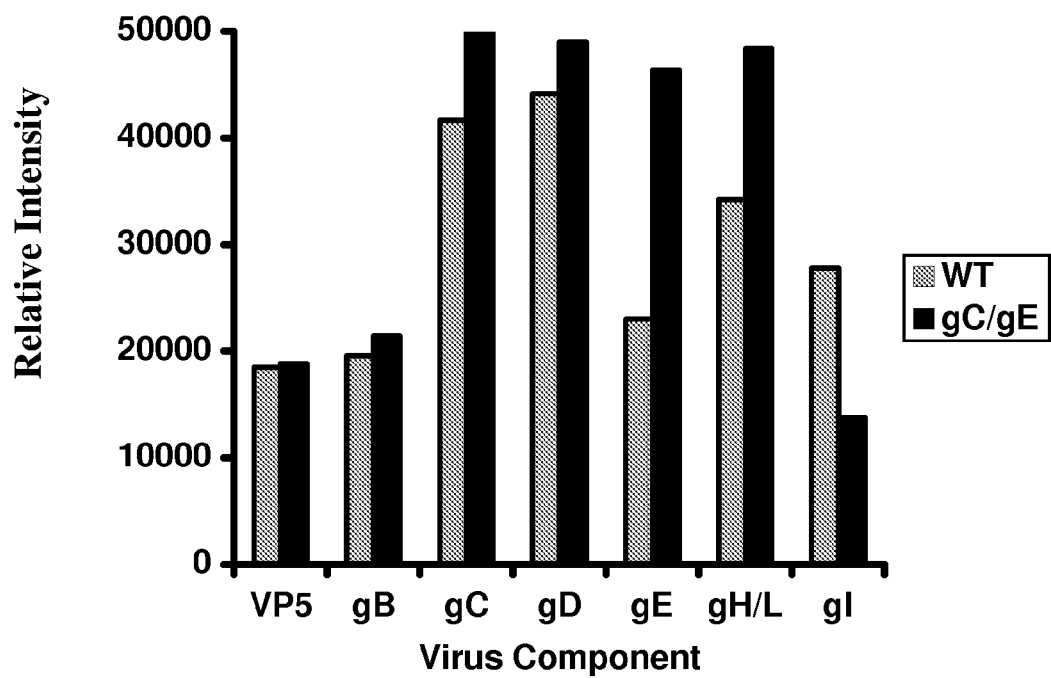
FIG. 43: The gC/gE mutant virus expresses similar or slightly greater concentrations of HSV-1 glycoproteins on the virion surface than WT virus. Purified gC/gE mutant and WT viruses were evaluated for VP5, gB, gC, gD, gE, gH/gL, and gI expression by Western blot and densitometry analysis to compare relative glycoprotein concentrations.

Densitometry analysis on Western blots of purified WT and gC/gE mutant viruses was performed to evaluate the relative concentrations of the glycoproteins, including those essential for virus entry, gB, gD, gH/gL. Analysis of HSV-1 capsid protein VP5 was included to ensure comparable loading of WT and gC/gE mutant virus particles on the gel. Some differences in the relative concentrations of HSV-1 glycoproteins expressed on the WT and the gC/gE mutant virus were detected (FIG. 43); however, concentrations of gB, gD, and gH/gL were slightly higher on the gC/gE mutant than WT virus suggesting that the greater neutralizing activity is not caused by lower concentrations of target glycoproteins on the mutant virus.

Figure 44A:
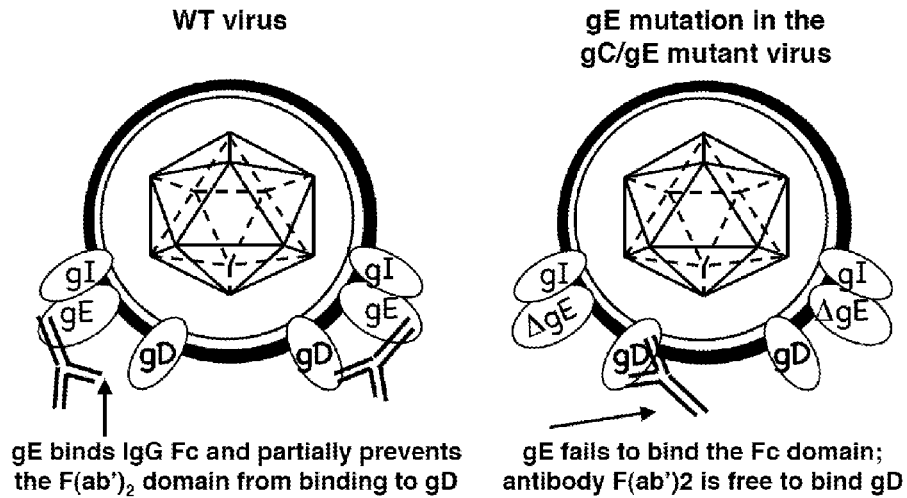
FIG. 44: The role of the HSV-1 FcγR in antibody neutralization. (A) Possible model to explain the greater susceptibility of the gC/gE mutant virus to neutralization by antibody alone. On the left side of the WT virus model, gE binds the Fc domain of IgG preventing the $F(ab')_2$ from binding antigen (shown here as gD). On the right side of the WT virus model, antibody bipolar bridging is shown in which the Fab domain binds to gD and the Fc domain of the same IgG molecule binds to gE. If antibody binding occurs as shown on the left side, but not the right side of the WT virus model, the HSV-1 FcγR (comprised of gE/gI) may prevent some $F(ab')_2$ domains from interacting with their target antigen. In the model of the gC/gE mutant virus, ΔgE fails to bind the IgG Fc domain, allowing the $F(ab')_2$ domain to bind antigen (shown as gD) and neutralize the virus. (B) A nonfunctional viral FcγR does not explain the increased susceptibility of the gC/gE mutant virus to antibody neutralization. Viruses were incubated with pooled human IgG from HIV negative donors and the amount of neutralization determined.

FIG. 44A depicts possible mechanisms by which the HSV-1 FcγR may interfere with antibody neutralization. By binding the Fc domain of IgG, the HSV-1 FcγR on WT virus may prevent the F(ab')₂ domain from interacting with its target antigen (left side of WT model). In contrast, the gE mutation in the gC/gE virus eliminates FcγR activity, which may facilitate interactions between the F(ab')₂ domain and the antibody target resulting in greater neutralization.

Figure 44B:
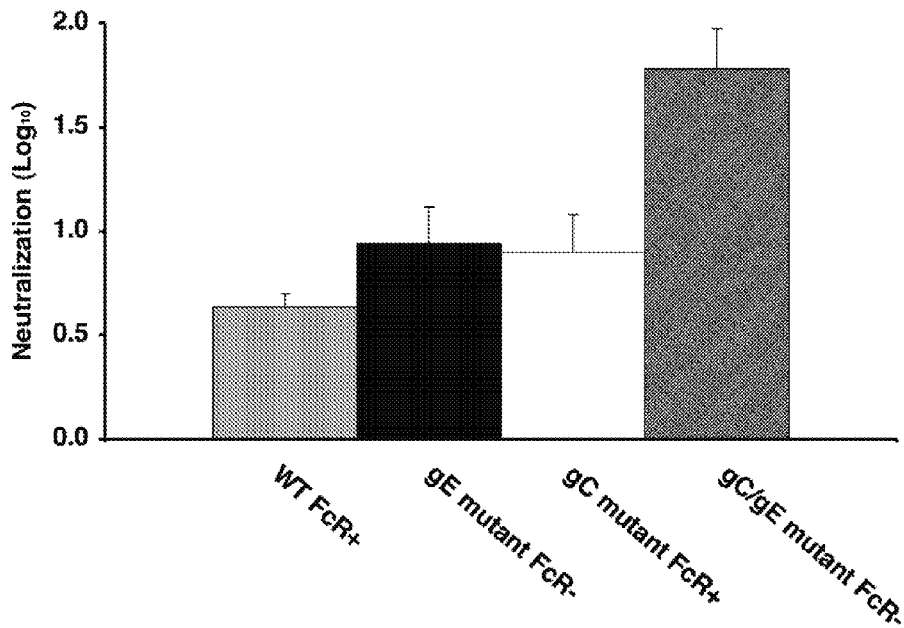

To evaluate this possibility, IgG pooled from HIV negative human donors was used to compare neutralization of a gE mutant virus that is defective in FcγR activity (NS-gE339) with a mutant virus that has an intact FcγR, but has a mutation in gC (NS-gCΔC3). Viruses were incubated with PBS or 100 μg pooled human IgG as the source of HSV antibodies. Antibody was equally effective neutralizing the FcγR intact and FcγR defective viruses and was even more active against the gC/gE double mutant virus (NS-gCΔC3, gE339) (FIG. 44B). Since the gC/gE double mutant virus was more readily neutralized than either single mutant virus from which it was derived, we conclude that the mutations in gC and gE both contribute to increasing the susceptibility of the gC/gE mutant virus to neutralizing antibody.

We next evaluated whether the gC and gE mutations expose previously shielded epitopes on other viral glycoproteins to neutralizing antibody, possibly because of altered glycoprotein conformation on the virion envelope. Assays were performed comparing neutralization of WT and gC/gE mutant viruses following incubation with rabbit antibodies that selectively interact with gB, gC, gD, gH/gL, or gI. Antibodies to gB, gD, gH/gL neutralized the viruses, as expected, since these glycoproteins are required for virus entry; however, differences between the viruses were not significant. Antibodies to gC and gI, which are not required for entry, failed to neutralize either virus.

Figure 45A:
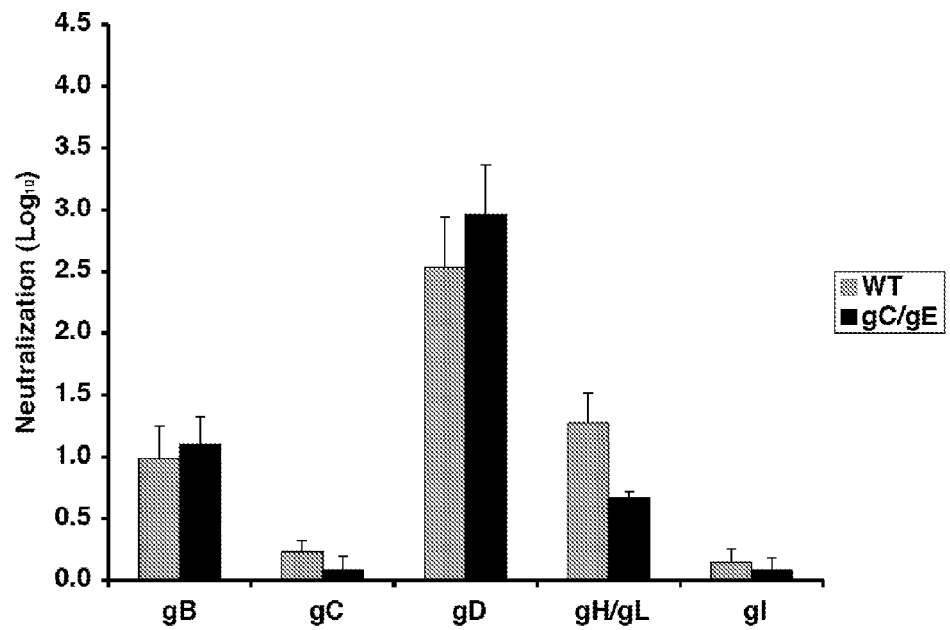
FIG. 45: gC and gE immune evasion domains shield critical neutralizing epitopes. (A) WT and gC/gE mutant viruses were incubated rabbit serum against gB, gC, gD, gH/gL, or gI. Results shown represent the neutralization ($Log_{10}$)+/−SE of 2-3 determinations with each individual antibody. (B) WT and gC/gE mutant viruses were incubated with rabbit serum against each individual glycoprotein. Results shown represent the neutralization +/−SE of 2-3 assays for each antibody.
Figure 45B:
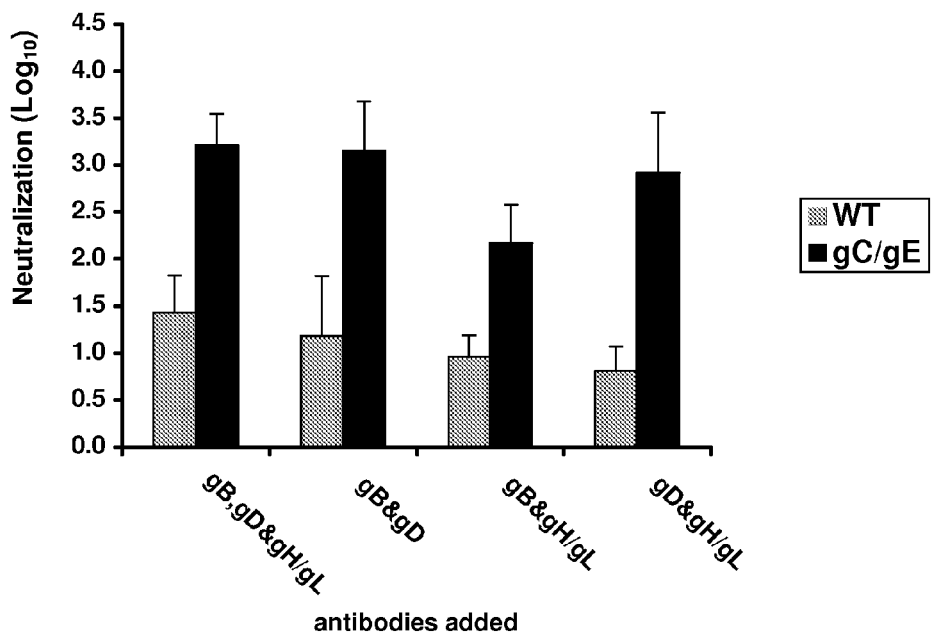

Since the human sera used in FIGS. 42B and 44B contain antibodies to multiple glycoproteins, we performed neutralization experiments using combinations of antibodies directed against gB, gD, and gH/gL (FIG. 45B). When used in combination, greater neutralization was detected for the gC/gE mutant than the WT virus, suggesting that the mutations within gC and gE expose neutralizing epitopes on multiple glycoproteins. Differences between the WT and gC/gE mutant viruses were comparable whether or not gH/gL antibodies were included in the neutralization reaction, indicating that the epitopes blocked are primarily on gB and gD.

Figure 46A:
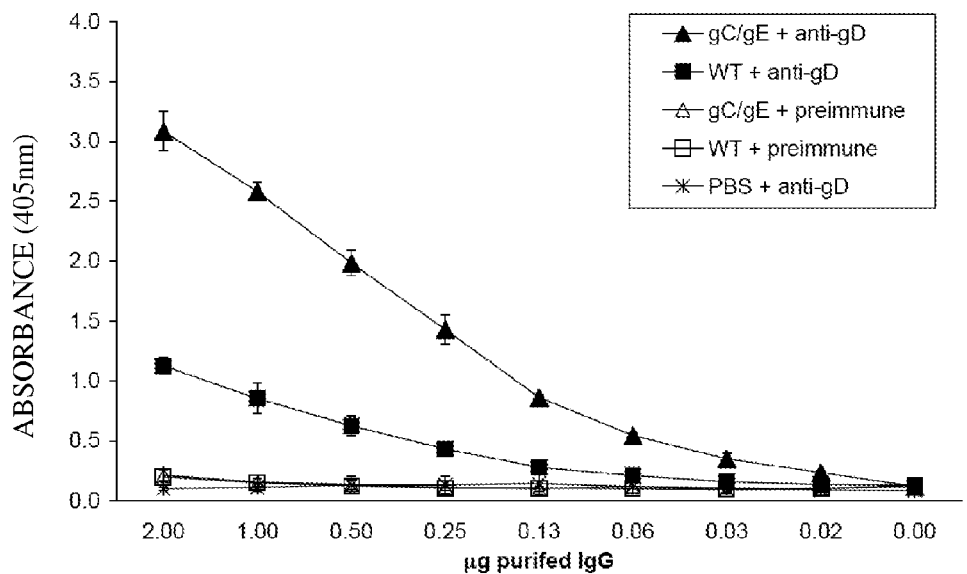
FIG. 46: Binding of anti-glycoprotein immunoglobulin to HSV-1 WT and gC/gE mutant viruses. (A) Comparing anti-gD binding to gC/gE mutant and WT virus. (B) Comparing anti-gB binding to gC/gE mutant and WT virus. (C) Comparing anti-gH/gL binding to gC/gE mutant and WT virus. Figures A-C represent the mean of three independent experiments. Error bars indicate standard deviation. (D) Binding of chicken anti-gD immunoglobulins. Figure D was performed once.
Figure 46B:
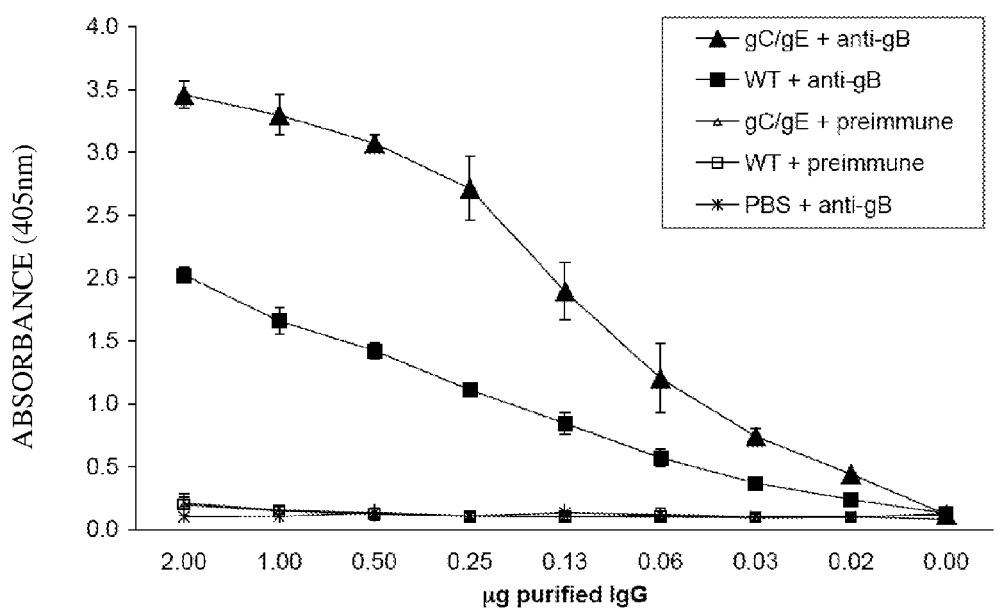
Figure 46C:
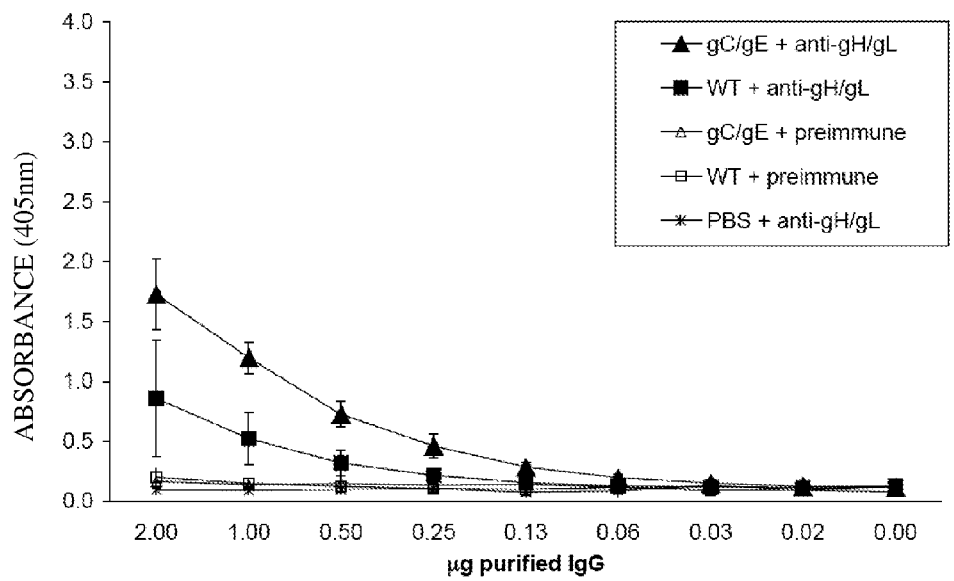
Figure 46D:
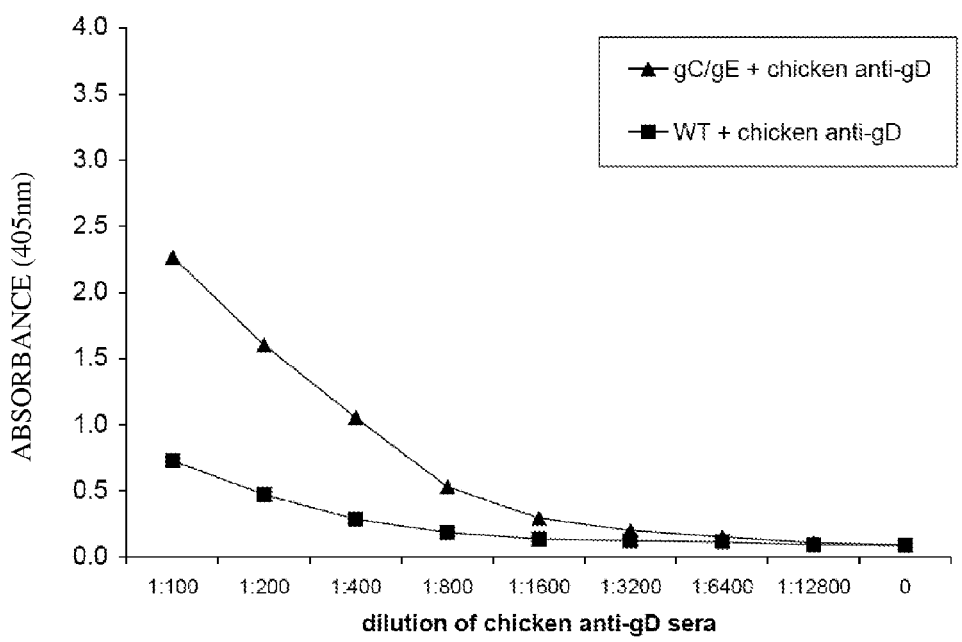

A viral ELISA was performed using WT and gC/gE mutant viruses to further evaluate whether the mutations on the gC/gE mutant virus expose epitopes on gB, gD and gH/gL. The gC/gE mutant virus bound greater concentrations of gD (FIG. 46A), gB (FIG. 46B) and gH/gL (FIG. 44C) antibodies than WT virus. Additional experiments were performed using chicken anti-gD antibodies. Chickens produce IgY antibodies that do not have domains that bind to Fc receptors. These antibodies were used to evaluate the potential contribution of the viral FcγR in the ELISA experiments. When chicken anti-gD antibody was added to WT or gC/gE mutant virus, greater binding was detected to the gC/gE mutant than WT virus (FIG. 46D). These results indicate that differences in antibody binding occur independent of Fc binding to the viral FcγR and support the hypothesis that gC and gE block epitopes on viral glycoproteins essential for entry, particularly on gB and gD.

Mutations in gC and gE enable access of antibodies to viral glycoproteins, including gB, gD and gH/gL, suggesting that gC and gE on WT virus shield epitopes on viral glycoproteins from neutralizing antibodies (see model FIG. 47).

HIV subjects maintain high levels of neutralizing antibody and complement throughout the course of the HIV infection. Therefore, blocking immune evasion domains on gC and gE via subunit vaccines may allow endogenous antibody and complement to be more effective against HSV in HIV patients.

What is claimed is:

1. An immunogenic composition comprising:
   a. a recombinant Herpes Simplex Virus (HSV)-2 glycoprotein D (gD) protein or immunogenic fragment thereof; and
   b. a recombinant HSV-2 glycoprotein C (gC) protein fragment, wherein said fragment comprises a C3b-binding domain thereof, or an immunogenic fragment of said C3b-binding domain;
   wherein administration of said composition to a human subject elicits an anti HSV-2 gC antibody that blocks an immune evasion function of said recombinant HSV gC protein.

2. The composition of claim 1, further comprising a recombinant HSV-1 protein selected from a gD-1 protein, a gC-1 protein, and a gE-1 protein.

3. The composition of claim 1, further comprising an adjuvant.

4. The composition of claim 3, wherein said adjuvant comprises a CpG-containing nucleotide molecule, an aluminum salt adjuvant, or a combination thereof.

5. A method of inducing an anti-HSV-2 immune response in a subject, the method comprising the step of administering to said subject the composition of claim 1.

6. The method of claim 5 further comprising the step of administering to said subject a booster immunization, wherein said booster immunization comprises a recombinant HSV-2 gD protein or immunogenic fragment thereof.

7. The method of claim 6, wherein said recombinant HSV-2 gD protein or immunogenic fragment thereof is present in said booster immunization an amount of 2-10 micrograms per dose.

8. A method of treating, suppressing, inhibiting, or reducing an incidence of an Herpes Simplex Virus (HSV)-2 infection in a subject, the method comprising the step of administering to said subject an immunogenic composition comprising (a) a recombinant HSV-2 glycoprotein D (gD) protein or immunogenic fragment thereof; and (b) a recombinant HSV-2 glycoprotein C (gC) protein fragment, wherein said fragment comprises a C3b-binding domain thereof, or an immunogenic fragment of said C3b-binding domain, wherein administration of said composition elicits an anti-HSV-2 gC antibody that blocks an immune evasion function of said recombinant HSV gC protein.

9. The method of claim 8, wherein said HSV-2 infection is a primary HSV-2 infection.

10. The method of claim 8, wherein said HSV-2 infection is a flare, recurrence, or HSV labialis following a primary HSV infection.

11. The method of claim 8, wherein said HSV-2 infection is a genital HSV-2 infection.

12. The method of claim 8, wherein said HSV-2 infection is an oral HSV-2 infection.

13. The method of claim 8, wherein said composition is administered intramuscularly.

14. The method of claim 8, wherein said composition is administered before exposure to HSV-2.

15. The method of claim 10, wherein said composition is administered after exposure to HSV-2.

16. The method of claim 8 further comprising the step of administering to said subject a booster immunization, wherein said booster immunization comprises said recombinant HSV-2 gD protein or immunogenic fragment thereof.

17. The method of claim 16, wherein said recombinant HSV gD protein or immunogenic fragment thereof is present in said booster immunization an amount of 2-10 micrograms per dose.

18. The method of claim 8, wherein said HSV-2 infection is a reactivation of a latent HSV infection.

19. The method of claim 8, wherein said composition further comprises an adjuvant.

* * * * *

SEQUENCE LISTING

<160> NUMBER OF SEQ ID NOS: 16

<210> SEQ ID NO 1
<211> LENGTH: 394
<212> TYPE: PRT
<213> ORGANISM: human herpesvirus 1

<400> SEQUENCE: 1

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Leu Ala Asp Pro Asn Arg Phe Arg Arg Lys Asp Leu Pro

```
                35                  40                  45
Val Leu Asp Gln Leu Thr Asp Pro Pro Gly Val Arg Arg Val Tyr His
 50                  55                  60

Ile Gln Ala Gly Leu Pro Asp Pro Phe Gln Pro Ser Leu Pro Ile
 65                  70                  75                  80

Thr Val Tyr Tyr Ala Val Leu Glu Arg Ala Cys Arg Ser Val Leu Leu
                 85                  90                  95

Asn Ala Pro Ser Glu Ala Pro Gln Ile Val Arg Gly Ala Ser Glu Asp
            100                 105                 110

Val Arg Lys Gln Pro Tyr Asn Leu Thr Ile Ala Trp Phe Arg Met Gly
        115                 120                 125

Gly Asn Cys Ala Ile Pro Ile Thr Val Met Glu Tyr Thr Glu Cys Ser
    130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Lys Gly Ser Cys Lys Tyr Ala Leu Pro Leu Arg Ile Pro Pro
    210                 215                 220

Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Val Tyr Ser Leu Lys Ile Ala Gly Trp His Gly Pro Lys Ala Pro
            260                 265                 270

Tyr Thr Ser Thr Leu Leu Pro Pro Glu Leu Ser Glu Thr Pro Asn Ala
        275                 280                 285

Thr Gln Pro Glu Leu Ala Pro Glu Ala Pro Asp Ser Ala Leu Leu
    290                 295                 300

Glu Asp Pro Val Gly Thr Val Ala Pro Gln Ile Pro Pro Asn Trp His
305                 310                 315                 320

Ile Pro Ser Ile Gln Asp Ala Ala Thr Pro Tyr His Pro Pro Ala Thr
                325                 330                 335

Pro Asn Asn Met Gly Leu Ile Ala Gly Ala Val Gly Gly Ser Leu Leu
            340                 345                 350

Ala Ala Leu Val Ile Cys Gly Ile Val Tyr Trp Met Arg Arg Arg Thr
        355                 360                 365

Gln Lys Ala Pro Lys Arg Ile Arg Leu Pro His Ile Arg Glu Asp Asp
    370                 375                 380

Gln Pro Ser Ser His Gln Pro Leu Phe Tyr
385                 390

<210> SEQ ID NO 2
<211> LENGTH: 393
<212> TYPE: PRT
<213> ORGANISM: human herpesvirus 2

<400> SEQUENCE: 2

Met Gly Arg Leu Thr Ser Gly Val Gly Thr Ala Ala Leu Leu Val Val
  1               5                  10                  15

Ala Val Gly Leu Arg Val Val Cys Ala Lys Tyr Ala Leu Ala Asp Pro
```

```
                 20                  25                  30
Ser Leu Lys Met Ala Asp Pro Asn Arg Phe Arg Gly Lys Asn Leu Pro
             35                  40                  45

Val Leu Asp Gln Leu Thr Asp Pro Pro Gly Val Lys Arg Val Tyr His
         50                  55                  60

Ile Gln Pro Ser Leu Glu Asp Pro Phe Gln Pro Ser Ile Pro Ile
 65                  70                  75                  80

Thr Val Tyr Tyr Ala Val Leu Glu Arg Ala Cys Arg Ser Val Leu Leu
                 85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
            115                 120                 125

Asp Asn Cys Ala Ile Pro Ile Thr Val Met Glu Tyr Thr Glu Cys Pro
            130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
            195                 200                 205

Arg Ala Arg Ala Ser Cys Lys Tyr Ala Leu Pro Leu Arg Ile Pro Pro
            210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
            275                 280                 285

Thr Gln Pro Glu Leu Val Pro Glu Asp Pro Glu Asp Ser Ala Leu Leu
            290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Arg Ala Gln
            355                 360                 365

Met Ala Pro Lys Arg Leu Arg Leu Pro His Ile Arg Asp Asp Asp Ala
            370                 375                 380

Pro Pro Ser His Gln Pro Leu Phe Tyr
385                 390

<210> SEQ ID NO 3
<211> LENGTH: 511
<212> TYPE: PRT
<213> ORGANISM: human herpesvirus 1

<400> SEQUENCE: 3

Met Ala Pro Gly Arg Val Gly Leu Ala Val Val Leu Trp Gly Leu Leu
```

-continued

```
1               5                   10                  15
Trp Leu Gly Ala Gly Val Ala Gly Gly Ser Glu Thr Ala Ser Thr Gly
            20                  25                  30

Pro Thr Ile Thr Ala Gly Ala Val Thr Asn Ala Ser Glu Ala Pro Thr
            35                  40                  45

Ser Gly Ser Pro Gly Ser Ala Ala Ser Pro Glu Val Thr Pro Thr Ser
            50                  55                  60

Thr Pro Asn Pro Asn Val Thr Gln Asn Lys Thr Thr Pro Thr Glu
65                  70                  75                  80

Pro Ala Ser Pro Pro Thr Thr Pro Lys Pro Thr Ser Thr Pro Lys Ser
                    85                  90                  95

Pro Pro Thr Ser Thr Pro Asp Pro Lys Pro Lys Asn Asn Thr Thr Pro
                100                 105                 110

Ala Lys Ser Gly Arg Pro Thr Lys Pro Pro Gly Pro Val Trp Cys Asp
            115                 120                 125

Arg Arg Asp Pro Leu Ala Arg Tyr Gly Ser Arg Val Gln Ile Arg Cys
130                 135                 140

Arg Phe Arg Asn Ser Thr Arg Met Glu Phe Arg Leu Gln Ile Trp Arg
145                 150                 155                 160

Tyr Ser Met Gly Pro Ser Pro Pro Ile Ala Pro Ala Pro Asp Leu Glu
                165                 170                 175

Glu Val Leu Thr Asn Ile Thr Ala Pro Pro Gly Gly Leu Leu Val Tyr
            180                 185                 190

Asp Ser Ala Pro Asn Leu Thr Asp Pro His Val Leu Trp Ala Glu Gly
            195                 200                 205

Ala Gly Pro Gly Ala Asp Pro Pro Leu Tyr Ser Val Thr Gly Pro Leu
            210                 215                 220

Pro Thr Gln Arg Leu Ile Ile Gly Glu Val Thr Pro Ala Thr Gln Gly
225                 230                 235                 240

Met Tyr Tyr Leu Ala Trp Gly Arg Met Asp Ser Pro His Glu Tyr Gly
                245                 250                 255

Thr Trp Val Arg Val Arg Met Phe Arg Pro Pro Ser Leu Thr Leu Gln
                260                 265                 270

Pro His Ala Val Met Glu Gly Gln Pro Phe Lys Ala Thr Cys Thr Ala
            275                 280                 285

Ala Ala Tyr Tyr Pro Arg Asn Pro Val Glu Phe Asp Trp Phe Glu Asp
            290                 295                 300

Asp Arg Gln Val Phe Asn Pro Gly Gln Ile Asp Thr Gln Thr His Glu
305                 310                 315                 320

His Pro Asp Gly Phe Thr Thr Val Ser Thr Val Thr Ser Glu Ala Val
                325                 330                 335

Gly Gly Gln Val Pro Pro Arg Thr Phe Thr Cys Gln Met Thr Trp His
            340                 345                 350

Arg Asp Ser Val Thr Phe Ser Arg Asn Ala Thr Gly Leu Ala Leu
            355                 360                 365

Val Leu Pro Arg Pro Thr Ile Thr Met Glu Phe Gly Val Arg His Val
            370                 375                 380

Val Cys Thr Ala Gly Cys Val Pro Glu Gly Val Thr Phe Ala Trp Phe
385                 390                 395                 400

Leu Gly Asp Asp Pro Ser Pro Ala Ala Lys Ser Ala Val Thr Ala Gln
            405                 410                 415

Glu Ser Cys Asp His Pro Gly Leu Ala Thr Val Arg Ser Thr Leu Pro
            420                 425                 430
```

```
Ile Ser Tyr Asp Tyr Ser Glu Tyr Ile Cys Arg Leu Thr Gly Tyr Pro
        435                 440                 445

Ala Gly Ile Pro Val Leu Glu His His Gly Ser His Gln Pro Pro Pro
    450                 455                 460

Arg Asp Pro Thr Glu Arg Gln Val Ile Glu Ala Ile Glu Trp Val Gly
465                 470                 475                 480

Ile Gly Ile Gly Val Leu Ala Ala Gly Val Leu Val Thr Ala Ile
                485                 490                 495

Val Tyr Val Val Arg Thr Ser Gln Ser Arg Gln Arg His Arg Arg
                500                 505                 510

<210> SEQ ID NO 4
<211> LENGTH: 480
<212> TYPE: PRT
<213> ORGANISM: human herpesvirus 2

<400> SEQUENCE: 4

Met Ala Leu Gly Arg Val Gly Leu Ala Val Gly Leu Trp Gly Leu Leu
1               5                   10                  15

Trp Val Gly Val Val Val Leu Ala Asn Ala Ser Pro Gly Arg Thr
                20                  25                  30

Ile Thr Val Gly Pro Arg Gly Asn Ala Ser Asn Ala Ala Pro Ser Ala
            35                  40                  45

Ser Pro Arg Asn Ala Ser Ala Pro Arg Thr Thr Pro Thr Pro Pro Gln
    50                  55                  60

Pro Arg Lys Ala Thr Lys Ser Lys Ala Ser Thr Ala Lys Pro Ala Pro
65                  70                  75                  80

Pro Pro Lys Thr Gly Pro Pro Lys Thr Ser Ser Glu Pro Val Arg Cys
                85                  90                  95

Asn Arg His Asp Pro Leu Ala Arg Tyr Gly Ser Arg Val Gln Ile Arg
            100                 105                 110

Cys Arg Phe Pro Asn Ser Thr Arg Thr Glu Phe Arg Leu Gln Ile Trp
        115                 120                 125

Arg Tyr Ala Thr Ala Thr Asp Ala Glu Ile Gly Thr Ala Pro Ser Leu
    130                 135                 140

Glu Glu Val Met Val Asn Val Ser Ala Pro Pro Gly Gly Gln Leu Val
145                 150                 155                 160

Tyr Asp Ser Ala Pro Asn Arg Thr Asp Pro His Val Ile Trp Ala Glu
                165                 170                 175

Gly Ala Gly Pro Gly Ala Ser Pro Arg Leu Tyr Ser Val Val Gly Pro
            180                 185                 190

Leu Gly Arg Gln Arg Leu Ile Ile Glu Glu Leu Thr Leu Glu Thr Gln
        195                 200                 205

Gly Met Tyr Tyr Trp Val Trp Gly Arg Thr Asp Arg Pro Ser Ala Tyr
    210                 215                 220

Gly Thr Trp Val Arg Val Arg Val Phe Arg Pro Pro Ser Leu Thr Ile
225                 230                 235                 240

His Pro His Ala Val Leu Glu Gly Gln Pro Phe Lys Ala Thr Cys Thr
                245                 250                 255

Ala Ala Thr Tyr Tyr Pro Gly Asn Arg Ala Glu Phe Val Trp Phe Glu
            260                 265                 270

Asp Gly Arg Arg Val Phe Asp Pro Ala Gln Ile His Thr Gln Thr Gln
        275                 280                 285

Glu Asn Pro Asp Gly Phe Ser Thr Val Ser Thr Val Thr Ser Ala Ala
    290                 295                 300
```

-continued

```
Val Gly Gly Gln Gly Pro Pro Arg Thr Phe Thr Cys Gln Leu Thr Trp
305                 310                 315                 320

His Arg Asp Ser Val Ser Phe Ser Arg Arg Asn Ala Ser Gly Thr Ala
                325                 330                 335

Ser Val Leu Pro Arg Pro Thr Ile Thr Met Glu Phe Thr Gly Asp His
            340                 345                 350

Ala Val Cys Thr Ala Gly Cys Val Pro Glu Gly Val Thr Phe Ala Trp
        355                 360                 365

Phe Leu Gly Asp Asp Ser Ser Pro Ala Glu Lys Val Ala Val Ala Ser
370                 375                 380

Gln Thr Ser Cys Gly Arg Pro Gly Thr Ala Thr Ile Arg Ser Thr Leu
385                 390                 395                 400

Pro Val Ser Tyr Glu Gln Thr Glu Tyr Ile Cys Arg Leu Ala Gly Tyr
                405                 410                 415

Pro Asp Gly Ile Pro Val Leu Glu His His Gly Ser His Gln Pro Pro
            420                 425                 430

Pro Arg Asp Pro Thr Glu Arg Gln Val Ile Arg Ala Val Glu Gly Ala
        435                 440                 445

Gly Ile Gly Val Ala Val Leu Val Ala Val Val Leu Ala Gly Thr Ala
    450                 455                 460

Val Val Tyr Leu Thr His Ala Ser Ser Val Arg Tyr Arg Arg Leu Arg
465                 470                 475                 480

<210> SEQ ID NO 5
<211> LENGTH: 552
<212> TYPE: PRT
<213> ORGANISM: human herpesvirus 1

<400> SEQUENCE: 5

Met Asp Arg Gly Ala Val Val Gly Phe Leu Leu Gly Val Cys Val Val
1               5                   10                  15

Ser Cys Leu Ala Gly Thr Pro Lys Thr Ser Trp Arg Arg Val Ser Val
                20                  25                  30

Gly Glu Asp Val Ser Leu Leu Pro Ala Pro Gly Pro Thr Gly Arg Gly
            35                  40                  45

Pro Thr Gln Lys Leu Leu Trp Ala Val Glu Pro Leu Asp Gly Cys Gly
    50                  55                  60

Pro Leu His Pro Ser Trp Val Ser Leu Met Pro Pro Lys Gln Val Pro
65                  70                  75                  80

Glu Thr Val Val Asp Ala Ala Cys Met Arg Ala Pro Val Pro Leu Ala
                85                  90                  95

Met Ala Tyr Ala Pro Pro Ala Pro Ser Ala Thr Gly Gly Leu Arg Thr
            100                 105                 110

Asp Phe Val Trp Gln Glu Arg Ala Ala Val Val Asn Arg Ser Leu Val
        115                 120                 125

Ile Tyr Gly Val Arg Glu Thr Asp Ser Gly Leu Tyr Thr Leu Ser Val
    130                 135                 140

Gly Asp Ile Lys Asp Pro Ala Arg Gln Val Ala Ser Val Val Leu Val
145                 150                 155                 160

Val Gln Pro Ala Pro Val Pro Thr Pro Pro Thr Pro Ala Asp Tyr
                165                 170                 175

Asp Glu Asp Asp Asn Asp Glu Gly Glu Asp Glu Ser Leu Ala
            180                 185                 190

Gly Thr Pro Ala Ser Gly Thr Pro Arg Leu Pro Pro Ser Pro Ala Pro
        195                 200                 205
```

Pro Arg Ser Trp Pro Ser Ala Pro Glu Val Ser His Val Arg Gly Val
210                 215                 220

Thr Val Arg Met Glu Thr Pro Glu Ala Ile Leu Phe Ser Pro Gly Glu
225                 230                 235                 240

Ala Phe Ser Thr Asn Val Ser Ile His Ala Ile Ala His Asp Asp Gln
                245                 250                 255

Thr Tyr Thr Met Asp Val Val Trp Leu Arg Phe Asp Val Pro Thr Ser
                260                 265                 270

Cys Ala Glu Met Arg Ile Tyr Glu Ser Cys Leu Tyr His Pro Gln Leu
                275                 280                 285

Pro Glu Cys Leu Ser Pro Ala Asp Ala Pro Cys Ala Ala Ser Thr Trp
290                 295                 300

Thr Ser Arg Leu Ala Val Arg Ser Tyr Ala Gly Cys Ser Arg Thr Asn
305                 310                 315                 320

Pro Pro Pro Arg Cys Ser Ala Glu Ala His Met Glu Pro Phe Pro Gly
                325                 330                 335

Leu Ala Trp Gln Ala Ala Ser Val Asn Leu Glu Phe Arg Asp Ala Ser
                340                 345                 350

Pro Gln His Ser Gly Leu Tyr Leu Cys Val Val Tyr Val Asn Asp His
                355                 360                 365

Ile His Ala Trp Gly His Ile Thr Ile Asn Thr Ala Ala Gln Tyr Arg
370                 375                 380

Asn Ala Val Val Glu Gln Pro Leu Pro Gln Arg Gly Ala Asp Leu Ala
385                 390                 395                 400

Glu Pro Thr His Pro His Val Gly Ala Pro Pro His Ala Pro Pro Thr
                405                 410                 415

His Gly Ala Leu Arg Leu Gly Ala Val Met Gly Ala Ala Leu Leu Leu
                420                 425                 430

Ser Ala Leu Gly Leu Ser Val Trp Ala Cys Met Thr Cys Trp Arg Arg
435                 440                 445

Arg Ala Trp Arg Ala Val Lys Ser Arg Ala Ser Gly Lys Gly Pro Thr
450                 455                 460

Tyr Ile Arg Val Ala Asp Ser Glu Leu Tyr Ala Asp Trp Ser Ser Asp
465                 470                 475                 480

Ser Glu Gly Glu Arg Asp Gln Val Pro Trp Leu Ala Pro Pro Glu Arg
                485                 490                 495

Pro Asp Ser Pro Ser Thr Asn Gly Ser Gly Phe Glu Ile Leu Ser Pro
                500                 505                 510

Thr Ala Pro Ser Val Tyr Pro Arg Ser Asp Gly His Gln Ser Arg Arg
                515                 520                 525

Gln Leu Thr Thr Phe Gly Ser Gly Arg Pro Asp Arg Arg Tyr Ser Gln
530                 535                 540

Ala Ser Asp Ser Ser Val Phe Trp
545                 550

<210> SEQ ID NO 6
<211> LENGTH: 545
<212> TYPE: PRT
<213> ORGANISM: human herpesvirus 2

<400> SEQUENCE: 6

Met Ala Arg Gly Ala Gly Leu Val Phe Phe Val Gly Val Trp Val Val
1               5                   10                  15

Ser Cys Leu Ala Ala Ala Pro Arg Thr Ser Trp Lys Arg Val Thr Ser
                20                  25                  30

```
Gly Glu Asp Val Val Leu Leu Pro Ala Pro Ala Glu Arg Thr Arg Ala
         35                  40                  45

His Lys Leu Leu Trp Ala Ala Glu Pro Leu Asp Ala Cys Gly Pro Leu
 50                  55                  60

Arg Pro Ser Trp Val Ala Leu Trp Pro Arg Arg Val Leu Glu Thr
 65                  70                  75                  80

Val Val Asp Ala Ala Cys Met Arg Ala Pro Glu Pro Leu Ala Ile Ala
                 85                  90                  95

Tyr Ser Pro Pro Phe Pro Ala Gly Asp Glu Gly Leu Tyr Ser Glu Leu
             100                 105                 110

Ala Trp Arg Asp Arg Val Ala Val Val Asn Glu Ser Leu Val Ile Tyr
         115                 120                 125

Gly Ala Leu Glu Thr Asp Ser Gly Leu Tyr Thr Leu Ser Val Val Gly
     130                 135                 140

Leu Ser Asp Glu Ala Arg Gln Val Ala Ser Val Val Leu Val Val Glu
145                 150                 155                 160

Pro Ala Pro Val Pro Thr Pro Thr Pro Asp Asp Tyr Asp Glu Glu Asp
                 165                 170                 175

Asp Ala Gly Val Thr Asn Ala Arg Arg Ser Ala Phe Pro Pro Gln Pro
             180                 185                 190

Pro Pro Arg Arg Pro Pro Val Ala Pro Pro Thr His Pro Arg Val Ile
         195                 200                 205

Pro Glu Val Ser His Val Arg Gly Val Thr Val His Met Glu Thr Leu
     210                 215                 220

Glu Ala Ile Leu Phe Ala Pro Gly Glu Thr Phe Gly Thr Asn Val Ser
225                 230                 235                 240

Ile His Ala Ile Ala His Asp Asp Gly Pro Tyr Ala Met Asp Val Val
                 245                 250                 255

Trp Met Arg Phe Asp Val Pro Ser Ser Cys Ala Asp Met Arg Ile Tyr
             260                 265                 270

Glu Ala Cys Leu Tyr His Pro Gln Leu Pro Glu Cys Leu Ser Pro Ala
         275                 280                 285

Asp Ala Pro Cys Ala Val Ser Ser Trp Ala Tyr Arg Leu Ala Val Arg
     290                 295                 300

Ser Tyr Ala Gly Cys Ser Arg Thr Thr Pro Pro Arg Cys Phe Ala
305                 310                 315                 320

Glu Ala Arg Met Glu Pro Val Pro Gly Leu Ala Trp Leu Ala Ser Thr
                 325                 330                 335

Val Asn Leu Glu Phe Gln His Ala Ser Pro Gln His Ala Gly Leu Tyr
             340                 345                 350

Leu Cys Val Val Tyr Val Asp Asp His Ile His Ala Trp Gly His Met
         355                 360                 365

Thr Ile Ser Thr Ala Ala Gln Tyr Arg Asn Ala Val Val Glu Gln His
     370                 375                 380

Leu Pro Gln Arg Gln Pro Glu Pro Val Glu Pro Thr Arg Pro His Val
385                 390                 395                 400

Arg Ala Pro His Pro Ala Pro Ser Ala Arg Gly Pro Leu Arg Leu Gly
                 405                 410                 415

Ala Val Leu Gly Ala Ala Leu Leu Ala Ala Leu Gly Leu Ser Ala
             420                 425                 430

Trp Ala Cys Met Thr Cys Trp Arg Arg Arg Ser Trp Arg Ala Val Lys
         435                 440                 445

Ser Arg Ala Ser Ala Thr Gly Pro Thr Tyr Ile Arg Val Ala Asp Ser
     450                 455                 460
```

```
Glu Leu Tyr Ala Asp Trp Ser Ser Asp Ser Glu Gly Glu Arg Asp Gly
465                 470                 475                 480

Ser Leu Trp Gln Asp Pro Pro Glu Arg Pro Asp Ser Pro Ser Thr Asn
                485                 490                 495

Gly Ser Gly Phe Glu Ile Leu Ser Pro Thr Ala Pro Ser Val Tyr Pro
            500                 505                 510

His Ser Glu Gly Arg Lys Ser Arg Arg Pro Leu Thr Thr Phe Gly Ser
        515                 520                 525

Gly Ser Pro Gly Arg Arg His Ser Gln Ala Ser Tyr Pro Ser Val Leu
    530                 535                 540

Trp
545

<210> SEQ ID NO 7
<211> LENGTH: 14
<212> TYPE: DNA
<213> ORGANISM: Unknown
<220> FEATURE:
<223> OTHER INFORMATION: CpG-containing oligonucleotide

<400> SEQUENCE: 7
ctagacgtta gcgt                                                      14

<210> SEQ ID NO 8
<211> LENGTH: 8
<212> TYPE: DNA
<213> ORGANISM: Unknown
<220> FEATURE:
<223> OTHER INFORMATION: CpG-containing oligonucleotide

<400> SEQUENCE: 8 tcaacgtt                                                              8

<210> SEQ ID NO 9
<211> LENGTH: 20
<212> TYPE: DNA
<213> ORGANISM: Unknown
<220> FEATURE:
<223> OTHER INFORMATION: CpG-containing oliginucleotide

<400> SEQUENCE: 9
tccatgacgt tcctgacgtt                                                20

<210> SEQ ID NO 10
<211> LENGTH: 24
<212> TYPE: DNA
<213> ORGANISM: Unknown
<220> FEATURE:
<223> OTHER INFORMATION: CpG-containing oliginucleotide

<400> SEQUENCE: 10
tcgtcgtttc gtcgttttgt cgtt                                           24

<210> SEQ ID NO 11
<211> LENGTH: 22
<212> TYPE: DNA
<213> ORGANISM: Unknown
<220> FEATURE:
<223> OTHER INFORMATION: CpG-containing oliginucleotide

<400> SEQUENCE: 11
tcgtcgttgt cgttttgtcg tt                                             22
```

```
<210> SEQ ID NO 12
<211> LENGTH: 22
<212> TYPE: DNA
<213> ORGANISM: Unknown
<220> FEATURE:
<223> OTHER INFORMATION: CpG-containing oliginucleotide

<400> SEQUENCE: 12
tcgtcgtttt cggcgcgcgc cg                                          22

<210> SEQ ID NO 13
<211> LENGTH: 24
<212> TYPE: DNA
<213> ORGANISM: Unknown
<220> FEATURE:
<223> OTHER INFORMATION: CpG-containing oliginucleotide

<400> SEQUENCE: 13
tgctgctttt gtgcttttgt gctt                                        24

<210> SEQ ID NO 14
<211> LENGTH: 20
<212> TYPE: DNA
<213> ORGANISM: Unknown
<220> FEATURE:
<223> OTHER INFORMATION: CpG-containing oliginucleotide

<400> SEQUENCE: 14
tccatgagct tcctgagctt                                             20

<210> SEQ ID NO 15
<211> LENGTH: 21
<212> TYPE: DNA
<213> ORGANISM: Unknown
<220> FEATURE:
<223> OTHER INFORMATION: CpG-containing oliginucleotide

<400> SEQUENCE: 15
ggggacgacg tcgtgggggg g                                           21

<210> SEQ ID NO 16
<211> LENGTH: 20
<212> TYPE: DNA
<213> ORGANISM: Unknown
<220> FEATURE:
<223> OTHER INFORMATION: CpG-containing oliginucleotide

<400> SEQUENCE: 16
gggggagcat gctgggggg                                              20
```